(12) United States Patent
Auerbach et al.

(10) Patent No.: US 6,939,875 B2
(45) Date of Patent: Sep. 6, 2005

(54) COMPOUNDS THAT MODULATE PPAR ACTIVITY AND METHODS FOR THEIR PREPARATION

(75) Inventors: Bruce J. Auerbach, Ann Arbor, MI (US); Larry D. Bratton, Whitmore Lake, MI (US); Gary F. Filzen, Ann Arbor, MI (US); Andrew G. Geyer, Novi, MI (US); Bharat K. Trivedi, Farmington Hills, MI (US); Paul C. Unangst, Ann Arbor, MI (US)

(73) Assignee: Warner-Lambert Company, Morris Plains, NJ (US)

( * ) Notice: Subject to any disclaimer, the term of this patent is extended or adjusted under 35 U.S.C. 154(b) by 3 days.

(21) Appl. No.: 10/979,617

(22) Filed: Nov. 2, 2004

(65) Prior Publication Data

US 2005/0153996 A1 Jul. 14, 2005

Related U.S. Application Data

(62) Division of application No. 10/347,749, filed on Jan. 22, 2003.
(60) Provisional application No. 60/386,026, filed on Jun. 5, 2002, and provisional application No. 60/370,508, filed on Apr. 5, 2002.

(51) Int. Cl.[7] .................. C07D 213/02; A61K 31/44
(52) U.S. Cl. .................. 514/277; 514/345; 514/568; 546/301; 546/342; 562/426; 562/465
(58) Field of Search ................. 546/301, 342; 562/426, 465; 514/277, 345, 568

(56) References Cited

U.S. PATENT DOCUMENTS

| 5,447,656 A | 9/1995 | Jungbauer et al. |
| 6,506,757 B1 | 1/2003 | Tajima et al. |
| 2003/0207915 A1 | 11/2003 | Cheng et al. |
| 2003/0207916 A1 | 11/2003 | Cheng et al. |
| 2003/0207924 A1 | 11/2003 | Cheng et al. |

FOREIGN PATENT DOCUMENTS

| DE | 3526235 | 5/1986 |
| DE | 4002374 A1 | 8/1991 |
| EP | 0578054 A1 | 1/1994 |
| EP | 0625513 A1 | 11/1994 |
| EP | 0930299 | 7/1999 |
| JP | 09194418 | 7/1997 |
| WO | WO9604228 A1 | 2/1996 |
| WO | WO97/28137 A1 | 8/1997 |
| WO | WO 97/28149 A1 | 8/1997 |
| WO | WO9946232 A1 | 9/1999 |
| WO | WO 01/00603 A1 | 1/2001 |
| WO | WO 01/16120 A1 | 3/2001 |
| WO | WO02/50048 A1 | 6/2002 |
| WO | WO02/062774 A1 | 8/2002 |
| WO | WO 02/092590 A1 | 11/2002 |
| WO | WO 02/100403 A1 | 12/2002 |
| WO | WO 03/024395 A2 | 3/2003 |

OTHER PUBLICATIONS

Nishimura, Koji: "Preparation of Indole Derivatives as Chymase Inhibitors and Drugs containing the same as the active Ingredient" XP002258311.
Nanteuil De G et al: "5–Imidaol–1–yl–1H–Benzimidazoles Inhibiteurs De L Interleukine–1: UNE Nouvelle Voie Pour Le Traitement De L'Arthrose" XP001147539.
T. Gordon et al., The American Journal of Medicine, 1977;62:707–714.
Rissanen et al., British Medical Journal,301:835–837 (1990).
W.R. Oliver et al., PNAS, vol. 98, pp. 5306–5311, (2001).
S.M. Berge et al., "Pharmaceutical Salts", Journal of Pharmaceutical Sciences, 1977;66:1–19.
Belleney, J. et al., J. Heterocyclic Chem., 1984;21:1431.

Primary Examiner—Zinna Northington Davis
(74) Attorney, Agent, or Firm—Michelle A. Sherwood

(57) ABSTRACT

This invention discloses compounds that alter PPAR activity. The invention also discloses pharmaceutically acceptable salts of the compounds, pharmaceutically acceptable compositions comprising the compounds or their salts, and methods of using them as therapeutic agents for treating or preventing disipidemia, hypercholesteremia, obesity, eating disorders, hyperglycemia, atherosclerosis, hypertriglyceridemia, hyperinsulinemia and diabetes in a mammal as well as methods of supressing appetite and modulating leptin levels in a mammal. The present invention also discloses methods for making the disclosed compounds.

24 Claims, No Drawings

COMPOUNDS THAT MODULATE PPAR ACTIVITY AND METHODS FOR THEIR PREPARATION

CROSS REFERENCE TO RELATED APPLICATION

This application is a divisional application of U.S. Ser. No. 10/347,749, filed Jan. 22, 2003, which claims priority to U.S. Provisional Applications Ser. Nos. 60/370,508, filed Apr. 5, 2002 and 60/386,026, filed Jun. 5, 2002.

FIELD OF THE INVENTION

The present invention relates to compounds and pharmaceutical formulations that can be used to treat conditions mediated by nuclear hormone receptors, more specifically, to compounds and pharmaceutical formulations that modulate Peroxisome Proliferator Activation Receptor (PPAR) activity.

BACKGROUND OF THE INVENTION

Hypercholesterolemia, dyslipidemia, diabetes, and obesity are well-recognized risk factors in the onset of atherosclerosis and coronary heart disease. The diseases are characterized by high levels of cholesterol and lipids in the blood. The blood cholesterol pool is generally dependent on dietary uptake of cholesterol from the intestine, and from the biosynthesis of cholesterol throughout the body, especially the liver. The majority of cholesterol in plasma is carried on apolipoprotein B-containing lipoproteins, such as low-density lipoproteins (LDL) and very-low-density lipoproteins (VLDL). The risk of coronary artery disease in man increases when LDL and VLDL levels increase. Conversely, high levels of cholesterol carried in high-density lipoproteins (HDL) is protective against coronary artery disease (Am. J. Med., 1977;62:707–714).

The statins represent perhaps the most important class of lipid-lowering drugs. These compounds inhibit HMG-CoA reductase which is implicated in the rate-limiting step in cellular cholesterol biosynthesis. Representative statins include atorvastatin, lovastatin, pravastatin, and simvastatin. The effectiveness of these compounds depends on LDL receptor regulation. Other important antilipidemia drugs include fibrates such as gemfibril and clofibrate, bile acid sequestrants such as cholestyramine and colestipol, probucol, and nicotinic acid analogs.

To date, a number of oral antidiabetic agents have been developed. The most commonly used hypoglygernic drugs are the sulfonylureas. Sulfonylureas are generally used to stimulate insulin. The biguanide metformin is generally used to improve insulin sensitivity and to decrease hepatic glucose output. Acarbose is used to limit postprandial hyperglycemia. Thiazolidine 2,4 diones are used to enhance insulin action without increasing insulin secretion.

Obesity is a chronic disease that is highly prevalent in modern society and is associated not only with a social stigma, but also with decreased life span and numerous medical problems, including diabetes mellitus, insulin resistance, hypertension, hypercholesterolemia, thromboembolic disease, and coronary heart disease. Rissanen et al, British Medical Journal, 301:835–837 (1990). Treatment of obesity remains a problem and it is unclear whether dieting results in decreased long-term risk of early death. A further important obesity intervention is physical activity. Exercise, however, in general, has been found to be only moderately successful in promoting weight loss. A program combining both dieting and exercise as well as behaviour modification is widely viewed as the optimal approach to weight loss. Studies have demonstrated that the combination of both food restriction and exercise promote a substantial loss of fat while maitaining lean tissue.

Peroxisome Proliferator Activation Receptors (PPAR) are implicated in a number of biological processes and disease states including hypercholesterolemia, dyslipidemia, and diabetes. PPARs are members of the nuclear receptor superfamily of transcription factors that includes steroid, thyroid, and vitamin D receptors. They play a role in controlling expression of proteins that regulate lipid metabolism. Furthermore, the PPARs are activated by fatty acids and fatty acid metabolites. There are three PPAR subtypes PPAR α, PPAR β (also referred to as PPAR δ), and PPAR γ. Each receptor shows a different pattern of tissue expression, and differences in activation by structurally diverse compounds. PPAR γ, for instance, is expressed most abundantly in adipose tissue and at lower levels in skeletal muscle, heart, liver, intestine, kidney, vascular endothelial and smooth muscle cells as well as macrophages. PPAR receptors are associated with regulation of insulin sensitivity and blood glucose levels, macrophage differentiation, inflammatory response, and cell differentiation. Accordingly, PPARs have been associated with obesity, diabetes, carcinogenesis, hyperplasia, atherosclerosis, dyslipidemia, and hypercholesterolemia.

In addition, PPARα agonists lower plasma triglycerides and LDL cholesterol and are therefore useful in treating hypertriglyceridemia, dyslipidemia and obesity. PPAR γ is associated with the development of non-insulin-dependent diabetes mellitus (NIDDM), hypertension, coronary artery disease, dyslipidemia and certain malignancies. Finally, activation of PPAR β has been demonstrated to increase HDL levels. (Leibowitz, WO97/28149, August 1997.) More recently, a PPAR β selective agonist was reported to have shown a dose-related increase in serum HDL-C and decrease in LDL-C and VLDL-TG in insulin-resistant middle aged rhesus monkeys. (W. R. Oliver et al., PNAS, v. 98, pp. 5306–5311, 2001)

Antilipidemic, antidiabetic and anti-obesity agents are still considered to have non-uniform effectiveness. The effectivieness of antidiabetic and antilipidemic therapies is limited, in part because of poor patient compliance due to unacceptable side effects. These side effects include diarrhea and gastrointestinal discomfort, and in the case of antidiabetics, edema, hypoglycemia and hepatoxicity. Furthermore, each type of drug does not work equally well in all patients.

For the reasons set forth above, there is a need for novel antilipidemic, antidiabetic, and anti-obesity agents that can be used alone or in combination. Furthermore, activation of multiple PPARs, for instance, PPARβ alone or in combination with the simultaneous activation of PPAR α and/or PPAR γ, may be desirable in formulating a treatment for dyslipidemia in which HDL is increased and LDL lowered.

SUMMARY OF THE INVENTION

The present invention provides compounds capable of modulating PPAR activity. Compounds of the present invention are described by Formula I:

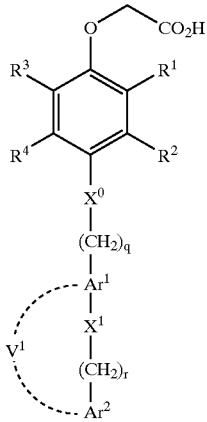

and pharmaceutically acceptable salts thereof, where:

$X^0$ and $X^1$ are independently absent, O, S, —$CH_2$—, —$CH_2$—$CH_2$—, —CH=CH—, —CH≡CH—, —$S(O)_2$—, or —S(O)—;

$Ar^1$ and $Ar^2$ are each independently unsubstituted or substituted aryl or heteroaryl, provided that $Ar^1$ is not thiazolyl or oxazolyl;

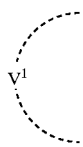

is absent; or when present,

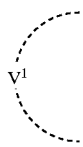

is a saturated or unsaturated hydrocarbon chain which is substituted or unsubstituted, wherein said chain has from 1 to 4 atoms so that

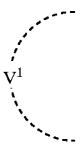

$Ar^1$, $X^1$, $(CH_2)_r$, and $Ar^2$, together form a five to eight membered ring;

$R^1$ and $R^2$ are selected from hydrogen, lower alkyl, lower alkoxy, haloalkyl, —O—$(CH_2)_mCF_3$, halogen, nitro, cyano, —OH, —SH, —$CF_3$, —$S(O)_p$alkyl, $S(O)_p$aryl, —$(CH_2)_m$ $OR^5$, —$(CH_2)_mNR^6R^7$, —$COR^5$, —$CO_2R^5$, or —$NR^6R^7$, or together with the atoms to which they are attached form a five to eight member ring;

$R^3$ and $R^4$ are selected from hydrogen, lower alkyl, lower alkoxy, haloalkyl, —O—$(CH_2)_mCF_3$, halogen, nitro, cyano, —OH, —SH, —$CF_3$, —$S(O)_p$alkyl, $S(O)_p$aryl, —$(CH_2)_m$ $OR^5$, —$(CH_2)_mNR^6R^7$, —$COR^5$, —$CO_2H$, —$CO_2R^5$, or —$NR^6R^7$;

provided that at least one of $R^1$–$R^4$ is H, lower alkyl, lower alkoxy, haloalkyl, —O—$(CH_2)_mCF_3$, halogen, nitro, cyano, —OH, —SH, —$CF_3$, —$S(O)_p$alkyl, $S(O)_p$aryl, —$(CH_2)_mOR^5$, —$(CH_2)_mNR^6R^7$, or $NR^6R^7$;

$R^5$ is hydrogen, alkyl, alkenyl, alkynyl, or aryl;

$R^6$ and $R^7$ are each independently hydrogen, alkyl, alkenyl, alkynyl, —COalkyl, —COaryl, cycloalkyl, —$CO_2$alkyl, —$CO_2$aryl, or $R^6$ and $R^7$ together with the atoms to which they are attached form a 4 to 7 membered ring having 1 to 3 heteroatoms;

m is 0 to 5;

p is 0, 1, or 2;

q is 0 to 6; and r is 0 to 6.

The invention also provides a compound of formula (II):

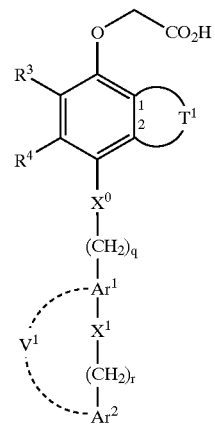

and pharmaceutically acceptable salts thereof, where:

$X^0$ and $X^1$ are independently absent, O, S, —$CH_2$—, —$CH_2$—$CH_2$—, —CH=CH—, —CH≡CH—, —$S(O)_2$—, or —S(O)—;

$Ar^1$ and $Ar^2$ are each independently unsubstituted or substituted aryl or heteroaryl, provided that $Ar^1$ is not thiazolyl or oxazolyl;

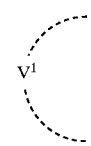

is absent; or when present,

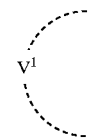

is a saturated or unsaturated hydrocarbon chain which is substituted or unsubstituted, wherein said chain has from 1 to 4 atoms so that

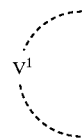

$Ar^1$, $X^1$, $(CH_2)_r$, and $Ar^2$, together form a five to eight member ring;

$R^3$ and $R^4$ are selected from hydrogen, lower alkyl, lower alkoxy, haloalkyl, —O—$(CH_2)_mCF_3$, halogen, nitro, cyano, —OH, —SH, —$CF_3$, —$S(O)_p$alkyl, $S(O)_p$aryl, —$(CH_2)_m$$OR^5$, —$(CH_2)_mNR^6R^7$, —$COR^5$, —$CO_2H$, —$CO_2R^5$, or —$NR^6R^7$;

$R^5$ is hydrogen, alkyl, alkenyl, alkynyl, or aryl;

$R^6$ and $R^7$ are each independently hydrogen, alkyl, alkenyl, alkynyl, —COalkyl, —COaryl, cycloalkyl, —$CO_2$alkyl, —$CO_2$aryl, —$SO_2$alkyl, —$SO_2$aryl, or $R^6$ and $R^7$ together with the atoms to which they are attached form a 4 to 7 membered ring having 1 to 3 heteroatoms;

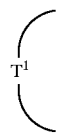

is a saturated or unsaturated, substituted or unsubstituted hydrocarbon chain or hydocarbon-heteroatom chain having from 3 to 6 atoms wherein the carbon atom of position 2 is connected to the carbon atom of position 3 to form a five to eight member ring;

m is 0 to 5;

p is 0 to 2;

q is 0 to 6; and r is 0 to 6.

In still another embodiment of the present invention, a method of treating, preventing or controlling hypercholesteremia and dyslipidemia in a mammal is provided. The method comprises administering to the mammal in need thereof a therapeutically effective amount of the compounds of the present invention. Additionally, the compounds of the present invention are also useful in the method of the present invention for treating, preventing, or controlling obesity, eating disorders, hyperglycemia, atherosclerosis, hypertriglyceridemia, hyperinsulinemia and diabetes. Furthermore, the compounds of the present invention are also useful in the methods of supressing appetite in a mammal, modulating leptin levels in a mammal, and treating a patient exhibiting glucose disorders associated with circulating glucocorticoids, growth hormone, catecholamines, glucagon, or parathyroid hormone. For each disease state treatable, preventable, or controllable by the method of the present invention, a therapeutically effective amount of the compounds of the present invention are administered to the mammal in need thereof.

In yet another embodiment of the present invention, a method for preparing compounds with Formulae I–II, or a pharmaceutically acceptable salt thereof, is provided. The method of this embodiment comprises reacting

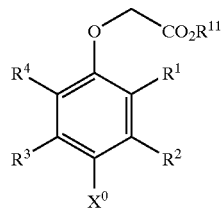

in a solvent in the presence of a base such as cesium carbonate: with

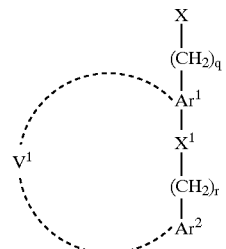

where $X^0$ is OH or SH;

n, q, r, $R^1$, $R^2$, $R^3$, $R^4$, $X^1$,

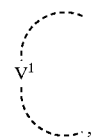

$Ar^1$ and $Ar_2$ are as defined above for Formula I;

$R^{11}$ is a lower alkyl; and

X is a halogen.

In yet another embodiment of the present invention, an alternative method for preparing compounds with Formulae I–II, or a pharmaceutically acceptable salt thereof, is provided. The method of this embodiment comprises reacting

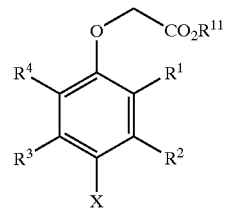

where X is a halide, $R^1$–$R^4$ have any of the meanings defined above, and $R^{11}$ is a lower alkyl with:

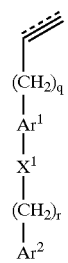

where - - - is a bond or is absent and wherein n, q, r, $X^0$, $X^1$,

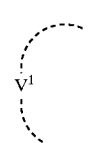

$Ar^1$ and $Ar^2$ are as defined above for Formula I;

in the presence of a catalyst such as a palladium catalyst to form

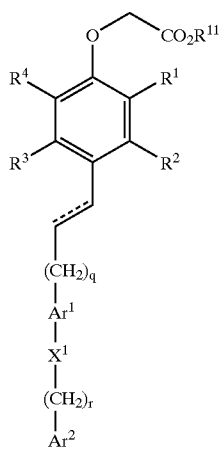

where - - - is a bond or is absent.

The double bond may optionally be removed, for instance, by hydrogenation and the resulting ester is preferably hydrolyzed to form the compounds of Formulas I or II.

In still another embodiment, the invention provides a process for preparing the compound of formula I-4 which is:

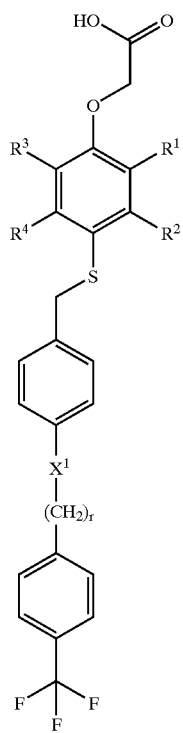

I-4 or a pharmaceutically acceptable salt thereof, comprising:
(a) conversion of phenol 1A to the thiocyante 1B;

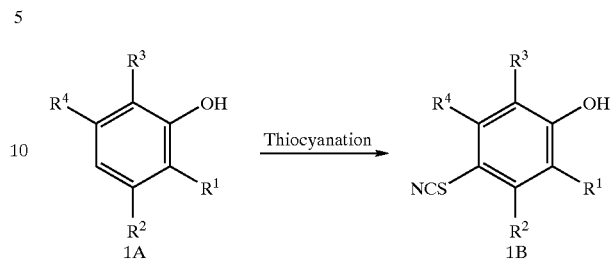

(b) alkylation of phenol moiety of thiocyanate 1B to acetoxyester 1C;

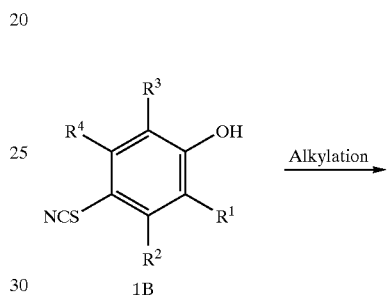

(c) reduction of the thiocyanate moiety in 1C to form thiol 1D;

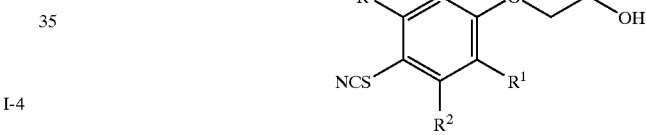

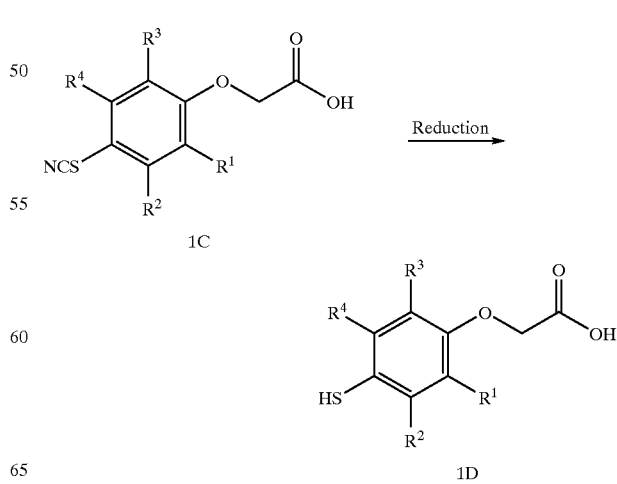

(d) alkylation of thiol 1D with chloride 3C to form 4a;

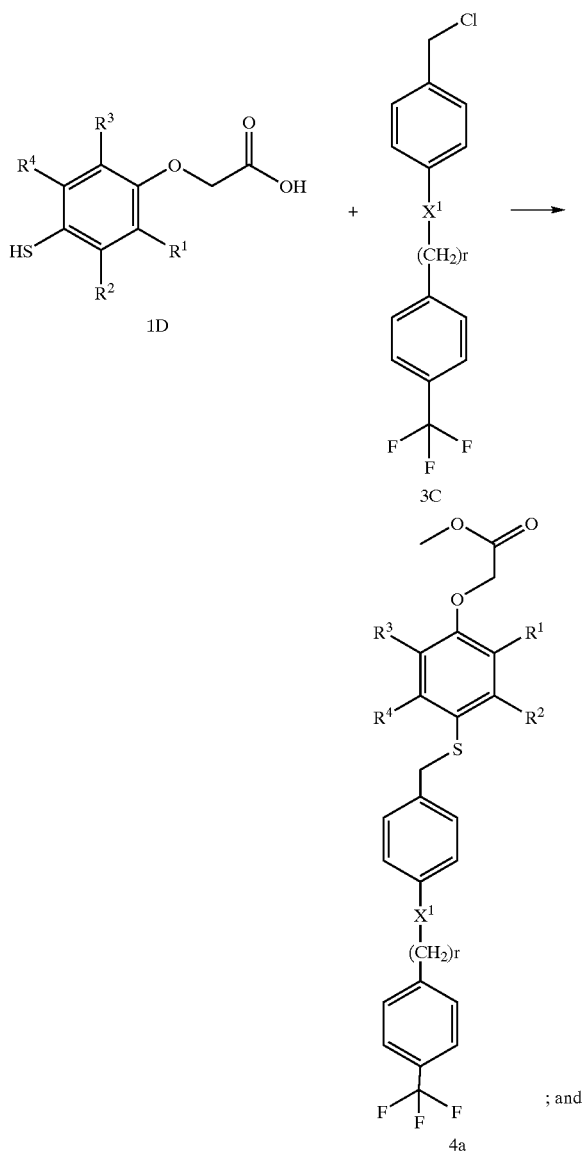

(e) saponification of the ester moiety in 4a to form I-4;
where
$R^1$ is hydrogen or together with $R^2$ forms a 5 membered carbocyclic ring;
$R^2$ is methoxy or together with $R^1$ forms a 5 membered carbocyclic ring;
$R^3$ is hydrogen or methyl;
$R^4$ is hydrogen;
$X^1$ is absent or O; and
r is 0 or 1.

DETAILED DESCRIPTION OF THE INVENTION

The following definitions are used, unless otherwise described: halo is fluoro, chloro, bromo, or iodo. Alkyl, alkoxy, alkenyl, alkynyl, etc. denote both straight and branched groups; but reference to an individual radical such as "propyl" embraces only the straight chain radical, a branched chain isomer such as "isopropyl" being specifically referred to.

The term "alkyl" as used herein refers to a straight or branched hydrocarbon of from 1 to 11 carbon atoms and includes, for example, methyl, ethyl, n-propyl, isopropyl, n-butyl, sec-butyl, isobutyl, tert-butyl, n-pentyl, n-hexyl, and the like. The alkyl group can also be substituted with one or more of the substituents selected from lower alkoxy, lower thioalkoxy, —O(CH$_2$)$_{1-5}$CF$_3$, halogen, nitro, cyano, =O, =S, —OH, —SH, —CF$_3$, —OCF$_3$, —CO$_2$H, CO$_2$C$_1$–C$_6$alkyl, —NH$_2$, —NHC$_1$–C$_6$alkyl, —CONR'R", or —N(C$_1$–C$_6$alkyl)$_2$ where R' and R" are independently alkyl, akenyl, alkynyl, aryl, or joined together to form a 4 to 7 member ring. Preferred alkyl groups have from 1 to 6 carbon atoms (C$_1$–C$_6$alkyl).

The term "lower alkyl" as used herein refers to a subset of alkyl which means a straight or branched hydrocarbon radical having from 1 to 6 carbon atoms and includes, for example, methyl, ethyl, n-propyl, isopropyl, n-butyl, sec-butyl, isobutyl, tert-butyl, n-pentyl, n-hexyl, and the like. Optionally, herein lower alkyl is referred to as "C$_1$–C$_6$alkyl."

The term "haloalkyl" as used herein refers to a lower alkyl radical, as defined above, bearing at least one halogen substituent, for example, chloromethyl, fluoroethyl, trifluoromethyl, or 1,1,1-trifluoroethyl and the like. Haloalkyl can also include perfluoroalkyl wherein all hydrogens of a loweralkyl group are replaced with fluorine atoms.

The term "alkenyl" means a straight or branched unsaturated hydrocarbon radical having from 2 to 12 carbon atoms and includes, for example, ethenyl, 1-propenyl, 2-propenyl, 1-butenyl, 2-butenyl, 1-pentenyl, 2-pentenyl, 3-methyl-3-butenyl, 1-hexenyl, 2-hexenyl, 3-hexenyl, 3-heptenyl, 1-octenyl, 1-nonenyl, 1-decenyl, 1-undecenyl, 1-dodecenyl, and the like.

The term "alkynyl" means a straight or branched hydrocarbon radical having from 2 to 12 carbon atoms having at least one triple bond and includes, for example, 1-propynyl, 1-butynyl, 3-butynyl, 1-pentynyl, 3-pentynyl, 3-methyl-3-butynyl, 1-hexynyl, 3-hexynyl, 3-heptynyl, 1-octynyl, 1-nonynyl, 1-decynyl, 1-undecynyl, 1-dodecynyl, and the like.

The term "alkylene" as used herein refers to a divalent group derived from a straight or branched chain saturated hydrocarbon having from 1 to 10 carbon atoms by the removal of two hydrogen atoms, for example methylene, 1,2-ethylene, 1,1-ethylene, 1,3-propylene, 2,2-dimethylpropylene, and the like. The alkylene groups of this invention can be optionally substituted. The alkylene group can also be substituted with one or more of the substituents selected from lower alkyl, lower alkoxy, lower thioalkoxy, —O(CH$_2$)$_{1-5}$CF$_3$, halogen, nitro, cyano, =O, =S, —OH, —SH, —CF$_3$, —CO$_2$H, —CO$_2$C$_1$–C$_6$alkyl, —NH$_2$, —NHC$_1$–C$_6$alkyl, —CONR'R", or —N(C$_1$–C$_6$alkyl)$_2$ where R' and R" are independently alkyl, akenyl, alkynyl, aryl, or joined together to form a 4 to 7 member ring. Preferred alkylene groups have from 1 to 6 carbon atoms (C$_1$–C$_6$ alkyl).

The term "cycloalkyl" means a hydrocarbon ring containing from 3 to 12 carbon atoms, for example, cyclopropyl, cyclobutyl, cyclopentyl, cyclohexyl, cycloheptyl, cycloctyl, decalinyl, norpinanyl, and adamantyl. Where possible, the cycloalkyl group may contain double bonds, for example, 3-cyclohexen-1-yl. The cycloalkyl ring may be unsubstituted or substituted by 1 to 3 substituents selected from alkyl, alkoxy, thioalkoxy, hydroxy, thiol, nitro, halogen, amino, alkyl and dialkylamino, formyl, carboxyl, CN, —NH—CO—R', —CO—NHR'—, —CO$_2$R', —COR', aryl, or heteroaryl, wherein alkyl, aryl, and heteroaryl are as defined herein. Examples of substituted cycloalkyl groups include fluorocyclopropyl, 2-iodocyclobutyl, 2,3-dimethylcyclopentyl, 2,2-dimethoxycyclohexyl, and 3-phenylcyclopentyl.

The term "heteroatom" as used herein represents oxygen, nitrogen, or sulfur (O, N, or S) as well as sulfoxyl or sulfonyl (SO or $SO_2$) unless otherwise indicated.

The term "heterocycloalkyl" means a monocyclic, fused, bridged, or spiro bicyclic heterocyclic ring systems. Monocyclic heterocyclic rings contain from about 3 to 12 ring atoms, with from 1 to 5 heteroatoms selected from N, O, and S, and preferably from 3 to 7 member atoms, in the ring. Bicyclic heterocyclics contain from 7 to 17 member atoms, preferably 7 to 12 member atoms, in the ring. Bicyclic heterocyclics contain from about 7 to about 17 ring atoms, preferably from 7 to 12 ring atoms. Bicyclic heterocyclics rings may be fused, spiro, or bridged ring systems. Examples of heterocyclic groups include cyclic ethers (oxiranes) such as ethyleneoxide, tetrahydrofuran, dioxane, and substituted cyclic ethers, wherein the substituents are those described above for the alkyl and cycloalkyl groups. Typical substituted cyclic ethers include propyleneoxide, phenyloxirane (styrene oxide), cis-2-butene-oxide (2,3-dimethyloxirane), 3-Chlorotetrahydrofuran, 2,6-dimethyl-1,4-dioxane, and the like. Heterocycles containing nitrogen are groups such as pyrrolidine, piperidine, piperazine, tetrahydrotriazine, tetrahydropyrazole, and substituted groups such as 3-aminopyrrolidine, 4-methylpiperazin-1-yl, and the like. Typical sulfur containing heterocycles include tetrahydrothiophene, dihydro-1,3-dithiol-2-yl, and hexahydrothiepin-4-yl. Other commonly employed heterocycles include dihydro-oxathiol-4-yl, tetrahydro-oxazolyl, tetrahydro-oxadiazolyl, tetrahydrodioxazolyl, tetrahydro-oxathiazolyl, hexahydrotriazinyl, tetrahydro-oxazinyl, morpholinyl, thiomorpholinyl, tetrahydropyrimidinyl, dioxolinyl, octahydrobenzofuranyl, octahydrobenzimidazolyl, and octahydrobenzothiazolyl. For heterocycles containing sulfur, the oxidized sulfur heterocycles containing SO or $SO_2$ groups are also included. Examples include the sulfoxide and sulfone forms of tetrahydrothiophene.

The term "hydrocarbon chain" as used herein refers to a straight hydrocarbon of from 2 to 6 carbon atoms. The hydrocarbon chain is optionally substituted with one or more substituents selected from lower alkyl, lower alkoxy, lower thioalkoxy, $-O(CH_2)_{0-2}CF_3$, halogen, nitro, cyano, =O, =S, —OH, —SH, $-CF_3$, $-CO_2H$, $-CO_2(C_1-C_6$alkyl), $-NH_2$, $-NHC_1-C_6$alkyl, —CONR'R", or $-N(C_1-C_6$alkyl)$_2$ where R' and R" are independently alkyl, akenyl, alkynyl, aryl, or joined together to form a 4 to 7 member ring.

The term "aryl" means a cyclic or polycyclic aromatic ring having from 5 to 12 carbon atoms, and being unsubstituted or substituted with up to 4 groups selected from $C_1-C_6$alkyl, cycloalkyl, heteroaryl, dialkylaminoalkoxy, or those recited above as substituents for alkyl. The term aryl includes both monovalent species, for example where $Ar_2$ is aryl, and divalent species, for example where $Ar_1$ is aryl. Examples of aryl groups include, but are not limited to, phenyl, biphenyl, naphthyl, 2-chlorophenyl, 3-chlorophenyl, 4-chlorophenyl, 2-methylphenyl, 3-methylphenyl, 4-methylphenyl, 2-methoxyphenyl, 3-methoxyphenyl, 4-methoxyphenyl, 2-chloro-3-methylphenyl, 2-chloro-4-methylphenyl, 2-chloro-5-methylphenyl, 3-chloro-2-methylphenyl, 3-chloro-4-methylphenyl, 4-chloro-2-methylphenyl, 4-chloro-3-methylphenyl, 5-chloro-2-methylphenyl, 2,3-dichlorophenyl, 2,5-dichlorophenyl, 3,4-dichlorophenyl, 2,3-dimethylphenyl, 3,4-dimethylphenyl, 4-trifluoromethyl and the like.

The term "heteroaryl" means an aromatic mono-, bi-, or or polycyclic ring incorporating one or more (i.e. 1–4) heteroatoms selected from N, O, and S. The term heteroaryl includes both monovalent species, for example where $Ar_2$ is heteroaryl, and divalent species, for example where $Ar_1$ is heteroaryl. It is understood that a heterocycle is optionally substituted with up to 4 groups selected from $C_1-C_6$ alkyl, cycloalkyl, heteroaryl, dialkylaminoalkoxy, or those recited above as substituents for alkyl. Examples of suitable monocyclic heteroaryl include, but are not limited to substituted or unsubstituted thienyl, furanyl, pyrrolyl, imidazolyl, pyrazolyl, isothiazolyl, isoxazolyl, triazoiyl, tetrazolyl, pyridinyl, pyrazinyl, pyrimidinyl, piperidinyl, pyrrolidinyl, piperazinyl, azetidinyl, aziridinyl, morpholinyl, thietanyl, oxetaryl. Preferred monocyclic diheterocycles include, but are not limited to 1-, 2-, 4-, or 5-imidazolyl, 1-, 3-, 4-, or 5-pyrazolyl, 3-, 4-, or 5-isothiazolyl, 3-, 4-, or 5-isoxazolyl, 1,3-, or 5-triazolyl, 1-, 2-, or 3-tetrazolyl, 2-pyrazinyl, 2-, 4-, or 5-pyrimidinyl, 1- or 2-piperazinyl, 2-, 3-, or 4-morpholinyl. Examples of suitable bicyclic and polycylic heteroaryl groups include, but are not limited to include but are not limited to 1-, 2-, 3-, 5-, 6-, 7-, or 8-indolizinyl, 1-, 3-, 4-, 5-, 6-, or 7-isoindolyl, 2-, 3-, 4-, 5-,6-, or 7-indolyl, 2-, 3-, 4-, 5-, 6-, or 7-indazolyl, 2-, 4-, 5-, 6-, 7-, or 8-purinyl, 1-, 2-, 3-, 4-, 6-, 7-, 8-, or 9-quinolizinyl, 2-, 3-, 4-, 5-, 6-, 7-, or 8-quinoliyl, 1-, 3-, 4-, 5-, 6-, 7-, or 8-isoquinoliyl, 1-, 4-, 5-, 6-, 7-, or 8-phthalazinyl, 2-, 3-, 4-, 5-, or 6-naphthyridinyl, 2-, 3-, 5-, 6-, 7-, or 8-quinazolinyl, 3-, 4-, 5-, 6-, 7-, or 8-cinnolinyl, 2-, 4-, 6-, or 7-pteridinyl, 1-, 2-, 3-, 4-, 5-, 6-, 7-, or 8-4aH carbazolyl, 1-, 2-, 3-, 4-, 5-, 6-, 7-, or 8-carbzaolyl, 1-, 3-, 4-, 5-, 6-, 7-, 8-, or 9-carbolinyl, 1-, 2-, 3-, 4-, 6-, 7-, 8-, 9-, or 10-phenanthridinyl, 1-, 2-, 3-, 4-, 5-, 6-, 7-, 8-, or 9-acridinyl, 1-, 2-, 4-, 5-, 6-, 7-, 8-, or 9-perimidinyl, 2-, 3-, 4-, 5-, 6-, 8-, 9-, or 10-phenathrolinyl, 1-, 2-, 3-, 4-, 6-, 7-, 8-, or 9-phenazinyl, 1-, 2-, 3-, 4-, 6-, 7-, 8-, 9-, or 10-phenothiazinyl, 1-, 2-, 3-, 4-, 6-, 7-, 8-, 9-, or 10-phenoxazinyl, 2-, 3-, 4-, 5-, 6-, or 1-, 3-, 4-, 5-, 6-, 7-, 8-, 9-, or 10-benzisoqinolinyl, 2-, 3-, 4, or thieno[2,3-b]furanyl, 2-, 3-, 5-, 6-, 7-, 8-, 9-, 10-, or 11-7H-pyrazino[2,3-c] carbazolyl, 2-, 3-, 5-, 6-, or 7-2H-furo[3,2-b]-pyranyl, 2-, 3-, 4-, 5-, 7-, or 8-5H-pyrido[2,3-d]-o-oxazinyl, 1-, 3-, or 5-1H-pyrazolo[4,3-d]-oxazolyl, 2-, 4-, or 5-4H-imidazo[4,5-d] thiazolyl, 3-, 5-, or 8-pyrazino[2,3-d]pyridazinyl, 2-, 3-, 5-, or 6-imidazo[2,1-b]thiazolyl, 1-, 3-, 6-, 7-, 8-, or 9-furo[3, 4-c]cinnolinyl, 1-, 2-, 3-, 4-, 5-, 6-, 7-, 8-, 9-, 10, or 11-4H-pyrido[2,3-c]carbazolyl, 2-, 3-, 6-, or 7-imidazo[1,2-b][1,2,4]triazinyl, 7-benzo[b]thienyl, 2-, 4-, 5-, 6-, or 7-benzoxazolyl, 2-, 4-, 5-, 6-, or 7-benzimidazolyl, 2-, 4-, 5-, 6-, or 7-benzothiazolyl, 1-, 2-, 4-, 5-, 6-, 7-, 8-, or 9-benzoxapinyl, 2-, 4-, 5-, 6-, 7-, or 8-benzoxazinyl, 1-, 2-, 3-, 5-, 6-, 7-, 8-, 9-, 10-, or 11-1H-pyrrolo[1,2-b][2] benzazapinyl. Typical fused heteroary groups include, but are not limited to 2-, 3-, 4-, 5-, 6-, 7-, or 8-quinolinyl, 1-, 3-, 4-, 5-, 6-, 7-, or 8-isoquinolinyl, 2-, 3-, 4-, 5-, 6-, or 7-indolyl, 2-, 3-, 4-, 5-, 6-, or 7-benzo[b]thienyl, 2-, 4-, 5-, 6-, or 7-benzoxazolyl, 2-, 4-, 5-, 6-, or 7-benzimidazolyl, 2-, 4-, 5-, 6-, or 7-benzothiazolyl.

The term "hydrocarbon-heteroatom chain" as used herein refers to a hydrocarbon chain wherein one or more carbon atoms are replaced with a heteroatom. The hydrocarbon-heteroatom chain is optionally substituted with one or more substituents selected from lower alkyl, lower :alkoxy, lower thioalkoxy, $-O(CH_2)_{0-2}CF_3$, halogen, nitro, cyano, =O, =S, —OH, —SH, $-CF_3$, $-CO_2H$, $-CO_2C_1-C_6$alkyl, —$NH_2$, —$NHC_1$–$C_6$alkyl, —CONR'R", or —$N(C_1$–$C_6$alkyl$)_2$ where R' and R" are independently alkyl, akenyl, alkynyl, aryl, or joined together to form a 4 to 7 member ring.

The term "heteroalkylene" as used herein, refers to an alkylene radical as defined above that includes one or more heteroatoms such as oxygen, sulfur, or nitrogen (with valence completed by hydrogen or oxygen) in the carbon chain or terminating the carbon chain.

The terms "lower alkoxy" and "lower thioalkoxy" as used herein refers to O-alkyl or S-alkyl of from 1 to 6 carbon atoms as defined above for "lower alkyl."

The term "cycloalkenyl" means a cycloalkyl group having one or more carbon-carbon double. Example includes cyclobutene, cyclopentene, cyclohexene, cycloheptene, cyclobutadiene, cyclopentadiene, and the like.

The symbol "⌒" means a bond to a group wherein a 4 to 8 membered ring is formed. Typically this symbol will appear in pairs.

When a bond is represented by a line such as " - - - " this is meant to represent that the bond may be absent or present provided that the resultant compound is stable and of satisfactory valency.

The term "patient" means all mammals including humans. Examples of patients include humans, cows, dogs, cats, goats, sheep, pigs, and rabbits.

A "therapeutically effective amount" is an amount of a compound of the present invention that when administered to a patient ameliorates a symptom of dyslipidemia, non-insulin dependent diabetes mellitus, obesity, hyperglycemia, hypercholesteremia, hyperlipidemia, atherosclerosis, hypertriglyceridemia, hyperinsulinemia, glucose disorders associated with circulating glucocorticoids, growth hormone, catecholamines, glucagon, or parathyroid hormone. Additionally, a "therapeutically effective amount" is an amount of a compound of the present invention that when administered to a patient ameliorates a symptom of an eating disorder, suppresses appetite, or modulates leptin levels.

The term "a pharmaceutically acceptable salt" refers to the relatively non-toxic, inorganic and organic base or acid addition salts of compounds of the present invention. These salts can be prepared in situ during the final isolation and purification of the compounds or by separately reacting the purified compound in its free form with a suitable organic or inorganic base or acid and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate, and laurylsulphonate salts, and the like. These also include cations based on the alkali and alkaline earth metals, such as sodium, lithium, potassium, calcium, magnesium, and the like, as well as non-toxic ammonium, quaternary ammonium, and amine cations including, but not limited to ammonium, tetramethylammonium, tetraethylammonium, methylamine, dimethylamine, trimethylamine, triethylamine, ethylamine, and the like. (See, for example, Berge S. M., et al., "Pharmaceutical Salts," *J. Pharm. Sci.*, 1977;66:1–19, which is incorporated herein by reference.) The free base form may be regenerated by contacting the salt form with a base. While the free base may differ from the salt form in terms of physical properties, such as solubility, the salts are equivalent to their respective free bases for the purposes of the present invention.

Compounds of the present invention are described by Formula I:

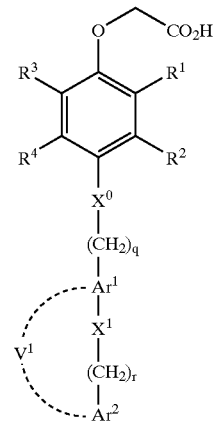

I and pharmaceutically acceptable salts thereof, where:

$X^0$ and $X^1$ are independently absent, O, S, —$CH_2$—, —$CH_2$—$CH_2$—, —CH=CH—, —CH≡CH—, —$S(O)_2$—, or —S(O)—;

$Ar^1$ and $Ar^2$ are each independently unsubstituted or substituted aryl or heteroaryl, provided that $Ar^1$ is not thiazolyl or oxazolyl;

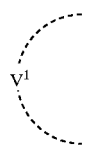

is absent; or when present,

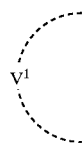

is a saturated or unsaturated hydrocarbon chain which is substituted or unsubstituted, wherein said chain has from 1 to 4 atoms so that

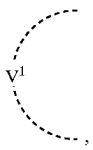

$Ar^1$, $X^1$, $(CH_2)_r$, and $Ar^2$, together form a five to eight membered ring;

$R^1$ and $R^2$ are selected from hydrogen, lower alkyl, lower alkoxy, haloalkyl, —O—$(CH_2)_mCF_3$, halogen, nitro, cyano, —OH, —SH, —$CF_3$, —$S(O)_p$alkyl, $S(O)_p$aryl, —$(CH_2)_m$$OR^5$, —$(CH_2)_mNR^6R^7$, —$COR^5$, —$CO_2R^5$, or —$NR^6R^7$, or together with the atoms to which they are attached form a five to eight member ring;

$R^3$ and $R^4$ are selected from hydrogen, lower alkyl, lower alkoxy, haloalkyl, —O—$(CH_2)_mCF_3$, halogen, nitro, cyano, —OH, —SH, —$CF_3$, —$S(O)_p$alkyl, $S(O)_p$aryl, —$(CH_2)_m$$OR^5$, —$(CH_2)_mNR^6R^7$, —$COR^5$, —$CO_2H$, —$CO_2R^5$, or—$NR^6R^7$;

provided that at least one of $R_1$–$R_4$ is H, lower alkyl, lower alkoxy, haloalkyl, —O—$(CH_2)_mCF_3$, halogen, nitro, cyano, —OH, —SH, —$CF_3$, —$S(O)_p$alkyl, $S(O)_p$aryl, —$(CH_2)_mOR^5$, —$(CH_2)_mNR^6R^7$, or $NR^6R^7$;

$R^5$ is hydrogen, alkyl, alkenyl, alkynyl, or aryl;

$R^6$ and R are each independently hydrogen, alkyl, alkenyl, alkynyl, —COalkyl, —COaryl, cycloalkyl, —$CO_2$alkyl, —$CO_2$aryl, or $R^6$ and $R^7$ together with the atoms to which they are attached form a 4 to 7 membered ring having 1 to 3 heteroatoms;

m is 0 to 5;

p is 0, 1, or 2;

q is 0 to 6; and r is 0 to 6.

In compounds of Formula I, $R^1$, $R^2$, $R^3$, and $R^4$ are preferably selected from hydrogen, alkyl, or alkoxy. More preferably, $R^2$ and $R^3$ are hydrogen; and $R^1$ and $R^4$ are alkyl or alkoxy. In a particularly preferred embodiment of Formula I, $R^2$ and $R^3$ are hydrogen; $R^1$ is alkyl; and $R^4$ is alkoxy. Preferred alkoxy include methoxy, ethoxy, isopropoxy, n-propoxy, t-butoxy, n-butoxy, or isobutoxy. Similarly, preferred alkyl include methyl, ethyl, isopropyl, n-propyl, t-butyl, n-butyl, or isobutyl. In a most preferred embodiment of Formula I, q is 1, $Ar^1$ is phenyl, $X^1$ is absent, r is 0, $V^1$ is absent, and $Ar^2$ is 4-trifluoromethylphenyl.

In compounds of Formula I,

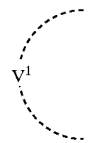

is preferably $(CH_2)_t$ wherein t is 1 to 4. Additionally,

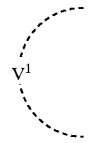

is optionally substituted with at least one substituent, wherein the substituent include but are not limited to lower alkyl, lower alkoxy, lower thioalkoxy, —$O(CH_2)_{0-2}CF_3$, halogen, nitro, cyano, =O, =S, —OH, —SH, —$CF_3$, $OCF_3$, —$CO_2H$, —$CO_2C_1$-$C_6$alkyl, —$NH_2$, —$NHC_1$-$C_6$alkyl, —CONR'R", or —$N(C_1$-$C_6$alkyl$)_2$ where R' and R" are independently alkyl, akenyl, alkynyl, aryl, or joined together to form a 4 to 7 member ring.

In a preferred embodiment of Formula I, $R^1$ and $R^2$ are joined together to form a five to eight member ring having Formula II. Such a ring includes, for example, cycloalkyl, aryl, heterocycloalkyl, or a heteroaryl rings where each such ring is optionally substituted as described above.

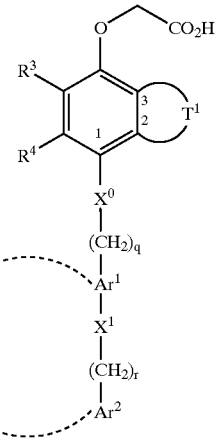

and pharmaceutically acceptable salts thereof, where:

$X^0$ and $X^1$ are independently absent, O, S, —$CH_2$—, —$CH_2$—$CH_2$—, —CH=CH—, —CH≡CH—, —$S(O)_2$—, or —$S(O)$—;

$Ar^1$ and $Ar^2$ are each independently unsubstituted or substituted aryl or heteroaryl, provided that $Ar^1$ is not thiazolyl or oxazolyl;

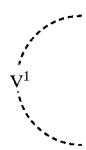

is absent; or when present,

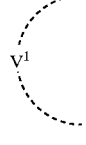

a saturated or unsaturated hydrocarbon chain which is substituted or unsubstituted, wherein said chain has from 1 to 4 atoms so that

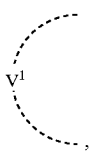

$Ar^1$, $X^1$, $(CH_2)_r$, and $Ar^2$, together form a five to eight member ring;

$R^3$ and $R^4$ are selected from hydrogen, lower alkyl, lower alkoxy, haloalkyl, —O—$(CH_2)_mCF_3$, halogen, nitro, cyano, —OH, —SH, —$CF_3$, —$S(O)_p$alkyl, $S(O)_p$aryl, —$(CH_2)_m OR^5$, —$(CH_2)_mNR^6R^7$, —$COR^5$, —$CO_2H$, —$CO_2R^5$, or —$NR^6R^7$;

$R^5$ is hydrogen, alkyl, alkenyl, alkynyl, or aryl;

$R^6$ and $R^7$ are each independently hydrogen, alkyl, alkenyl, alkynyl, —COalkyl, —COaryl, cycloalkyl, —$CO_2$alkyl, —$CO_2$aryl, —$SO_2$alkyl, —$SO_2$aryl, or $R^6$ and $R^7$ together with the atoms to which they are attached form a 4 to 7 membered ring having 1 to 3 heteroatoms;

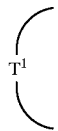

is a saturated or unsaturated, substituted or unsubstituted hydrocarbon chain or hydocarbon-heteroatom chain having from 3 to 6 atoms wherein the carbon atom of position 2 is connected to the carbon atom of position 3 to form a five to eight member ring;

m is 0 to 5;

p is 0 to 2;

q is 0 to 6; and r is 0 to 6.

Preferably,

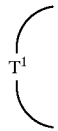

is —CH$_2$CH$_2$CO—O—, —CH$_2$—CH$_2$—O—CO—, —CH$_2$—CH$_2$—CH$_2$—CH$_2$—, —HC=CH—HC=CH—, —N=CH—HC=CH—, —HC=N—HC=CH—, —HC=CH—N=CH—, —HC=CH—HC=N—, —CH$_2$—CH$_2$—CH$_2$—, —CH$_2$—CH$_2$—O—CH$_2$—, —CH$_2$—O—CH$_2$CH$_2$—, —CH$_2$—HC=CH—CH$_2$—, —CH$_2$—HC=CH—, —CH$_2$CH$_2$—N R$^4$—CH$_2$—, —COCH=CH—O—, —O—CH=CH—CO—, —CH=CH—NR$^4$—, —NR$^4$—CH=CH—, —CH=CH—CH$_2$—, —CH$_2$—CH$_2$—NR$^4$—, —NR$^4$—CH$_2$—CH$_2$—, —O—CH$_2$—CH$_2$—, —CH$_2$—CH$_2$—O—, —CH$_2$—CH$_2$CO—, —CH$_2$—CO—CH$_2$—, —CO—CH$_2$—CH$_2$—, —CH$_2$—CH$_2$—CH$_2$—CO—, —CO—CH$_2$—CH$_2$—CH$_2$—, —CH$_2$—CO—CH$_2$—CH$_2$—, —CH$_2$—CH$_2$—CO—CH$_2$, —CH$_2$—CH$_2$—CH$_2$—NR$^4$—, —NR$^4$—CH$_2$—CH$_2$—CH$_2$—, —O—CH$_2$—CH$_2$—CH$_2$—, —CH$_2$—CH$_2$—CH$_2$—O—, —CO—NR$^4$—CH$_2$—CH$_2$—, NR$^4$CO—CH$_2$—CH$_2$—, —CH$_2$—CH$_2$NR$^4$—CO—, or —CH$_2$—CH$_2$—CO—NR$^4$—. It will be understood that the left-most atom of these groups in attached to the atom labeled "3" in Formula I and the right-most atom of these groups is attached to the atom label "2" in Formula I.

In the present embodiment,

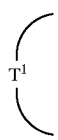

optionally substituted with 1 or more substituents selected from the group consisting of lower alkyl, lower alkoxy, lower thioalkoxy, —O(CH$_2$)$_{1-5}$CF$_3$, halogen, nitro, cyano, =O, =S, —OH, —SH, —CF$_3$, —CO$_2$H, —CO$_2$C$_1$-C$_6$alkyl, —N$_2$, —NHC$_1$-C$_6$alkyl, —OCH$_2$O—, and —N(C$_1$-C$_6$alkyl)$_2$.

In compounds of Formula II, R$^3$, and R$^4$ are preferably selected from hydrogen, alkyl, or alkoxy. More preferably, R$^3$ and R$^4$ are hydrogen; and

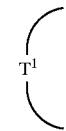

is a saturated or unsaturated, unsubstituted hydrocarbon chain having from 3 to 6 atoms wherein the carbon atom of position 2 is connected to the carbon atom of position 3 to form a five to eight member ring such as a cyclopentyl or cyclohexyl ring. In a most preferred embodiment of Formula II, q is 1, Ar$^1$ is phenyl, X$^1$ is O, r is 1, V$^1$ is absent, and Ar$^2$ is 4-trifluoromethylphenyl.

Also in this embodiment,

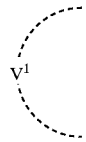

is preferably (CH$_2$)$_t$ wherein t is 1 to 4. Additionally, is optionally substituted with at least one substituent, wherein the substituent include but are not limited to lower alkyl, lower alkoxy, lower thioalkoxy, —O(CH$_2$)$_{0-2}$CF$_3$, halogen, nitro, cyano, =O, =S, —OH, —SH, —CF$_3$, —OCF$_3$, —CO$_2$H, —CO$_2$C$_1$-C$_6$alkyl, —NH$_2$, —NHC$_1$-C$_6$alkyl, —CONR'R", or —N(C$_1$-C$_6$alkyl)$_2$ where R' and R" are independently alkyl, akenyl, alkynyl, aryl, or joined together to form a 4 to 7 member ring.

Examples of compounds of Formula I and Formula II include

[4-(Biphenyl-4-ylmethylsulfanyl)-5-methoxy-2-methyl-phenoxy]-acetic acid;

[4-(Biphenyl-4-ylmethylsulfanyl)-2-methyl-phenoxy]-acetic acid;

[2-Methyl-4-(4'-trifluoromethyl-biphenyl-4-ylmethylsulfanyl)-phenoxy]-acetic acid;

[5-Methoxy-2-methyl-4-(4'-trifluoromethyl-biphenyl-4-ylmethylsulfanyl)-phenoxy]-acetic acid;

[5-Methoxy-2-methyl-4-(2',4',6'-trimethyl-biphenyl-4-ylmethylsulfanyl)-phenoxy]-acetic acid;

[4-(4'-Chloro-3'-trifluoromethyl-biphenyl-4-ylmethylsulfanyl)-2-methyl-phenoxy]-acetic acid;

[4-(2',4'-Dichloro-biphenyl-4-ylmethylsulfanyl)-5-methoxy-2-methyl-phenoxy]-acetic acid;

[4-(3',4'-Dichloro-biphenyl-4-ylmethylsulfanyl)-5-methoxy-2-methyl-phenoxy]-acetic acid;

[5-Methoxy-2-methyl-4-(3'-trifluoromethyl-biphenyl-4-ylmethylsulfanyl)-phenoxy]-acetic acid;

[4-(4'-Fluoro-biphenyl-4-ylmethylsulfanyl)-5-methoxy-2-methyl-phenoxy]-acetic acid;

[5-Methoxy-2-methyl-4-(3'-trifluoromethoxy-biphenyl-4-ylmethylsulfanyl)-phenoxy]-acetic acid;

[7-(4'-Trifluoromethyl-biphenyl-4-ylmethylsulfanyl)-indan-4-yloxy]-acetic acid;

[4-(4Benzyloxy-benzylsulfanyl)-2-methyl-phenoxy]-acetic acid;

{5-Methoxy-2-methyl-4-[4-(4-trifluoromethyl-benzyloxy)-benzylsulfanyl]-phenoxy}-acetic acid;
{2-Methyl-4-[4-(4-trifluoromethyl-benzyloxy)-benzylsulfanyl]-phenoxy}-acetic acid;
[5-Methoxy-2-methyl-4-(3'-trifluoromethoxy-biphenyl-3-ylmethylsulfanyl)-phenoxy]-acetic acid;
[4-(9H-Fluoren-2-ylmethylsulfanyl-2-methyl-phenoxy]-acetic acid;
{{5-Methoxy-2-methyl-4-[4-(5-trifluoromethyl-pyridin-2-yl)-benzylsulfanyl]-phenoxy}-acetic acid;
{5-Methoxy-2-methyl-4-[6-4-trifluoromethyl-phenyl)-pyridin-3-ylmethylsulfanyl]-phenoxy}-acetic acid;
[5-Chloro-2-methyl-4-(4'-trifluoromethyl-biphenyl-4-ylmethylsulfanyl)-phenoxy]-acetic acid;
[3-Methoxy-4-(4'-trifluoromethyl-biphenyl-4-ylmethylsulfanyl)-phenoxy]-acetic acid;
{2-Methyl-4-[2-(4'-trifluoromethyl-biphenyl-4-yl)-ethylsulfanyl]-phenoxy}-acetic acid;
{5-Methoxy-2-methyl-4-[2-(4'-trifluoromethyl-biphenyl-4-yl)-ethylsulfanyl]-phenoxy}-acetic acid;
{2-Methyl-4-[2-(4'-trifluoromethyl-biphenyl-4-yl)-vinyl]-phenoxy}-acetic acid;
{2-Methyl-4-[2-(4'-trifluoromethyl-biphenyl-4-yl)ethyl]-phenoxy}-acetic acid;
{7-[4-(5-Trifluoromethyl-pyridin-2-yl)-benzylsulfanyl]-indan-4-yloxy}-acetic acid;
{5-Methyl-7-[4-(5-trifluoromethyl-pyridin-2-yl)-benzylsulfanyl]-indan-4-yloxy}-acetic acid;
[5-Methyl-7-(4'-trifluoromethyl-biphenyl-4-ylmethylsulfanyl)-indan-4-yloxy]-acetic acid;
(4-{4-[2-(3-Fluoro-phenyl)-vinyl]-benzylsulfanyl}-5-methoxy-2-methyl-phenoxy)-acetic acid;
{2-Methyl-4-[4-(5-trifluoromethyl-pyridin-2-yl)-benzylsulfanyl]-phenoxy}-acetic acid;
{4-[4-(2,4-Difluoro-benzyloxy)-benzylsulfanyl]-2-methyl-phenoxy}-acetic acid;
{4-[4-(2,4-Dichloro-benzyloxy)-benzylsulfanyl]-2-methyl-phenoxy}-acetic acid;
{4-[4-(4-Methoxy-benzyloxy)-benzylsulfanyl]-2-methyl-phenoxy}-acetic acid;
{4-[4-(4-tert-Butyl-benzyloxy)-benzylsulfanyl]-2-methyl-phenoxy}-acetic acid;
{2-Methyl-4-[4-(4-trifluoromethoxy-benzyloxy)-benzylsulfanyl]-phenoxy}-acetic acid;
{6-Methyl-8-[4-(5-trifluoromethyl-pyridine-2-yl)-benzylsulfanyl]-chroman-5-yloxy}-acetic acid;
{5-Chloro-2-methyl-4-[4-(5-trifluoromethyl-pyridin-2-yl)-benzylsulfanyl]-phenoxy}-acetic acid;
[5-hydroxy-2-methyl-4-4'-trifluoromethyl-biphenyl-4-ylmethylsulfanyl)-phenoxy]-acetic acid;
[5-Methoxy-2-methyl-4-(3-methyl-4'-trifluoromethyl-biphenyl-4-ylmethylsulfanyl)-phenoxy]-acetic acid;
{7-[4-(4-trifluoromethyl-benzyl)-benzylsulfanyl]-indan-4-yloxy}-acetic acid;
{4-[5-(4-Chloro-phenyl)-isoxazol-3-ylmethylsulfanyl]-5-methoxy-2-methyl-phenoxy}-acetic acid;
{2-Methyl-4-[5-(4-trifluoromethyl-phenyl)-isoxazol-3-ylmethylsulfanyl]-phenoxy}-acetic acid;
{5-Methoxy-2-methyl-4-[5-(4-trifluoromethyl-phenyl)-isoxazol-3-ylmethylsulfanyl]-phenoxy}-acetic acid;
{7-[5-(4-Trifluoromethyl-phenyl)-isoxazol-3-ylmethylsulfanyl]-indan-4-yloxy}-acetic acid;
{2-Methyl-4-[3-(4-trifluoromethyl-phenyl)-isoxazol-5-ylmethylsulfanyl]-phenoxy}-acetic acid;
{5-Methoxy-2-methyl-4-[3-(4-trifluoromethyl-phenyl)-isoxazol-5-ylmethylsulfanyl]-phenoxy}-acetic acid;
[2-Methyl-4-(4-phenoxy-benzylsulfanyl)-phenoxy]-acetic acid;
[7-(4'-Trifluoromethyl-biphenyl-3-ylmethylsulfanyl)-indan-4-yloxy]-acetic acid;
[5-Methoxy-2-methyl-4-(4'-trifluoromethyl-biphenyl-3-ylmethylsulfanyl)-phenoxy]-acetic acid;
[5-Methoxy-2-methyl-4-(4'-trifluoromethyl-biphenyl-4-ylmethanesulfonyl)-phenoxy]-acetic acid;
[5-Methoxy-2-methyl-4-(4'-trifluoromethyl-biphenyl-4-ylmethanesulfinyl)-phenoxy]-acetic acid;
[2-Propyl-4-(4'-trifluoromethyl-biphenyl-4-ylmethylsulfanyl)-phenoxy]-acetic acid;
{7-[3-(5-Trifluoromethyl-pyridin-2-yl)-benzylsulfanyl]-indan-4-yloxy}-acetic acid;
(5-Methoxy-2-methyl-4-{2-[1-(4-trifluoromethyl-benzyl)-1H-indol-3-yl]-ethylsulfanyl}-phenoxy)-acetic acid;
[7-(4'-Trifluoromethyl-biphenyl-2-ylmethylsulfanyl)-indan-4-yloxy]-acetic acid;
{5-Methoxy-2-methyl-4-[2-(4-trifluoromethyl-benzyloxy)-benzylsulfanyl]-phenoxy}-acetic acid;
{4-[4-(4-Fluoro-benzyloxy)-benzylsulfanyl]-2-methyl-phenoxy}-acetic acid;
{4-[4-(4-Chloro-benzyloxy)-benzylsulfanyl]-2-methyl-phenoxy}-acetic acid;
4-[4-(2,5-Dichloro-benzyloxy)-benzylsulfanyl]-2-methyl-phenoxy}-acetic acid;
{2-Methyl-4-[4-(pyridine-2-ylmethoxy)-benzylsulfanyl]-phenoxy}-acetic acid;
{5-Chloro-2-methyl-4-[4-(4-trifluoromethyl-benzyloxy)-benzylsulfanyl]-phenoxy}-acetic acid;
{7-[4-(2,4-Dichloro-benzyloxy)-benzylsulfanyl]-indan-4-yloxy}-acetic acid;
{7-[4-(4-Trifluoromethyl-benzyloxy)-benzylsulfanyl]-indan-4-yloxy}-acetic acid;
{5-Methyl-7-[4-(4-trifluoromethyl-benzyloxy)-benzylsulfanyl]-indan-4-yloxy}-acetic acid;
{7-[4-(4-Fluoromethyl-benzyloxy)-benzylsulfanyl]-indan-4-yloxy}-acetic acid;
{7-[4-(2,4-Difluoro-benzyloxy)-benzylsulfanyl]-indan-4-yloxy}-acetic acid;
{7-[4-(4-tert-Butyl-benzyloxy)-benzylsulfanyl]-indan-4-yloxy}-acetic acid;
{7-[4-(4-Methoxy-benzyloxy)-benzylsulfanyl]-indan-4-yloxy}-acetic acid;
[7-(4-Benzyloxy-benzylsulfanyl)-indan-4-yloxy]-acetic acid;
{7-[4-(4-Chloro-benzyloxy)-benzylsulfanyl]-indan-4-yloxy}-acetic acid;
{7-[4-(2,5-Dichloro-benzyloxy)-benzylsulfanyl]-indan-4-yloxy}-acetic acid;
{7-[4-(3,4-Dichloro-benzyloxy)-benzylsulfanyl]-indan-4-yloxy}-acetic acid;
{7-[4-(4-Chloro-3-trifluoromethyl-benzyloxy)-benzylsulfanyl]-indan-4-yloxy}-acetic acid;
{7-[4-(4-Fluoro-3-trifluoromethyl-benzyloxy)-benzylsulfanyl]-indan-4-yloxy}-acetic acid;
{7-[4-(4-Trifluoromethoxy-benzyloxy)-benzylsulfanyl]-indan-4-yloxy}-acetic acid;
{7-[4-(4-Fluoro-2-trifluoromethyl-benzyloxy)-benzylsulfanyl]-indan-4-yloxy}-acetic acid;
{7-[4-(3,5-Dichloro-benzyloxy)-benzylsulfanyl]-indan-4-yloxy}-acetic acid;
{7-[4-Methoxy-3-(4-trifluoromethyl-benzyloxy)-benzylsulfanyl]-indan-4-yloxy}-acetic acid;
{7-[3-(4-Trifluoromethyl-benzyloxy)-benzylsulfanyl]-indan-4-yloxy}-acetic acid;
{7-[3-(4-Chloro-3-trifluoromethyl-benzyloxy)-benzylsulfanyl]-indan-4-yloxy}-acetic acid;

{7-[2-(4-Trifluoromethyl-benzyloxy)-benzylsulfanyl]-indan-4-yloxy}-acetic acid;
{7-[3,5-Dichloro-4-(4-trifluoromethyl-benzyloxy)-benzylsulfonyl]-indan-4-yloxy}-acetic acid;
{8-[4-(4-Trifluoromethyl-benzyloxy)-benzylsulfanyl]-chroman-5-yloxy}-acetic acid;
{8-[3-(4-Trifluoromethyl-benzyloxy)-benzylsulfanyl]-chroman-5-yloxy}-acetic acid;
{8-[4-(2,5-Dichloro-benzyloxy)-benzylsulfanyl]-chroman-5-yloxy}-acetic acid;
{8-[4-(5-Trifluoromethyl-pyridine-2-yl)-benzylsulfanyl]-chroman-5-yloxy}-acetic acid;
{7-[5-(2-Chloro-phenyl)-isoxazol-3-ylmethylsulfanyl]-indan-4-yloxy}-acetic acid;
{7-[3-(2,6-Dichloro-phenyl)-5-methyl-isoxazol-4-ylmethylsulfanyl]-indan-4-yloxy}-acetic acid;
{7-[3-(4-Trifluoromethyl-phenyl)-isoxazol-5-ylmethylsulfanyl]-indan-4-yloxy}-acetic acid;
{7-[2-(4'-Trifluoromethyl-biphenyl-4-yl)-ethylsulfanyl]-indan-4-yloxy}-acetic acid;
{7-[2-(4'-Trifluoromethyl-biphenyl-4-yl)-ethyl]-indan-4-yloxy}-acetic acid;
{5-Methyl-7-[4-5-trifluoromethyl-pyridin-2-yl)-benzylsulfanyl]-2,3-dihydro-benzofuran-4-yloxy}-acetic acid;
[8-(4'-Trifluoromethyl-biphenyl-4-ylmethylsulfanyl)-chroman-5-yloxy]-acetic acid;
{8-[5-(4-Chloro-phenyl)-isoxazol-3-ylmethylsulfanyl]-chroman-5-yloxy}-acetic acid;
{4-[5-(4-Chloro-phenyl)-isoxazol-3-ylmethylsulfanyl]-2-methyl-phenoxy}-acetic acid;
{7-[5-(4-Chloro-phenyl)-isoxazol-3-ylmethylsulfanyl]-indan-4-yloxy}-acetic acid;
{7-[3-(4-Chloro-phenyl)-isoxazol-5-ylmethylsulfanyl]-indan-4-yloxy}-acetic acid;
{5-Chloro-2-methyl-4-[5-(4-trifluoromethyl-phenyl)-isoxazol-3-ylmethylsulfanyl]-phenoxy}-acetic acid;
2-[2-butyl-4-({4-[4-(trifluoromethyl)phenyl]phenyl}methylthio)phenoxy]acetic acid;
{6-methyl-8-[4-(4-trifluoromethyl-benzyloxy)-benzylsulfanyl]-chroman-5-yloxy}-acetic acid;
{4-[5-(4-trifluoromethyl-phenyl)-isoxazol-3-ylmethylsulfanyl]-5,6,7,8-tetrahydro-naphthalen-1-yloxy}-acetic acid;
(4-{2-Butyl-5-chloro-1-[4-(1-cyano-cyclopentyl)-benzyl]-1H-imidazol-4-ylmethylsulfanyl}-2-methyl-phenoxy)-acetic acid;
[4-(5-Biphenyl-4-yl-2-thiophen-2-yl-4,5-dihydro-oxazol-4-ylmethylsulfanyl)-5-methoxy-2-methyl-phenoxy]-acetic acid;
{4-[2-(4-Bromo-phenoxy)-ethylsulfanyl]-2,6-dimethyl-phenoxy}-acetic acid;
[4-(3-{2-[4(2-Diethylamino-ethoxy)-phenyl]-benzimidazol-1-yl}-propylsulfanyl)-5-methoxy-2-methyl-phenoxy]-acetic acid;
[4-(5-Biphenylyl-2-thiophen-2-yl-4,5-dihydro-oxazol-4-ylmethylsulfanyl)-2-methyl-phenoxy]-acetic acid;
(4-{2-[3-(4-Fluoro-phenyl)-benzo[b]thiophen-7-yl]-ethylsulfanyl}-2-methyl-phenoxy)-acetic acid;
{2-Methyl-4-[2-(5-phenyl-naphthalen-1-yloxy)ethylsulfanyl]-phenoxy}-acetic acid;
[2-Methyl-4-(3-phenoxy-benzylsulfanyl)-phenoxy]-acetic acid;
[2,5-Dimethyl-4-(5-p-tolyl-1,3,4-oxadiazol-2-ylmethylsulfanyl)-phenoxy]-acetic acid;
[2-Methyl-4-(4-pyrazol-1-yl-benzylsulfanyl)-phenoxy]-acetic acid;
[2-Methyl-4-(5-methyl-3-phenyl-isoxazol-4-ylmethylsulfanyl)-phenoxy]-acetic acid;
[4-(Biphenyl-2-ylmethylsulfanyl)-2-methyl-phenoxy]-acetic acid;
{4-[5-(4-Chloro-phenyl)-isoxazol-3-ylmethylsulfanyl]-2-methyl-phenoxy}-acetic acid;
[2-Methyl-4-(5-p-tolyl-1,3,4-oxadiazol-2-ylmethylsulfanyl)-phenoxy]-acetic acid;
{4-[3-(4-Chloro-phenyl)-1,2,4-oxadiazol-5-ylmethylsulfanyl]-2-methyl-phenoxy}-acetic acid;
[2,5-Dimethyl-4-(4-pyrazol-1-yl-benzylsulfanyl)-phenoxy]-acetic acid;
[4-(Biphenyl-2-ylmethylsulfanyl)-2,5-dimethyl-phenoxy]-acetic acid;
[4-(4-Benzyloxy-benzylsulfanyl)-5,6,7,8-tetrahydro-naphthalen-1-yloxy]-acetic acid;
[4-(4-Benzyloxy-benzylsulfanyl)-2,6-dimethyl-phenoxy]-acetic acid;
[4-(4-Benzyloxy-benzylsulfanyl)-2,5,-dimethyl-phenoxy]-acetic acid;
[4-(4-Benzyloxy-benzylsulfanyl)-2-methyl-phenoxy]-acetic acid;
[4-(4-Benzyloxy-benzylsulfanyl)-phenoxy]-acetic acid;
[4-(Biphenyl-4-ylmethylsulfanyl)-5,6,7,8-tetrahydro-naphthalen-1-yloxy]-acetic acid;
[4-(Biphenyl-4-ylmethylsulfanyl)-2,6-dimethyl-phenoxy]-acetic acid;
[4-(Biphenyl-4-ylmethylsulfanyl)-2,5-dimethyl-phenoxy]-acetic acid;
[4-(Biphenyl-4-ylmethylsulfanyl)-phenoxy]-acetic acid;
{4-[3-(2-Fluoro-phenoxy)-benzylsulfanyl]-2,6-dimethyl-phenoxy}-acetic acid;
[4-(2-{4-[2-(3-Chloro-4-cyclohexyl-phenyl)-ethyl]-piperazin-1-yl}-ethylsulfanyl)-2-methyl-phenoxy]-acetic acid;
[5-Methoxy-2-methyl-4-(2-{4-[2-(3-phenyl-benzofuran-7-yl)-ethyl]-piperazin-1-yl}-ethylsulfanyl)-phenoxy]-acetic acid;
{4-[2-(2,6-Diphenyl-piperidin-1-yl)-ethylsulfanyl]-5-methoxy-2-methyl-phenoxy}-acetic acid;
[2-Methyl-4-(2-{4-[2-(3-phenyl-benzofuran-7-yl)-ethyl]-piperazin-1-yl}-ethylsulfanyl)-phenoxy]-acetic acid;
{4-[2-(2,6-Diphenyl-piperidin-1yl)-ethylsulfanyl]-2-methyl-phenoxy}-acetic acid;
and pharmaceutically acceptable salts thereof.

A subset of exemplary compounds of Formula I and Formula II include
[4-(Biphenyl-4-ylmethylsulfanyl)-5-methoxy-2-methyl-phenoxy]-acetic acid;
[5-Methoxy-2-methyl-4-(4'-trifluoromethyl-biphenyl-4-ylmethylsulfanyl)-phenoxy]-acetic acid;
[4-(2',4'-Dichloro-biphenyl-4-ylmethylsulfanyl)-5-methoxy-2-methyl-phenoxy]-acetic acid;
[5-Methoxy-2-methyl-4-(3'-trifluoromethyl-biphenyl-4-ylmethylsulfanyl)-phenoxy]-acetic acid;
[4-(4'-Fluorobiphenyl-4-ylmethylsulfanyl)-5-methoxy-2-methyl-phenoxy]-acetic acid;
[7-(4'-Trifluoromethyl-biphenyl-4-ylmethylsulfanyl)-indan-4-yloxy]-acetic acid;
{5-Methoxy-2-methyl-4-[4-(4-trifluoromethyl-benzyloxy)-benzylsulfanyl]-phenoxy}-acetic acid;
[5-Methoxy-2-methyl-4-(3'-trifluoromethoxy-biphenyl-3-ylmethylsulfanyl)-phenoxy]-acetic acid;
{{5-Methoxy-2-methyl-4-[4-(5-trifluoromethyl-pyridin-2-yl)-benzylsulfanyl]-phenoxy}-acetic acid;
{5-Methoxy-2-methyl-4-[6-(4-trifluoromethyl-phenyl)-pyridin-3-ylmethylsulfanyl]-phenoxy}-acetic acid;

[3-Methoxy-4-(4'-trifluoromethyl-biphenyl-4-ylmethylsulfanyl)-phenoxy]-acetic acid;

{5-Methoxy-2-methyl-4-[2-(4'-trifluoromethyl-biphenyl-4-yl)-ethylsulfanyl]-phenoxy}-acetic acid;

(4-{4-[2-(3-Fluoro-phenyl)-vinyl]-benzylsulfanyl}-5-methoxy-2-methyl-phenoxy)-acetic acid;

[5-Methoxy-2-methyl-4-(3-methyl-4'-trifluoromethyl-biphenyl-4-ylmethylsulfanyl)-phenoxy]-acetic acid;

{4-[5-(4-Chloro-phenyl)-isoxazol-3-ylmethylsulfanyl]-5-methoxy-2-methyl-phenoxy}-acetic acid;

{5-Methoxy-2-methyl 4-[5-(4-trifluoromethyl-phenyl)-isoxazol-3-ylmethylsulfanyl]-phenoxy}-acetic acid;

{5-Methoxy-2-methyl-4-[3-(4-trifluoromethyl-phenyl)-isoxazol-5-ylmethylsulfanyl]-phenoxy}-acetic acid;

[5-Methoxy-2-methyl-4-(4'-trifluoromethyl-biphenyl-3-ylmethylsulfanyl)-phenoxy]-acetic acid;

{7-[4-(4-Trifluoromethyl-benzyloxy)-benzylsulfanyl]-indan-4-yloxy}-acetic acid;

{5-Methyl-7-[4-(5-trifluoromethyl-pyridin-2-yl)-benzylsulfanyl]-2,3-dihydro-benzofuran-4-yloxy}-acetic acid;

and pharmaceutically acceptable salts thereof.

Certain of the compounds of the present invention possess one or more chiral centers and each center may exist in the R or S configuration. The present invention includes all diastereomeric, enantiomeric, and epimeric forms as well as the appropriate mixtures thereof. Stereoisomers may be obtained, if desired, by methods known in the art as, for example, the separation of stereoisomers by chiral chromatographic columns. Additionally, the compounds of the present invention may exist as geometric isomers. The present invention includes all cis, trans, syn, anti, entgegen (E), and zusammen (Z) isomers as well as the appropriate mixtures thereof In some situations, compounds may exist as tautomers. All tautomers are included within Formulas I and II and are provided by this invention.

In addition, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

The present invention includes all pharmaceutically acceptable, nonn-toxic esters of the compounds of Formulae I and II. Such esters include $C_1$–$C_6$ alkyl esters where the alkyl group is a straight or branched chain. Acceptable esters also include $C_5$–$C_7$ cycloalkyl esters as well as arylalkyl esters such as, but not limited to benzyl. $C_1$–$C_4$ esters are preferred. Esters of the compounds of the present invention may be prepared according to conventional methods.

The compounds of the present invention are suitable to be administered to a patient for the treatment, control, or prevention of hypercholesteremia, dyslipidemia, obesity, hyperglycemia, hypercholesteremia, atherosclerosis, hypertriglyceridemia, and hyperinsulinemia. The compounds of the present invention are also suitable to be administered to a patient for the supression of appetite and modulation of leptin. Accordingly, the compounds may be administered to a patient alone or as part of a composition that contains other components such as excipients, diluents, and carriers, all of which are well-known in the art. The compositions can be administered to humans and/or animals either orally, rectally, parenterally (intravenously, intramuscularly, or subcutaneously), intracisternally, intravaginally, intraperitoneally, intravesically, locally (powders, ointments, or drops), or as a buccal or nasal spray.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil), and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid; (b) binders, as for example, carboxymethylcellulose, alignates, gelatin, polyvinylpyrrolidone, sucrose, and acacia; (c) humectants, as for example, glycerol; (d) disintegrating agents, as for example, agar, calcium carbonate, potato or tapioca starch, alginic acid, certain complex silicates, and sodium carbonate; (e) solution retarders, as for example paraffin; (f) absorption accelerators, as for example, quaternary ammonium compounds; (g) wetting agents, as for example, cetyl alcohol and glycerol monostearate; (h) adsorbents, as for example, kaolin and bentonite; and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar, as well as high molecular weight polyethyleneglycols, and the like.

Solid dosage forms such as tablets, dragees, capsules, pills, and granules can be prepared with coatings and shells, such as enteric coatings and others well-known in the art. They may contain opacifying agents, and can also be of such composition that they release the active compound or compounds in a certain part of the intestinal tract in a delayed manner. Examples of embedding compositions which can be used are polymeric substances and waxes. The active compounds can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propyleneglycol, 1,3- butyleneglycol, dimethylformamide, oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan or mixtures of these substances, and the like.

Besides such inert diluents, the composition can also include adjuvants, such as wetting agents, emulsifying and suspending agents, sweetening, flavoring, and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are preferably suppositories which can be prepared by mixing the compounds of the present invention with suitable non-irritating excipients or carriers such as cocoa butter, polyethyleneglycol, or a suppository wax, which are solid at ordinary temperatures but liquid at body temperature and therefore, melt in the rectum, or vaginal cavity and release the active component.

Dosage forms for topical administration of a compound of this invention include ointments, powders, sprays, and inhalants. The active component is admixed under sterile conditions with a physiologically acceptable carrier and any preservatives, buffers, or propellants as may be required. Ophthalmic formulations, eye ointments, powders, and solutions are also contemplated as being within the scope of this invention.

The compounds of the present invention can be administered to a patient at dosage levels in the range of about 0.1 to about 2,000 mg per day. For a normal human adult having a body weight of about 70 kilograms, a dosage in the range of about 0.01 to about 10 mg per kilogram of body weight per day is preferable. However, the specific dosage used can vary. For example, the dosage can depend on a numbers of factors including the requirements of the patient, the severity of the condition being treated, and the pharmacological activity of the compound being used. The determination of optimum dosages for a particular patient is well-known to those skilled in the art.

PREPARATION OF COMPOUNDS OF THE INVENTION

The present invention contains compounds that can be synthesized in a number of ways familiar to one skilled in organic synthesis. The compounds outlined herein can be synthesized according to the methods described below, along with methods typically utilized by a synthetic chemist, and combinations or variations of those methods, which are generally known to one skilled in the art of synthetic chemistry. The synthetic route of compounds in the present invention is not limited to the methods outlined below. It is assumed one skilled in the art will be able to use the schemes outlined below to synthesize compounds claimed in this invention. Individual compounds may require manipulation of the conditions in order to accommodate various functional groups. A variety of protecting groups generally known to one skilled in the art may be required. Purification, if necessary, can be accomplished on a silica gel column eluted with the appropriate organic solvent system. Also, reverse phase HPLC or recrystallization may be employed.

Many of the compounds with Formulas I and II are preferably made by reacting:

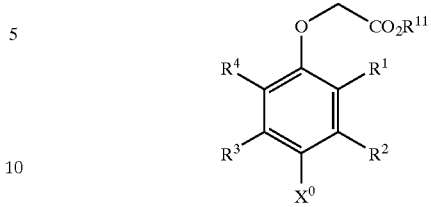

in a solvent in the presence of a base such as cesium carbonate, with the aryl halide:

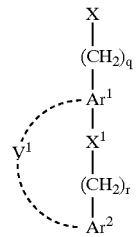

wherein:

n, $R^1$, $R^2$, $R^3$, $R^4$, $X^0$, $X^1$, $V^1$, $Ar^1$, and $Ar^2$ are the same as defined above for Formula I;

$R^{11}$ is a lower alkyl; and

X is a halogen.

The resulting ester is then preferably hydrolyzed to form the compounds of Formulas I and II. Specifically, compounds of Formulas I and II can be prepared using the synthetic route outlined in Scheme 1-6.

Scheme 1 covers the preparation of compounds of Formulas I and II wherein $X^0$ is S, q is 0–3,

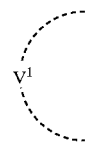

is absent, $X^1$ is absent and r is 0. Compounds of the general formula A are thiocyanated with a mixture of bromine and sodium thiocyanate to give compounds of the general formula B. Compounds of the general formula B are then alkylated with an alkyl haloacarboxylate to give compounds of the general formula C. The preferred alkyl haloacarboxylate is methyl bromoacetate. Alternate routes to compounds of formula C will be readily apparent to a person skilled in the art of organic synthesis. Compounds of the general formula D are then prepared by reduction of C with dithiothreitol in methanol. Compounds of the general formula D are then alkylated with compounds of the general formula Y in the same manner as for B to give E. Compounds of the general formula Y are prepared as described in Scheme 7 (below) or are readily available from commercial sources. Compounds of the general formula E are then, saponified with LiOH in the THF to give the final compound F.

Scheme 1

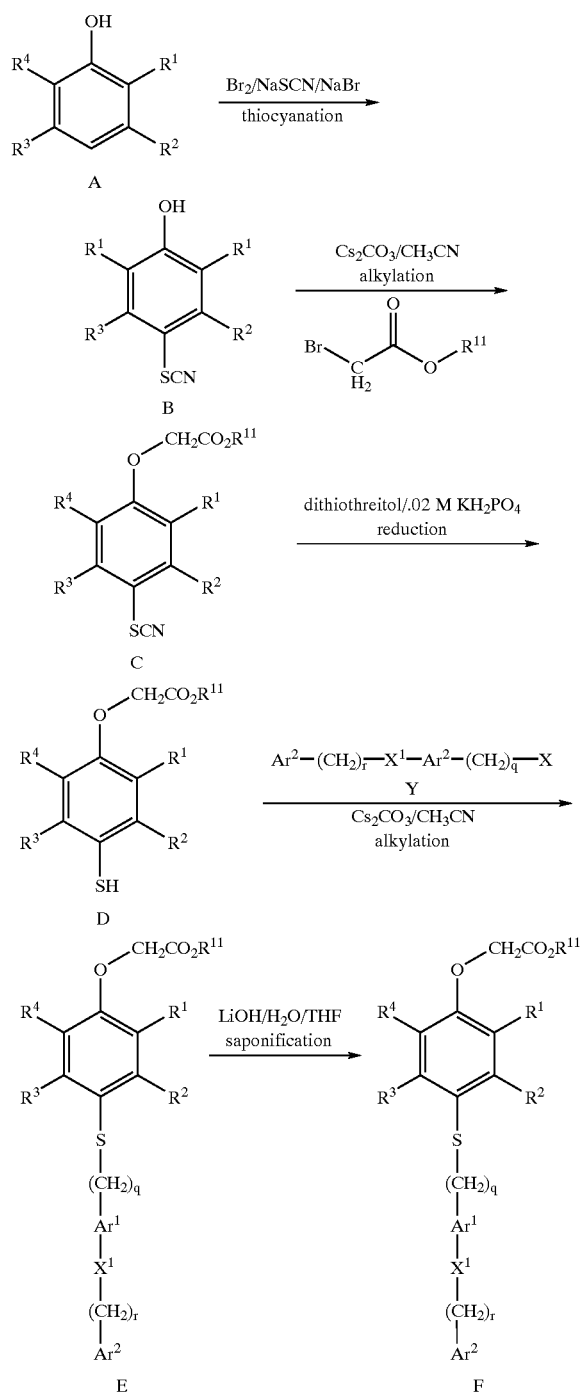

Scheme 2 covers the preparation of compounds of Formula I–II wherein $X^0$ is O, q is 0–3, $X^1$ is absent, is absent, and r is 0. Compounds of the general formula A are alkylated with an alkyl haloacarboxylate to give compounds of the general formula G. The preferred alkyl halocarboxylate is methyl bromoacetate. Alternate routes to compounds of formula G when Y is O will be readily apparent to a person skilled in the art of organic synthesis. Compounds of the general formula G are then acylated using Friedel-Crafts conditions to give compounds of the general formula H which are then oxidized with m-chloroperoxybenzoic acid followed by hydrolysis to give phenolic compounds of the general formula I. Compounds of the general formula I are then reacted in a similar manner as for D to give after saponification with LiOH in THF, compounds of the general formula K.

Scheme 2

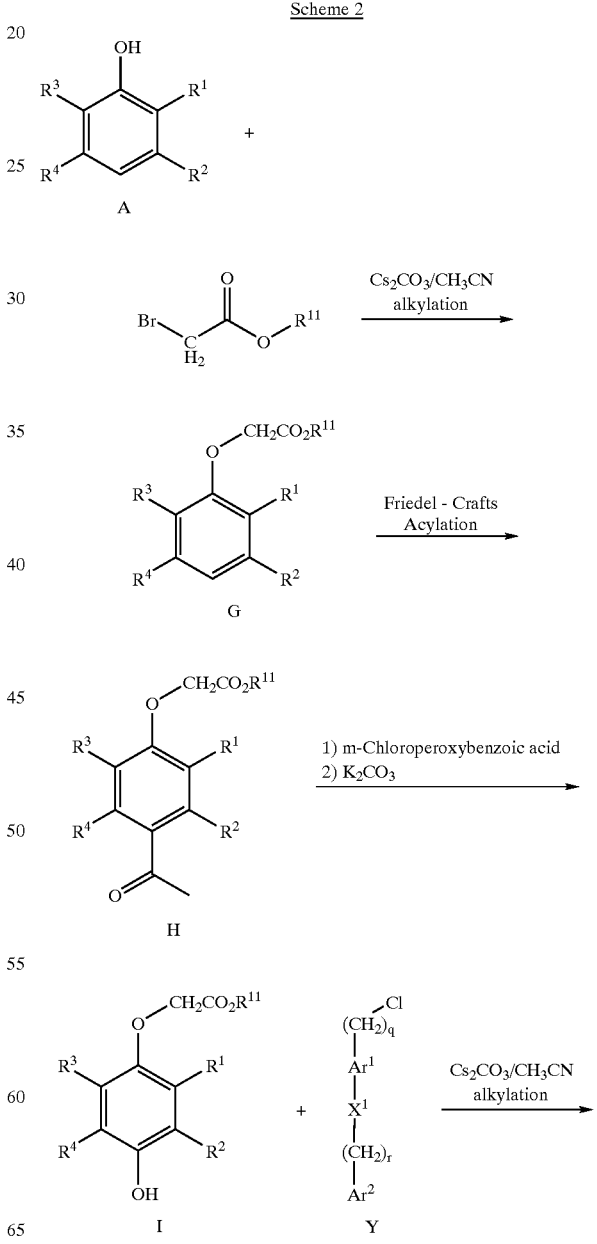

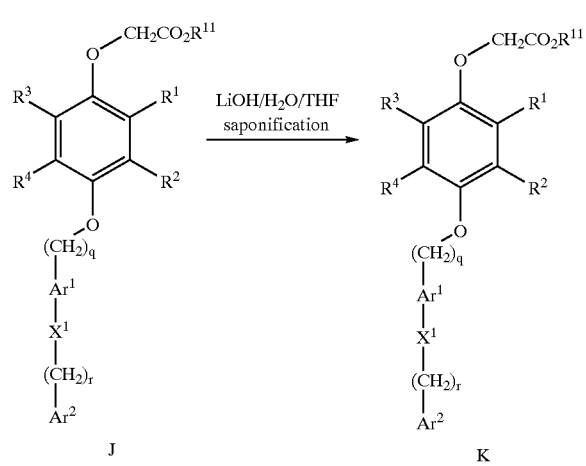

Scheme 3 covers the preparation of compounds of formula I–II wherein $X^0$ is —$CH_2$—$CH_2$—, —C≡C—, q is 0–3, $X^1$ is absent, is absent, and r is 0. Compounds of the general formula A are brominated with bromine, using acetic acid as solvent to give L. Alternatively, N-bromosuccinimide may be used in place of bromine and dichloromethane in place of acetic acid as solvent. Compounds of the general formula L are then alkylated with an alkyl haloacarboxylate to give compounds of the general formula M. The preferred alkyl halocarboxylate is methyl bromoacetate. Alternate routes to compounds of formula M will be readily apparent to a person skilled in the art of organic synthesis. Compounds of the general formula M are then reacted in the presence of tetrakis(triphenylphosphine)palladium(0) and biphenyl compounds of the general formula EE to give compounds of the general formula N. Compounds of the general formula EE are prepared as described in Scheme 9 or are readily available from commercial sources. Compounds of the general formula N are then saponified with LIOH in THF to give the final compound O.

Scheme 3

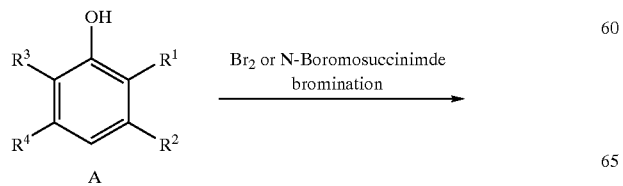

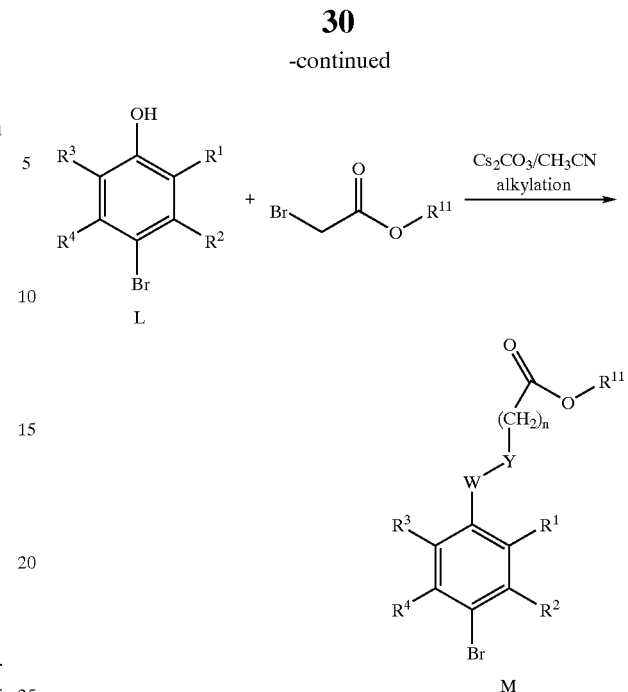

Scheme 4 covers the preparation of compounds of formula I–II wherein $X^0$ is —$CH_2$—$CH_2$—, q is 0–3, $X^1$ is absent, is absent, and r is 0. Accordingly, compounds of the general N can be reduced with hydrogen and palladium as catalyst to give compounds of the general formula P which are then saponified LiOH in THF to give the final compound Q.

Scheme 4

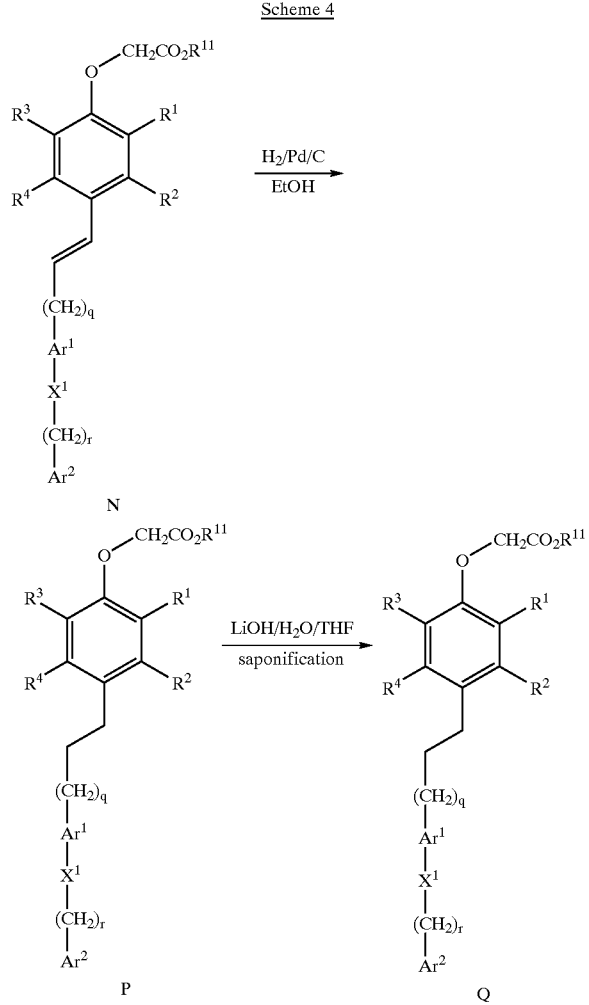

Scheme 5 covers the preparation of compounds of formula I–II wherein $X^0$ is absent, q is 0, $X^1$ is absent,

is absent, and r is 0 are prepared. Compounds of the general formula M are allowed to react with tetrakis(triphenylphosphine) palladium(0) and biphenyl compounds of the general formula HH to give compounds of the general formula R. Compounds of the general formula HH are prepared as described in Scheme 10 or are readily available from commercial sources. Compounds of the general formula R are then saponified with LiOH in THF to give the final compound S.

Scheme 5

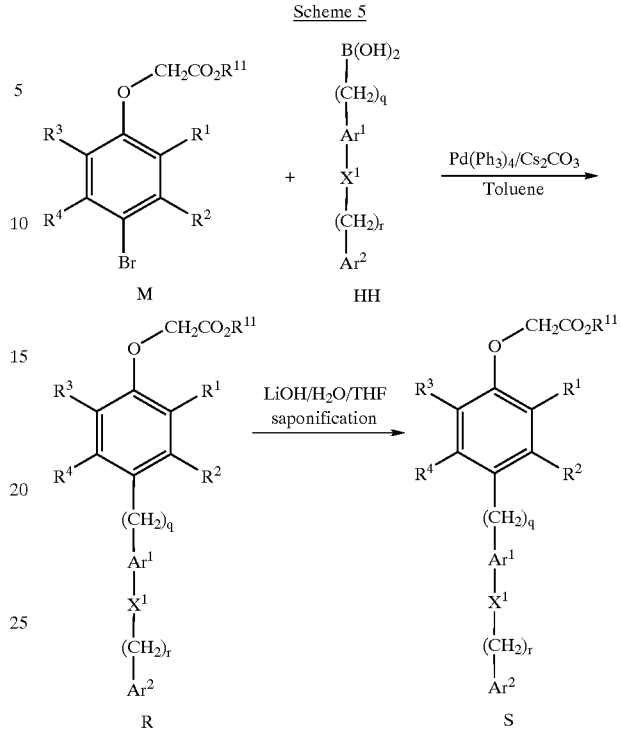

With reference to Scheme 6, compounds of formula I–II wherein $X^0$ is S or O, q is 1–3, $X^1$ is O, and r is 1–3 are prepared using the same conditions utilized for the preparation of K.

Scheme 6

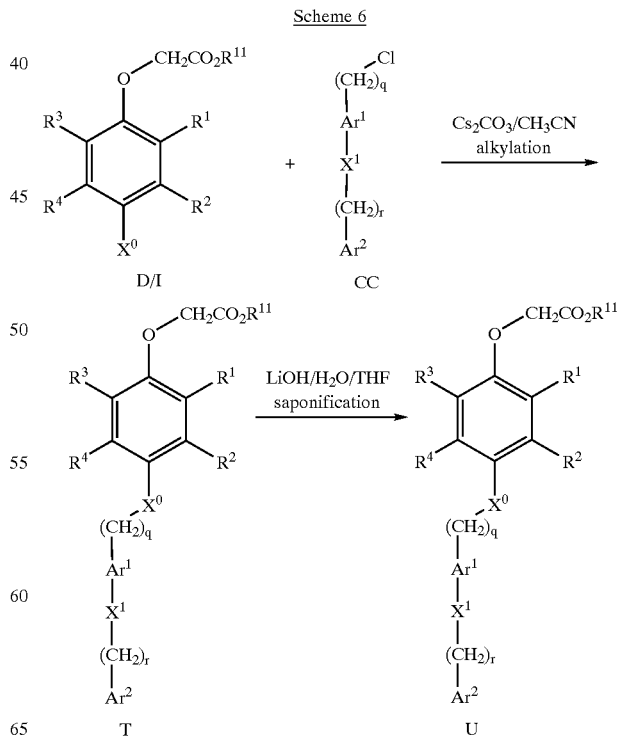

With reference to Scheme 7, compounds of the general formula X are prepared by reacting aryl boronic acid W with aryl bromide V in the presence of Pd(0) and cesium carbonate. Compounds of the general formula X are then reacted with methanesulfonyl chloride to give chlorides of the general formula Y.

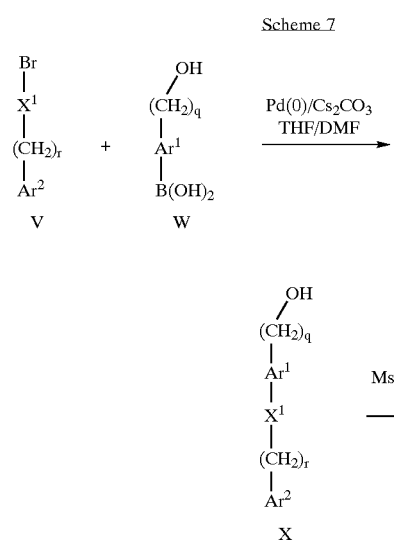

With reference to Scheme 8, compounds of the general formula CC are prepared wherein an appropriate hydroxy benzyl alcohol AA is alkylated with an appropriate bromide Z. The resulting compound BB is then reacted with methanesulfonyl chloride to give chlorides of the general formula CC.

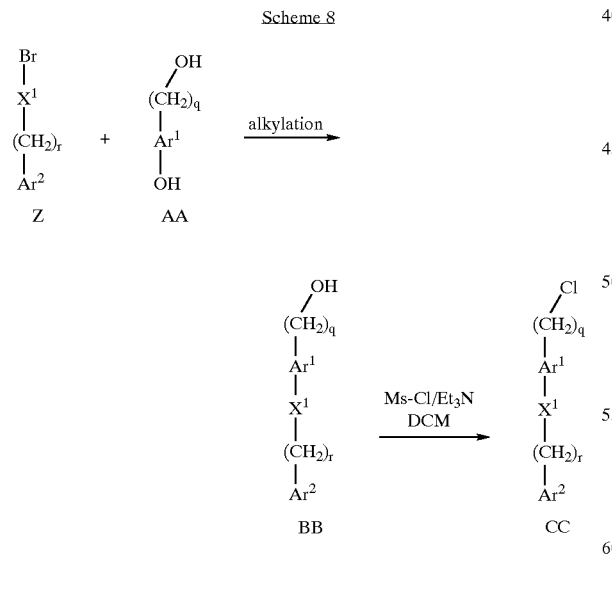

With reference to Scheme 9, compounds of the general formula EE are prepared by reacting aryl boronic acid V with aryl bromide DD in the presence of Pd(0) and cesium carbonate.

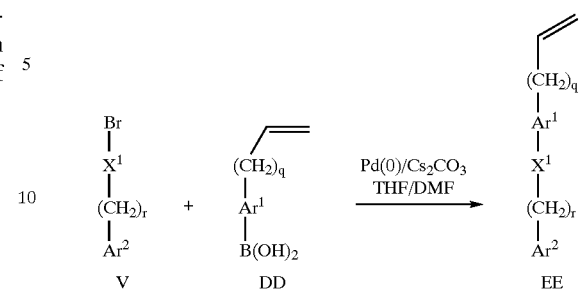

With reference to Scheme 10, compounds of the general formula HH are prepared by reacting aryl bromide V with boronic acid FF to give GG. Compounds of the general formula GG are then reacted with an alkyl lithium reagent and then quenched with a borate which is hydrolyzed to give compounds of the general formula HH.

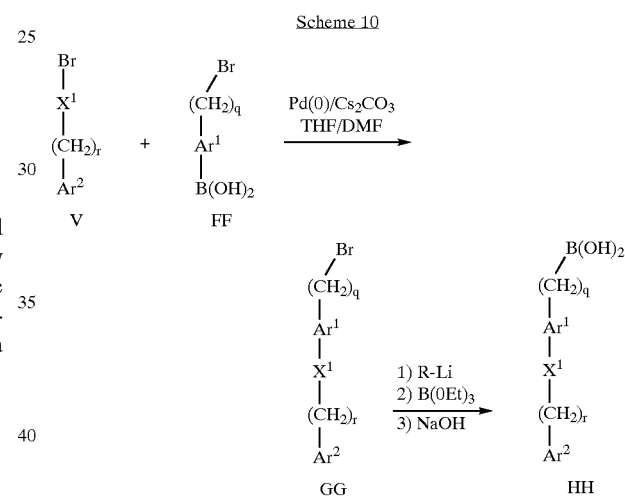

With reference to Scheme 11, compounds of formula I–II wherein $X^0$ is S or O, q is 1–3, $X^1$ is absent, r is O, and $V^1$ is a saturated or unsaturated hydrocarbon chain which is substituted or unsubstituted are prepared using the same conditions utilized for the preparation of K. Compounds of the general formula NN are prepared as described in Scheme 12 or are readily available from commercial sources.

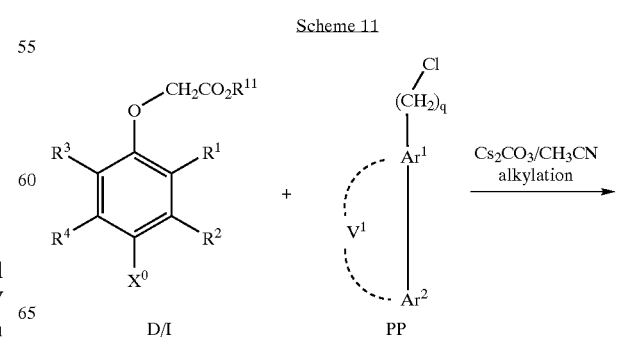

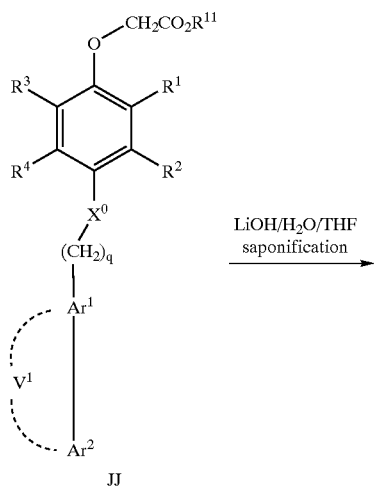

JJ

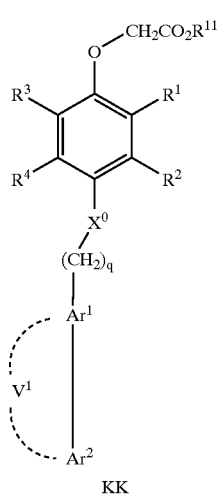

KK

With reference to Scheme 12, compounds of the general formula NN can be prepared by reacting an appropriately substituted aryl amine LL under Sandmeyer conditions followed by heating to give intermediate MM. The resulting intermediate MM is then reacted with methanesulfonyl chloride to give chlorides of the general formula NN.

Scheme 12

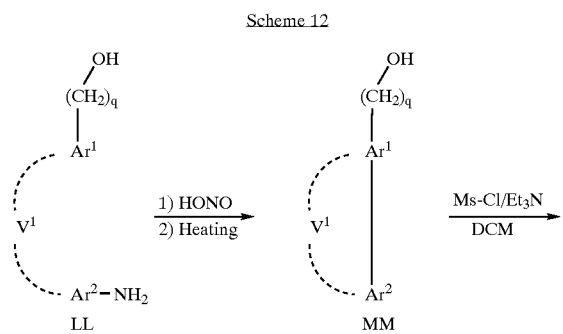

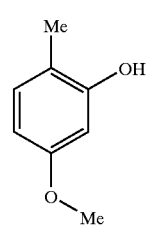

NN

Not all compounds of Formulas I–II falling into a given class may be compatible with some of the reaction conditions described. Such restrictions are readily apparent to those skilled in the art of organic synthesis, and alternative methods must then be used.

The following non-limiting descriptions also demonstrate methods for the synthesis of compounds of Formulae I and II.

EXAMPLE 1

Synthesis of [4-(Biphenyl-4 ylmethylsulfanyl)-5-methoxy-2-methyl-phenoxy]-acetic acid (compound 1)

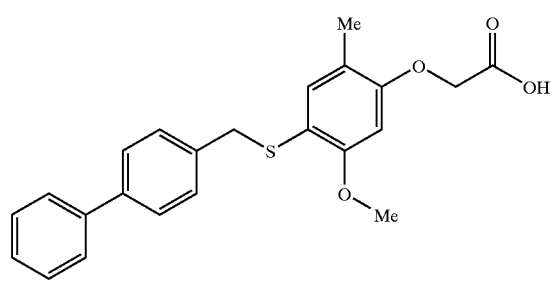

Step 1. Preparation of 5-Methoxy-2-methyl-phenol (compound 1A)

1A

Me
OH

O
Me

2-Hydroxy-4-methoxy-benzaldehyde (3 g, 19.7 mmol), ammonium formate (6.2 g, 99 mmol) and palladium/carbon (900 mg @10%) were added to 26 ml glacial acetic acid and heated at 110° C. for 1 h. The reaction was cooled, filtered, and diluted with water (100 ml). The crude product was extracted with chloroform (3×50 ml), washed with water, brine, and dried over anhydrous sodium sulfate. The resulting solution was concentrated and used for the next step without further purification. MS m/z 139 (M+1).

Step 2. Preparation of 5-Methoxy-2-methyl-4-thiocyanato-phenol (compound 1B)

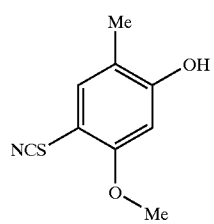

1B

The product from Example 1A (3.5 g, 25 mmol), sodium thiocyanate (6.48 g, 80 mmol), and sodium bromide (2.6 g, 25 mmol) were dissolved in 30 ml anhydrous methanol. Bromine (4.4 g, 28 mmol) was added drop wise over 15 minutes and allowed to stir at ambient temperature for 1 h. Brine was added (50 ml) and the crude product was extracted into ethyl acetate (3×100 ml). The combined organic extracts were washed with brine, dried over anhydrous sodium sulfate, decanted, and concentrated to afford the title product in good purity. 400 MHz $^1$H NMR (DMSO-$d_6$) δ 10.13 (s, 1H), 7.25 (s, 1H), 6.54 (s, 1H), 3.77 (s, 3H), 2.0 (s, 3H); MS m/z 196 (M+1).

Step 3. Preparation of (5-Methoxy-2-methyl-4-thiocyanato-phenoxy)-acetic acid methyl ester (compound 1C)

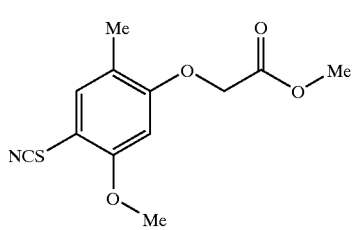

1C

The product from Example 1B (620 mg, 3.2 mmol), methyl bromoacetate (854 mg, 3.5 mmol), and cesium carbonate (3.1 g, 9.6 mmol) were stirred in 10 ml anhydrous acetonitrile at ambient temperature for 1 h. The reaction was filtered through Celite®, concentrated, and purified using normal phase chromatography. 400 MHz $^1$H NMR (DMSO-$d_6$) δ 7.33 (s, 1H), 6.72 (s, 1H), 4.93 (s, 2H), 3.84 (s, 3H), 3.66 (s, 3H), 2.09 (s, 3H); MS m/z 268 (M+1).

Step 4. Preparation of (4Mercapto-5-methoxy-2-methyl-phenoxy)-acetic acid methyl ester (compound 1D)

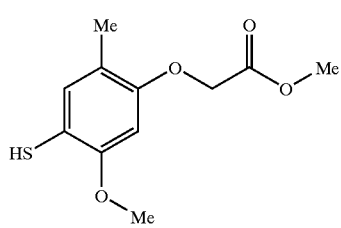

1D

The product from Example 1C (1.1 g, 4.1 mmol) and dithiothreitol (824 mg, 5.4 mmol) were dissolved in 20 ml methanol with 2.5 ml water. The solution was refluxed for 4 h, cooled, concentrated, and purified by normal phase chromatography. 400 MHz $^1$H NMR (DMSO-$d^6$) δ 7.02 (s, 1H), 6.54 (s, 1H), 4.79 (s, 2H), 4.41 (s, 1H), 3.72 (s, 3H), 3.64 (s, 3H), 2.02 (s, 3H); MS m/z 243 (M+1).

Step 5. Preparation of 4-Bromomethyl-biphenyl (compound 1E)

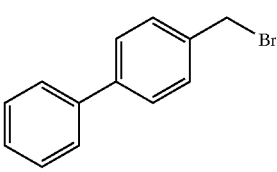

1E

Biphenyl-4-yl-methanol (500 mg, 2.72 mmol) phosphorus tribromide (809 mg, 2.99 mmol), and lithium bromide (260 mg, 2.99 mmol) were dissolved in 10 ml DMF and stirred at ambient temperature for 1 h. Water (10 ml) was added and the crude product was extracted into dichloromethane, dried over anhydrous sodium sulfate, filtered through silica gel, and concentrated. MS m/z 167 (M+1-Br).

Step 6. Preparation of [4-(Biphenyl-4-ylmethylsulfanyl)-5-methoxy-2-methyl-phenoxy]-acetic acid methyl ester (compound 1F)

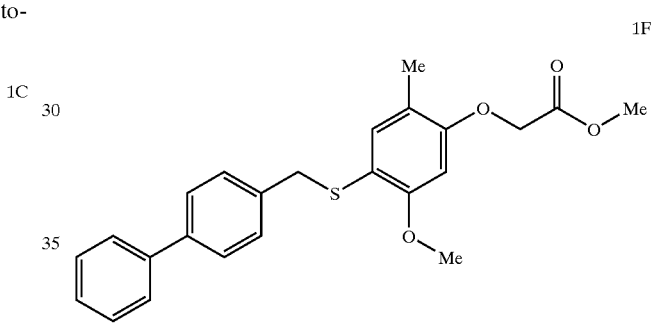

1F

The product from Example 1D (100 mg, 0.38 mmol), the product from Example 1E (92 mg, 0.38 mmol) and cesium carbonate (250 mg, 0.76 mmol) were added to 5 ml acetonitrile and stirred at ambient temperature for 4 hr. The reaction was filtered through Celite®, concentrated and purified through normal phase chromatography. MS m/z 409 (M+1).

Step 7. Preparation of [4-(Biphenyl-4-ylmethylsulfanyl)-5-methoxy-2-methyl-phenoxy]-acetic acid (compound 1)

The product from Example 1F (101 mg) was dissolved in 10 ml THF/water solution (10:1). Lithium hydroxide monohydrate (300 mg) was added and stirred for 30 minutes. 2 Normal aqueous HCl was added to pH<5 and then washed with ethyl acetate. The organic extract was dried over anhydrous sodium sulfate, decanted, and concentrated. The title product was recrystallized from chloroform/hexanes. mp 60–62° C.; 400 MHz $^1$H NMR (DMSO-$d_6$) δ 12.94 (br(s), 1H), 7.58 (d, 2H, J=8 Hz), 7.52 (d, 2H, J=8 Hz), 7.39 (t, 2H, J=7.2 Hz), 7.30 (m, 3H), 7.02 (s, 1H), 6.52 (s, 1H), 4.69 (s, 2H), 4.01 (s, 2H), 3.73 (s, 3H), 2.01 (s, 3H). MS m/z 393 (M−1). Anal. Calc'd for $C_{32}H_{22}O_4S \cdot 3H_2O$ C, 69.05; H, 5.07; found: C, 69.04; H, 5.35.

EXAMPLE 2

Synthesis of [4-Biphenyl-4-ylmethylsulfanyl)-2-methyl-phenoxy]-acetic acid (compound 2)

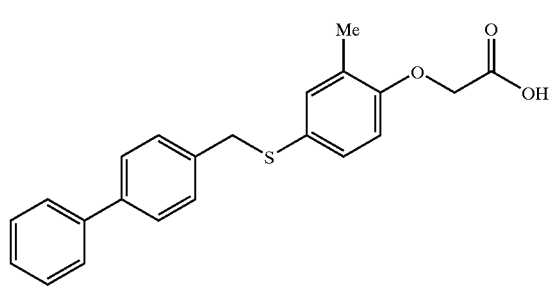

Step 1. Preparation of 2-Methyl-4-thiocyanato-phenol (compound 2A)

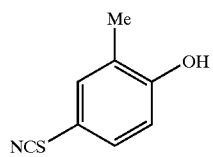

The title compound was prepared in a manner analogous to Example 1B from 2-methylphenol. 400 MHz $^1$H NMR (DMSO-$d_6$) δ 10.09 (s, 1H), 7.36 (s, 1H), 7.30 (d, 1H, J=8.1 Hz), 6.83 (d, 1H, J=8.1 Hz), 2.08 (s, 3H); MS m/z 166 (M+1).

Step 2. Preparation of (2-Methyl-4-thiocyanato-phenoxy)-acetic acid methyl ester (compound 2B)

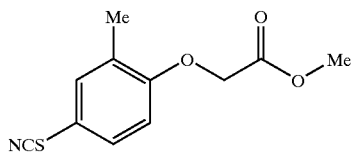

The title compound was prepared from 2 Example 2A in a manner analogous to Example 1C. 400 MHz $^1$H NMR (DMSO-$d_6$) δ 7.46 (s, 1H), 6.95 (d, 1H, J=8.5 Hz), 6.80 (d, 1H, J=8.5 Hz), 4.86 (s, 2H), 3.65 (s, 3H), 2.17 (s, 3H); MS m/z 238 (M+1).

Step 3. Preparation of (4-Mercapto-2-methyl-phenoxy)-acetic acid methyl ester (compound 2C)

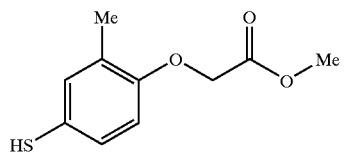

The title compound was prepared from (2-methyl-4-thiocyanato-phenoxy)-acetic acid methyl ester in a manner analogous to Example 1D. 400 MHz $^1$H NMR (DMSO-$d_6$) δ 7.05 (s, 1H), 7.00 (d, 1H, J=10.3 Hz), 6.70 (d, 1H, J=10.3 Hz), 5.00 (s, 1H), 4.73 (s, 1H), 3.63 (s, 3H), 2.09 (s, 3H); MS m/z 213 (M+1).

Step 4. Preparation of [4-(Biphenyl-4-ylmethylsulfanyl)-2-methyl-phenoxy]-acetic acid methyl ester (compound 2D)

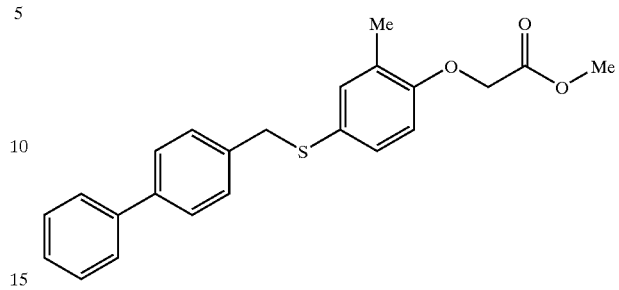

The title compound was prepared in the manner analogous to Example 1F using 2C and 1E. MS m/z 379 (M+1).

Step 5. Preparation of [4-(Biphenyl-4ylmethylsulfanyl)-2-methyl-phenoxy]-acetic acid (compound 2)

The title compound was prepared in the manner analogous to Example 1. mp 138° C.; 400 MHz $^1$H NMR (DMSO-$d_6$) δ 7.59 (d, 2H, J=9.5 Hz); 7.53 (d, 2H, J=9.5 Hz), 7.40 (m, 2H), 7.31(m, 3H), 7.14 (d, 1H, J=1.7 Hz), 7.09 (d, 1H, J=10.7 Hz), 6.70 (d, 1H, J=10.7 Hz), 4.62 (s, 2H), 4.11 (s, 2H), 2.09 (s, 3H); MS m/z 363 (M−1).

EXAMPLE 3

Synthesis of [2-Methyl-4-(4'-trifluoromethyl-biphenyl-4-ylmethylsulfanyl)-phenoxy]-acetic acid (compound 3)

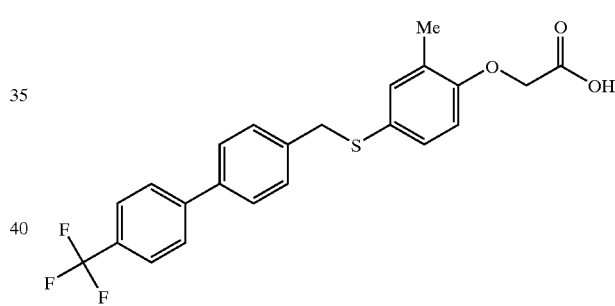

Step 1. Preparation of (4'-Trifluoromethyl-biphenyl-4-yl)-methanol (compound 3A)

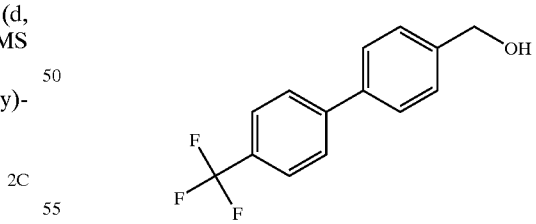

1-Bromo-4-trifluoromethyl-benzene (814 mg, 3.62 mmol), 4-hydroxymethylphenylboronic acid (600 mg, 3.98 mmol), cesium carbonate (2.36 g, 7.24 mmol), and PdCl$_2$(dppf) (132 mg, 0.181 mmol) were added to 10 ml of a 1:1 solution of DMF/THF. The reaction was flushed with nitrogen and heated to 90° C. for 1 h. The reaction was cooled, poured into diethyl ether and washed with water (2×50 ml), brine (1×50 ml) and dried over anhydrous sodium sulfate. The crude product was filtered through silica gel, eluted: with diethyl ether, and concentrated to provide the title compound. MS m/z 251 (M−1).

Step 2. Preparation of 4-Chloromethyl-4'-trifluoromethyl-biphenyl (compound 3B)

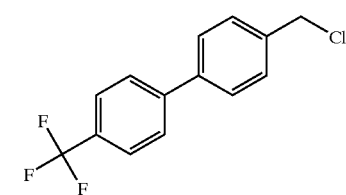

The product from Example 3A was dissolved in 10 ml methylene chloride. Triethylarnine (468 mg, 4.62 mol) and methanesulfonyl chloride (422 mg, 3.68 mmol) were then added and stirred for 18 h. The reaction was poured into water and extracted with methylene chloride. The organic solution was dried over anhydrous sodium sulfate, decanted and concentrated to provide the title compound that was used without further purification. MS m/z 235 (M-Cl+1).

Step 3. Preparation of [2-Methyl-4(4'-trifluoromethyl-biphenyl-4-ylmethylsulfanyl)-phenoxy]-acetic acid methyl ester (compound 3C)

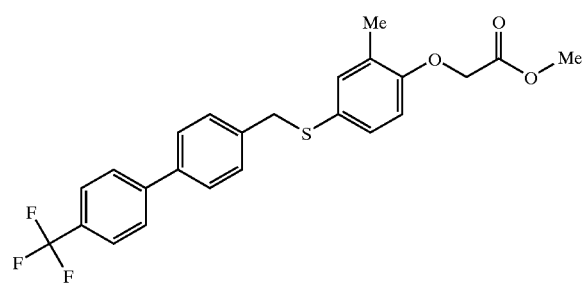

The title compound was prepared in the manner analogous to Example 1F using 3B and 2C. MS m/z 447 (M+1).

Step 4. Preparation of [2-Methyl-4-(4'-trifluoromethyl-biphenyl-4-ylmethylsulfanyl)-phenoxy]-acetic acid (compound 3)

The title compound was prepared in the manner analogous to Example 1 using 3C. mp 140–141° C.; 400 MHz $^1$H NMR (DMSO-$d_6$) δ 12.95 (br(s), 1H), 7.82 (d, 2H, J=8.4 Hz), 7.74 (d, 2H, J=8.4 Hz), 7.61 (d, 2H, J=8.4 Hz), 7.35 (d, 2H, J=8.4 Hz), 7.10 (m, 2H), 6.70 (d, 1H, J=8.4 Hz), 4.62 (s, 2H), 4.13 (s, 2H), 2.08 (s, 3H); MS m/z 431 (M−1). Anal. Calc'd for $C_{23}H_{19}F_3O_3S \cdot 0.7\ H_2O$ C, 62.07; H, 4.62; found: C, 61.98; H, 4.22.

EXAMPLE 4

Synthesis of [5-Methoxy-2-methyl-4-(4'-trifluoromethyl-biphenyl-4-ylmethylsulfanyl)-phenoxy]-acetic acid (compound 4)

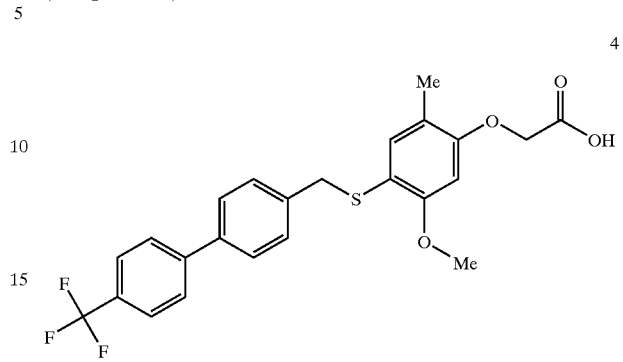

Step 1. Preparation of [5-Methoxy-2-methyl-4-(4'-trifluoromethyl-biphenyl-4-ylmethylsulfanyl)-phenoxy]-acetic acid methyl ester (compound 4A)

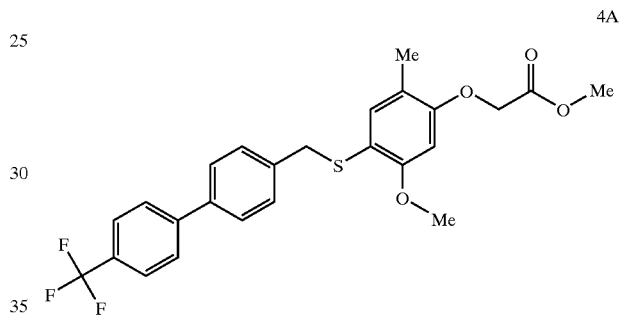

The title compound was prepared in the manner analogous to Example 1F using 1D and 3B. MS m/z 477 (M+1).

Step 2. Preparation of [5-Methoxy-2-methyl-4-(4'-trifluoromethyl-biphenyl-4-ylmethylsulfanyl)-phenoxy]-acetic acid (compound 4)

The title compound was prepared in the manner analogous to Example 1 using 4A. mp 170–171° C.; 400 MHz $^1$H NMR (DMSO-$d_6$) δ 7.81 (d, 2H, J=8 Hz), 7.60 (d, 2H, J 8.4 Hz), 7.32 (d, 2H, J=8.4 Hz), 7.02 (s, 1H), 6.52 (s, 1H), 4.70 (s, 2H), 4.03 (s, 2H), 3.73 (s, 3H), 2.00 (s, 3H). MS m/z 463 (M+1). Anal. Calc'd for $C_{24}H_{21}F_3NO_4S \cdot 0.1\ H_2O$ C, 62.09; H, 4.60; found: C, 62.00; H, 4.36.

EXAMPLE 5

Synthesis of [5-Methoxy-2-methyl-4-(2',4',6'-trimethyl-biphenyl-4-ylmethylsulfanyl)-phenoxy]-acetic acid (compound 5)

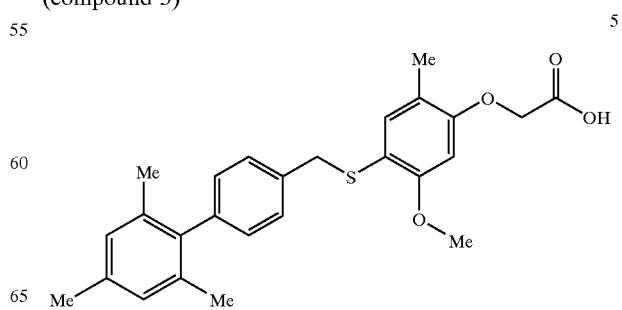

Step 1. Preparation of [5-Methoxy-2-methyl-4-(2',4',6'-trimethyl-biphenyl-4-ylmethylsulfanyl)-phenoxy]-acetic acid methyl ester (compound 5A)

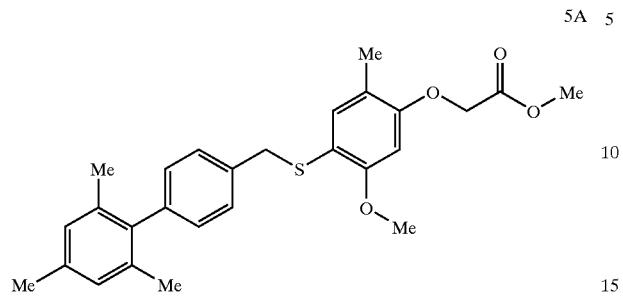

2-Bromo-1,3,5-trimethyl-benzene (396 mg, 2mmol), 4-hydroxymethylphenylboronic acid (334 mg, 2.2 mmol), cesium carbonate (1.3 g, 4 mmol), and PdCl$_2$(dppf) (82 mg, 0.1 mmol) were added to 5 ml of a 1:1 solution of DMF/THF. The reaction was flushed with nitrogen and heated to 90° C. for 1 h. The reaction was cooled, poured into diethyl ether and washed with water (2×10 ml), brine (1×10 ml) and dried over anhydrous sodium sulfate. The organic solution was filtered through silica gel, eluted with diethyl ether, and concentrated. The crude product was dissolved in 10 ml dichloromethane. Added to this solution were triethylamine (202 mg, 2 mmol) then methanesulfonyl chloride (184 mg, 1.6 mmol) and allowed to stir at ambient temperature for 18 h. The reaction was poured into water and extracted with methylene chloride. The organic solution was dried over anhydrous sodium sulfate, decanted and concentrated to provide the crude alkyl chloride. The product from Example 1D (387 mg, 1.6 mmol), the crude 4'-chloromethyl-2,4,6-trimethyl-biphenyl, and cesium carbonate (1 g, 3.06 mmol) were stirred in 10 ml acetonitrile for 3 h, filtered, concentrated, and purified by normal phase chromatography to afford the title product. MS m/z 451 (M+1).

Step 2. Preparation of [5-Methoxy-2-methyl-4-(2',4',6'-trimethyl-biphenyl-4-ylmethylsulfanyl)-phenoxy]-acetic acid The title compound was prepared in the manner analogous to Example 1 using 5A. mp 141° C.; 400 MHz $^1$H NMR (DMSO-d$_6$) δ 12.81 (br(s), 1H), 7.04 (d, 2H, J=8.4 Hz), 6.77 (m, 3H), 6.69 (s, 2H), 6.36 (s, 1H), 4.43 (s, 2H), 3.82 (s, 2H), 3.58 (s, 3H), 2.03 (s, 3H), 1.82 (s, 3H), 1.67 (s, 6H). MS m/z 437 (M+1).

EXAMPLE 6

Synthesis of [4-(4'-Chloro-3'-trifluoromethyl-biphenyl-4-ylmethylsulfanyl)-2-methyl-phenoxy]-acetic acid (compound 6)

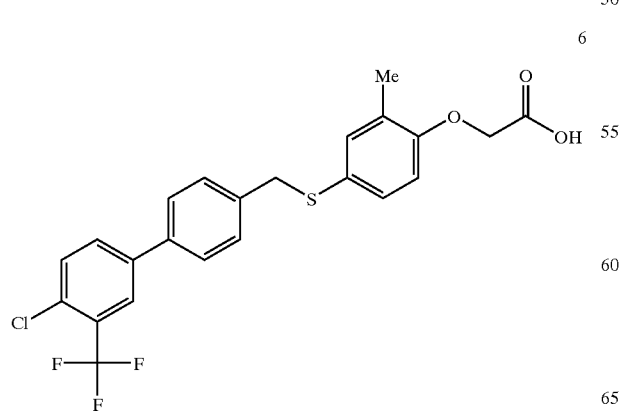

Step 1. Preparation of (4'-Chloro-3'-trifluoromethyl-biphenyl-4-yl)-methanol (compound 6A)

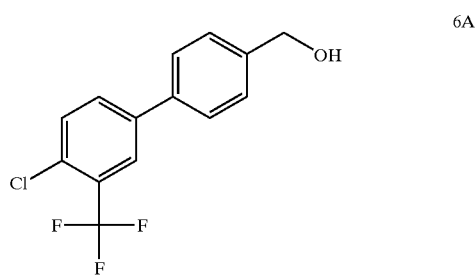

The title compound was prepared in the manner analogous to Example 3A using 4-bromo-1-chloro-2-trifluoromethyl-benzene. MS m/z 288 (M+1).

Step 2. Preparation of 4-Chloro-4'-chloromethyl-3'-trifluoromethyl-biphenyl (compound 6B)

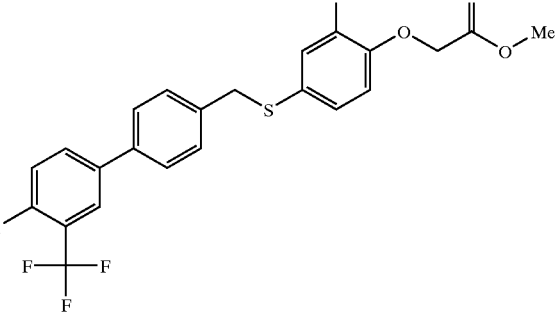

The title compound was prepared in the manner analogous to Example 3B using 6A. MS m/z 305 (M).

Step 3. Preparation of [4-(4'-Chloro-3'-trifluoromethyl-biphenyl-4ylmethylsulfanyl)-2-methyl-phenoxy]-acetic acid methyl ester (compound 6C)

The title compound was prepared in the manner analogous to Example 1F using 2C and 6B. MS m/z 481 (M+1).

Step 4. Preparation of [4-(4'-Chloro-3'-trifluoromethyl-biphenyl-4-ylmethylsulfanyl)-2-methyl-phenoxy]-acetic acid (compound 6)

The title compound was prepared in the manner analogous to Example 1 using 6C. 400 MHz $^1$H NMR (DMSO-d$_6$) δ 7.97 (s, 1H), 7.92 (d, 1H, J=10.5 Hz), 7.74 (d, 1H, J=10.5 Hz), 7.64 (d, 2H, J=8.9 Hz), 7.34 (d, 2H, J=8.9 Hz), 7.14 (s, 1H), 7.08 (d, 1H, J=11.0 Hz), 6.70 (d, 1H, J=11.0 Hz), 4.62 (s, 2H), 4.12 (s, 2H), 2.08 (s, 3H); MS m/z 465 (M−1).

EXAMPLE 7

Synthesis of [4-(2',4'-Dichloro-biphenyl-4-ylmethylsulfanyl)-5-methoxy-2-methyl-phenoxyl-acetic acid (compound 7)

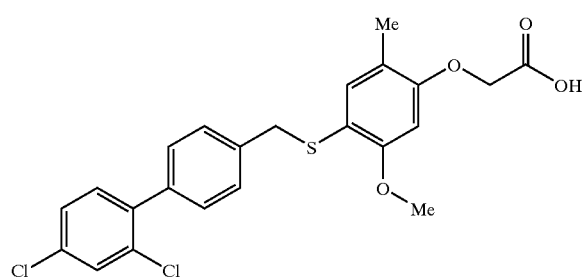

Step 1. Preparation of [4(2',4'-Dichloro-biphenyl-4ylmethylsulfanyl)-5-methoxy-2-methyl-phenoxy]-acetic acid methyl ester (compound 7A)

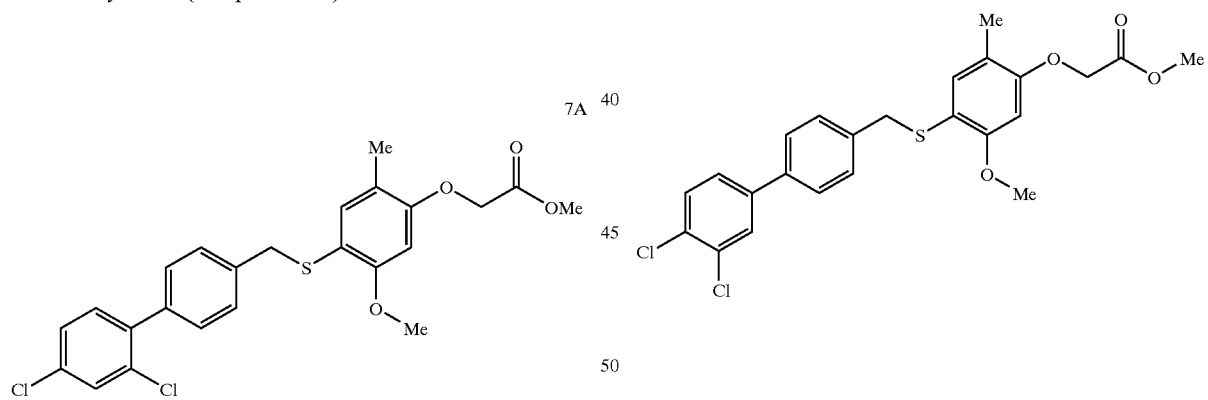

The title compound was prepared in the manner analogous to Example 5A using 1D and 1-bromo-2,4-dichloro-benzene. MS m/z 479 (M+2).

Step 2. Preparation of [4-(2',4'-Dichloro-biphenyl-4-ylmethylsulfanyl)-5-methoxy-2-methyl-phenoxy]-acetic acid (compound 7)

The title compound was prepared in the manner analogous to Example 1 using 7A. 400 MHz $^1$H NMR (DMSO-d$_6$) δ 12.95 (br(s, 1H), 7.67 (dd, 1H, J'=2 Hz, J=8.4 Hz), 7.43 (d, 1H, J=2.4 Hz), 7.37 (s, 1H), 7.28 (s, 4H), 7.02 (s, 1H), 6.52 (s, 1H), 4.70 (s, 2H), 4.02 (s, 2H), 3.72 (s, 3H), 2.01 (s, 3H); MS m/z 465 (M+2).

EXAMPLE 8

Synthesis of [4-(3',4'-Dichloro-biphenyl-4-ylmethylsulfanyl)-5-methoxy-2-methyl-phenoxy]-acetic acid (compound 8)

Step 1. Preparation of [4-(3',4'-Dichloro-biphenyl-4-ylmethylsulfanyl)-5-methoxy-2-methyl-phenoxy]-acetic acid methyl ester (compound 8A)

The title compound was prepared in the manner analogous to Example 5A using 1D and 4-bromo-1,2-dichloro-benzene. MS m/z 479 (M+2).

Step 2. Preparation of [4-(3',4'-Dichloro-biphenyl-4-ylmethylsulfanyl)-5-methoxy-2-methyl-phenoxy]-acetic acid (compound 8)

The title compound was prepared in the manner analogous to Example 1 using 8A. mp 161–162° C.; 400 MHz $^1$H NMR (DMSO-d$_6$) δ 7.87 (d, 1H, J=2 Hz), 7.57–7.66 (m, 4H), 7.29 (d, 2H, J=8.4 Hz), 7.01 (s, 1H),6.52. (s, 1H), 4.69 (s, 2H), 4.02 (s, 2H), 3.72 (s, 3H), 2.03 (s, 3H); MS m/z 494 (M+1).

EXAMPLE 9

Synthesis of [5-Methoxy-2-methyl-4-(3'-trifluoromethyl-biphenyl-4-ylmethylsulfanyl)-phenoxy]-acetic acid (compound 9)

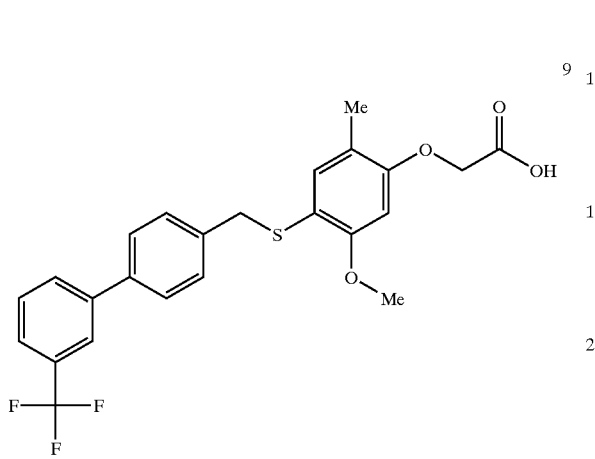

Step 1. Preparation of [5-Methoxy-2-methyl-4-(3'-trifluoromethyl-biphenyl-4-ylmethylsulfanyl)-phenoxy]-acetic acid methyl ester (compound 9A)

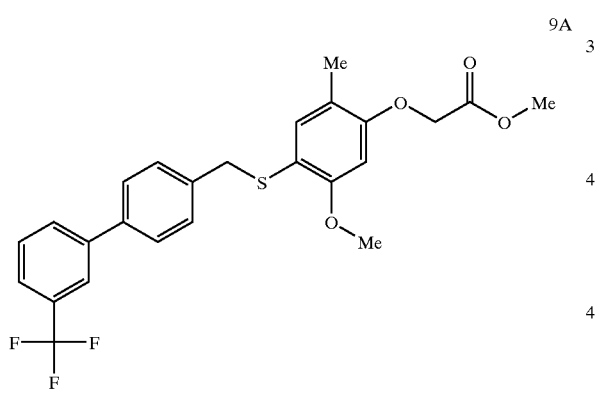

The title compound was prepared in the manner analogous to Example 5A using 1D and 1-bromo-3-trifluoromethyl-benzene. MS m/z 477 (M+1).

Step 2. Preparation of [5-Methoxy-2-methyl-4-(3'-trifluoromethyl-biphenyl-4-ylmethylsulfanyl)-phenoxy]-acetic acid (compound 9)

The title compound was prepared in the manner analogous to Example 1 using 9A. mp 138–139° C.; 400 MHz $^1$H NMR (DMSO-d$_6$) δ 12.95 (br(s), 1H), 7.91 (m, 2), 7.63 (m, 4H), 7.32 (d, 2H, J=8.4 Hz), 7.02 (s, 1H), 6.52 (s, 1H), 4.69 (s, 2H), 4.03 (s, 2H), 3.73 (s, 3H), 2.06 (s, 3H); MS m/z 463 (M+1).

EXAMPLE 10

Synthesis of [4-(4'-Fluoro-biphenyl-4-ylmethylsulfanyl)-5-methoxy-2-methyl-phenoxy]-acetic acid (compound 10)

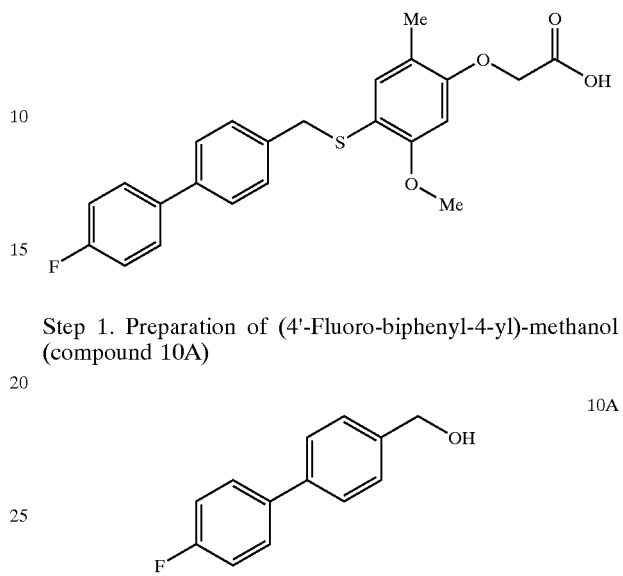

Step 1. Preparation of (4'-Fluoro-biphenyl-4-yl)-methanol (compound 10A)

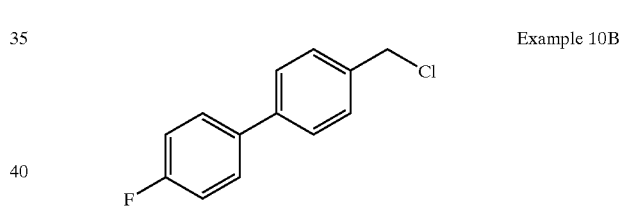

The title compound was prepared in the manner analogous to Example 3A using 1-bromo-4-fluorobenzene. MS m/z 185 (M-H$_2$O).

Step 2. Preparation of 4-Chloromethyl-4'-fluoro-biphenyl (compound 10B).

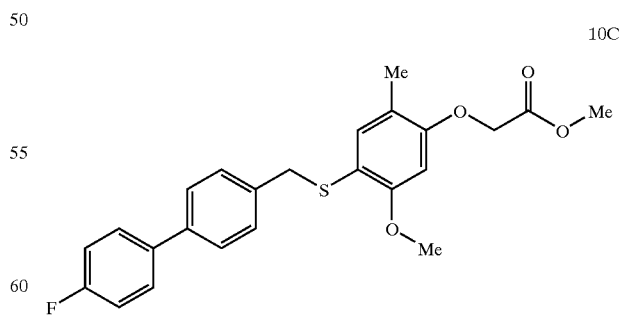

EXAMPLE 10B

The title compound was prepared in the manner analogous to Example 3B using 10A. MS m/z 222 (M+2).

Step 3. Preparation of [4(4'-Fluoro-biphenyl-4-ylmethylsulfanyl)-5-methoxy-2-methyl-phenoxy]-acetic acid methyl ester (compound 10C)

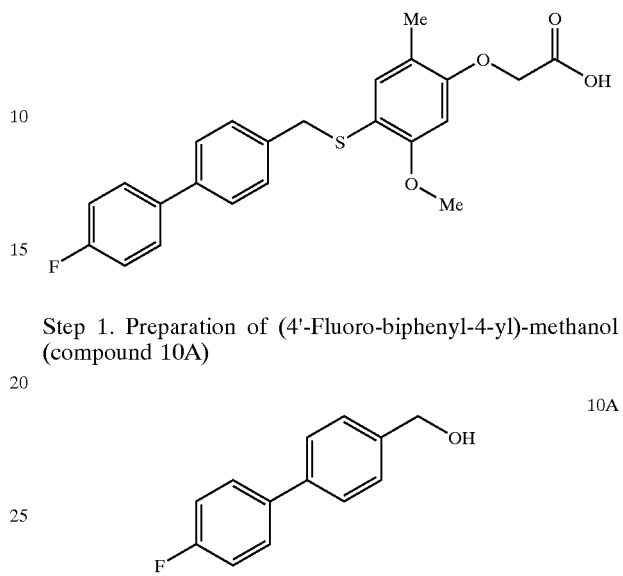

The title compound was prepared in the manner analogous to Example 1F using 10B and 1D. MS m/z 427 (M+1).

Step 4. Preparation of [4-(4'-Fluoro-biphenyl-4-ylmethylsulfanyl)-5-methoxy-2-methyl-phenoxy]-acetic acid The title compound was prepared in the manner analogous to Example 1 using 10C. 400 MHz ¹H NMR (DMSO-d₆) δ 12.93 (br(s), 1H), 7.62 (m, 2H), 7.49 (d, 2H, J=8.4 Hz), 7.27 (d, 2H, J=8.4 Hz), 7.22 (m, 2H), 7.02 (s, 1H), 6.52 (s, 1H), 4.69 (s, 2H), 4.01 (s, 2H), 3.73 (s, 3H), 2.01 (s, 3H). MS m/z 411 (M−1).

EXAMPLE 11

Synthesis of [5-Methoxy-2-methyl-4-(3'-trifluoromethoxy-biphenyl-4-ylmethylsulfanyl)-phenoxy]-acetic acid (compound 11)

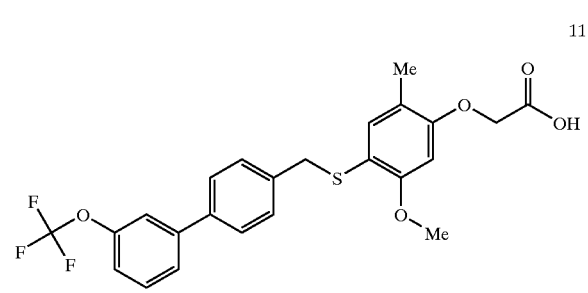

Step 1. Preparation of [5-Methoxy-2-methyl-4(3'-trifluoromethoxy-biphenyl-4-ylmethylsulfanyl)-phenoxy]-acetic acid methyl ester (compound 11A)

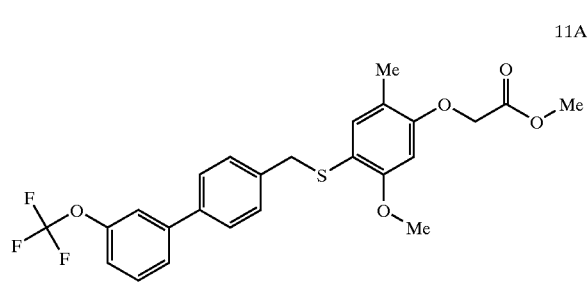

The title compound was prepared in the manner analogous to Example 5A using 1D and 1-bromo-3-trifluoromethoxy-benzene. MS m/z 493 (M+1).

Step 2. Preparation of [5-Methoxy-2-methyl-4-(3'-trifluoromethoxy-biphenyl-4-ylmethylsulfanyl)-phenoxy]-acetic acid (compound 11)

The title compound was prepared in the manner analogous to Example 1 using 11A. mp 137° C.; 400 m/z ¹H NMR (DMSO-d₆) δ 12.95 (br(s), 1H), 7.66 (d, 1H, J=8.8 Hz), 7.56 (m, 4H), 7.30 (m, 3H), 7.02 (s, 1H), 6.52 (s, 1H), 4.69 (s, 2H), 4.02 (s, 2H), 3.73 (s, 3H), 2.01 (s, 3H). MS m/z 493 (M+1).

EXAMPLE 12

Synthesis of [7-(4'-Trifluoromethyl-biphenyl-4-ylmethylsulfanyl)-indan-4-yloxy]-acetic acid (compound 12)

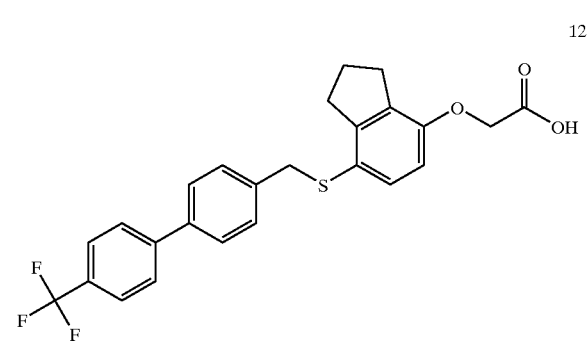

Step 1. Preparation of Indan-4-ol (compound 12A)

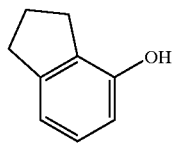

A mixture of 4-hydroxy-indan-1-one (5.0 g, 33.7 mmol), sodium cyanoborohydride (6.4 g, 101.1 mmol), and zinc iodide (32.3 g, 101.1 mmol) in dichloroethane, was heated at reflux for two hours. The reaction mixture was then filtered through 50 g SiO₂ while still warm, eluting further with dichloroethane. The filtrate was collected and concentrated under vacuum. The residue was added to diethyl ether and the resulting white precipitate was filtered off. The filtrate was collected and concentrated in vacuo to give 4.2 g of the title, compound with purity high enough for subsequent use. 400 MHz ¹H NMR (DMSO-d₆) δ 9.06 (s, 1H), 6.86 (t, 1H, J=7.8 Hz), 6.59 (d, 1H, J=7.8 Hz), 6.48 (d, 1H, J=7.8 Hz), 2.75 (t, 2H, J=7.3 Hz), 2.67 (t, 2H, J=7.3 Hz), 1.92 (m, 2H).

Step 2. Preparation of 7-Thiocyanato-indan-4-ol (compound 12B)

The title compound was prepared in the manner analogous to Example 1B using 12A. MS m/z 192 (M+1).

Step 3. Preparation of (7-Mercapto-indan-4-yloxy)-acetic acid methyl ester (compound 12C)

7-Thiocyanato-indan-4ol (Example 12B) (1.47 g, 7.7 mmol), cesium carbonate (3.77 g, 11.6 mmol) and methyl bromoacetate (1.24 g, 8.08 mmol) were stirred in 20 ml acetonitrile at ambient temperature for 4 h. The reaction was filtered and concentrated. The crude product was treated under the conditions of Example 1D to afford the title product. MS m/z 239 (M+1).

Step 4. Preparation of [7-(4'-Trifluoromethyl-biphenyl-4-ylmethylsulfanyl)-indan-4-yloxy]-acetic acid methyl ester (compound 12D)

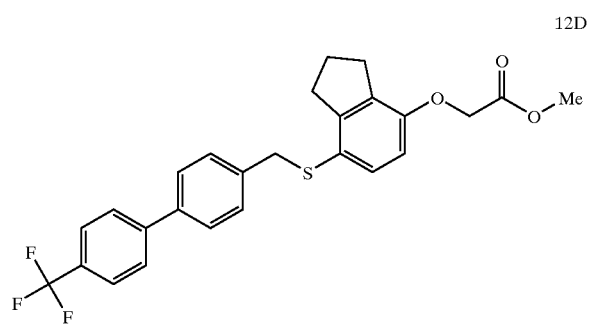

The title compound was prepared in the manner analogous to Example 1F using 12C and 3B. MS m/z 473 (M+1).

Step 5. Preparation of 17-(4'-Trifluoromethyl-biphenyl-4-ylmethylsulfanyl)-indan-4-yloxy]-acetic acid (compound 12)

The title compound was prepared in the manner analogous to Example 1 using 12D. mp 158–159° C.; 400 MHz $^1$H NMR (DMSO-$d_6$) δ 12.94 (br(s), 1H), 7.82 (d, 2H, J=8 Hz), 7.74 (d, 2H, J=8.8 Hz), 7.60 (d, 2H, J=6.4 Hz), 7.31 (d, 2H, J=8 Hz), 7.08 (d, 1H, J=8.8 Hz), 6.58 (d, 1H, J=8.4 Hz), 4.61 (s, 2H), 4.06 (s, 2H), 2.72 (m, 4H), 1.90 (q, 2H); MS m/z 457 (M−1).

EXAMPLE 13

Synthesis of [4-(4-Benzyloxy-benzylsulfanyl)-2-methyl-phenoxy]-acetic acid (compound 13)

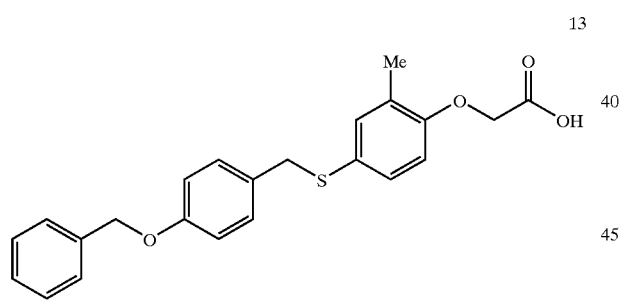

Step 1. Preparation of [4-(4Benzyloxy-benzylsulfanyl)-2-methyl-phenoxy]-acetic acid methyl ester (compound 13A)

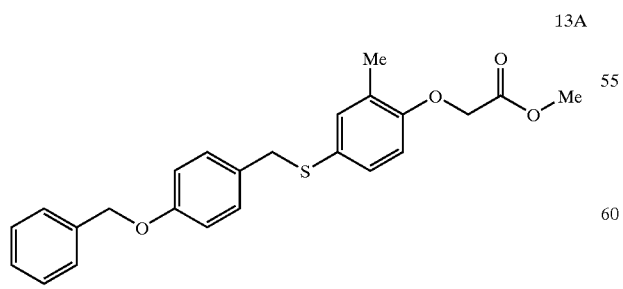

The title compound was prepared in the manner analogous to Example 1F using 1-chloromethyl-4-benzyloxy-benzene and 2C. MS m/z 409 (M+1).

Step 2. Preparation of [4-(4-Benzyloxy-benzylsulfanyl)-2-methyl-phenoxy]-acetic acid (compound 13)

The title compound was prepared in the manner analogous to Example 1 and 13A. mp 120–121° C.; 400 MHz $^1$H NMR (DMSO-$d_6$) δ 7.39–7.25 (m, 5H), 7.15–7.03 (m, 4), 6.85 (d, 2H, J=8.5 Hz), 6.68 (d, 1H, J 8.4 Hz), 5.00 (s, 2H), 4.62 (s, 2H), 4.00 (s, 2H), 2.08 (s, 3H); MS m/z 395 (M+1).

EXAMPLE 14

Synthesis of {5-Methoxy-2-methyl-4-[4-(4-trifluoromethyl-benzyloxy)-benzylsulfanyl]-phenoxy}-acetic acid (compound 14)

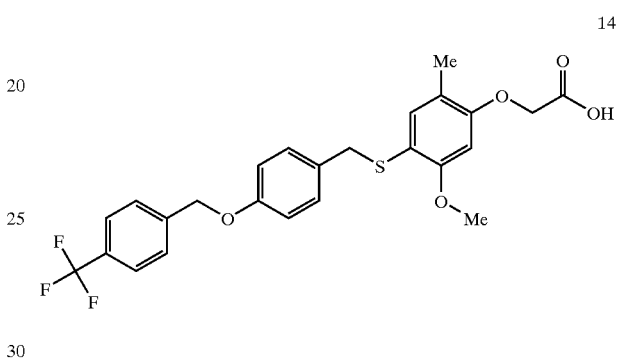

Step 1. Preparation of [4-(4-Trifluoromethyl-benzyloxy)-phenyl]-methanol (compound 14A)

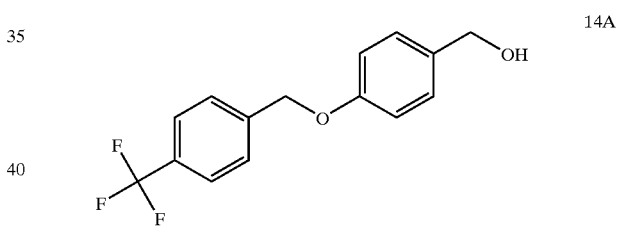

4-Hydroxymethyl-phenol (1 g, 8.06 mmol), 1-Chloromethyl-4-trifluoromethyl-benzene (1.57 g, 8.06 mmol), and cesium carbonate (5.26 g, 16.12 mmol) were refluxed in acetonitrile for 20 h, cooled, filtered, and concentrated to give the title compound. MS m/z 265 (M-H$_2$O+1).

Step 2. Preparation of 4-Chloromethyl-(4-trifluoromethyl-benzyloxy-benzene) (compound 14B)

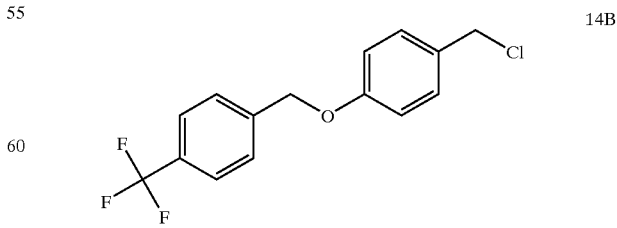

The title compound was prepared in the manner analogous to Example 3B using 14A. MS m/z 265 (M-Cl+1).

Step 3. Preparation of {5-Methoxy-2-methyl-4-[4-(4-trifluoromethyl-benzyloxy)-benzylsulfanyl]-phenoxy}-acetic acid methyl ester (compound 14C)

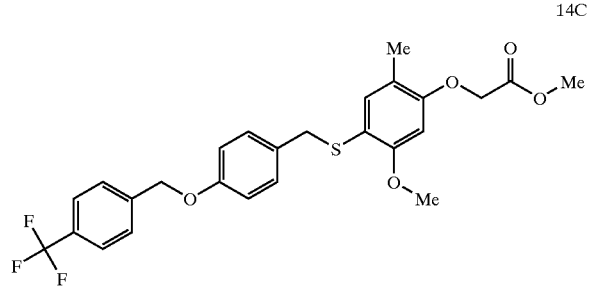

14C

The title compound was prepared in the manner analogous to Example 1F using 14B and 1D. MS m/z 507 (M+1).

Step 4. Preparation of {5-Methoxy-2-methyl-4-[4-(4-trifluoromethyl-benzyloxy)-benzylsulfanyl]-phenoxy}-acetic acid (compound 14)

The title compound was prepared in the manner analogous to Example 1 using 14C. mp 145° C.; 400 MHz $^1$H NMR (DMSO-$d_6$) δ 12.94 (br(s), 1H), 7.70 (d, 2H, J=8 Hz), 7.76 (d, 2H, J=8 Hz), 7.14 (d, 2H, J=8.8 Hz), 6.97 (s, 1H), 6.87 (m, 2H), 6.50 (s, 1H), 5.14 (s, 2H), 4.68 (s, 2H), 3.91 (s, 2H), 3.71 (s, 3H), 2.00 (s, 3H); MS m/z 491 (M−1).

EXAMPLE 15

Synthesis of {2-Methyl-4-[4-(4-trifluoromethyl-benzyloxy)-benzylsulfanyl]-phenoxy}-acetic acid (compound 15)

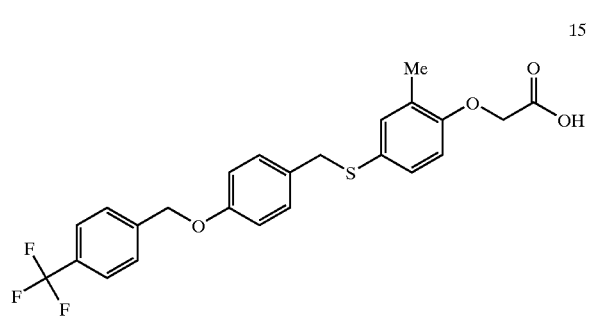

15

Step 1. Preparation of {2-Methyl-4-[4-(4-trifluoromethyl-benzyloxy)-benzylsulfanyl]-phenoxy}-acetic acid methyl ester (compound 15A)

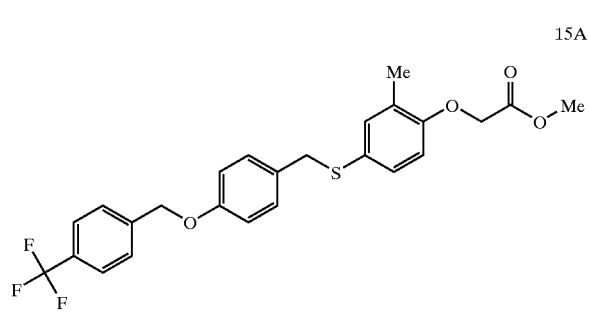

15A

The title compound was prepared in the manner analogous to Example 1F using 2C and 14B. MS m/z 477 (M+1).

Step 2. Preparation of {2-Methyl-4-[4-(4-trifluoromethyl-benzyloxy)-benzylsulfanyl]-phenoxy}-acetic acid (compound 15)

The title compound was prepared in the manner analogous to Example 1 using 15A. mp 133° C.; 400 MHz $^1$H NMR (DMSO-$d_6$) δ 7.70 (d, 2H, J=8 Hz), 7.76 (d, 2H, J=8 Hz), 7.14 (d, 2H, J=8.8 Hz), 7.09 (m, 1H), 7.04 (dd, 1H, J=2.4 Hz, J'=8.4 Hz), 6.87 (m, 2H), 6.68 (d, 1H, J=8.4 Hz), 5.14 (s, 2H), 4.61 (s, 2H), 3.99 (s, 2H), 2.08 (s, 3H); MS m/z 461 (M−1).

EXAMPLE 16

Synthesis of [5-Methoxy-2-methyl-4-(3'-trifluoromethoxy-biphenyl-3-ylmethylsulfanyl)-phenoxy]-acetic acid (compound 16)

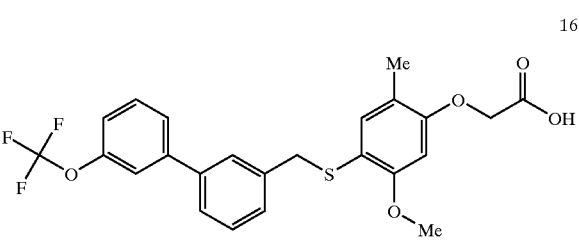

16

Step 1. Preparation of (3'-Trifluoromethoxy-biphenyl-3-yl)-methanol (compound 16A)

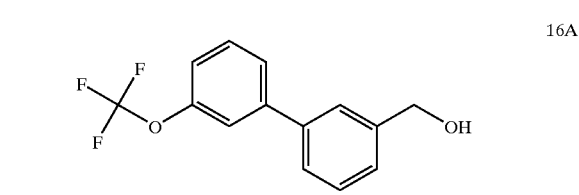

16A

The title compound was prepared in the manner analogous to Example 3A using 3-hydroxymethylphenylboronic acid and 1-bromo-3-trifluoromethoxy-benzene. MS m/z 251 (M−1).

Step 2. Preparation of 3-Chloromethyl-3'-trifluoromethoxy-biphenyl (compound 16B)

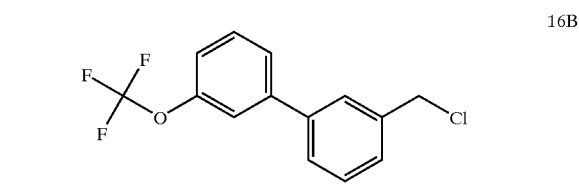

16B

The title compound was prepared in the manner analogous to Example 3B using 16A. MS m/z 251 (M−1).

Step 2. Preparation of [5-Methoxy-2-methyl-4-(3'-trifluoromethoxy-biphenyl-3-ylmethylsulfanyl)-phenoxy]-acetic acid methyl ester (compound 16C)

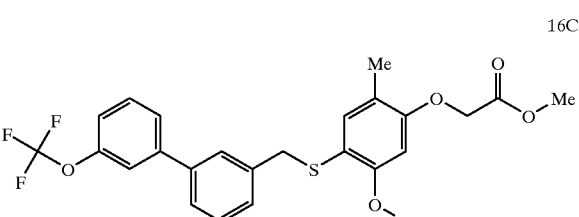

16C

The title compound was prepared in the manner analogous to Example 1F using 16B and 1D. MS m/z 491 (M−1).

Step 4. Preparation of [5-Methoxy-2-methyl-4-(3'-trifluoromethoxy-biphenyl-3-ylmethylsulfanyl)-phenoxy]-acetic acid (compound 16)

The title compound was prepared in the manner analogous to Example 1 using 16C. mp 92–94° C.; 400 MHz $^1$H NMR (DMSO-d$_6$) δ 12.96 (br(s), 1H), 7.55–7.24 (m, 8H), 7.01 (s, 1H), 6.52 (s, 1H), 4.68 (s, 2H), 4.03 (s, 2H), 3.72 (s, 3H), 1.99 (s, 3H); MS m/z 479 (M+1).

EXAMPLE 17

Synthesis of [4-(9H-Fluoren-2-ylmethylsulfanyl-2-methyl-phenoxy]-acetic acid (compound 17)

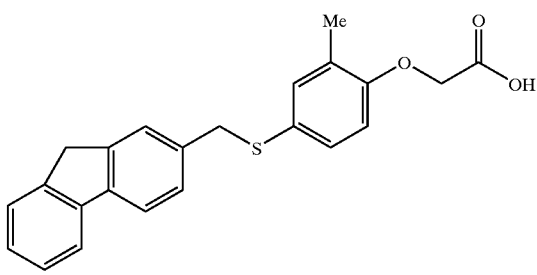

Step 1. Preparation of (9H-Fluoren-2-yl)-methanol (compound 17A)

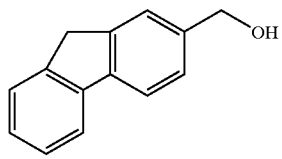

9H-Fluorene-2-carbaldehyde (500 mg, 2.6 mmol) was dissolved in 10 ml methanol. Sodium borohydride (200 mg, 5.2 mmol) was added and allowed to stir at ambient temperature for 1 h. Water (10 ml) was added and the crude product was extracted into ethyl acetate (50 ml), washed with brine (50 ml), dried over anhydrous sodium sulfate, decanted and concentrated to afford the title product in good purity. MS m/z 195 (M+1).

Step 2. Preparation of 2-Chloromethyl-9H-fluorene (compound 17B)

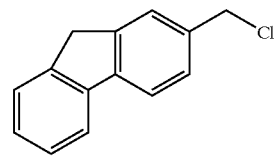

The title compound was prepared in the manner analogous to Example 3B using 17A. MS m/z 179 (M-Cl+1).

Step 3. Preparation of [4-(9H-Fluoren-2-ylmethylsulfanyl-2-methyl-phenoxy]-acetic acid methyl ester (compound 17C)

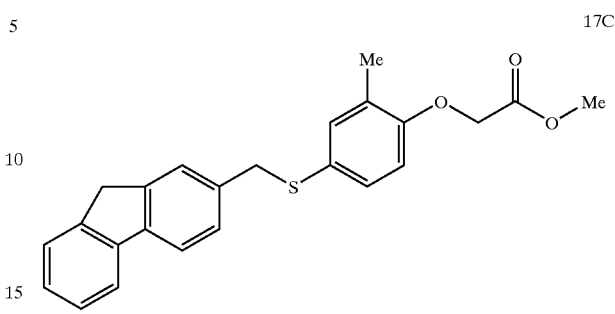

The title compound was prepared in the manner analogous to Example 1F using 17B and 2C. MS m/z 422 (M+1).

Step 4. Preparation of [4-(9H-Fluoren-2-ylmethylsulfanyl-2-methyl-phenoxy]-acetic acid (compound 17)

The title compound was prepared in the manner analogous to Example 1 using 17C. 400 MHz $^1$H NMR (DMSO-d$_6$) δ 12.93 (br(s), 1H), 7.80 (d, 1H, J=7.6 Hz), 7.23 (d, 1H, J=8 Hz), 7.5 (d, 1H, J=7.6 Hz), 7.43 (s, 1H), 7.31 (t, 1H, J'=6.4 Hz), 7.24 (m, 2H), 7.15 (m, 1H), 7.08 (dd, 1H, J=2.4 Hz, J=8.4 Hz), 6.7 (d, 1H, J=8.8 Hz), 4.62 (s, 2H), 4.13 (s, 2H), 3.82 (s, 2H), 2.09 (s, 3H). MS m/z 375 (M-1). Anal. Calc'd for $C_{23}H_{20}O_3S \cdot 0.3 H_2O$ C, 72.34; H, 5.44; found: C, 72.46; H, 5.20.

EXAMPLE 18

Synthesis of {{5-Methoxy-2-methyl-4-[4-(5-trifluoromethyl-pyridin-2-yl)-benzylsulfanyl]-phenoxy}-acetic acid (compound 18)

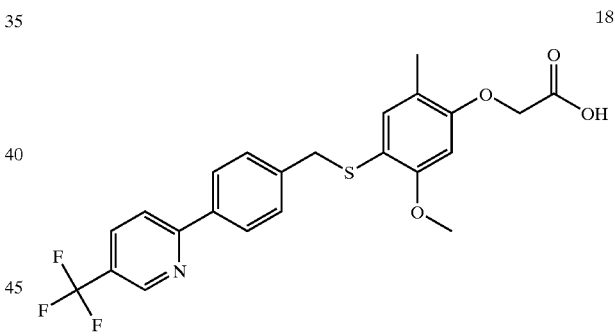

Preparation of [4-(5-Trifluoromethyl-pyridin-2-yl)-phenyl]-methanol (compound 18A)

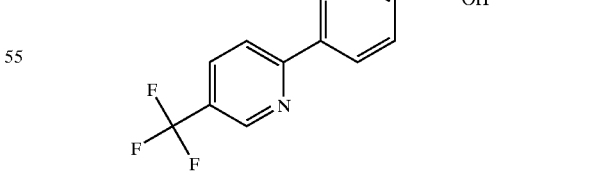

The title compound was prepared from 2-Chloro-5-trifluoromethyl-pyridine and 4-(hydroxymethyl)boronic acid PdCl$_2$(dppb) catalyst in the manner analogous to Example 3A. 400 MHz $^1$H NMR (DMSO-d$_6$) δ 8.98 (s, 1H), 8.2 (dd, 1H, J=2.4 Hz, J'=8.4 Hz), 8.09 (m, 3H), 7.42 (d, 2H, J=8.54 Hz), 5.23 (t, 1H), 4.54 (d, 2H, J=6 Hz); MS m/z 254 (M+1).

Preparation of 2-(4-Chloromethyl-phenyl)-5-trifluoromethyl-pyridine (compound 18B)

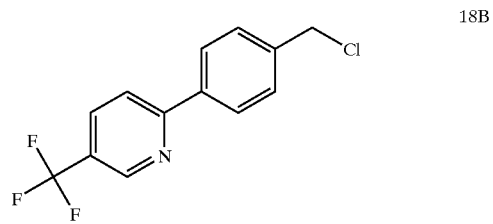

The title compound was prepared in the manner analogous to Example 3B using 18A. MS m/z 272 (M+1).

Preparation of {5-Methoxy-2-methyl-4-[4-(5-trifluoromethyl-pyridin-2-yl)-benzylsulfanyl]-phenoxy}-acetic acid methyl ester (compound 18C)

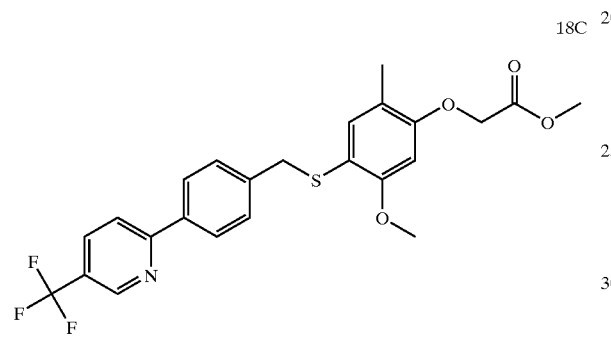

The title compound was prepared in the manner analogous to Example 1F using 1D and 18B. MS m/z 478 (M+1).

Preparation of {5-Methoxy-2-methyl-4-[4-(5-trifluoromethyl-pyridin-2-yl)-benzylsulfanyl]-phenoxy}-acetic acid (compound 18)

The title compound was prepared from the product of Example 18C in the manner analogous to Example 1. mp 225° C. (dec.); 400 MHz $^1$H NMR (DMSO-$d_6$) δ 8.97 (s, 1H), 8.2 (dd, 1H, J=2.4 Hz, J'=8.4 Hz), 8.13 (m, 1H), 8.01 (d, 2H, J=8.4 Hz), 7.34 (s, 2H, J=8.4 Hz), 6.95 (s, 1H), 6.42 (s, 1H), 4.23 (s, 2H), 4.01 (s, 2H), 3.69 (s, 3H), 1.96 (s, 3H) MS m/z 464 (M+1).

EXAMPLE 19

Synthesis of 45-Methoxy-2-methyl-4-[6-(4-trifluoromethyl-phenyl)-pyridin-3-ylmethylsulfanyl]-phenoxy}-acetic acid (compound 19)

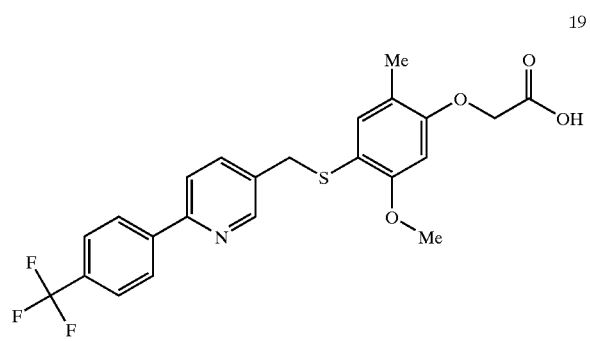

Step 1. Preparation of [4-(6-Chloro-pyridin-3-ylmethylsulfanyl)-5-methoxy-2-methyl-phenoxy]-acetic acid methyl ester (compound 19A)

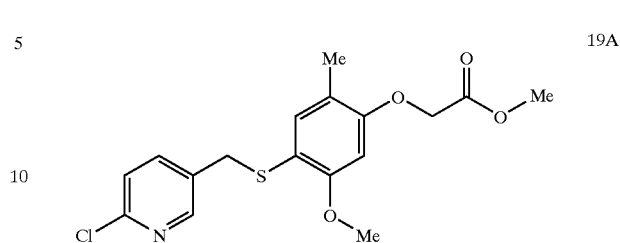

The title compound was prepared from 2-Chloro-5-chloromethyl-pyridine and 1D in a manner analogous to Example 1F. MS m/z 370 (M+2).

Step 2. Preparation of {5-Methoxy-2-methyl-4-[6-(4-trifluoromethyl-phenyl)-pyridin-3-ylmethylsulfanyl]-phenoxy}-acetic acid methyl ester (compound 19B)

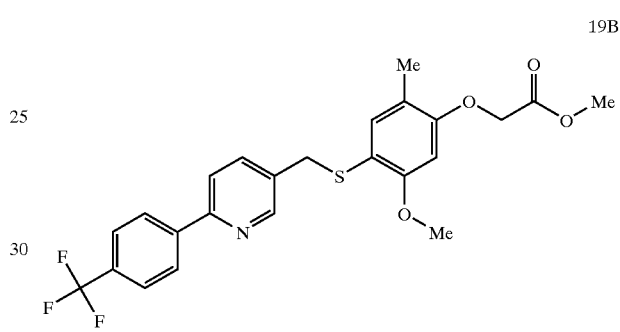

The title compound was prepared from the product of Example 19A and 1-bromo-4-trifluoromethyl-benzene in a manner analogous to Example 3A. MS m/z 478 (M+1).

Step 3. Preparation of {5-Methoxy-2-methyl-4-[6-(4-trifluoromethyl-phenyl)-pyridin-3-ylmethylsulfanyl]-phenoxy}-acetic acid (compound 19)

The title compound was prepared from the product of Example 19B in the manner analogous to Example 1. mp 203° C. (dec.); 400 MHz $^1$H NMR (DMSO-$d_6$) δ 8.34 (d, 1H, J=1.6 Hz), 8.21 (d, 2H, J=8 Hz), 7.92 (d, 1H, J=8.4 Hz), 7.77 (d, 2H, J=8.4 Hz), 7.65 (dd 1H, J'=2.4 Hz, J=8.4 Hz), 6.93 (s, 1H), 6.39 (s, 1H), 4.15 (s, 2H), 4.00 (s, 2H), 3.66 (s, 3H), 1.95 (s, 3H). MS m/z 464 (M+1).

EXAMPLE 20

Synthesis of [5-Chloro-2-methyl-4-(4'-trifluoromethyl-biphenyl-4-ylmethylsulfanyl)-phenoxy]-acetic acid (compound 20)

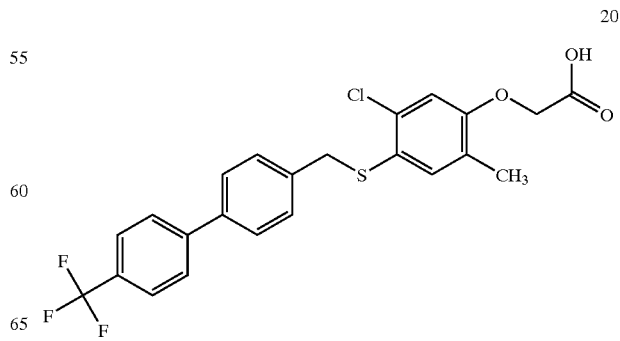

Step 1. Preparation of 5-Chloro-2-methyl-4-thiocyanato-phenol (compound 20A)

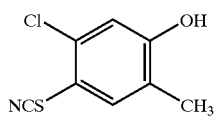

20A

The title compound was prepared in a manner analogous to Example 1B from 5-chloro-2-methyl-phenol. 400 MHz $^1$H NMR (DMSO-d$_6$) δ 10.60 (s, 1H), 7.54 (s, 1H), 6.98 (s, 1H), 2.07 (s, 3H).

Step 2. Preparation of (5-Chloro-2-methyl-4-thiocyanato-phenoxy)-acetic acid methyl ester(compound 20B)

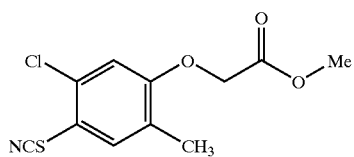

20B

The title compound was prepared from the product of Example 20A in a manner analogous to Example 1C. 400 MHz $^1$H NMR (DMSO-d$_6$) δ 7.62 (s, 1H), 7.40 (s, 1H), 4.94 (s, 2H), 3.65 (s, 3H), 2.15 (s, 3H).

Step 3. Preparation of (5-Chloro-4-mercapto-2-methyl-phenoxy)-acetic acid methyl ester (compound 20C)

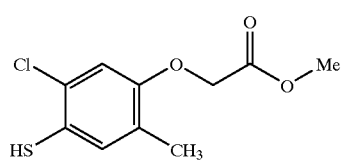

20C

The title compound was prepared from (5-chloro-2-methyl-4-thiocyanato-phenoxy)-acetic acid methyl ester in a manner analogous to Example 1D. 400 MHz $^1$H NMR (DMSO-d$_6$) δ 7.27 (s, 1H), 6.97 (s, 1H), 5.31 (s, 1H), 4.79 (s, 2H), 3.64 (s, 3H), 2.07 (s, 3H).

Step 4. Preparation of [5-Chloro-2-methyl-4-(4'-trifluoromethyl-biphenyl-4-ylmethylsulfanyl)phenoxy]-acetic acid methyl ester (compound 20D)

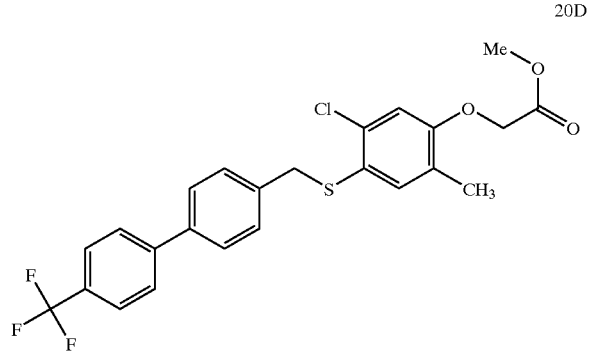

20D

The title compound was prepared in the manner analogous to Example 1F using 3B and 20C. 400 MHz $^1$H NMR (DMSO-d$_6$) δ 7.82 (d, 2H, J=8.3 Hz), 7.74 (d, 2H, J=8.3 Hz), 7.62 (d, 2H, J=8.3 Hz), 7.39 (d, 2H, J=8.3 Hz), 7.27 (s, 1H), 7.00 (s, 1H), 4.82 (s, 2H), 4.20 (s, 2H), 3.64 (s, 3H), 2.09 (s, 3H); MS m/z 480 (M+).

Step 5. Preparation of [5-Chloro-2-methyl-4-(4'-trifluoromethyl-biphenyl-4-ylmethylsulfanyl)-phenoxy]-acetic acid (compound 20)

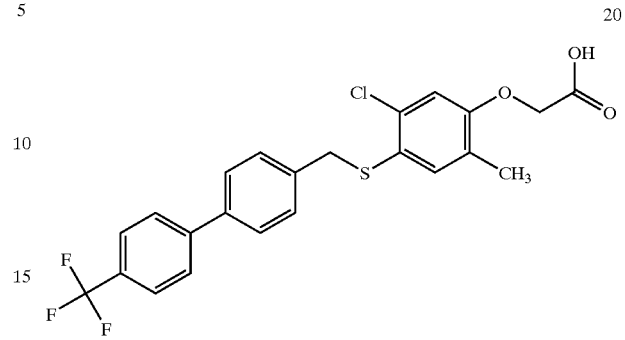

20

The title compound was prepared in the manner analogous to Example 1 using 20D. mp 161–162° C.; 400 MHz $^1$H NMR (DMSO-d$_6$) δ 7.83 (d, 2H, J=8.3 Hz), 7.74 (d, 2H, J=8.3 Hz), 7.62 (d, 2H, J=8.3 Hz), 7.51 (d, 2H, J=8.3 Hz), .7.26 (s, 1H), 6.95 (s, 1H), 4.69 (s, 2H), 4.20 (s, 2H), 2.08 (s, 3H); MS m/z 467 (M+1).

EXAMPLE 21

Synthesis of [3-Methoxy-4-(4'-trifluoromethyl-biphenyl-4-ylmethylsulfanyl)-phenoxy]-acetic acid (compound 21)

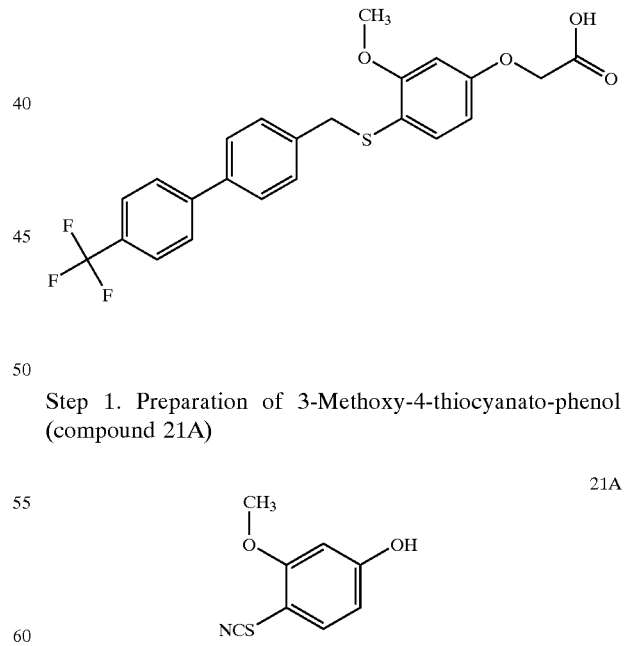

Step 1. Preparation of 3-Methoxy-4-thiocyanato-phenol (compound 21A)

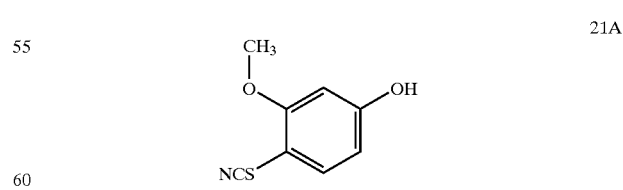

21A

The title compound was prepared in a manner analogous to Example 1B from 3-methoxy-phenol. 400 MHz $^1$H NMR (DMSO-d$_6$) δ 10.21 (s, 1H), 7.34 (d, 1H, J=8.3 Hz), 6.53 (s, 1H), 6.43 (d, 1H, J=8.3 Hz), 3.81 (s, 3H).

Step 2. Preparation of (3-Methoxy-4-thiocyanato-phenoxy)-acetic acid methyl ester (compound 21B)

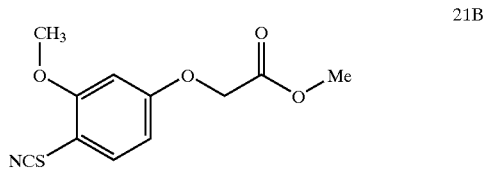

The title compound was prepared from the product of Example 21A in a manner analogous to Example 1C. MS m/z 227 (M-CN).

Step 4. Preparation of (4-Mercapto-3-methoxy-phenoxy)-acetic acid methyl ester (compound 21C)

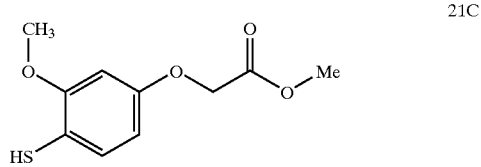

The title compound was prepared from (3-Methoxy-4-thiocyanato-phenoxy)-acetic acid methyl ester in a manner analogous to Example 1D. 400 MHz $^1$H NMR (DMSO-d$_6$) δ 7.13 (d, 1H, J=8.5 Hz), 6.56 (s, 1H), 6.39 (d, 1H, J=8.5 Hz), 4.72 (s, 2H), 4.51 (s, 1H), 3.75 (s, 3H), 3.64 (s, 3H).

Step 5. Preparation of [3-Methoxy-4-(4'-trifluoromethyl-biphenyl-4-ylmethylsulfanyl)-phenoxy]-acetic acid methyl ester (compound 21D)

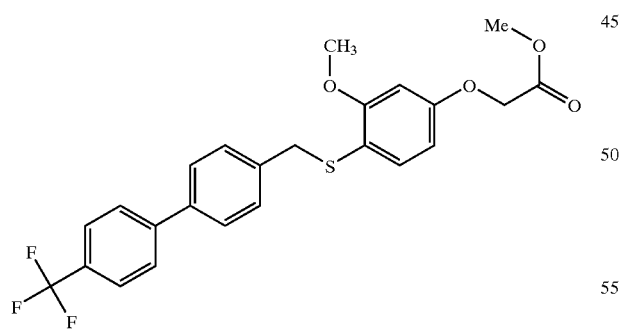

The title compound was prepared in the manner analogous to Example 1F using 3B and 21C. 400 MHz $^1$H NMR (DMSO-d$_6$) δ 7.81 (d, 2H, J=8.3 Hz), 7.53 (d, 2H, J=8.3 Hz), 7.59 (d, 2H, J=8.3 Hz), 7.32 (d, 2H, J=8.3 Hz), 7.11 (d, 1H, J=8.5 Hz), 6.56 (s, 1H), 6.37 (d, 1H, J=8.5 Hz), 4.73 (s, 2H), 4.04 (s, 2H), 3.76 (s, 3H), 3.63 (s, 3H); MS m/z 463 (M+1).

Step 6. Preparation of [3-Methoxy-4-(4'-trifluoromethyl-biphenyl-4-ylmethylsulfanyl)-phenoxy]-acetic acid (compound 21)

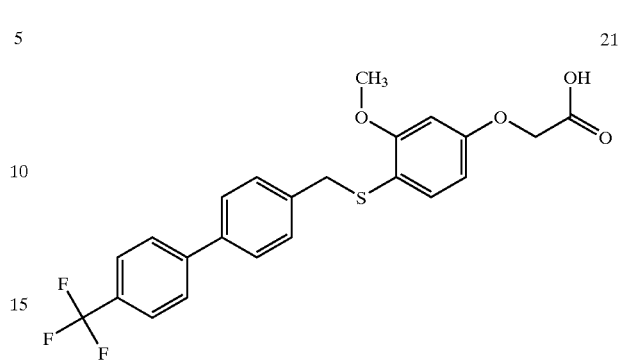

The title compound was prepared in the manner analogous to Example 1 using 21D. 400 MHz $^1$H NMR (DMSO-d$_6$) δ 7.83 (d, 2H, J=8.3 Hz), 7.76 (d, 2H, J=8.3 Hz), 7.61 (d, 2H, J=8.3 Hz), 7.34 (d, 2H, J=8.3 Hz), 7.13 (d, 1H, J=8.5 Hz), 6.56 (s, 1H), 6.39 (d, 1H, J=8.5 Hz), 4.63 (s, 2H), 4.06 (s, 2H), 3.77 (s, 3H); MS m/z 449 (M+1). Anal. Calc'd for $C_{23}H_{19}F_3O_4S$, C, 61.60; H, 4.27; found: C, 61.35; H, 4.25.

EXAMPLE 22

Synthesis of {2-Methyl-4-[2-(4'-trifluoromethyl-biphenyl-4-yl)-ethylsulfanyl]-phenoxy}-acetic acid (compound 22)

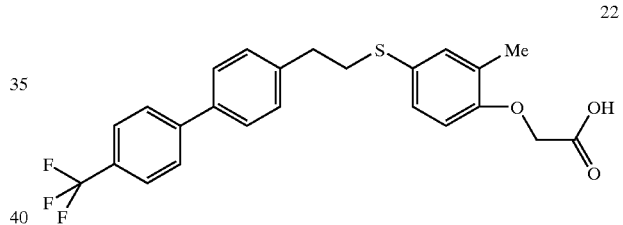

Step 1. Preparation of 2-(4'-Trifluoromethyl-biphenyl-4-yl)-ethanol (compound 22A)

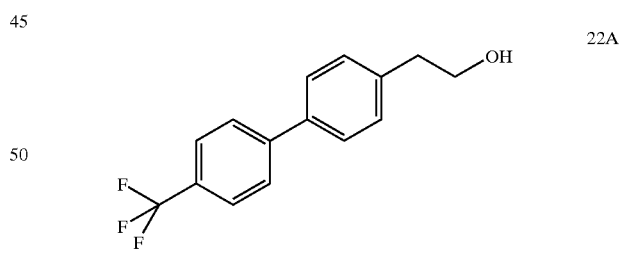

A mixture of 2-(4-bromo-phenyl)-ethanol (2.3 ml, 3.3 g, 16.4 mmol), 4-trifluoromethylphenylboronic acid (5.0 g, 26.3 mmol), 1.0 M aqueous sodium carbonate solution (44.0 ml), and tetrakis(triphenylphosphine)palladium (0.98 g, 0.85 mmol) in 180 ml of ethanol and 180 ml of toluene was heated at reflux for 4 h. The cooled reaction mixture was diluted with 500 ml of ethyl acetate and filtered through a bed of Celite filter-aid. The filtrate was washed with 5% aqueous sodium carbonate solution (2×750 ml) and brine (3×750 ml), then dried over anhydrous sodium sulfate and concentrated. The crude product was purified by normal phase chromatography. MS m/z 266 (M).

Step 2. Preparation of 4-(2-Bromo-ethyl)-4'-trifluoromethyl-biphenyl (compound 22B)

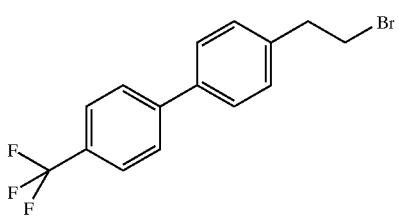

A solution of 2-(4'-trifluoromethyl-biphenyl-4-yl)-ethanol (2.8 g, 10.3 mmol) and carbon tetrabromide (3.8 g, 11.5 mmol) in 50 ml of dichloromethane was cooled in ice, and triphenylphosphine (2.9 g, 11.1 mmol) was added in portions over 10 minutes. The mixture was stirred at room temperature for 18 h, and the solvent was evaporated. The residue was stirred in 75 ml of ether, and the mixture was filtered. The insoluble material was washed on the funnel with fresh ether (3×75 ml). The combined ether filtrates were concentrated, and the crude product was purified by normal phase chromatography. MS m/z 328 (M−1).

Step 3. Preparation of {2-Methyl-4-[2-(4'-trifluoromethyl-biphenyl-4-yl)-ethylsulfanyl]-phenoxy}-acetic acid methyl ester (compound 22C)

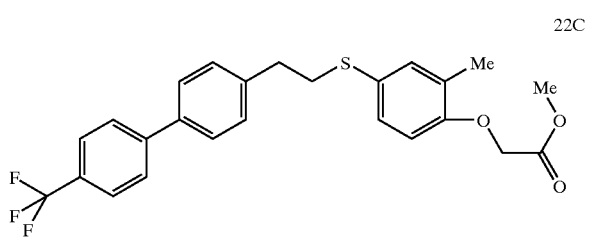

A solution 4-(2-bromo-ethyl)-4'-trifluoromethyl-biphenyl (0.66 g, 2.0 mmol) and (4-mercapto-2-methyl-phenoxy)-acetic acid methyl ester (0.42 g, 2.0 mmol) in 10 ml of acetonitrile was treated with cesium carbonate (1.3 g, 4.0 mmol), and the mixture was stirred at room temperature for 18 h. The reaction mixture was added to 200 ml of brine and extracted with ethyl acetate (4×75 ml). The combined extracts were washed with brine (2×200 ml), then dried over anhydrous sodium sulfate and concentrated. The crude product was purified by normal phase chromatography. MS m/z 461 (M+1).

Step 4. Preparation of {2-Methyl-4-[2-(4'-trifluoromethyl-biphenyl-4-yl)-ethylsulfanyl]-phenoxy}acetic acid (compound 22)

A solution of {2-methyl-4-[2-(4'-trifluoromethyl-biphenyl-4-yl)-ethylsulfanyl]-phenoxy}-acetic acid methyl ester (0.78 g, 1.7 mmol) in 10 ml of tetrahydrofuran and 2.0 ml of water was treated with lithium hydroxide monohydrate (0.21 g, 5.0 mmol), and the mixture was stirred at room temperature for 2 h. The reaction mixture was diluted with 5.0 ml of water and made strongly acidic by the addition of 4.0 N hydrochloric acid. The mixture was extracted with ethyl acetate (4×30 ml), and the combined extracts were washed with brine (2×50 ml), then dried over anhydrous sodium sulfate and concentrated. The crude product was recrystallized from ethyl acetate/hexane. mp 132–134° C.; IR (thin film) cm$^{-1}$: 1741, 1709, 1490, 1326, 1239, 1110; 400 MHz $^1$H NMR (DMSO-$d_6$) δ 7.82 (d, 2H, J=8.0 Hz), 7.74 (d, 2H, J=8.0 Hz), 7.61 (d, 2H, J=8.3 Hz), 7.31 (d, 2H, J=8.3 Hz), 7.15 (m, 2H), 6.75 (d, 1H, J=8.3 Hz), 4.64 (s, 2H), 3.11 (t, 2H, J=7.6 Hz), 2.82 (t, 2H, J=7.6 Hz), 2.12 (s, 3H); MS m/z 447 (M+1). Anal. Calc'd for $C_{24}H_{21}F_3O_3S$: C, 64.56; H, 4.74; found: C, 64.45; H, 4.58.

EXAMPLE 23

Synthesis of {5-Methoxy-2-methyl-4-[2-(4'-trifluoromethyl-biphenyl-4-yl)-ethylsulfanyl]-phenoxy}-acetic acid (compound 23)

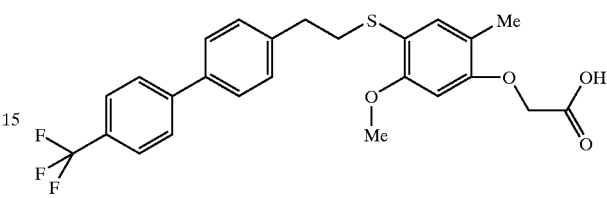

Step 1. Preparation of {5-Methoxy-2-methyl-4-[2-(4-trifluoromethyl-biphenyl-4-yl)-ethylsulfanyl]-phenoxy}-acetic acid methyl ester (compound 23A)

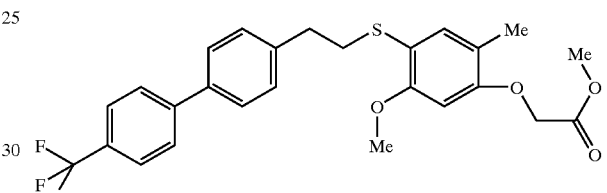

The title compound was prepared in the manner analogous to Example 22C using 4-(2-bromo-ethyl)-4'-trifluoromethyl-biphenyl and 1D. MS m/z 491 (M+1).

Step 2. Preparation of {5-Methoxy-2-methyl-4-[2-(4'-trifluoromethyl-biphenyl-4-yl)-ethylsulfanyl]-phenoxy}-acetic acid (compound 23)

The title compound was prepared in the manner analogous to Example 1 using {5-methoxy-2-methyl-4-[2-(4'-trifluoromethyl-biphenyl-4-yl)-ethylsulfanyl]-phenoxy}-acetic acid methyl ester. mp 169–171° C.; IR (thin film) cm$^{-1}$: 1718, 1500, 1330, 1162, 1109, 1052; 400 MHz $^1$H NMR (DMSO-$d_6$) δ 7.82 (d, 2H, J=8.3 Hz), 7.74 (d, 2H, J=8.6 Hz), 7.61 (d, 2H, J=8.3 Hz), 7.31 (d, 2H, J=8.3 Hz), 7.06 (s, 1H), 6.53 (s, 1H), 4.69 (s, 2H), 3.73 (s, 3H), 3.02 (t, 2H, J=7.5 Hz), 2.78 (t, 2H, J=7.5 Hz), 2.06 (s, 3H); MS m/z 477 (M+1). Anal. Calc'd for $C_{25}H_{23}F_3O_4S$: C, 63.02; H, 4.87; found: C, 62.77; H, 4.62.

EXAMPLE 24

Synthesis of {2-Methyl-4-[2-(4'-trifluoromethyl-biphenyl-4-yl)-vinyl]-phenoxy}-acetic acid (compound 24)

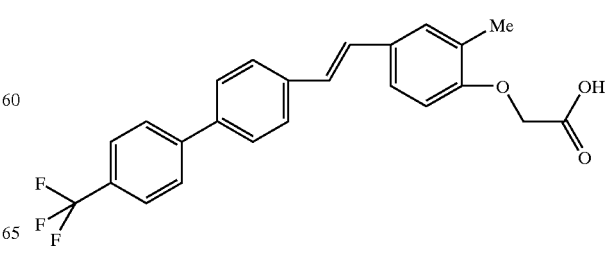

Step 1. Preparation of (4-Bromo-2-methyl-phenoxy)-acetic acid methyl ester (compound 24A)

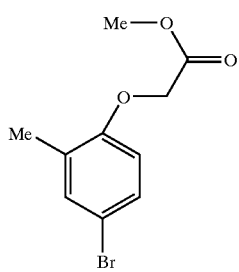

A solution of o-tolyloxy-acetic acid methyl ester (Belleney J., et al., *J. Heterocyclic Chem.*, 1984; 21:1431; 3.7 g, 20.5 mmol) in 70 ml of acetonitrile was treated in portions over 10 minutes with N-bromosuccinimide (3.8 g, 21.3 mmol). The mixture was stirred at room temperature for 18 h, and the solvent was evaporated. The residue was stirred in 75 ml of carbon tetrachloride, and the mixture was filtered. The insoluble material was washed on the funnel with fresh carbon tetrachloride (2×50 ml). The combined filtrates were concentrated, and the crude product was purified by normal phase chromatography. MS m/z 258 (M−1).

Step 2. Preparation of 4-Trifluoromethyl-4'-vinyl-biphenyl (compound 24B)

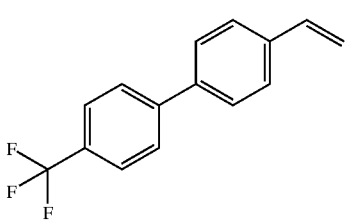

The title compound was prepared in the manner analogous to Example 3A using 1-bromo-4-vinyl-benzene and 4-trifluoromethylphenylboronic acid. MS m/z 248 (M).

Step 3. Preparation of {2-Methyl-4-[2-(4'-trifluoromethyl-biphenyl-4-yl)-vinyl]-phenoxy}-acetic acid methyl ester and {2-methyl-4-[2-(4'-trifluoromethyl-biphenyl-4-yl)-vinyl]-phenoxy}-acetic acid (compound 24)

A mixture of 4-trifluoromethyl-4'-vinyl-biphenyl (1.9 g, 7.7 mmol), (4-Bromo-2-methyl-phenoxy)-acetic acid methyl ester (2.0 g, 7.7 mmol), anhydrous sodium acetate (1.2 g, 14.6 mmol), N,N-dimethylglycine (0.23 g, 2.2 mmol), and palladium acetate (0.025 g, 0.11 mmol) in 10 ml of 1-methyl-pyrrolidin-2-one was heated at 130° C. for 10 h. The reaction mixture was partitioned between 250 ml of brine and 300 ml of ethyl acetate. The total mixture was filtered through a bed of Celite filter-aid. The organic layer was washed with 5% aqueous sodium carbonate solution (3×250 ml) and brine (2×250 ml), then dried over anhydrous sodium sulfate and concentrated. The residue was purified by normal phase chromatography to give {2-methyl-4-[2-(4'-trifluoromethyl-biphenyl-4-yl)-vinyl]-phenoxy}-acetic acid methyl ester; MS m/z 427 (M+1).

During the above sodium carbonate washings, a precipitate formed and was removed by filtration. The solid was stirred for 18 h in a solution of 150 ml of water, 50 ml of methanol, and 50 ml of 4.0 N hydrochloric acid. The acidified product was filtered and recrystallized from aqueous acetonitrile to give {2-methyl-4-[2-(4'-trifluoromethyl-biphenyl-4-yl)-vinyl]-phenoxy}-acetic acid. mp 243–245° C.; IR (thin film) cm$^{-1}$: 1746, 1717, 1502, 1323, 1125, 1069; 400 MHz $^1$H NMR (DMSO-d$_6$) δ 7.88 (d, 2H, J=8.0 Hz), 7.76 (d, 2H, J=8.3 Hz), 7.71 (d, 2H, J=8.5 Hz), 7.64 (d, 2H, J=8.5 Hz), 7.43 (d, 1H, J=1.7 Hz), 7.32 (dd, 1H, J=2.1, 8.5 Hz), 7.21 (d, 1H, J=16.5 Hz), 7.10 (d, 1H, J=16.4 Hz), 6.79 (d, 1H, J=8.5 Hz), 4.68 (s, 2H), 2.18 (s, 3H); MS m/z 413 (M+1). Anal. Calc'd for $C_{24}H_{19}F_3O_3$: C, 69.90; H, 4.64; found: C, 69.77; H, 4.57.

EXAMPLE 25

Synthesis of {2-Methyl-4-[2-(4'-trifluoromethyl-biphenyl-4-yl)-ethyl]-phenoxy}-acetic acid (compound 25)

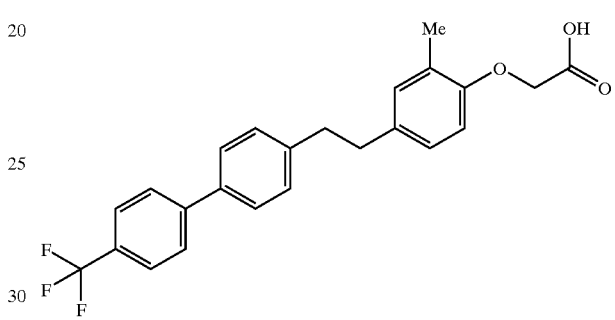

A solution of {2-methyl-4-[2-4'-trifluoromethyl-biphenyl-4-yl)-vinyl]-phenoxy}-acetic acid (0.98 g, 2.4 mmol) in 100 ml of tetrahydrofuran was hydrogenated over 0.16 g of 20% palladium on carbon catalyst. The catalyst was removed by filtration, and the filtrate was evaporated. The crude product was recrystallized from aqueous acetonitrile. mp 174–176° C.; IR (thin film) cm$^{-1}$: 1747, 1711, 1500, 1318, 1160, 1123; 400 MHz $^1$H NMR (DMSO-d$_6$) δ 7.83 (d, 2H, J=8.1 Hz), 7.74 (d, 2H, J=8.3 Hz), 7.60 (d, 2H, J=6.5 Hz), 7.32 (d, 2H, J=8.3 Hz), 7.01 (d, 1H, J=2.0 Hz), 6.94 (dd, 1H, J=2.0, 8.3 Hz), 6.66 (d, 1H, J=8.3 Hz), 4.59 (s, 2H), 2.83 (m, 2H), 2.76 (m, 2H), 2.11 (s, 3H); MS m/z 413 (M−1). Anal. Calc'd for $C_{24}H_{21}F_3O_3$: C, 69.56; H, 5.11; found: C, 69.28; H, 4.96.

EXAMPLE 26

Synthesis of {7-[4-(5-Trifluoromethyl-pyridin-2-yl)-benzylsulfanyl]-indan-4-yloxy}-acetic acid (compound 26)

Step 1. Preparation of {7-[4-(5-Trifluoromethyl-pyridin-2-yl)-benzylsulfanyl]-indan-4-yloxy}-acetic acid methyl ester (compound 26A)

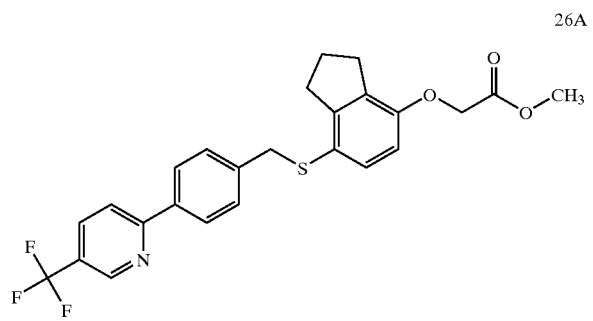

26A

The title compound was prepared in the manner analogous to Example 1F using 18B and 12C. MS m/z 474 (M+1).

Step 2. Preparation of {7-[4-(5-Trifluoromethyl-pyridin-2-yl)-benzylsulfanyl]-indan-4-yloxy}-acetic acid (compound 26)

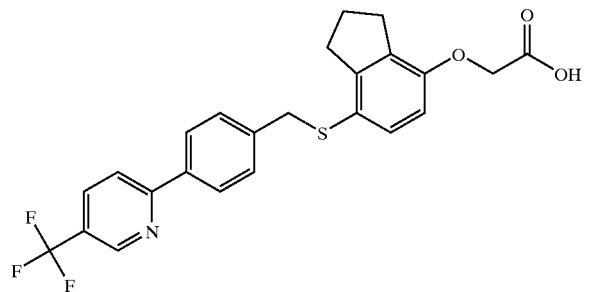

26

The title compound was prepared from the product of Example 26A in the manner analogous to Example 1. mp 220° C. (dec.); 400 MHz $^1$H NMR (DMSO-$d_6$) δ 12.94 (s, 1H), 8.97 (s, 1H), 8.2 (dd, 1H, J=2 Hz, J'=8.8 Hz), 8.13 (d, 1H, J=8.4 Hz), 8.01 (d, 2H, J=8.4 Hz), 7.34 (d, 2H, J=8.8 Hz), 7.07 (d, 1H, J=8.4 Hz), 6.57 (d, 1H, J=8 Hz), 4.61 (s, 2), 4.07 (s, 2H), 2.72 (m, 4H), 1.89 (m, 2H). MS m/z 460 (M+1).

EXAMPLE 27

Synthesis of {5-Methyl-7-[4-(5-trifluoromethyl-pyridin-2-yl)-benzylsulfanyl]-indan-4-yloxy}-acetic acid (compound 27)

Step 1. Preparation of {5-Methyl-7-[4-(5-trifluoromethyl-pyridin-2-yl)-benzylsulfanyl]-indan-4-yloxy}-acetic acid methyl ester (compound 27A)

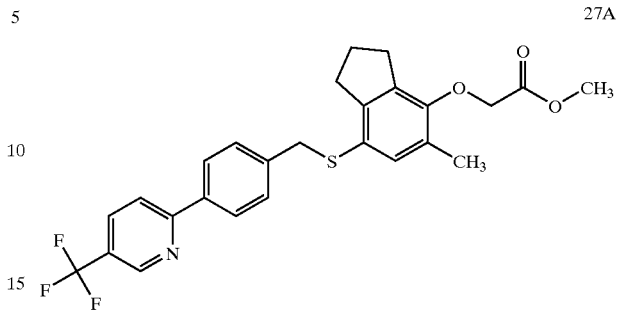

27A

The title compound was prepared from the products of Example 18B and (7-mercapto-5-methyl-indan-4-yloxy)-acetic acid methyl ester (prepared in a similar manner as described for Example 12C) in a manner analogous to Example 1F. MS m/z 488 (M+1).

Step 2. Preparation of {5-Methyl-7-[4-(5-trifluoromethyl-pyridin-2-yl)-benzylsulfanyl]-indan-4yloxy}-acetic acid (compound 27)

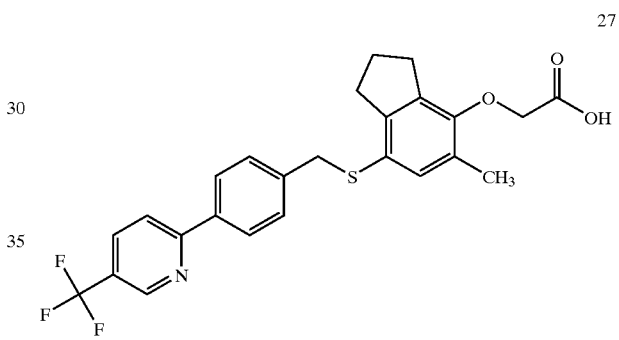

27

The title compound was prepared from the product of Example 27A in the manner analogous to Example 1. mp 186° C. ; 400 MHz $^1$H NMR (DMSO-$d_6$) δ 12.94 (s, 1H), 8.97 (s, 1H), 8.24 (dd, 1H, J=2 Hz, J'=8.8 Hz), 8.14 (d, 1H, J=8.4 Hz), 8.01 (d, 2H, J=8.4 Hz), 7.34 (d, 2H, J=8.8 Hz), 6.99 (s, 1H), 4.41 (s, 2H), 4.13 (s, 2H), 2.83 (t, 2H, J=7.2 Hz), 2.62 (t, 2H, J=7.2 Hz), 2.13 (s, 3H), 1.87 (m, 2H). MS m/z 474 (M+1).

EXAMPLE 28

Synthesis of [5-Methyl-7-(4'-trifluoromethyl-biphenyl-4-ylmethylsulfanyl)-indan-4-yloxy]-acetic acid (compound 28)

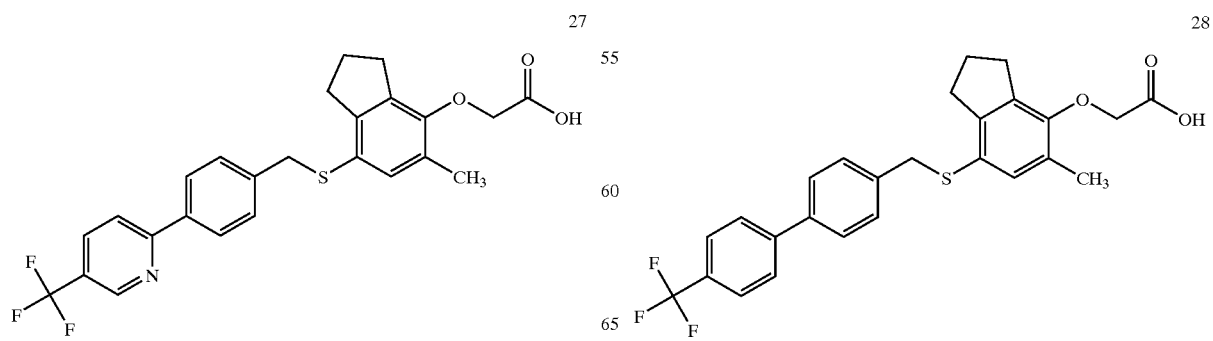

Step 1. Preparation of [5-Methyl-7-(4'-trifluoromethyl-biphenyl-4-ylmethylsulfanyl)-indan-4-yloxy]-acetic acid methyl ester (compound 28A)

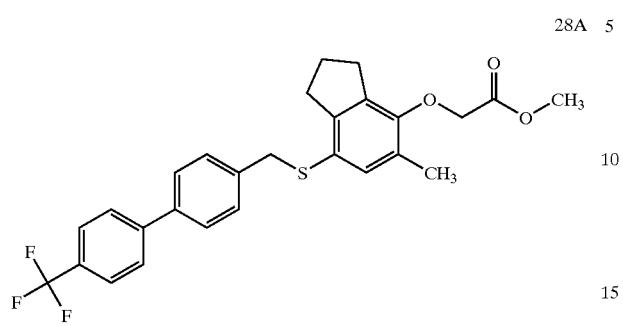

The title compound was prepared from the product of Example 3B and (7-Mercapto-5-methyl-indan-4-yloxy)-acetic acid methyl ester in a manner analogous to Example 1F. MS m/z 487 (M+1).

Step 2. Preparation of [5-Methyl-7-(4'-trifluoromethyl-biphenyl-4-ylmethylsulfanyl)-indan-4-yloxy]-acetic acid (compound 28)

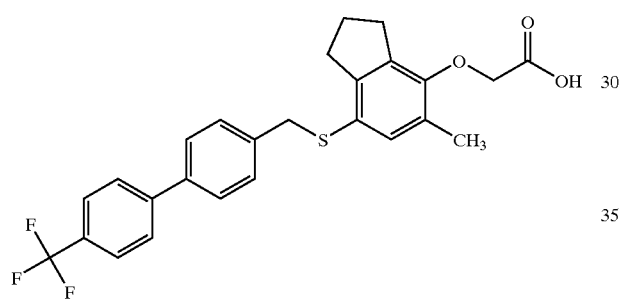

The title compound was prepared from the product of Example 28A in the manner analogous to Example 1. mp 177° C.; 400 MHz $^1$H NMR (DMSO-d$_6$) δ 12.82 (s, 1H), 7.82(d, 2H, J=8 Hz),7.75 (d, J=8 Hz), 7.61 (d, 2H, J=8 Hz), 7.35 (d, 2H, J=8 Hz), 6.99 (s, 1H), 4.41 (s, 2H), 4.12 (s, 2H), 2.83 (t, 2H, J=7.2 Hz), 2.62 (t, 2H, J=7.2 Hz), 2.13 (s, 3H), 1.89 (m, 2H). MS m/z 473 (M+1).

EXAMPLE 29

Synthesis of (4-{4-[2-(3-Fluoro-phenyl)-vinyl]-benzylsulfanyl}-5-methoxy-2-methyl-phenoxy)-acetic acid (compound 29)

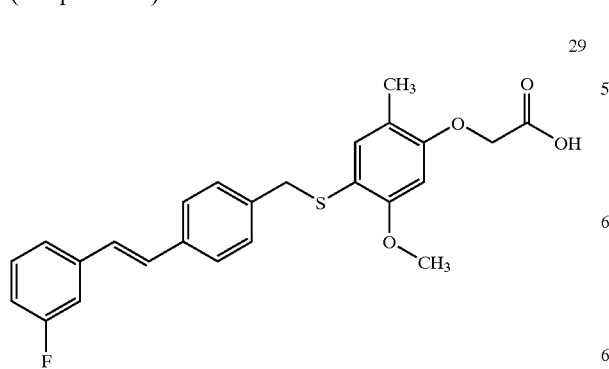

Step 1. Preparation of {4-[2-(3-Fluoro-phenyl)-vinyl]-phenyl}-methanol (compound 29A)

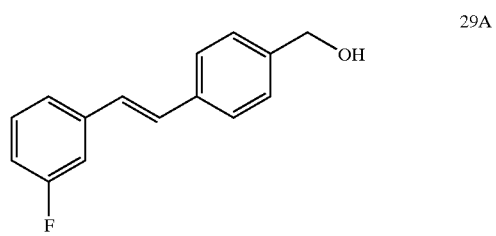

(4-Bromo-phenyl)-methanol (1 g, 5.35 mmol), 3-fluorostyrene (718 mg, 5.89 mmol), palladium acetate (60 mg, 0.3 mmol), and triphenylphosphine (140 mg, 0.6 mmol) were heated in triethylamine at 90° C. in a sealed tube for 18 h. The reaction was concentrated and purified by normal phase chromatography to afford the title compound. MS m/z 227 (M−1).

Step 2. Preparation of {4-[2-(3-Fluoro-phenyl)-vinyl]-phenyl}-chloromethane (compound 29B)

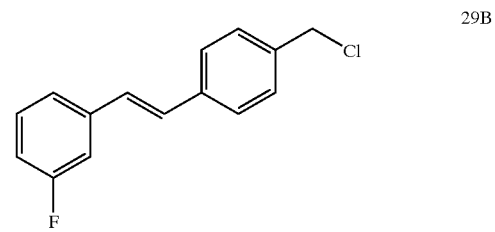

The title compound was prepared from the product of Example 29A in a manner analogous to Example 3B. MS m/z 245 (M−1).

Step 3. Preparation of (4-{4-[2-(3-Fluoro-phenyl)-vinyl]-benzylsulfanyl}-5-methoxy-2-methyl-phenoxy)-acetic acid methyl ester (compound 29C)

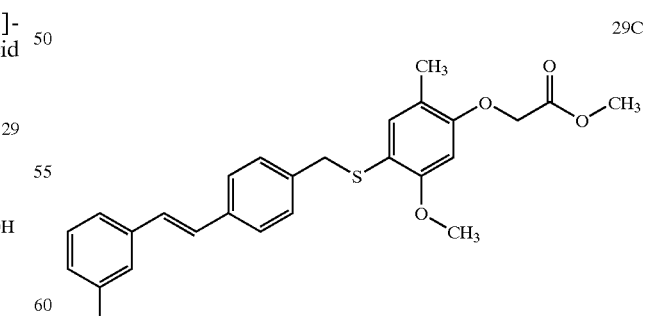

The title compound was prepared from the product of Example 29B and the product of Example 1D in a manner analogous to Example 1F. MS m/z 453 (M+1).

Step 4. Preparation of (4-{4-[2-(3-Fluoro-phenyl)-vinyl]-benzylsulfanyl}-5-methoxy-2-methyl-phenoxy)-acetic acid (compound 29)

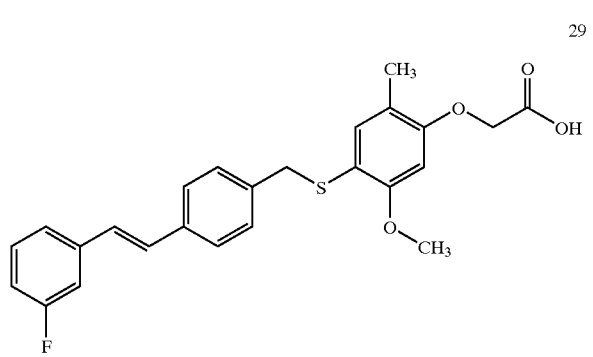

The title compound was prepared from the product of Example 29C in the manner analogous to Example 1. mp 154° C. (dec.); 400 MHz $^1$H NMR (DMSO-d$_6$) δ 12.94 (s, 1H), 7.46–7.34 (m, 5H), 7.27–7.15 (m, 4H), 7.06–6.99 (m, 2H), 6.52 (s, 1H), 4.69 (s, 2H), 3.98 (s, 2H), 3.73 (s, 3H), 2.00 (s, 3H), MS m/z 439 (M+1).

EXAMPLE 30

Synthesis of {2-Methyl-4-[4-(5-trifluoromethyl-pyridin-2-yl)-benzylsulfanyl]-phenoxy}-acetic acid (compound 30)

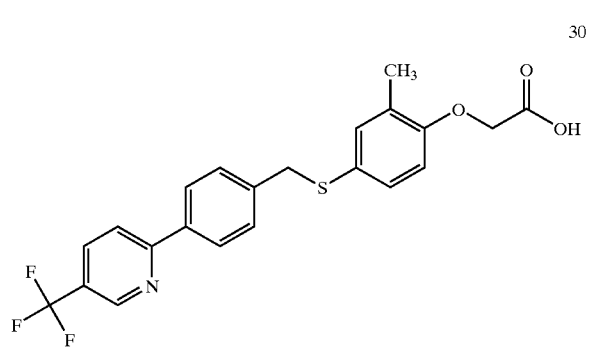

Step 1. Preparation of {2-Methyl-4-[4-(5-trifluoromethyl-pyridin-2-yl)-benzylsulfanyl]-phenoxy}-acetic acid methyl ester (compound 30A)

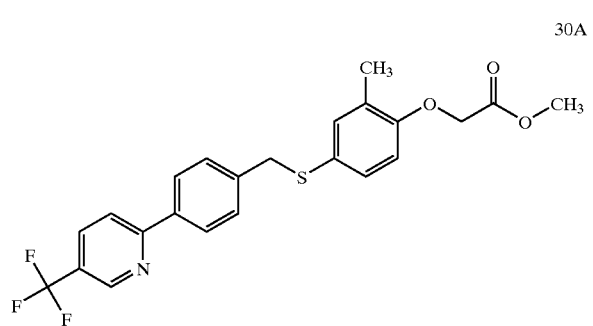

The title compound was prepared from the product of Example 2C and the product of Example 18B in a manner analogous to Example 1F. MS m/z 448 (M+1).

Preparation of {2-Methyl-4-[4-(5-trifluoromethyl-pyridin-2-y)-benzylsulfanyl]-phenoxy}-acetic acid

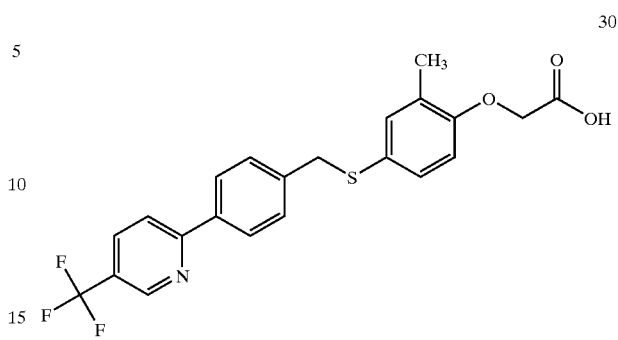

The title compound was prepared from the product of Example 30A in the manner analogous to Example 1. 400 MHz $^1$H NMR (DMSO-d$_6$) δ 8.97 (s, 1H), 8.2 (dd, 1H, J=2 Hz, J'=8.8 Hz), 8.13 (d, 1H, J=8.4 Hz), 8.01 (d, 2H, J=8.4 Hz), 7.36 (d, 2H, J=8.4 Hz), 7.07 (s, 1H), 7.01 (dd, 1H, J=8.4 Hz, J'=2.4 Hz), 6.57 (d, 1H, J=8.8 Hz), 4.09 (s, 2H), 4.06 (s, 2H), 2.04 (s, 3H). MS m/z 434 (M+1).

EXAMPLE 31

Synthesis of {4-[4-(2,4-Difluoro-benzyloxy)-benzylsulfanyl]-2-methyl-phenoxy}-acetic acid (compound 31)

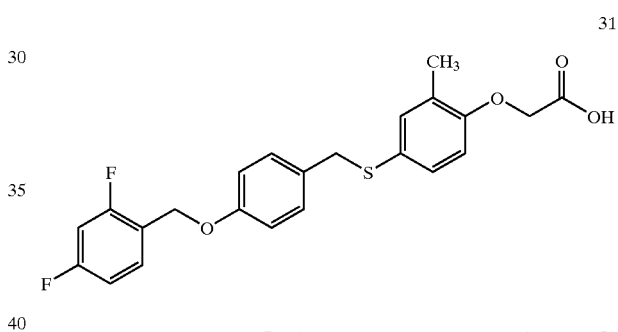

Step 1. Preparation of [4-(2,4-Difluoro-benzyloxy)phenyl]-methanol (compound 31A)

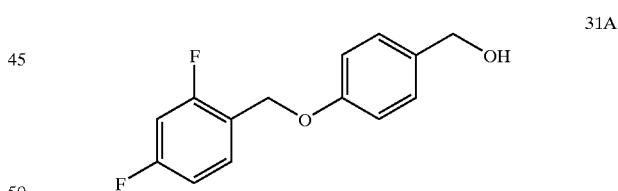

The title compound was prepared in the manner analogous to Example 14A using 1-bromomethyl-2,4-difluoro-benzene and 4-hydroxymethyl-phenol. MS m/z 233 (M-OH).

Step 2. Preparation of 1-(4-Chloromethyl-phenoxymethyl)-2,4-difluoro-benzene (compound 31B)

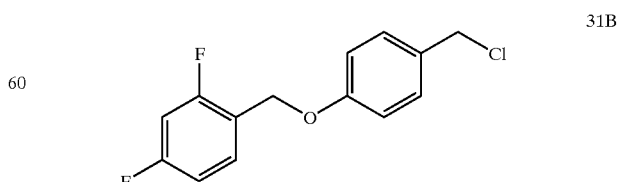

The title compound was prepared in the manner analogous to Example 3B using 31A. MS m/z 233 (M-Cl).

Step 3. Preparation of {4-[4-(2,4-Difluoro-benzyloxy)-benzylsulfanyl]-2-methyl-phenoxy}-acetic acid methyl ester (compound 31C)

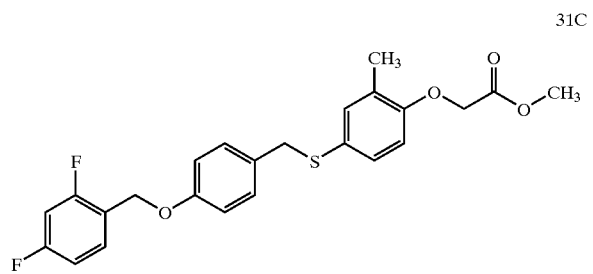

The title compound was prepared in the manner analogous to Example 1F using 31B and 2C. MS m/z 445 (M+1).

Step 4. Preparation of {4-[4-(2,4-Difluoro-benzyloxy)-benzylsulfanyl]-2-methyl-phenoxy}-acetic acid

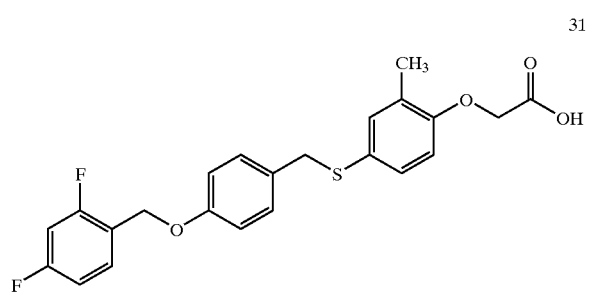

To a solution of the product from Example 31C (1.5 g, 3.3 mmol) in a mixture of 20 mL of tetrahydrofuran and 4 mL of water was added lithium hydroxide monohydrate (0.42 g, 9.9 mmol). The reaction mixture was stirred at room temperature for 18 hrs and then evaporated to afford a residue, which was suspended in 50 mL of water. The mixture was acidified with 1N hydrochloric acid to pH 2. The precipitated solid was collected be filtration, washed with water, and then dried to provide the title compound without any further purification. mp 139–141° C.; IR (KBr) cm$^{-1}$: 3081, 2917, 1735, 1604, 1508, 1233; 400 MHz $^1$H NMR (DMSO-d$_6$): δ 7.51–7.59 (m, 1H), 7.02–7.31 (m, 6H), 6.85–6.92 (m, 2H), 6.68 (d, 1H, J=8.6 Hz), 5.01 (s, 2H), 4.60 (s, 2H), 4.00 (s, 2H), 2.08 (s, 3H); MS m/z 429 (M−1). Anal. Calc'd for C$_{23}$H$_{20}$F$_2$O$_4$S: C, 64.17; H, 4.68; found: C, 64.11; H, 4.59.

EXAMPLE 32

Synthesis of {4-[4-(2,4-Dichloro-benzyloxy)-benzylsulfanyl]-2-methyl-phenoxy}-acetic acid (compound 32)

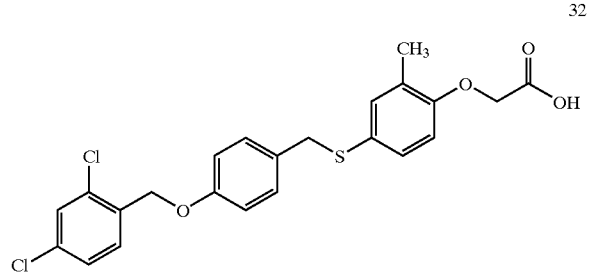

Step 1. Preparation of [4-(2,4-Dichloro-benzyloxy)-phenyl]-methanol (compound 32A)

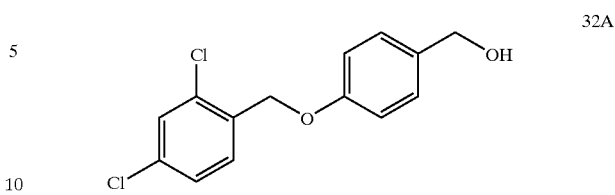

The title compound was prepared in the manner analogous to Example 14A using 2,4-dichloro-1-chloromethyl-benzene and 4-hydroxymethyl-phenol. MS m/z 265 (M-OH).

Step 2. Preparation of 2,4-Dichloro-1-(4-chloromethyl-phenoxymethyl)-benzene (compound 32B)

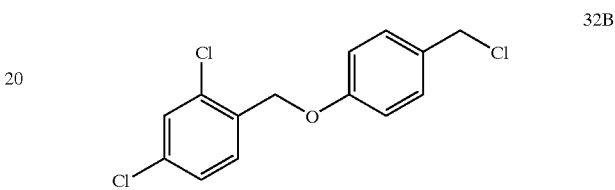

The title compound was prepared in the manner analogous to Example 3B using 32A. MS m/z 265 (M-Cl).

Step 3. Preparation of {4-[4-(2,4-Dichloro-benzyloxy)-benzylsulfanyl]-2-methyl-phenoxy}-acetic acid methyl ester (compound 32C)

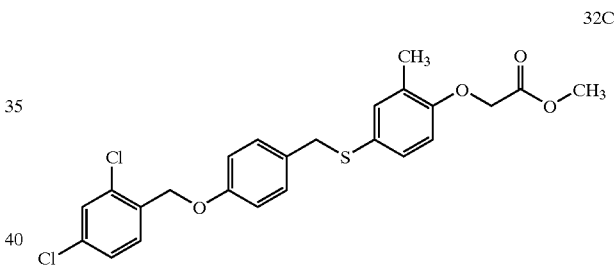

The title compound was prepared in the manner analogous to Example 1F using 32B and 2C. MS m/z 477 (M+1).

Step 4. Preparation of {4-[4-(2,4-Dichloro-benzyloxy)-benzylsulfanyl]-2-methyl-phenoxy}-acetic acid (compound 32)

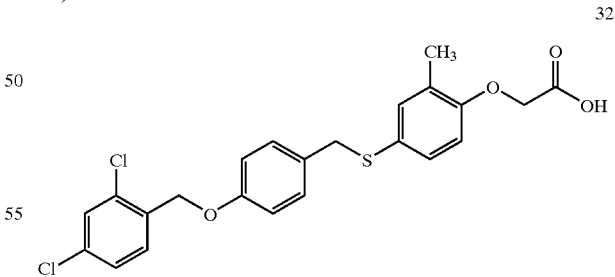

The title compound was prepared in the manner analogous to Example 1 using 32C. mp 143–145° C.; IR (KBr) cm$^{-1}$: 3062, 2936, 1724, 1492, 1227, 1192; 400 MHz $^1$H NMR (DMSO-d$_6$): δ 12.97 (br(s), 1H), 7.64 (d, 1H, J=2.0 Hz), 7.54 (d, 1H, J=8.3 Hz), 7.42 (dd, 1H, J=8.3, 2.0 Hz), 7.01–7.20 (m, 4H), 6.84–6.92 (m, 2H), 6.69 (d, 1H, J=8.5 Hz), 5.05 (s, 2H), 4.62 (s, 2H), 4.01 (s, 2H), 2.08 (s, 3H); MS m/z 461 (M−1). Anal. Calc'd for C$_{23}$H$_{20}$Cl$_2$O$_4$S: C, 59.62; H, 4.35; found: C, 59.33; H, 4.28.

EXAMPLE 33

Synthesis of {4-[4-(4-Methoxy-benzyloxy)-benzylsulfanyl]-2-methyl-phenoxy}-acetic acid (compound 33)

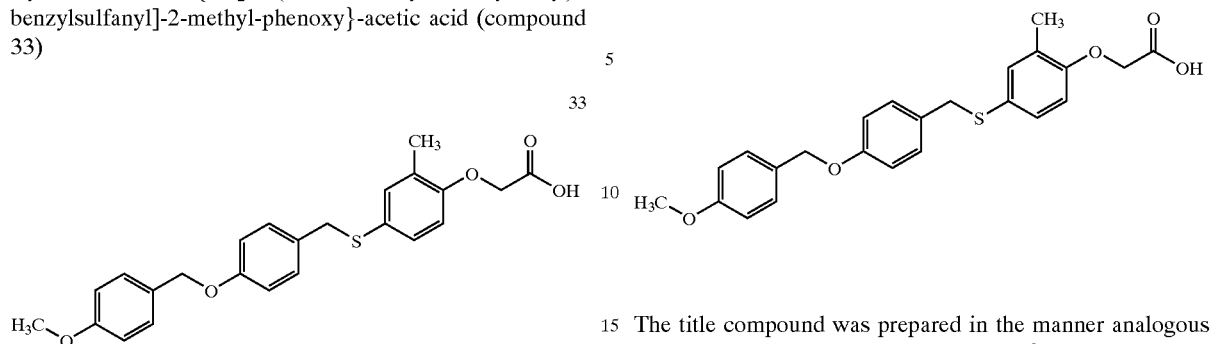

Step 1. Preparation of [4-(4-Methoxy-benzyloxy)-phenyl]-methanol (compound 33A)

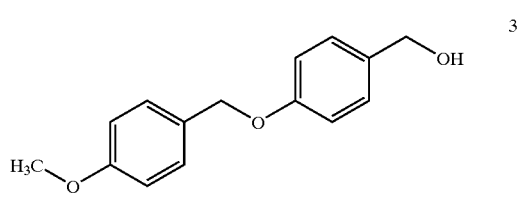

The title compound was prepared in the manner analogous to Example 14A using 1-chloromethyl-4-methoxy-benzene and 4-hydroxymethyl-phenol. MS m/z 227 (M-OH).

Step 2. Preparation of 4-Methoxy-1-(4-chloromethyl-phenoxymethyl)-benzene (compound 33B)

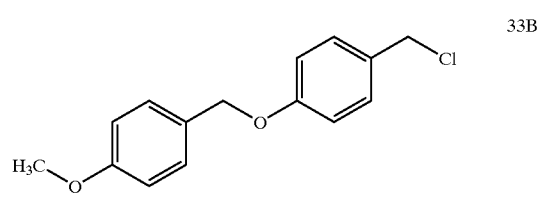

The title compound was prepared in the manner analogous to Example 3B using 33A. MS m/z 227 (M-Cl).

Step 3. Preparation of {4-[4-(4Methoxy-benzyloxy)-benzylsulfanyl]-2-methyl-phenoxy}-acetic acid methyl ester (compound 33C)

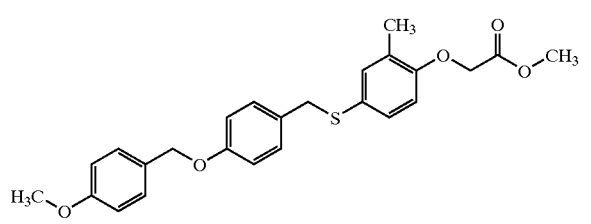

The title compound was prepared in the manner analogous to Example 1F using 33B and 2C. MS m/z 439 (M+1).

Step 4. Preparation of {4-[4(4-Methoxy-benzyloxy)-benzylsulfanyl]-2-methyl-phenoxy}-acetic acid (compound 33)

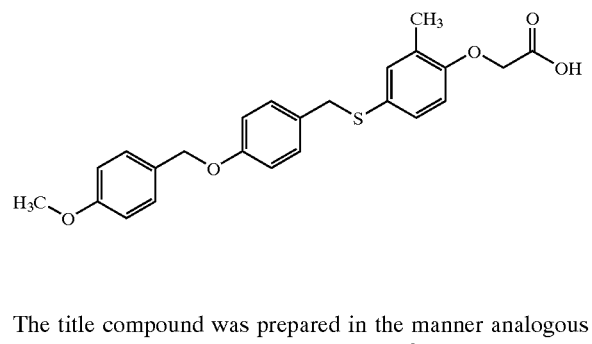

The title compound was prepared in the manner analogous to Example 1 using 33C. mp 150–152° C.; HPLC: area %=96.69, r.t.=2.93 min., γ=214 nm, mobile phase= acetonitrile/water with 0.10% TFA; IR (KBr) cm$^{-1}$: 2929, 1728, 1707, 1513, 1491, 1225; 400 MHz $^1$H NMR (DMSO-$d_6$): δ 12.98 (br(s), 1H), 7.27–7.34 (m, 2H), 7.02–7.16 (m, 4H), 6.81–6.91 (m, 4H), 6.69 (d, 1H, J=8.6 Hz), 4.91 (s, 2H), 4.61 (s, 2H), 3.99 (s, 2H), 3.69 (s, 3H), 2.08 (s, 3H); MS m/z 423 (M−1). Anal. Calc'd for $C_{24}H_{24}O_5S$: C, 67.90; H, 5.70; found: C, 67.48; H, 5.59.

EXAMPLE 34

Synthesis of {4-[4-(4-tert-Butyl-benzyloxy)-benzylsulfanyl]-2-methyl-phenoxy}-acetic acid (compound 34)

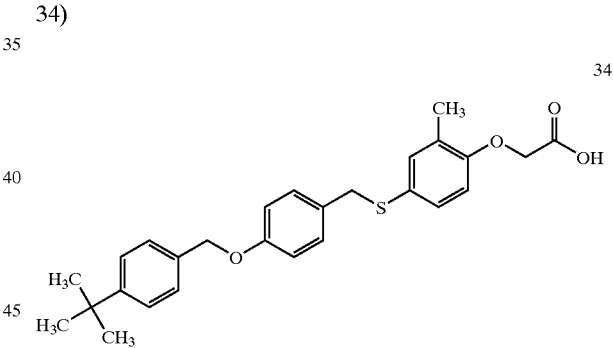

Step 1. Preparation of [4-(4-tert-Butyl-benzyloxy)-phenyl]-methanol (compound 34A)

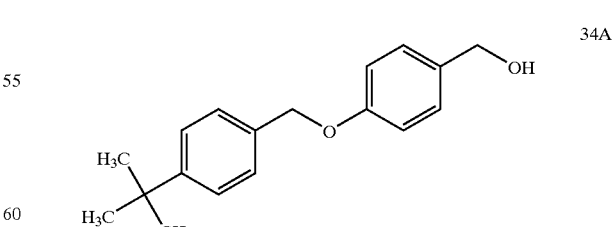

The title compound was prepared in the manner analogous to Example 14A using 1-bromomethyl-4-tert-butyl-benzene and 4-hydroxymethyl-phenol. MS m/z 253 (M-OH).

Step 2. Preparation of 4-tert-Butyl-1-(4-chloromethyl-phenoxymethyl)-benzene (compound 34B)

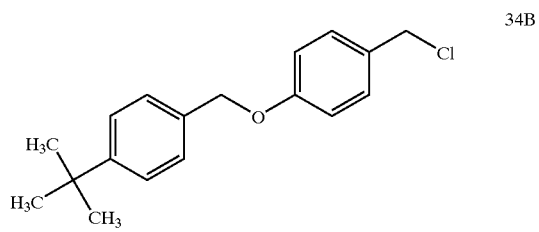

34B

The title compound was prepared in the manner analogous to Example 3B using 34A. MS m/z 253 (M−Cl).

Step 3. Preparation of {4-[4-(4-tert-Butyl-benzyloxy)-benzylsulfanyl]-2-methyl-phenoxy}-acetic acid methyl ester (compound 34C)

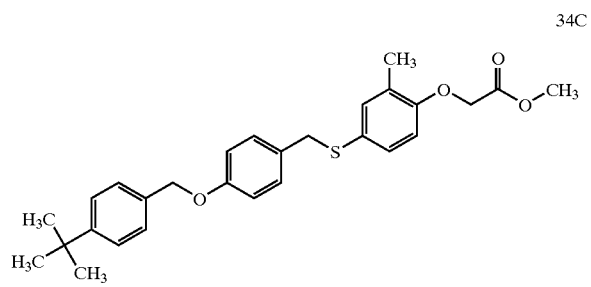

34C

The title compound was prepared in the manner analogous to Example 1F using 34B and 2C. MS m/z 465 (M+1).

Step 4. Preparation of {4-[4-(4-tert-Butyl-benzyloxy)-benzylsulfanyl]-2-methyl-phenoxy}-acetic acid (compound 34)

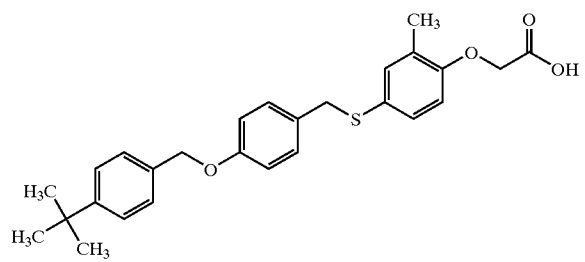

34

The title compound was prepared in the manner analogous to Example 1 using 34C. mp 135–137° C.; IR (KBr) cm$^{-1}$: 2961, 2908, 1751, 1495, 1233, 1194; 400 MHz $^1$H NMR (DMSO-d$_6$): δ 13.00 (br(s), 1H), 7.27–7.38 (m, 4H), 7.02–7.17 (m, 4H), 6.82–6.88 (m, 2H), 6.69 (d, 1H, J=8.5 Hz), 4.96 (s, 2H), 4.61 (s, 2H), 3.99 (s, 2H), 2.08 (s, 3H), 1.22 (s, 9H); MS m/z 451 (M+1). Anal. Calc'd for C$_{27}$H$_{30}$O$_4$S: C, 71.97; H, 6.71; found: C, 71.66; H, 6.52.

EXAMPLE 35

Synthesis of {2-Methyl-4-[4-(4-trifluoromethoxy-benzyloxy)-benzylsulfanyl]-phenoxy}-acetic acid (compound 35)

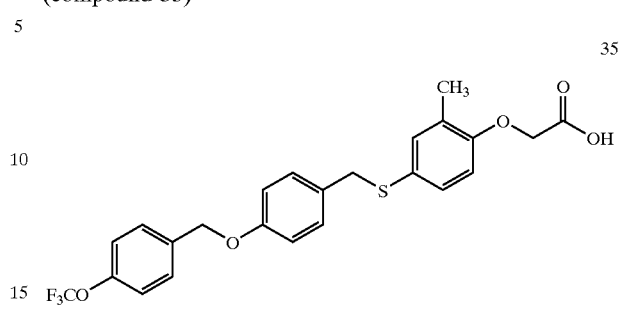

35

Step 1. Preparation of [4-(4-Acetoxy-benzylsulfanyl)-2-methyl-phenoxy]-acetic acid methyl ester (compound 35A)

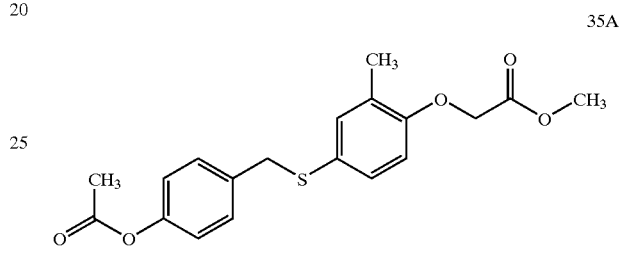

35A

The title compound was prepared in the manner analogous to Example 1F using acetic acid 4-chloromethyl-phenyl ester and 2C. MS m/z 361 (M+1).

Step 2. Preparation of [4-(4Hydroxy-benzylsulfanyl)-2-methyl-phenoxy]-acetic acid (compound 35B)

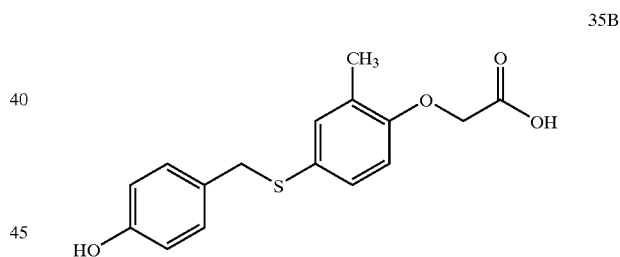

35B

The title compound was prepared in the manner analogous to Example 1 using 35A. MS m/z 303 (M−1).

Step 3. Preparation of [4-(4-Hydroxy-benzylsulfanyl)-2-methyl-phenoxy]-acetic acid methyl ester (compound 35C)

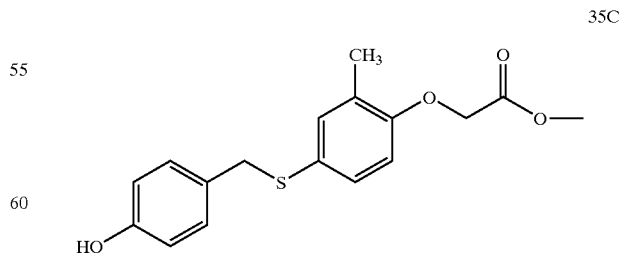

35C

To a solution of the product from Example 35B (0.43 g, 1.4 mmol) in 14 mL of 2,2-dimethoxy propane was added 1.4 mL of concentrated hydrochloric acid. The reaction mixture was stirred at room temperature for 18 hours. The mixture was concentrated and purified by flash chromatography to provide the title compound. MS m/z 317 (M−1).

Step 4. Preparation of {2-Methyl-4-[4(4-trifluoromethoxy-benzyloxy)-benzylsulfanyl]-phenoxy}-acetic acid methyl ester (compound 35D)

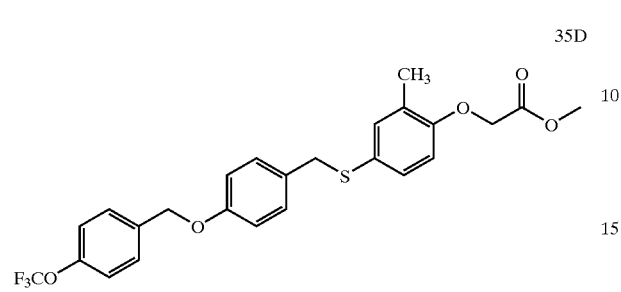

35D

The title compound was prepared in the manner analogous to Example 1F using 1-bromomethyl-4-trifluoromethoxy-benzene and 35C. MS m/z 493 (M+1).

Step 5. Preparation of {2-Methyl-4-[4-(4-trifluoromethoxy-benzyloxy)-benzylsulfanyl]-phenoxy}-acetic acid (compound 35)

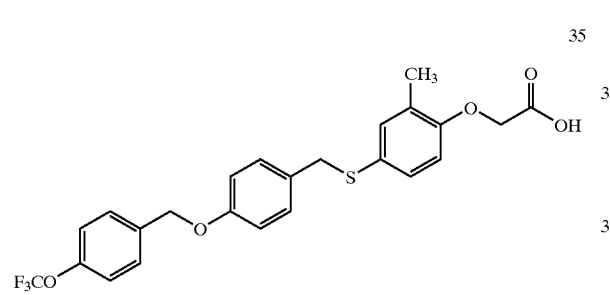

35

The title compound was prepared in the manner analogous to Example 1 using 35D. mp 141–142° C.; 400 MHz $^1$H NMR (DMSO-d$_4$): δ 12.96 (br(s), 1H), 7.46–7.57 (m, 2H), 7.28–7.38 (m, 2H), 7.00–7.20 (m, 4H), 6.82–6.91 (m, 2H), 6.69 (d, 1H, J=8.6 Hz), 5.05 (s, 2H), 4.62 (s, 2H), 4.00 (s, 2H), 2.08 (s, 3H); MS m/z 477 (M−1). Anal. Calc'd for C$_{24}$H$_{21}$F$_3$O$_5$S: C, 60.25; H, 4.42; found: C, 59.92; H, 4.07.

EXAMPLE 36

Synthesis of {6-Methyl-8-[4-(5-trifluoromethyl-pyridine-2-yl)-benzylsulfanyl]-chroman-5-yloxy}-acetic acid (compound 36)

Step 1. {6-Methyl-8-[4-(5-trifluoromethyl-pyridine-2-yl)-benzylsulfanyl]-chroman-5-yloxy}-acetic acid methyl ester (compound 36A)

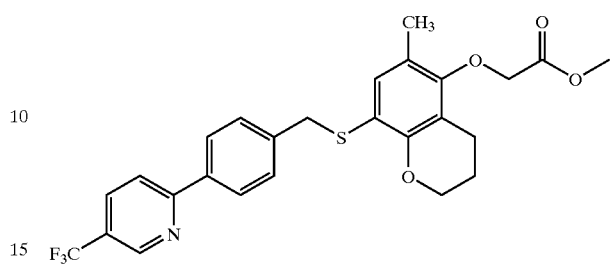

36A

The title compound was prepared in the manner analogous to Example 1F using (8-mercapto-6-methyl-chroman-5-yloxy)-acetic acid methyl ester and 18B. MS m/z 504 (M+1).

Step 2. {6-Methyl-8-[4-(5-trifluoromethyl-pyridine-2-yl)-benzylsulfanyl]-chroman-5-yloxy}-acetic acid methyl ester (compound 36)

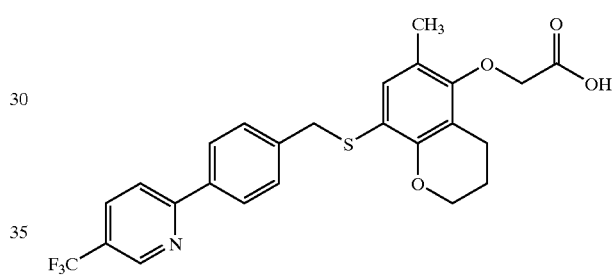

36

The title compound was prepared in the manner analogous to Example 1 using 36A. mp 156–157° C.; IR (KBr) cm$^{-1}$: 2928, 1731, 1710, 1603, 1329, 1113, 1082; 400 MHz $^1$H NMR (DMSO-d$_6$): δ 12.84 (br(s), 1H), 8.97 (s, 1H), 8.22 (dd, 1H, J=8.4, 2.0 Hz), 8.12 (d, 1H, J=8.4 Hz), 8.04 (d, 2H, J=8.2 Hz), 7.42 (d, 2H, J=8.2 Hz), 6.88 (s, 1H), 4.29 (s, 2H), 4.05–4.14 (m, 4H), 2.64 (t, 2H, J=6.3 Hz), 2.04 (s, 3H), 1.81 (pentet, 2H) ; MS m/z 490 (M+1). Anal. Calc'd for C$_{25}$H$_{22}$F$_3$NO$_4$S: C, 61.34; H, 4.53; N, 2.86; found: C, 60.96; H, 4.48; N, 2.79.

EXAMPLE 37

Synthesis of {5-Chloro-2-methyl-4-[4-(5-trifluoromethyl-pyridin-2-yl)-benzylsulfanyl]-phenoxy}-acetic acid (compound 37)

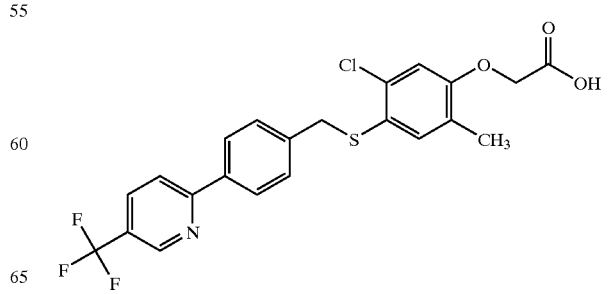

37

Step 1. Preparation of {5-Chloro-2-methyl-4-[4-(5-trifluoromethyl-pyridin-2-yl)-benzylsulfanyl]-phenoxy}-acetic acid methyl ester (compound 37A)

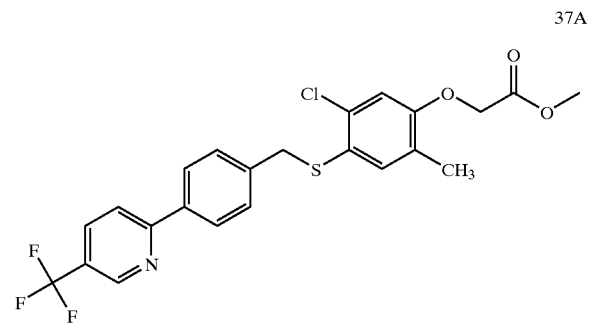

37A

Compound 37A was prepared in the manner analogous to Example 1F using the products from Example 18B and Example 20C. MS m/z 482 (M+).

Step 2. Preparation of {5-chloro-2-methyl-4-[4-(5-trifluoromethyl-pyridin-2-yl)-benzylsulfanyl]-phenoxy}-acetic acid (compound 37)

The title compound was prepared in the manner analogous to Example 1 using 37A. IR cm$^{-1}$:1708, 1122; 400 MHz $^1$H NMR (DMSO-d$_6$) δ 8.97 (s, 1H), 8.22 (d, 1H, J=8.3 Hz), 8.12 (d, 1H, J=8.3 Hz), 8.04 (d, 2H, J=8.3 Hz), 7.43 (d, 2H, J=8.3 Hz), 7.25 (s, 1H), 6.94 (s, 1H), 4.70 (s, 2H), 4.21 (s, 2H), 2.06 (s, 3H). Anal. Calc'd for C$_{22}$H$_{17}$ClF$_3$NO$_3$S: C, 56.47, H, 3.66, N 2.99; found: C, 56.48, H, 3.28, N 3.04.

EXAMPLE 38

Synthesis of [5-hydroxy-2-methyl-4-(4'-trifluoromethyl-biphenyl-4-ylmethylsulfanyl)-phenoxyl-acetic acid (compound 38)

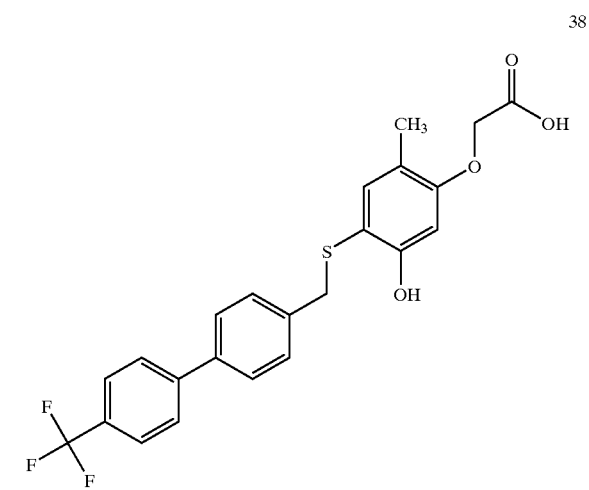

38

A solution of [5-Methoxy-2-methyl-4-(4'-trifluoromethyl-biphenyl-4-ylmethylsulfanyl)-phenoxy]-acetic acid, prepared according to Example 4,(1.0 g, 2.2 mmol) in 75 mL DCM at 0° C., was treated with dropwise addition of BBr$_3$ (5.5 mL of a 1.0 M solution in DCM). After 30 minutes, the reaction was carefully quenched with 50% NH$_4$OH. The reaction was then acidified to pH 1 with conc. HCl, and extracted with EtOAC. The organic layer was dried (Na$_2$SO$_4$) and concentrated in vacuo. The crude reaction mixture was then taken up in MeOH, followed by addition of 50 μL H$_2$SO$_4$, and then refluxing for 3 hours. The reaction was then diluted with EtOAc, washed 1×50 mL water, dried (Na$_2$SO$_4$), and the reaction concentrated in vacuo. The resulting ester was purified by recrystallization from EtOAC/Hexanes. The ester was then saponified in the same manner as described for Example 1, to give the title compound in 37% overall yield. IR cm$^{-1}$:3408, 1752, 1323; 400 MHz $^1$H NMR (DMSO-d$_6$) δ 9.56 (s, 1H), 7.82 (d, 2H, J=8.4 Hz), 7.74 (d, 2H, J=8.4 Hz), 7.31 (d, 2H, J=8.4 Hz), 6.92 (s, 1H), 6.30 (s, 1H), 4.55 (s, 2H), 4.00 (s, 2H), 1.95 (s, 3H). Anal. Calc'd for C$_{23}$H$_{19}$F$_3$NO$_4$S.0.1 H$_2$O C, 61.35; H, 4.30; found: C, 61.08; H, 3.92.

EXAMPLE 39

Synthesis of [5-Methoxy-2-methyl-4(3-methyl-4'-trifluoromethyl-biphenyl-4-ylmethylsulfanyl)-phenoxy]-acetic acid (compound 39)

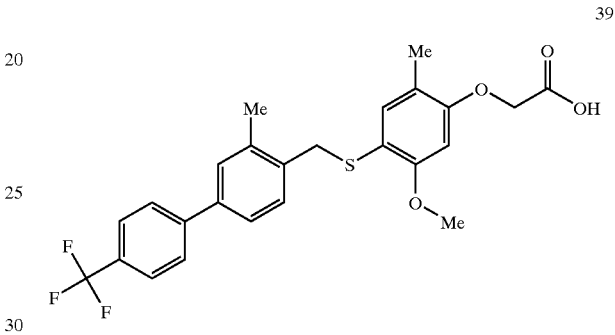

39

Step 1. Preparation of (3-Methyl-4'-trifluoromethyl-biphenyl-4-yl)-methanol (compound 39A)

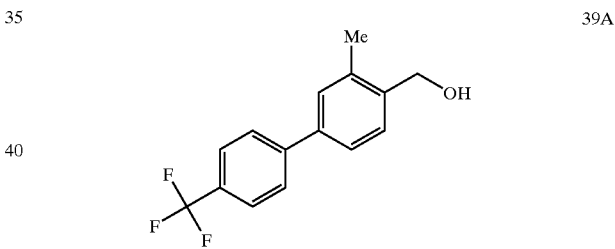

39A

The title compound was prepared in the manner analogous to Example 3A using (4-bromo-2-methyl-phenyl)-methanol and 4-(trifluoromethyl)benzeneboronic acid. MS m/z 249 (M-OH).

Step 2. Preparation of 4chloromethyl-3-methyl-4'-trifluoromethyl-biphenyl (compound 39B)

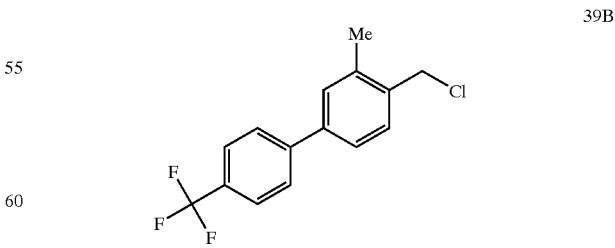

39B

The title compound was prepared in the manner analogous to Example 3B using 39A. 400 MHz $^1$H NMR (DMSO-d$_6$) δ 7.84 (d, 2H, J=8.3 Hz), 7.76 (d, 2H, J=8.3 Hz), 7.57 (s, 1H), 7.48 (m, 2H), 4.80 (s, 2H), 2.41 (s, 3H).

Step 3. Preparation of [5-Methoxy-2-methyl-4-(3-methyl-4'-trifluoromethyl-biphenyl-4-ylmethylsulfanyl)-phenoxy]-acetic acid methyl ester (compound 39C)

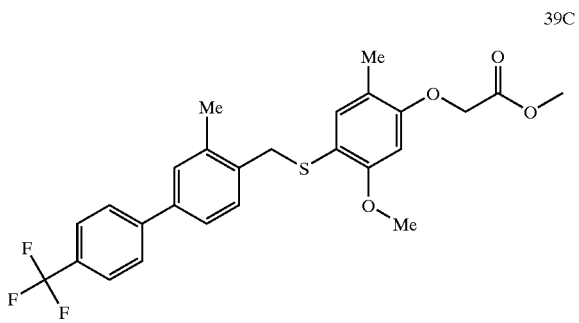

39C

The title compound was prepared in the manner analogous to Example 1F using 1D and 39B. MS m/z 491 (M+1).

Step 4. Preparation of [5-Methoxy-2-methyl-4-(methyl-4'-trifluoromethyl-biphenyl-4-ylmethylsulfanyl)-phenoxy]-acetic acid (compound 39)

The title compound was prepared in the manner analogous to Example 1 using 39C. IR cm$^{-1}$:1740, 1322; 400 MHz $^1$H NMR (DMSO-d$_6$) δ 7.81 (d, 2H, J=8.1 Hz), 7.73 (d, 2H, J=8.1 Hz), 7.51 (s, 1H), 7.39 (d, 1H, J=7.8 Hz), 7.16 (d, 1H, J=7.8 Hz), 7.04 (s, 1H), 6.53 (s, 1H), 4.71 (s, 2H), 4.00 (s, 2H), 3.73 (s, 3H), 2.39 (s, 3H), 2.02 (s, 3H); MS m/z 477 (M+1). Anal. Calc'd for C$_{25}$H$_{23}$F$_3$O$_4$S.0.1 H$_2$O; C, 62.78; H, 4.89; found: C, 62.57; H, 4.82.

EXAMPLE 40

Synthesis of {7-[4-(4-trifluoromethyl-benzyl)-benzylsulfanyl]-indan-4yloxy}-acetic acid (compound 40)

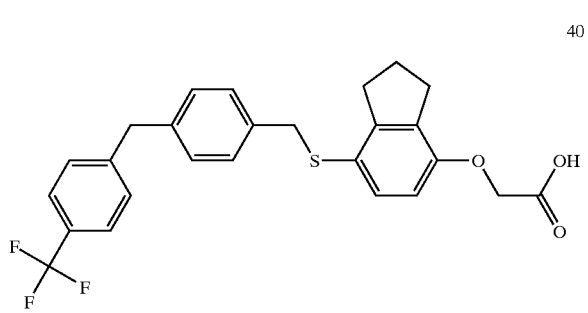

40

Step 1. Preparation of 4-(4-trifluoromethyl-benzyl)-benzoic acid methyl ester (compound 40A)

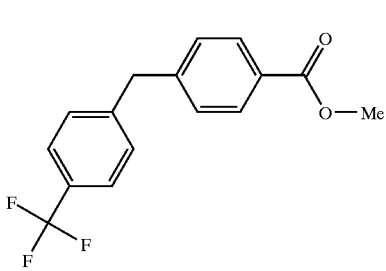

40A

A solution of 1-bromo-4-trifluoromethyl-benzene (10.0 g, 44.4 mmol) in THF at −78° C. was treated with dropwise addition of n-butyl lithium (33.3 mL of a 1.6 M solution in hexanes). After 20 minutes, 4-formyl-benzoic acid methyl ester in 50 mL THF was added. The reaction was allowed to come to room temperature and after 1 H, quenched with sat. NH$_4$Cl. The reaction was then concentrated in vacuo, taken up in EtOAc, and washed with 2 M HCl (1×100 mL), brine (1×100 mL), dried (Na$_2$SO$_4$) and the solvent removed in vacuo to give the alcohol intermediate. Purification by flash column chromatography (gradient elution: 5% EtOAc/hexane to 40% EtOAc/hexane) gave 6.2 g of the alcohol intermediate. 4.0 g (12.9 mmol) of the intermediate was then hydrogenated in EtOAc using 0.5 g of 10% Pd(OH)$_2$/C as catalyst. Filtration through Celite® , and concentration in vacuo gave the title compound (3.60 g, 95%). MS m/z 295 (M+1).

Step 2. Preparation of [4-(4-trifluoromethyl-benzyl)-phenyl]-methanol (compound 40B)

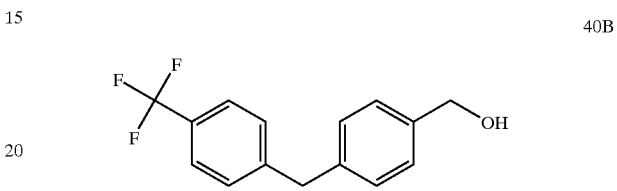

40B

A solution of 40A (3.6 g, 12.2 mmol) in 75 mL THF at room temperature was treated portionwise with lithium aluminum hydride (0.97 g, 25.6 mmol). After 1 hour, the reaction mixture was carefully quenched with sat. NH$_4$Cl. The reaction mixture was then extracted with EtOAc, and the organic layer washed with 2 M HCl (1×50 mL), brine (1×50 mL), dried (Na$_2$SO$_4$) and the solvent removed in vacuo. Purification by flash column chromatography (gradient elution: 5% EtOAc/hexane to 40% EtOAc/hexane) gave the title compound (2.8 g, 86%). MS m/z 265 (M−1).

Step 3. Preparation of Chloro-[4-(4-trifluoromethyl-benzyl)-phenyl]-methane (compound 40C)

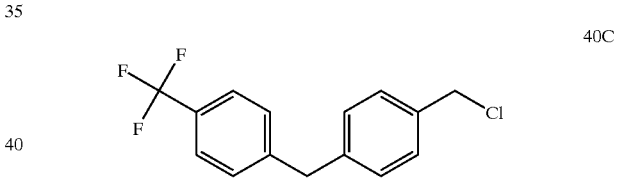

40C

The title compound was prepared in a similar manner as described for 3B using 40B and thionyl chloride. 400 MHz $^1$H NMR (DMSO-d$_6$) 7.59 (d, 2H, J=8.4 Hz), 7.40 (d, 2H, J=8.4 Hz), 7.31 (d, 2H, J=8.4 Hz), 7.20 (d, 2H, J=8.4 Hz), 4.67 (s, 2H), 3.99 (s, 2H).

Step 4. Preparation of {7-[4-(4-Trifluoromethyl-benzyl)-benzylsulfanyl]-indan-4-yloxy}-acetic acid methyl ester (compound 40D)

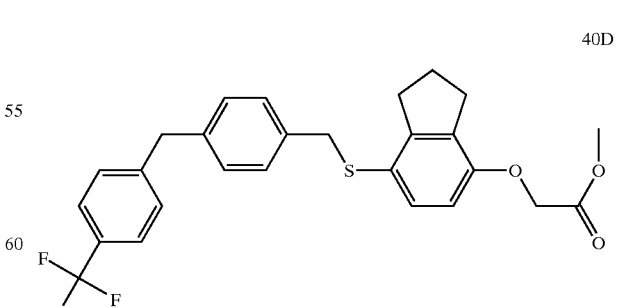

40D

The title compound was prepared in the manner analogous to Example 1F using the products from Example 12C and Example 40C. MS m/z 487 (M+1).

Step 5. Preparation of {7-[4-(4-trifluoromethyl-benzyl)-benzylsulfanyl]-indan-4-yloxy}-acetic acid (compound 40)

The title compound was prepared in the manner analogous to Example 1 using 40D. IR cm$^{-1}$: 1745, 1704,1325; 400 MHz $^1$H NMR (DMSO-d$_6$) δ 7.58 (d, 2H, J=8.1 Hz), 7.37 (d, 2H, J=8.1 Hz), 7.09 (s, 2H), 7.05 (d, 2H, J=8.3 Hz), 6.55 (d, 1H, J=8.3 Hz), 4.60 (s, 2H), 3.94 (s, 4H), 2.71 (t, 2H, J=8.3 Hz), 2.58 (t, 2H, J=8.3 Hz), 1.81 (m, 2H); MS m/z 473 (M+1). Anal. Calc'd for C$_{26}$H$_{23}$F$_3$O$_3$S.0.1 H$_2$O, C, 65.84; H, 4.93; found: C, 65.58; H, 4.96.

EXAMPLE 41

Synthesis of {4-[5-(4-Chloro-phenyl)-isoxazol-3-ylmethylsulfanyl]-5-methoxy-2-methyl-phenoxy}-acetic acid (compound 41)

41

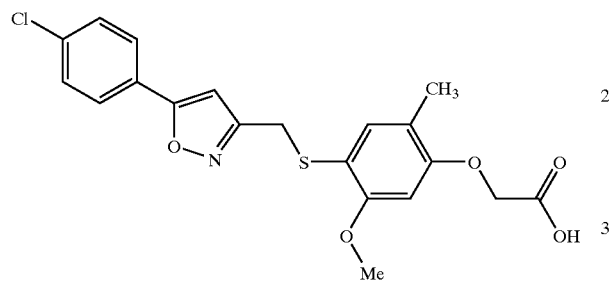

Step 1. Preparation of {4-[5-(4-Chloro-phenyl)-isoxazol-3-ylmethylsulfanyl]-5-methoxy-2-methyl-phenoxy}-acetic acid methyl ester (compound 41A)

41A

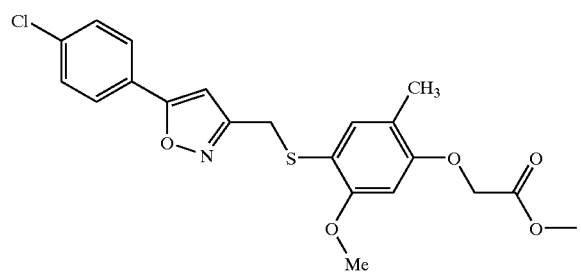

The title compound was prepared in the manner analogous to Example 1F using 1D and 3-chloromethyl-5-(4-chloro-phenyl)-isoxazole. MS m/z 434 (M+1).

Step 2. Preparation of {4-[5-(4-Chloro-phenyl)-isoxazol-3-ylmethylsulfanyl]-5-methoxy-2-methyl-phenoxy}-acetic acid (compound 41)

The title compound was prepared in the manner analogous to Example 1 using 41A. IR cm$^{-1}$:1747, 1432; 400 MHz $^1$H NMR (DMSO-d$_6$) δ 7.81 (d, 2H, J=8.8 Hz), 7.53 (d, 2H, J=8.8 Hz), 7.05 (s, 1H), 6.92 (s, 1H), 6.52 (s, 1H), 4.69 (s, 2H), 4.01 (s, 2H), 3.71 (s, 3H), 2.00 (s, 3H); MS m/z 420 (M+1). Anal. Calc'd for C$_{20}$H$_{18}$ClNO$_5$S, C 57.21; H, 4.32 N, 3.34; found: C, 56.84; H, 4.62, N, 2.96.

EXAMPLE 42

Synthesis of {2-Methyl-4-[5-(4-trifluoromethyl-phenyl)-isoxazol-3-ylmethylsulfanyl]-phenoxy}-acetic acid (compound 42)

42

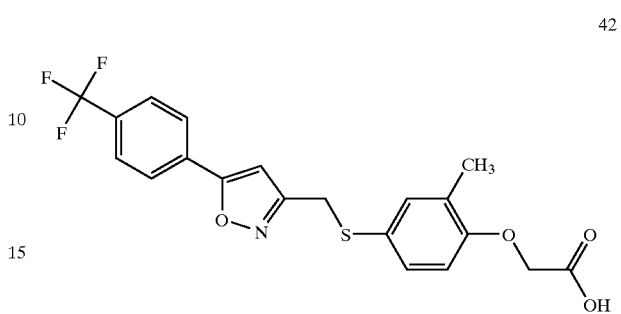

Step 1. Preparation of 5-(4-Trifluoromethyl-phenyl)-isoxazole-3-carboxylic acid ethyl ester (compound 42A)

42A

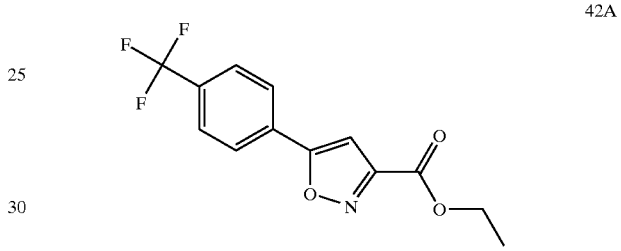

Sodium hydride (1.6 g, 63.7 mmol, 95%) was added to a solution of 1(4-trifluoromethyl-phenyl)-ethanone (10.0 g, 53.1 mmol) and oxalic acid diethyl ester (8.7 mL, 63.7 mmol) in 75 mL dry DMF at 0° C. The reaction was allowed to come to room temperature and then heated to 45° C. for 45 minutes. The reaction was then cooled, concentrated in vacuo, and the residue taken up in EtOAc. The organic layer was then washed with 2 M HCl (1×100 mL), dried (Na$_2$SO$_4$) and the solvent removed in vacuo. Purification by flash column chromatography (gradient elution: 5% EtOAc/hexane to 55% EtOAc/hexane) gave the intermediate 2,4-dioxo-4-(4-trifluoromethyl-phenyl)-butyric acid ethyl ester (12.2 g, 80%) which was then taken up in EtOH and refluxed in the presence of hydroxyl amine hydrochloride (10.2 g, 132.3 mmol) for 3H. The reaction was then cooled, diluted with EtOAc, washed with dilute NaHCO$_3$, brine, dried (Na$_2$SO$_4$), and concentrated in vacuo. Recrystallization from EtOAc/hexane gave 5.2 g of the title compound. MS m/z 286 (M+1).

Step 2. Preparation of [5-(4-Trifluoromethyl-phenyl)-isoxazol-3-yl]-methanol (compound 42B)

42B

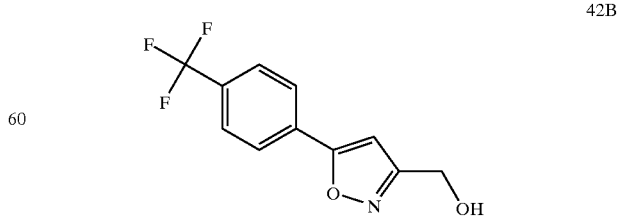

The title compound was prepared in a manner analogous to Example 40B using 42A. MS m/z 244 (M+1).

Step 3. Preparation of 3-chloromethyl-5-(4-trifluoromethyl-phenyl)-isoxazole (compound 42C)

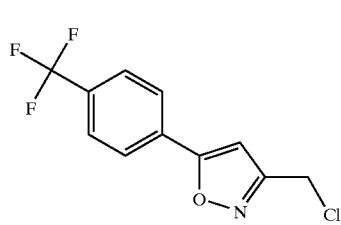

The title compound was prepared in a manner analogous to Example 3B using 42B. MS m/z 262 (M+1).

Step 4. Preparation of {2-methyl-4-[5-(4-trifluoromethyl-phenyl)-isoxazol-3-ylmethylsulfanyl]-phenoxy}-acetic acid methyl ester (compound 42

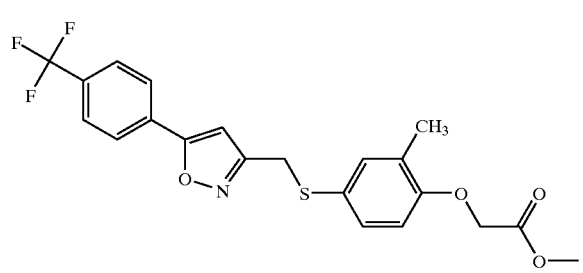

The title compound was prepared in a manner analogous to Example 1F using 42C and 2C. MS m/z 438 (M+1).

Step 5. Preparation of {2Methyl-4-[5-(4-trifluoromethyl-phenyl)-isoxazol-3-ylmethylsulfanyl]-phenoxy}-acetic acid (compound 42)

The title compound was prepared in a manner analogous to Example 1 using 42D. IR cm$^{-1}$:1746, 1326; 400 MHz $^1$H NMR (DMSO-d$_6$) δ 12.97 (br(s), 1H), 8.02 (d, 2H, J=8.0 Hz), 7.83 (d, 2H, J=8.0 Hz), 7.20 (s, 1H), 7.15 (s, 2H), 6.71 (d, 1H, J=8.5 Hz), 4.63 (s, 2H), 4.14 (s, 2H), 2.08 (s, 3H); MS m/z 424 (M+1). Anal. Calc'd for C$_{20}$H$_{16}$F$_3$NO$_4$S C, 56.73; H, 3.81; N, 3.31 found: C, 56.59; H, 3.58; N, 3.22.

EXAMPLE 43

Synthesis of {5-Methoxy-2methyl-4-[5-(4-trifluoromethyl-phenyl)-isoxazol-3-ylmethylsulfanyl]-phenoxy}-acetic acid (compound 43)

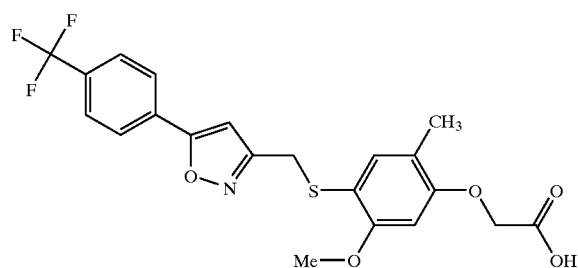

Step 1. Preparation of {5-Methoxy-2-methyl-4-[5-(4-trifluoromethyl-phenyl)-isoxazol-3-ylmethylsulfanyl]-phenoxy}-acetic acid methyl ester (compound 43A)

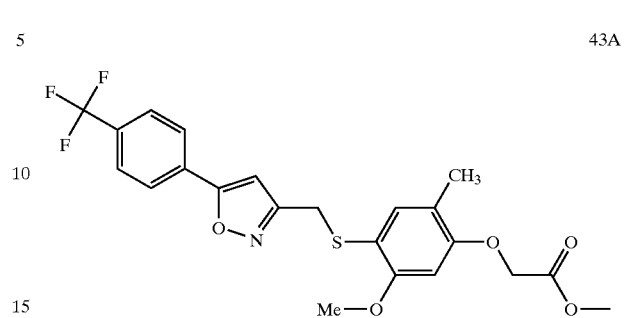

The title compound was prepared in a manner analogous to Example 1F using 42C and 1D. MS n/z 468 (M+1).

Step 2. Preparation of {5-Methoxy-2-methyl-4-15-(4-trifluoromethyl-phenyl)-isoxazol-3-ylmethylsulfanyl]-phenoxy}-acetic acid (compound 43)

The title compound was prepared in a manner analogous to Example 1 using 43A. IR cm$^{-1}$: 1745, 1322; 400 MHz $^1$H NMR (DMSO-d$_6$) δ 12.96 (br(s), 1H), 8.01 (d, 2H, J=8.3 Hz), 7.83 (d, 2H, J=8.3 Hz), 7.07 (s, 2H), 6.52 (s, 1H), 4.70 (s, 2H), 4.03 (s, 2H), 3.71 (s, 3H), 1.99 (s, 3H); MS m/z 454 (M+1). Anal. Calc'd for C$_{21}$H$_{18}$F$_3$NO$_5$S. 0.1H$_2$O C, 54.46; H, 3.92; N, 3.01 found: C, 54.54; H, 3.74; N, 2.93.

EXAMPLE 44

Synthesis of {7-[5-(4-Trifluoromethyl-phenyl)-isoxazol-3-ylmethylsulfanyl]-indan-4-yloxy}-acetic acid (compound 44)

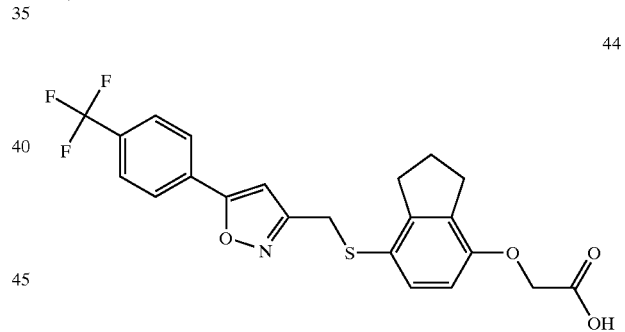

Step 1. Preparation of {7-[5-(4-Trifluoromethyl-phenyl)-isoxazol-3-ylmethylsulfanyl]-indan-4-yloxy}-acetic acid methyl ester (compound 44A)

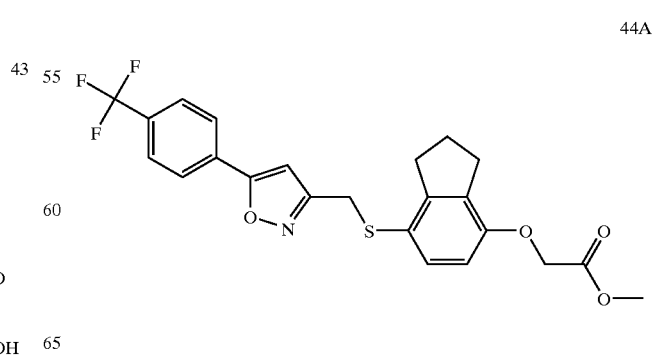

The title compound was prepared in a manner analogous to Example 1F using 42C and 12C. MS m/z 464 (M+1).

Step 2. Preparation of {7-[5-(4-Trifluoromethyl-phenyl)-isoxazol-3-ylmethylsulfanyl]-indan-4-yloxy}-acetic acid (compound 44)

The title compound was prepared in a manner analogous to Example 1 using 44A. 400 MHz $^1$H NMR (DMSO-$d_6$) δ 12.94 (br(s), 1H), 8.01 (d, 2H, J=8.4 Hz), 7.83 (d, 2H, J=8.4 Hz), 7.09 (s, 2H), 6.58 (d, 1H, J=8.6 Hz), 4.62 (s, 2H), 4.08 (s, 2H), 2.77 (m, 4H), 1.89 (m, 2H); MS m/z 450 (M+1). Anal. Calc'd for $C_{22}H_{18}F_3NO_4S$ C, 58.79; H, 4.04; N, 3.12 found: C, 58.59; H, 3.80; N, 3.01.

EXAMPLE 45

Synthesis of {2-Methyl-4-[3-(4-trifluoromethyl-phenyl)-isoxazol-5-ylmethylsulfanyl]-phenoxy}-acetic acid (compound 45)

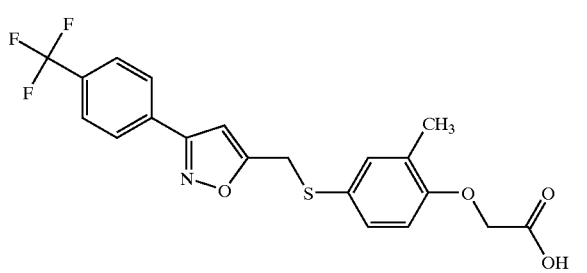

45

Step 1. Preparation of 5-chloromethyl-3-(4-trifluoromethyl-phenyl)-isoxazole (compound 45A)

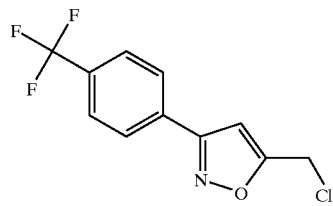

45A

A solution of 4-trifluoromethyl-benzaldehyde oxime (8.9 g, 47.1 mmol) in 100 mL DCM was added to a rapidly stirred solution of propargyl chloride (47.1 mmol), triethyl amine (4.71 mmol) and 91 mL of commercial bleach (6.5% by weight) all in 50 mL DCM at 0° C. After 1 hour the layers were separated and the organic layer dried ($Na_2SO_4$), and concentrated in vacuo. Purification by flash column chromatography (gradient elution: 5% EtOAc/hexane to 25% EtOAc/hexane) gave the title compound (2.9 g, 23%) MS m/z 262 (M+1).

Step 2. Preparation of {2-Methyl-4-[3-(4-trifluoromethyl-phenyl)-isoxazol-5-ylmethylsulfanyl]-phenoxy}-acetic acid methyl ester (compound 45B)

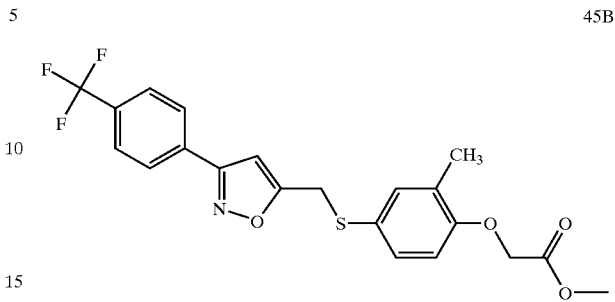

45B

The title compound was prepared in a manner analogous to Example 1F using 45A and 2C. MS m/z 438 (M+1).

Step 3. Preparation of {2-Methyl-4-[3-(4-trifluoromethyl-phenyl)-isoxazol-5-ylmethylsulfanyl]-3-phenoxy}-acetic acid (compound 45)

The title compound was prepared in a manner analogous to Example 1 using 45B. IR cm$^{-1}$: 1747; 400 MHz $^1$H NMR (DMSO-$d_6$) δ 12.97 (br(s), 1H), 7.99 (d, 2H, J=8.0 Hz), 7.81 (d, 2H, J=8.0 Hz), 7.21 (s, 1H), 7.16 (d, 1H, J=8.5 Hz), 6.86 (s, 1H), 6.74 (d, 1H, J=8.5 Hz), 4.63 (s, 2H), 4.30 (s, 2H), 2.09 (s, 3H); MS m/z 424 (M+1).

EXAMPLE 46

Synthesis of {5-Methoxy-2-methyl-4-[3(4-trifluoromethyl-phenyl)-isoxazol-5-ylmethylsulfanyl]-phenoxy}-acetic acid (compound 46)

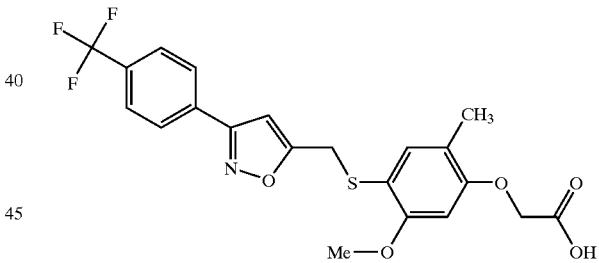

46

Step 1. Preparation of {5-Methoxy-2-methyl-4-[3-(4-trifluoromethyl-phenyl)-isoxazol-5-ylmethylsulfanyl]-phenoxy}-acetic acid methyl ester (compound 46A)

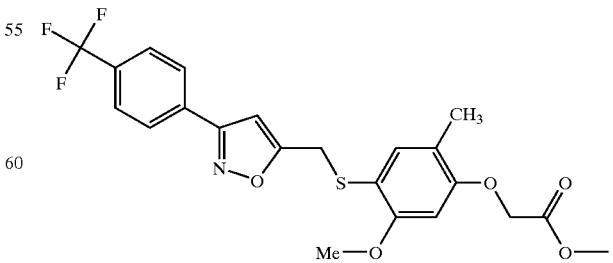

46A

The title compound was prepared in a manner analogous to Example 1F using 45A and 1D. MS m/z 468 (M+1).

Step 2. Preparation of {5-Methoxy-2-methyl-4-[3-(4-trifluoromethyl-phenyl)-isoxazol-5-ylmethylsulfanyl]-phenoxy}-acetic acid (compound 46)

The title compound was prepared in a manner analogous to Example 1 using 46A. IR cm$^{-1}$:1752,1711; 400 MHz $^1$H NMR (DMSO-d$_6$) δ 12.96 (br(s), 1H), 7.98 (d, 2H, J=8.1 Hz), 7.81 (d,2H, J=8.1 Hz), 7.09 (s, 1H),6.80 (s, 1H),6.54 (s, 1H),4.71 (s, 2H), 4.18 (s, 2H), 3.79 (s, 3H), 2.00 (s, 3H); MS m/z 454 (M+1)

EXAMPLE 47

Synthesis of [2-Methyl-4-(4-phenoxy-benzylsulfanyl)-phenoxy]-acetic acid (compound 47)

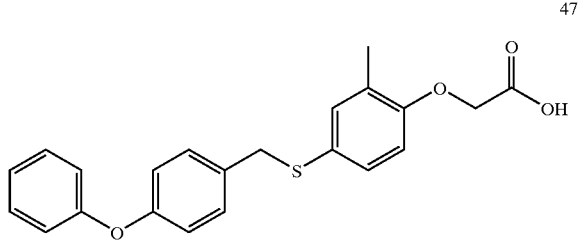

47

Step 1. Preparation of [2-Methyl-4-(4-phenoxy-benzylsulfanyl)-phenoxy]-acetic acid methyl ester (compound 47A)

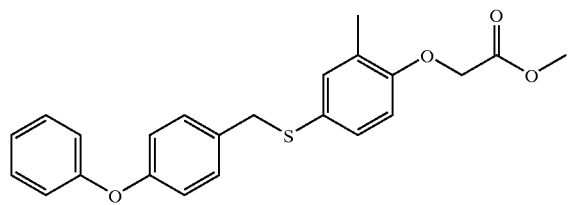

47A

The title compound was prepared in the manner analogous to Example 1F with 1-chloromethyl-4-phenoxy-benzene and 2C. MS m/z 321 (M-methylacetate).

Step 2. Preparation of [2-Methyl-4-(4-phenoxy-benzylsulfanyl)-phenoxy]-acetic acid (compound 47)

The title compound was prepared in the manner analogous to Example 1 using 47A. 400 MHz $^1$H NMR (DMSO-d$_6$) δ 12.95 (br(s), 1H), 7.33 (m, 2H), 7.22 (m, 2H), 7.07 (m, 3H), 6.93 (m, 2H), 6.87 (m, 2H), 6.71 (d, 1H, J=8.3 Hz), 4.62 (s, 2H), 4.04 (s, 2H), 2.09 (s, 3H). MS m/z 379 (M-1).

EXAMPLE 48

Synthesis of [7-(4'-Trifluoromethyl-biphenyl-3-ylmethylsulfanyl)-indan-4-yloxy]-acetic acid (compound 48)

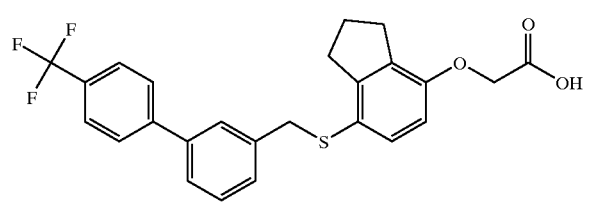

48

Step 1. Preparation of (4'-Trifluoromethyl-biphenyl-3-yl)-methanol (compound 48A)

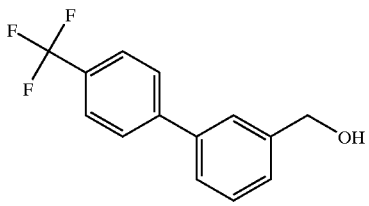

48A

The title compound was prepared in the manner analogous to Example 3A with 1-bromo-4-trifluoromethyl-benzene and 3-(hydroxymethyl)phenyl boronic acid. MS m/z 251 (M-1).

Step 2. Preparation of 3-Chloromethyl-4'-trifluoromethyl-biphenyl (compound 48B)

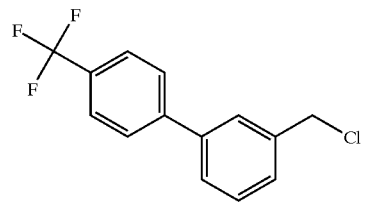

48B

The title compound was prepared in the manner analogous to Example 3B using 48A. MS m/z 236 (M+1-Cl).

Step 3. Preparation of [7-(4'-Trifluoromethyl-biphenyl-3-ylmethylsulfanyl)-indan-4-yloxy]-acetic acid methyl ester (compound 48C)

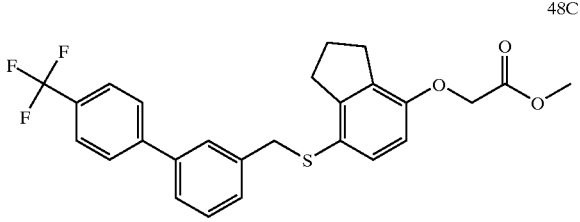

48C

The title compound was prepared in the manner analogous to Example 1F using 12C and 48B. MS m/z 473 (M+1).

Step 4. Preparation of [7-(4'-Trifluoromethyl-biphenyl-3-ylmethylsulfanyl)-indan-4-yloxy]-acetic acid (compound 48)

The title compound was prepared in the manner analogous to Example 1 using 48C. 400 MHz $^1$H NMR (DMSO-d$_6$) δ 12.96 (br(s), 1H), 7.75 (d, 2H, J=8.3 Hz), 7.67 (d, 2H, J=8.1 Hz), 7.52 (m, 1H), 7.37 (t, 1H, J=7.6 Hz), 7.29 (m, 2H), 7.13 (d, 1H, J=8.5 Hz), 6.61 (d, 1H, J=8.5 Hz), 4.63 (s, 2H), 4.05 (s, 2H), 2.71 (t, 2H), 2.58 (t, 2H), 1.81 (m, 2H). MS m/z 459 (M+1).

EXAMPLE 49

Synthesis or [5-Methoxy-2-methyl-4-(4'-trifluoromethyl-biphenyl-3-ylmethylsulfanyl)-phenoxy]-acetic acid (compound 49)

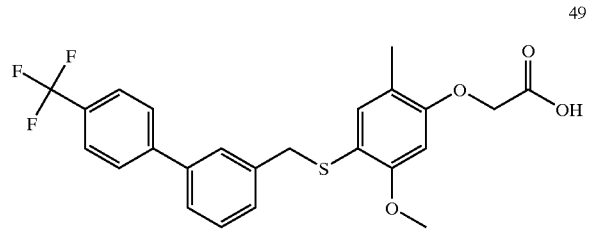

49

Step 1. Preparation of [5-Methoxy-2-methyl-4-(4'-trifluoromethyl-biphenyl-3-ylmethylsulfanyl)-phenoxy]-acetic acid methyl ester (compound 49A)

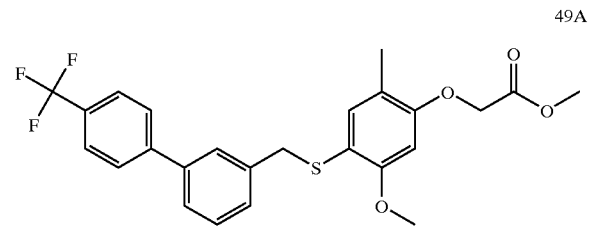

49A

The title compound was prepared in the manner analogous to Example 1F using 48B and 1D. MS m/z 477 (M+1).

Step 2. Preparation of [5-Methoxy-2-methyl-4-(4'-trifluoromethyl-biphenyl-3-ylmethylsulfanyl)-phenoxy]-acetic acid (compound 49)

The title compound was prepared in the manner analogous to Example 1 using 49A. 400 MHz $^1$H NMR (DMSO-$d_6$) δ 12.96 (br(s), 1H), 7.73 (d, 2H, J=9 Hz), 7.71 (d, 2H, J=9 Hz), 7.50 (m, 1H), 7.42 (m, 1H), 7.36 (t, 1H, J=7.8 Hz), 7.28 (m, 1H), 6.99 (s, 1H), 6.53 (s, 1H), 4.70 (s, 2H), 4.03 (s, 2H), 3.73 (s, 3H), 1.99 (s, 3H). MS m/z 463 (M+1).

EXAMPLE 50

Synthesis of [5-Methoxy-2-methyl-4-(4'-trifluoromethyl-biphenyl-4-ylmethanesulfonyl)-phenoxy]-acetic acid (compound 50)

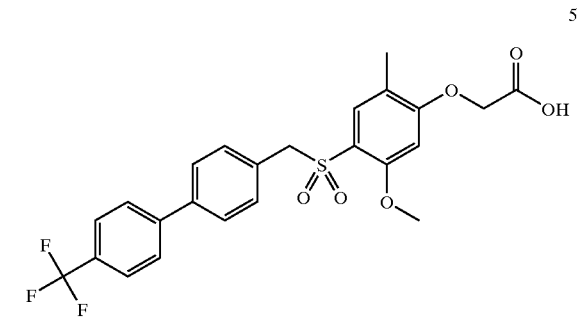

50

Step 1. Preparation of [5-Methoxy-2-methyl-4-(4'-trifluoromethyl-biphenyl-4-ylmethanesulfonyl)-phenoxy]-acetic acid methyl ester (compound 50A)

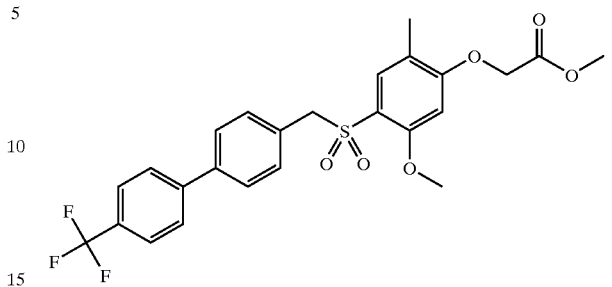

50A

Example 4 (200 mg) was dissolved in 5 ml dichloromethane. Excess m-chloroperbenzoic acid (300 mg) was added and the reaction was allowed to stir 3 h. The solvent was removed under vacuum and the crude product was purified by MPLC. MS m/z 509 (M+1).

Step 2. Preparation of [5-Methoxy-2-methyl-4-(4'-trifluoromethyl-biphenyl-4-ylmethanesulfonyl)-phenoxy]-acetic acid (compound 50)

The title compound was prepared in the manner analogous to Example 1 using 50A. 400 MHz $^1$H NMR (DMSO-$d_6$) δ 13.13 (br(s), 1H), 7.85 (d, 2H, J=8.1 Hz), 7.77 (d, 2H, J=8.3 Hz), 7.66 (d, 2H, J=8.6 Hz), 7.3 (m, 3H), 6.76 (s, 1H), 4.89 (s, 2H), 4.67 (s, 2H), 3.96 (s, 3H), 2.04 (s, 3H). MS m/z 495 (M+1).

EXAMPLE 51

Synthesis of [5-Methoxy-2-methyl-4-(4'-trifluoromethyl-biphenyl-4-ylmethanesulfinyl)-phenoxy]-acetic acid (compound 51)

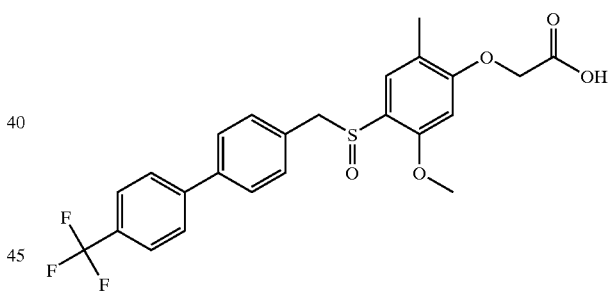

51

Step 1. Preparation of [5-Methoxy-2-methyl-4-(4'-trifluoromethyl-biphenyl-4-ylmethanesulfinyl)-phenoxy]-acetic acid methyl ester (compound 51A)

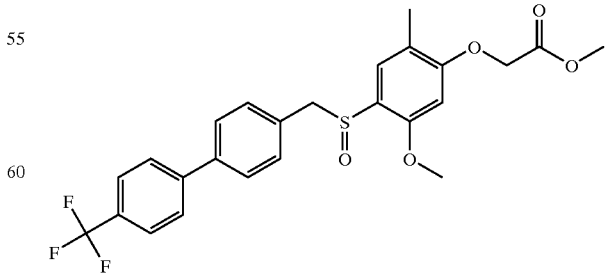

51A

Example 4 (0.5 g, 1.0 mmol) was dissolved in 25 ml dichloromethane followed by the addition of 2-benzenesulfonyl-3-phenyl-oxaziridine (0.274, 1.04 mmol). The reaction was stirred 1 h. 10 ml water was added, the layers were separated, and dichloromethane solution was dried over anhydrous sodium sulfate, decanted, and concentrated. The product was recrystallized from ethyl acetate to give the title product. MS m/z 493 (M+1).

Step 2. Preparation of [5-Methoxy-2-methyl-4-(4'-trifluoromethyl-biphenyl-4-ylmethanesulfinyl)-phenoxy]-acetic acid (compound 51)

The title compound was prepared in the manner analogous to Example 1 using 51A. 400 MHz $^1$H NMR (DMSO-d$_6$) δ 7.83 (d, 2H, J=8.78 Hz), 7.76 (d, 2H, J=8.30 Hz), 7.59 (d, 2H, J=8.30 Hz), 7.11 (d, 2H, J=8.30 Hz), 7.02 (s, 1H), 6.64 (s, 1H), 4.79 (s, 2H), 4.20 (d, 1H, J=12.7 Hz), 3.91 (d, 1H, J=12.4 Hz), 3.76 (s, 3H), 2.03 (s, 3H). MS m/z 479 (M+1).

EXAMPLE 52

Synthesis of [2-Propyl-4-(4'-trifluoromethyl-biphenyl-4-ylmethylsulfanyl)-phenoxy]-acetic acid (compound 52)

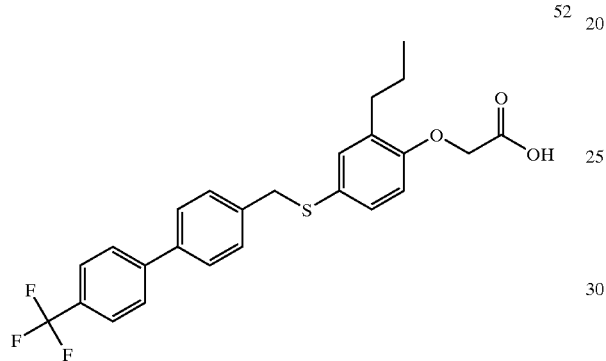

Step 1. Preparation of [2-Propyl-4-(4'-trifluoromethyl-biphenyl-4-ylmethylsulfanyl)-phenoxy]-acetic acid methyl ester (compound 52A)

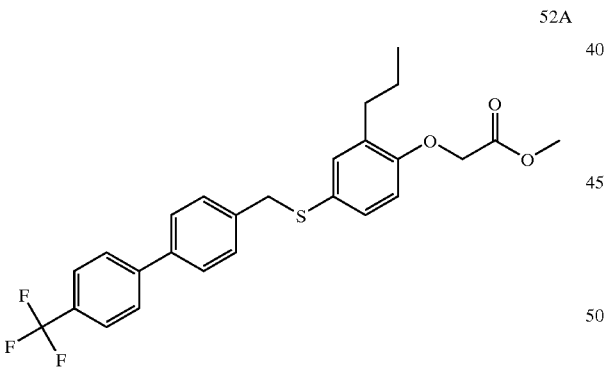

The title compound was prepared in the manner analogous to Example 1F using 48B and (4-Mercapto-2-propyl-phenoxy)-acetic acid methyl ester, prepared from 2-propylphenol in a manner analagous to Example 2. MS m/z 475 (M+1).

Step 2. Preparation of [2-Propyl-4-(4'-trifluoromethyl-biphenyl-4-ylmethylsulfanyl)-phenoxy]-acetic acid (compound 52)

The title compound was prepared in the manner analogous to Example 1 using 52A. 400 MHz $^1$H NMR (DMSO-d$_6$) δ 7.81 (d, 2H, J=8.5 Hz), 7.74 (d, 2H, J=8.5 Hz), 7.60 (d, 2H, J=8.1 Hz), 7.33 (d, 2H, J=8.3 Hz), 7.10 (m, 1H), 7.02 (m, 1H), 6.71 (d, 1H, J=8.5 Hz), 4.60 (s, 2H), 4.11 (s, 2H), 1.43 (m, 2H), 0.77 (m, 3H). MS m/z 459 (M−1).

EXAMPLE 53

Synthesis of {7-[3-(5-Trifluoromethyl-pyridin-2-yl)-benzylsulfanyl]-indan-4-yloxy}-acetic acid (compound 53)

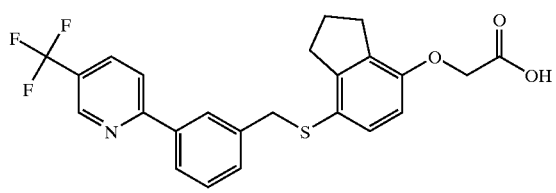

Step 1. Preparation of [3-(5-Trifluoromethyl-pyridin-2-yl)-phenyl]-methanol (compound 53A)

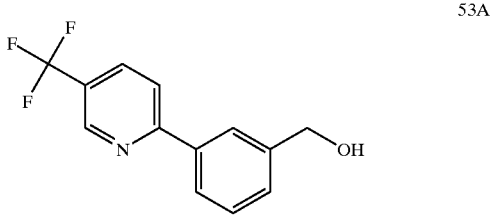

The title compound was prepared in the manner analogous to Example 3A using 3-(hydroxymethyl)phenyl boronic acid and 2-chloro-5-trifluoromethyl-pyridine. MS m/z 253 (M+1).

Step 2. Preparation of 2-(3-Chloromethyl-phenyl)-5-trifluoromethyl-pyridine (compound 53B)

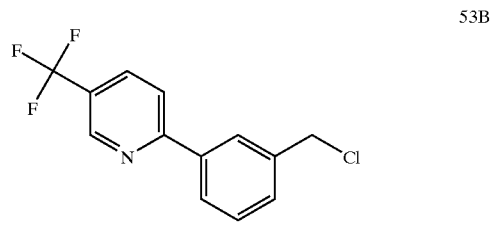

The title compound was prepared in the manner analogous to Example 3B using 53A. MS m/z 237 (M+1-Cl).

Step 3. Preparation of {7-[3-(5-Trifluoromethyl-pyridin-2-yl)-benzylsulfanyl]-indan-4-yloxy}-acetic acid methyl ester (compound 53C)

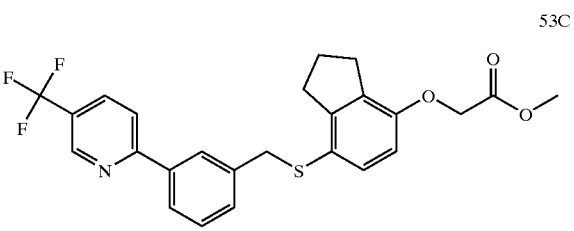

The title compound was prepared in the manner analogous to Example 1F using 12C and 53B. MS m/z 474 (M+1).

Step 4. Preparation of {7-[3-(5-Trifluoromethyl-pyridin-2-yl)-benzylsulfanyl]-indan-4-yloxy}-acetic acid (compound 53)

The title compound was prepared in the manner analogous to Example 1 using 53C. 400 MHz $^1$H NMR (DMSO-d$_6$) δ 8.98 (m, 1H), 8.23 (dd, 1H, J=1.7 Hz, J'=8.5 Hz), 7.99 (m, 2H), 7.87 (s, 1H), 7.39 (t, 1H, J=7.6 Hz), 7.33 (m, 1H), 7.11 (d, 1H, J=8.5 Hz), 6.58 (d, 1H, J=8.5 Hz), 4.61 (s, 2H), 4.08 (s, 2H), 2.70 (t, 2H, J=7.3 Hz), 2.63 (t, 2H, J=7.6 Hz), 1.84 (m, 2H). MS m/z 460 (M+1).

EXAMPLE 54
Synthesis of (5-Methoxy-2-methyl-4-{2-[1-(4-trifluoromethyl-benzyl)-1H-indol-3-yl]-ethylsulfanyl}-phenoxy)-acetic acid (compound 54)

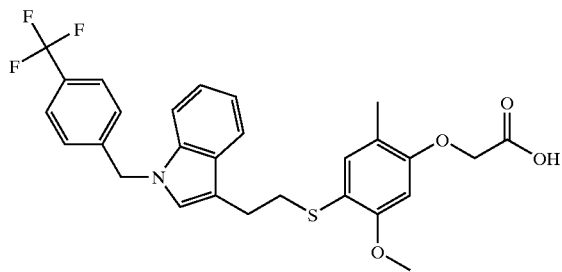

Step 1. Preparation of {4-[2-(1H-Indol-3-yl)-ethylsulfanyl]-5-methoxy-2-methyl-phenoxy}-acetic acid methyl ester (compound 54A)

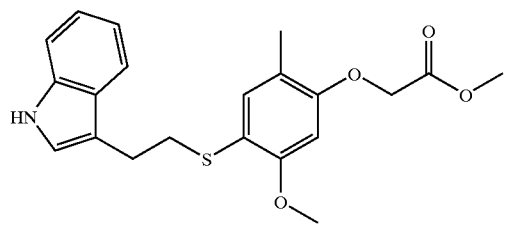

The compound 1D (1.622 g, 6.7 mmol) and 3-(2-bromo-ethyl)-1H-indole (1.50 g, 6.69 mmol) was dissolved in 5 ml DMF. Potassium carbonate (1.11 g, 8.03 mmol) was added followed by stirring at room temperature for 3 h. The reaction was filtered, concentrated and purified by MPLC to give the title compound. MS m/z 225 (M+1).

Step 2. Preparation of (5-Methoxy-2-methyl-4-{2-[1-(4-trifluoromethyl-benzyl)-1H-indol-3-yl]-ethylsulfanyl}-phenoxy)-acetic acid methyl ester (compound 54B)

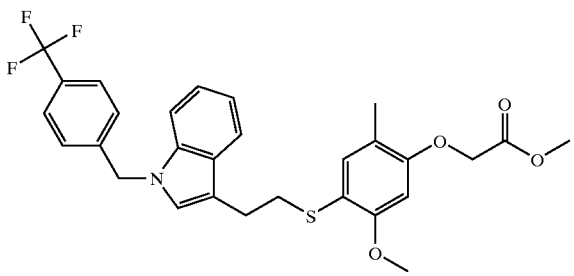

The compound 54A (0.300 g, 0.778 mmol) was dissolved in 5 ml DMF. NaH was added and stirred for ½ h. 4-trifluoromethylbenzyl bromide (0.223 g, 0.934 mmol) was added and the reaction was stirred for 1.5 h. 10 ml 2N HCl was added to pH<4. The DMF solution was partitioned between 30 ml water and 30 ml ethyl. acetate. The organic solution was washed 2×30 ml water 1×30 ml brine, dried over sodium sulfate, decanted, concentrated and purified by MPLC to give the title product. MS m/z 544 (m+1).

Step 3. Preparation of (5-Methoxy-2-methyl-4-{2-[1-(4-trifluoromethyl-benzyl)-1H-indol-3-yl]-ethylsulfanyl}-phenoxy)-acetic acid (compound 54)

The title compound was prepared in the manner analogous to Example 1 using 54B. 400 MHz $^1$H NMR (DMSO-d$_6$) δ 13.0 (br(s), 1H) 7.60 (d, 1H, J=8.1 Hz), 7.42 (d, 1H, J=7.96 Hz), 7.31 (m, 4H), 7.04 (m, 2H), 6.96 (m, 1H), 6.53 (s, 1H), 5.43 (s, 2H), 4.70 (s, 2H), 3.72 (s, 3H), 3.03 (t, 2H, J=8.8 Hz), 2.86 (t, 2H, J=7.6 Hz), 2.04 (s, 3H). MS m/z 530 (M+1).

EXAMPLE 55
Synthesis of [7-(4'-Trifluoromethyl-biphenyl-2-ylmethylsulfanyl)-indan-4-yloxy]-acetic acid (compound 55)

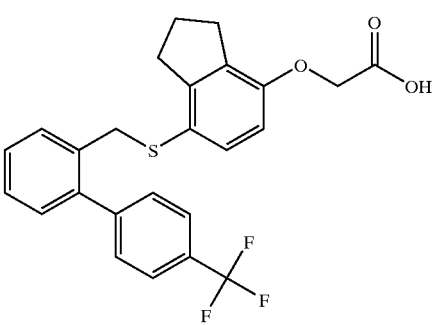

Step 1. Preparation of [7-(4'-Trifluoromethyl-biphenyl-2-ylmethylsulfanyl)-indan-4-yloxy]-acetic acid methyl ester (compound 55A)

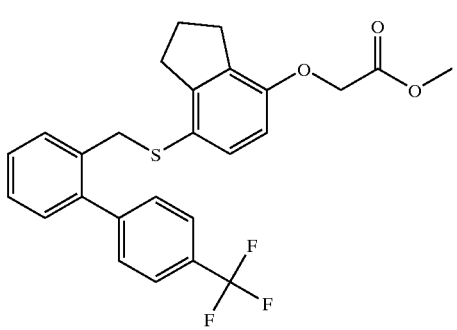

The title compound was prepared in the manner analogous to Example 1F using 12C. and 2-chloromethyl-4'-trifluoromethyl-biphenyl, which was prepared in a manner analogous to Examples 3A and 3B. MS m/z 473 (M+1).

Step 2. Preparation of [7-(4'-Trifluoromethyl-biphenyl-2-ylmethylsulfanyl)-indan-4-yloxy]-acetic acid (compound 55)

The title compound was prepared in the manner analogous to Example 1 using 55A. 400 MHz $^1$H NMR (DMSO-d$_6$) δ 12.97 (br(s), 1H), 7.68 (d, 2H, J=8.5 Hz), 7.32 (m, 5H), 7.11 (m, 1H), 6.77 (d, 1H, J=8.5 Hz), 6.47 (d, 1H, J=8.3 Hz), 4.62 (s, 2H), 3.87 (s, 2H), 2.70 (m, 2H), 1.76 (m, 2H). MS m/z 459 (M+1).

EXAMPLE 56

Synthesis of {5-Methoxy-2-methyl-4-[2-(4-trifluoromethyl-benzyloxy)-benzylsulfanyl]-phenoxy}-acetic acid (compound 56)

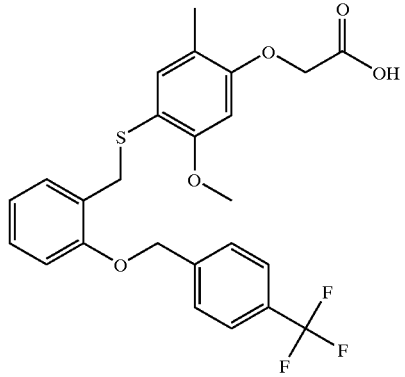

Step 1. Preparation of {5-Methoxy-2-methyl-4-[2-(4-trifluoromethyl-benzyloxy)-benzylsulfanyl]-phenoxy}-acetic acid methyl ester (compound 56A)

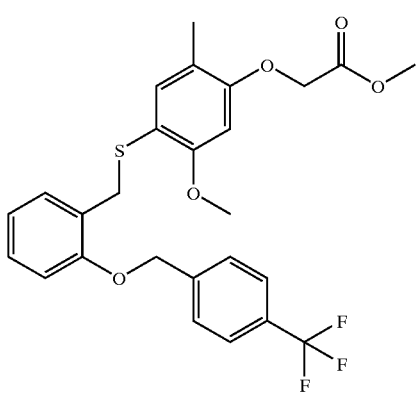

The title compound was prepared in the manner analogous to Example 1F using 81A and 1D. MS m/z 507 (M+1).

Step 2. Preparation of 5-Methoxy-2-methyl-4-[2-(4-trifluoromethyl-benzyloxy)-benzylsulfanyl]-phenoxy}-acetic acid (compound 56)

The title compound was prepared in the manner analogous to Example 1 using 56A. 400 MHz $^1$H NMR (DMSO-$d_6$) δ 12.95 (br(s), 1H), 7.67 (m, 4H), 7.12 (m, 2H), 6.96 (m, 2H), 6.80 (m, 1H), 6.49 (s, 1H), 5.19 (s, 2H), 4.68 (s, 2H), 3.99 (s, 2H), 3.67 (s, 3H), 1.96 (s, 3H). MS m/z 493 (M+1).

EXAMPLE 57

Synthesis of {4-[4-(4-Fluoro-benzyloxy)-benzylsulfanyl]-2-methyl-phenoxy}-acetic acid (compound 57)

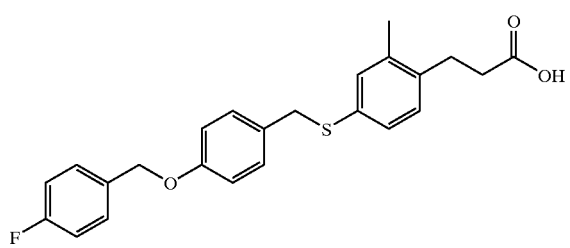

Step 1. Preparation of [4-(4-Fluoro-benzyloxy)-phenyl]-methanol (compound 57A)

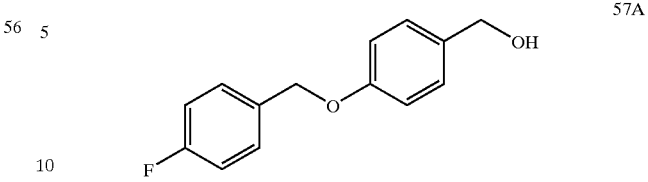

The title compound was prepared in the manner analogous to Example 14A using 1-bromomethyl-4-fluoro-benzene and 4-hydroxymethyl-phenol. MS m/z 215 (M-OH).

Step 2. Preparation of 1-(4-Chloromethyl-phenoxymethyl)-4difluoro-benzene (compound 57B)

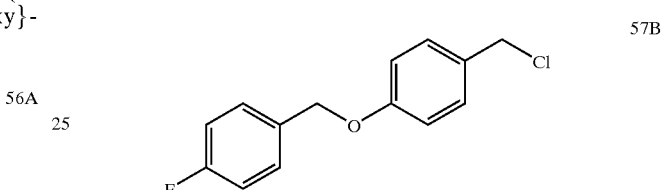

The title compound was prepared in the manner analogous to Example 3B using 57A. MS m/z 215 (M-Cl).

Step 3. Preparation of {4-[4-(4-Fluoro-benzyloxy)-benzylsulfanyl]-2-methyl-phenoxy}-acetic acid methyl ester (compound 57C)

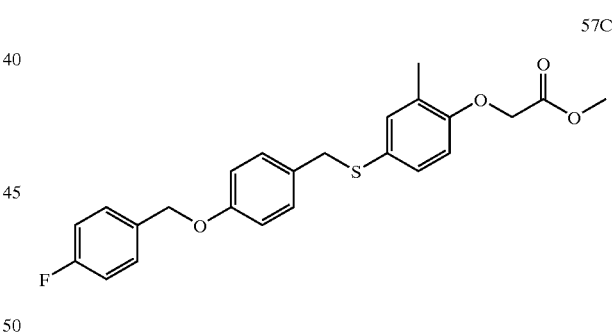

The title compound was prepared in the manner analogous to Example 1F using 57B and 2C. MS m/z 427 (M+1).

Step 4. Preparation of {4-[4-(4-Fluoro-benzyloxy)-benzylsulfanyl]-2-methyl-phenoxy}-acetic acid (compound 57)

The title compound was prepared in the manner analogous to Example 1 using the product from Example 57C. mp 154–155° C.; IR (KBr) cm$^{-1}$: 3050, 2925, 1727, 1495, 1228, 1156; 400 MHz $^1$H NMR (MSO-$d_6$): δ 13.00 (br(s), 1H), 7.37–7.48 (m, 2H) 6.99–7.22 (m, 6H), 6.80–6.90 (m, 2H), 6.69 (d, 1H, J=8.5 Hz), 4.98 (s, 2H), 4.61 (s, 2H), 4.00 (s, 2H), 2.08 (s, 3H); MS m/z 411 (M−1). Anal. Calc'd for $C_{23}H_{21}FO_4S$: C, 66.97; H, 5.13; found: C, 66.64; H, 4.88.

EXAMPLE 58

Synthesis of {4-[4-(4-Chloro-benzyloxy)-benzylsulfanyl]-2-methyl-phenoxy}-acetic acid (compound 58)

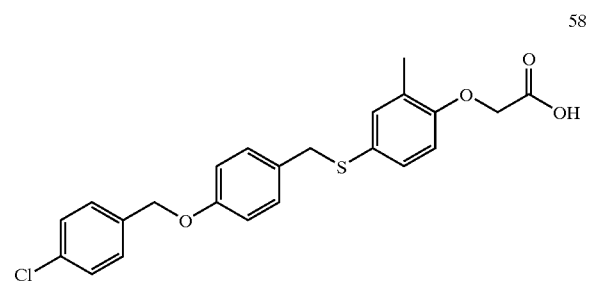

Step 1. Preparation of {4-[4(4Chloro-benzyloxy)-benzylsulfanyl]-2-methyl-phenoxy}-acetic acid methyl ester (compound 58A)

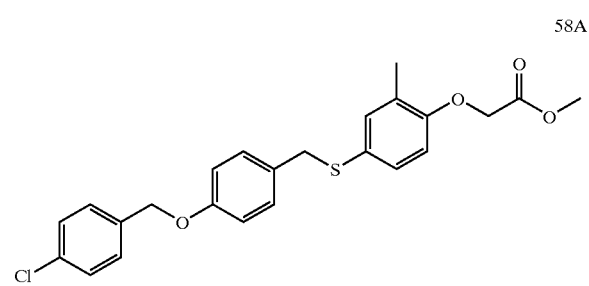

The title compound was prepared in the manner analogous to Example 1F using I-bromomethyl-4-chloro-benzene and the product from Example 35C. MS m/z 443 (M+1).

Step. 2. Preparation of {4-[4-(4-Chloro-benzyloxy)-benzylsulfanyl]-2-methyl-phenoxy)-acetic acid (compound 58)

The title compound was prepared in the manner analogous to Example 1 using 58A. mp 164° C.; IR (KBr) cm$^{-1}$: 3062, 1727, 1612, 1493, 1226, 1193; 400 MHz $^1$H NMR (DMSO-d$_6$): δ 12.99 (br(s), 1H), 7.36–7.44 (m, 4H), 7.01–7.17 (m, 4H), 6.81–6.89 (m, 2H), 6.69 (d, 1H, J=8.5 Hz), 5.01 (s, 2H), 4.61 (s, 2H), 4.00 (s, 2H), 2.08 (s, 3H); MS m/z 427 (M−1). Anal. Calc'd for C$_{23}$H$_{21}$ClO$_4$S: C, 64.40; H, 4.93; found: C, 64.43; H, 4.81.

EXAMPLE 59

Synthesis of 4-[4-(2,5-Dichloro-benzyloxy)-benzylsulfanyl]-2-methyl-phenoxy}-acetic acid (compound 59)

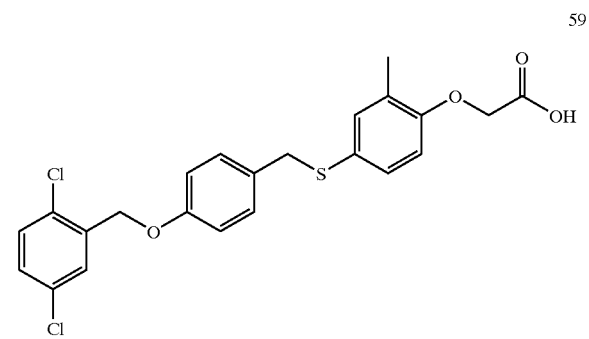

Step 1. Preparation of {4-[4-(2,5-Dichloro-benzyloxy)-benzylsulfanyl]-2-methyl-phenoxy}-acetic acid methyl ester (compound 59A)

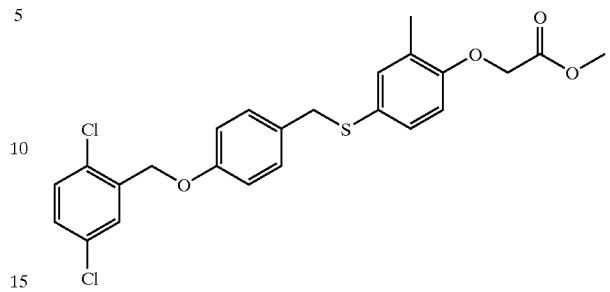

The title compound was prepared in the manner analogous to Example 1F using 2-bromomethyl-1,4-dichloro-benzene and the product prepared from Example 35C. m/z 265 (M-211).

Step 2. Preparation of {4-[4-(2,4-Dichlorobenzyloxy)-benzylsulfanyl]-2-methyl-phenoxy}-acetic acid (compound 59)

The title compound was prepared in the manner analogous to Example 1 using 59A. mp 101–103° C.; IR (KBr) cm$^{-1}$: 3077, 1715, 1608, 1496, 1437, 1234; 400 MHz $^1$H NMR (DMSO-d$_6$): δ 7.37–7.63 (m, 3H), 6.99–7.20 (m, 4H), 6.85–6.94 (m, 2H), 6.63 (d, 1H, J=8.5 Hz), 5.05 (s, 2H), 4.45 (s, 2H), 3.99 (s, 2H), 2.07 (s, 3H); HPLC: area %=97.61, r.t.=5.56 min., λ=214 nm, mobile phase=acetonitrile/water with 0.10% TFA; MS m/z 461 (M−1). Anal. Calc'd for C$_{23}$H$_{20}$Cl$_2$O$_4$S: C, 59.62; H, 4.35; found: C, 58.04; H, 4.26.

EXAMPLE 60

Synthesis of {2-Methyl-4-[4-(pyridine-2-ylmethoxy)-benzylsulfanyl]-phenoxy}-acetic acid (compound 60)

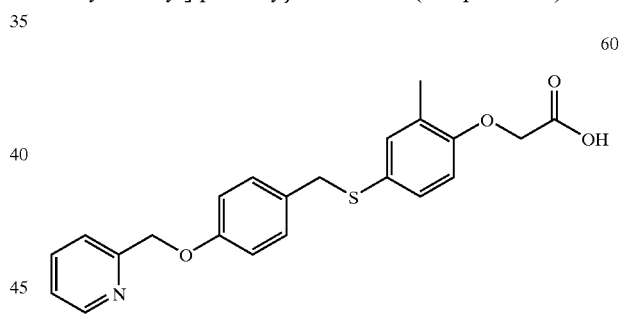

Step 1. Preparation of {2-Methyl-4-[4-(pyridine-2-ylmethoxy)-benzylsulfanyl]-phenoxy}-acetic acid methyl ester (compound 60A)

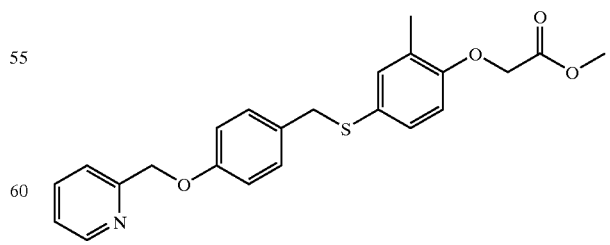

The title compound was prepared in the manner analogous to Example 1F using 2-bromomethyl-pyridine hydrochloride and the product prepared from Example 35C. MS m/z 410 (M+1).

Step 2. Preparation of {2-Methyl-4-[4-(pyridine-2-ylmethoxy)-benzylsulfanyl]-phenoxy)-acetic acid (compound 60)

The title compound was prepared in the manner analogous to Example 1 using 60A. mp 150° C.; IR (KBr) cm$^{-1}$: 2917, 1723, 1605, 1511, 1490,1217; 400 MHz $^1$H NMR (DMSO-d$_6$): δ 12.95 (brs, 1H), 8.49–8.55 (s, 1H), 7.73–7.81 (m, 1H), 7.40–7.48 (m, 1H), 7.24–7.33 (m, 1H), 7.00–7.19 (m, 4H), 6.83–6.93 (m, 2H), 6.69 (d, 1H, J=8.5 Hz), 5.08 (s, 2H), 4.62 (s, 2H), 4.00 (s, 2H), 2.08 (s, 3H); HPLC: area %=96.24, r.t.=1.95 min., γ=214 nm, mobile phase=acetonitrile/water with 0.10% TFA; MS m/z 396 (M+1). Anal. Calc'd for C$_{22}$H$_{21}$NO$_4$S: C, 66.82; H, 5.35; N, 3.54; found: C, 66.12; H, 5.09; N, 3.44.

EXAMPLE 61

Synthesis of {5-Chloro-2-methyl-4-[4-(4-trifluoromethyl-benzyloxy)-benzylsulfanyl]-phenoxy}-acetic acid (compound 61)

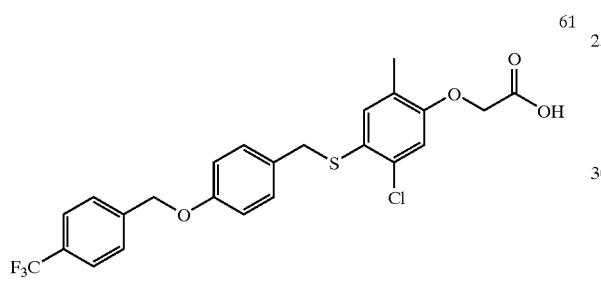

61

Step 1. Preparation of (5-Chloro-2-methyl-4-[4-(4trifluoromethyl-benzyloxy)-benzyl-sulfanyl]-phenoxy}-acetic acid methyl ester (compound 61A)

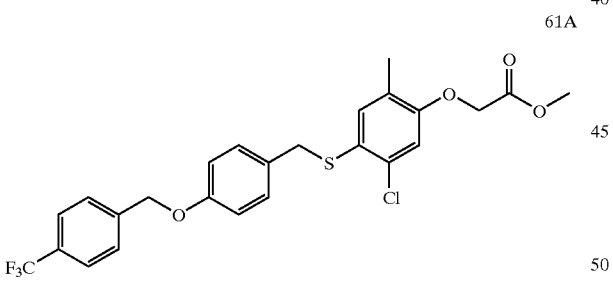

61A

The title compound was prepared in the manner analogous to Example 1F using 14B and 20C. MS m/z 265 (M–245).

Step 2. Preparation of {5-Chloro-2-methyl-4-[4-(4-trifluoromethyl-benzyloxy)-benzyl-sulfanyl]-phenoxy}-acetic acid (compound 61)

The title compound was prepared in the manner analogous to Example 1 using 61A. mp 142–143° C.; IR (KBr) cm$^{-1}$: 3074, 1747, 1321, 1234, 1175, 1124; 400 MHz $^1$H NMR (DMSO-d$_6$): δ 13.01 (br(s), 1H), 7.67–7.73 (m, 2H), 7.57–7.64 (m, 2H), 7.16–7.25 (m, 4H), 6.87–6.95 (m, 4H), 5.15 (s, 2H), 4.69 (s, 2H), 4.07 (s, 2H), 2.07 (s, 3H); MS m/z 495 (M–1). Anal. Calc'd for C$_{24}$H$_{20}$ClF$_3$O$_4$S: C, 58.01; H, 4.06; found: C, 57.73; H, 4.06.

EXAMPLE 62

Synthesis of {7-[4-(2,4Dichloro-benzyloxy)-benzylsulfanyl]-indan-4-yloxy}-acetic acid (compound 62)

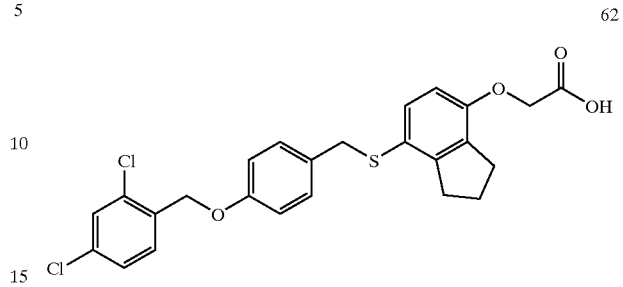

62

Step 1. Preparation of {7-[4(2,4-Dichloro-benzyloxy)-benzylsulfanyl]-indan-4-yloxy}-acetic acid methyl ester (compound 62A)

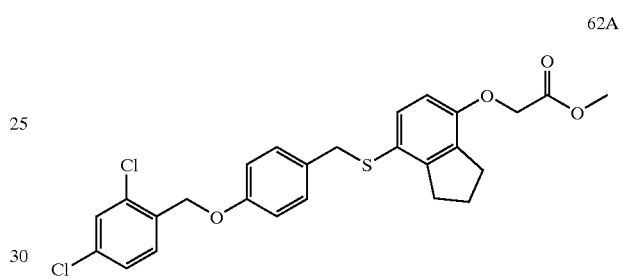

62A

The title compound was prepared in the manner analogous to Example 1F using 12C and 4chloromethyl-(2,4-dichloro-benzyloxy-benzene) prepared from 4-hydroxymethyl-phenol and 1-chloromethyl-2,4-dichloro-benzene in the manner analagous to Examples 14A and 14B. MS m/z 503 (M+1).

Step 2. Preparation of {7-[4-(2,4-Dichloro-benzyloxy)-benzylsulfanyl]-indan-4-yloxy}-acetic acid (compound 62)

The title compound was prepared in the manner analogous to Example 1 using 62A. mp 149–150° C.; IR (KBr) cm$^{-1}$: 3089, 1734, 1512, 1473, 1295, 1234; 400 MHz $^1$H NMR (DMSO-d$_6$): δ 13.11 (br(s), 1H), 7.40–7.71 (m, 3H), 6.88–7.19 (m, 5H), 6.58 (d, 1H, J=8.5 Hz), 5.07 (s, 2H), 4.61 (s, 2H), 3.96 (s, 2H), 2.77 (t, 2H, t, J=7.4 Hz), 2.69 (t, 2H, J=7.4 Hz), 1.91 (pentet, 2H); MS m/z 487 (M–1). Anal. Calc'd for C$_{25}$H$_{22}$Cl$_2$O$_4$S: C, 61.35; H, 4.53; found: C, 60.95; H, 4.41.

EXAMPLE 63

Synthesis of {7-[4-(4-Trifluoromethyl-benzyloxy)-benzylsulfanyl]-indan-4-yloxy}-acetic acid (compound 63)

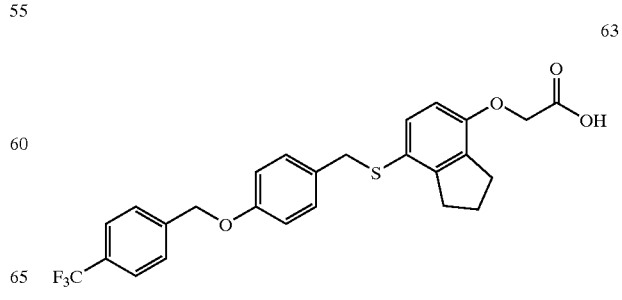

63

Step 1. Preparation of {7-[4-(4-Trifluoromethyl-benzyloxy)-benzylsulfanyl]-indan-4-yloxy}-acetic acid methyl ester (compound 63A)

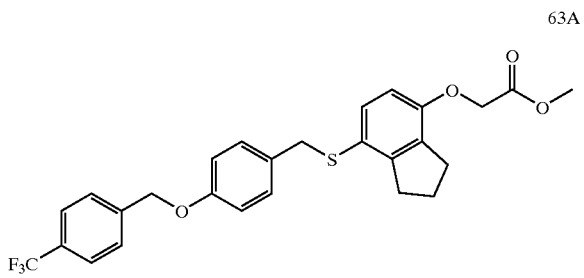

63A

The title compound was prepared in the manner analogous to Example 1F using 14B and 12C. MS m/z 265 (M−237).
Step 2. Preparation of {7-[4-(4-Trifluoromethyl-benzyloxy)-benzylsulfanyl]-indan-4-yloxy}-acetic acid (compound 63)
The title compound was prepared in the manner analogous to Example 1 using 63A. mp 145° C.; IR (KBr) cm$^{-1}$: 2968, 1740, 1510, 1325, 1248, 1110; 400 MHz $^1$H NMR (DMSO-d$_6$): δ 12.99 (br(s), 1H), 7.66–7.75 (m, 2H), 7.55–7.65 (m, 2H); 7.01–7.15 (m, 3H) 6.83–6.90 (m, 2H), 6.56 (d, 1H, J=8.5 Hz), 5.14 (s, 2H), 4.60 (s, 2H), 3.93 (s, 2H), 2.74 (t, 2H, t, J=7.6 Hz), 2.65 (t, 2H, J=7.4 Hz), 1.87 (pentet, 2H); MS m/z 487 (M−1). Anal. Calc'd for C$_{26}$H$_{23}$F$_3$O$_4$S: C, 63.92; H, 4.75; found: C, 63.95; H, 4.65.

EXAMPLE 64
Synthesis of {5-Methyl-7-[4-(4-trifluoromethyl-benzyloxy)-benzylsulfanyl]-indan-4-yloxy}-acetic acid (compound 64)

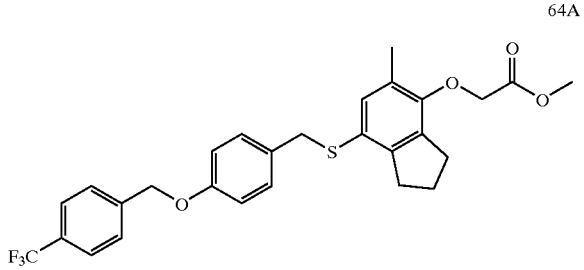

64

Step 1. Preparation of {5-Methyl-7-[4-(4-trifluoromethyl-benzyloxy)-benzylsulfanyl]-indan-4yloxy}-acetic acid methyl ester (compound 64A)

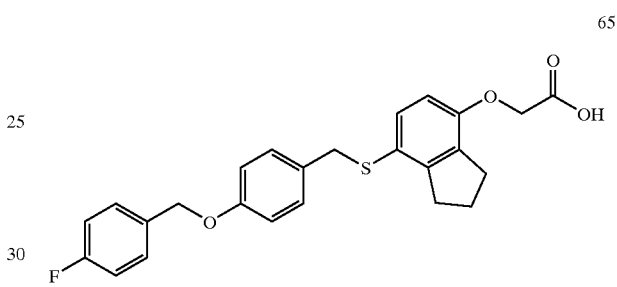

64A

The title compound was prepared in the manner analogous to Example 1F using 14B and (7-mercapto-5-methyl-indan-4-yloxy)-acetic acid methyl ester, which was prepared in a similar manner as described for Example 12C. MS m/z 265 (M−251).

Step 2. Preparation of {5-Methyl-7-[4-(4-trifluoromethyl-benzyloxy)-benzylsulfanyl]-indan-4-yloxy}-acetic acid (compound 64)

The title compound was prepared in the manner analogous to Example 1 using 64A. mp 165–167° C.; IR (KBr) cm$^{-1}$: 3039, 1707, 1516, 1329, 1163, 1112; 400 MHz $^1$H NMR (DMSO-d$_6$) δ 12.81 (br(s), 1H), 7.66–7.74 (m, 2H), 7.56–7.64 (m, 2H); 7.11–7.19 (m, 2H), 6.94 (s, 1H), 6.85–6.91 (m, 2H), 5.15 (s, 2H), 4.40 (s, 2H), 3.99 (s, 2H), 2.81 (t, 2H, J=7.4 Hz), 2.59 (t, 2H, J=7.4 Hz), 2.13 (s, 3H), 1.86 (pentet, 2H); MS m/z 501 (M−1). Anal. Calc'd for C$_{27}$H$_{25}$F$_3$O$_4$S: C, 64.53; H, 5.01; found: C, 64.33; H, 4.82.

EXAMPLE 65

Synthesis of {7-[4-(4-Fluoromethyl-benzyloxy)-benzylsulfanyl]-indan-4-yloxy}-acetic acid (compound 65)

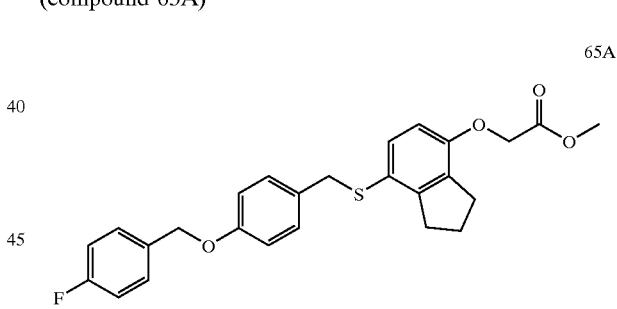

65

Step 1. Preparation of {7-[4-(4-Fluoromethyl-benzyloxy)-benzylsulfanyl]-indan-4-yloxy}-acetic acid methyl ester (compound 65A)

65A

The title compound was prepared in the manner analogous to Example 1F using 12C and 4-chloromethyl-(4-fluoro-benzyloxy-benzene), prepared from 4-hydroxymethyl-phenol and 1-bromomethyl-4-fluoro-benzene in a manner analagous to Examples 14A and 14B. MS m/z 453 (M+1).

Step 2. Preparation of {7-[4-(4-Fluoromethyl-benzyloxy)-benzylsulfanyl]-indan-4-yloxy}-acetic acid (compound 65)

The title compound was prepared in the manner analogous to Example 1 using 65A. mp 153–155° C.; IR (KBr) cm$^{-1}$: 3117, 3028, 1731, 1512, 1471, 1231; 400 MHz $^1$H NMR (DMSO-d$_6$): δ 12.94 (br(s), 1H), 7.39–7.47 (m, 2H), 7.01–7.20 (m, 5H); 6.82–6.89 (m, 2H) 6.56 (d, 1H, J=8.4 Hz), 4.99 (s, 2H), 4.61 (s, 2H), 3.94 (s, 2H), 2.75 (t, 2H, J=7.5 Hz), 2.67 (t, 2H, J=7.5 Hz), 1.89 (pentet, 2H); MS m/z 437 (M−1). Anal. Calc'd for C$_{25}$H$_{23}$FO$_4$S: C, 68.48; H, 5.29; found: C, 68.24; H, 5.15.

EXAMPLE 66
Synthesis of {7-[4-(2,4-Difluoro-benzyloxy)-benzylsulfanyl]-indan-4-yloxy}-acetic acid (compound 66)

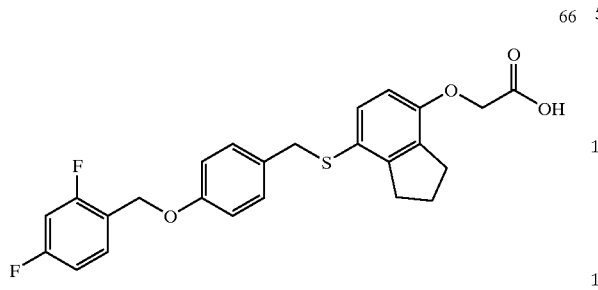

Step 1. Preparation of {17-[4(2,4-Difluoro-benzyloxy)-benzylsulfanyl]-indan-4-yloxy}-acetic acid methyl ester (compound 66A)

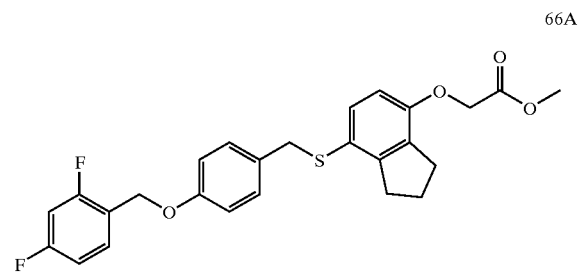

The title compound was prepared in the manner analogous to Example 1F using 12C and 4chloromethyl-(2,4-difluoro-benzyloxy-benzene) prepared from 4-hydroxymethyl-phenol and 1-bromomethyl-2,4-difluoro-benzene in the manner analagous to Examples 14A and 14B. MS m/z 471 (M+1).

Step 2. Preparation of {7-[4-(2,4-Difluoro-benzyloxy)-benzylsulfanyl]-indan-4-yloxy}-acetic acid (compound 66)
The title compound was prepared in the manner analogous to Example 1 using 66A. mp 158–160° C.; IR (KBr) cm$^{-1}$: 3065, 3043, 1751, 1510, 1433, 1239; 400 MHz $^1$H NMR (DMSO-d$_6$): δ 12.94 (br(s), 1H), 7.51–7.61 (m, 1H), 7.21–7.30 (m, 1H); 7.01–7.16 (m, 4H) 6.83–6.92 (m, 2H), 6.57 (d, 1H, J=8.5 Hz), 5.01 (s, 2H), 4.61 (s, 2H), 3.94 (s, 2H), 2.76 (t, 2H, J=7.4 Hz), 2.68 (t, 2H, J=7.4 Hz), 1.90 (pentet, 2H); MS m/z 455 (M−1). Anal. Calc'd for C$_{25}$H$_{22}$F$_2$O$_4$S: C, 65.78; H, 4.86; found: C, 65.58; H, 4.83.

EXAMPLE 67
Synthesis of {7-[4-(4-tert-Butyl-benzyloxy)-benzylsulfanyl]-indan-4-yloxy}-acetic acid (compound 67)

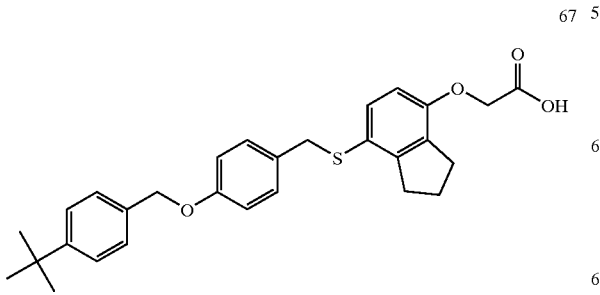

Step 1. Preparation of {7-[4(4-tert-Butyl-benzyloxy)-benzylsulfanyl]-indan-4-yloxy}-acetic acid methyl ester (compound 67A)

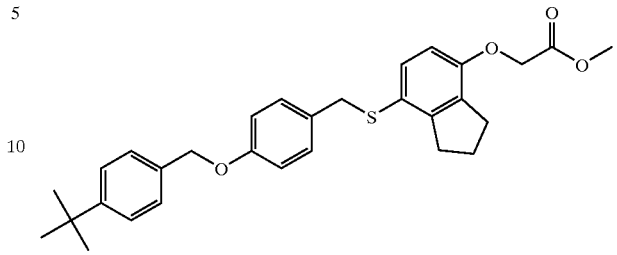

The title compound was prepared in the manner analogous to Example 1F using 12C and 4-chloromethyl-(4-tert-butyl-benzyloxy-benzene) prepared from 4-hydroxymethyl-phenol and 1-bromomethyl-4-tert-butyl-benzene in the manner analagous to Examples 14A and 14B. m/z 491 (M+1).

Step 2. Preparation of {7-[4(4-tert-Butyl-benzyloxy)-benzylsulfanyl]-indan-4-yloxy}-acetic acid (compound 67)
The title compound was prepared in the manner analogous to Example 1 using 67A. mp 152–153° C.; IR (KBr) cm$^{-1}$: 3134, 3032, 1745, 1708, 1473, 1228; 400 MHz $^1$H NMR (DMSO-d$_6$): δ 12.94 (br(s), 1H), 7.25–7.39 (m, 4H), 7.01–7.14 (m, 3H) 6.80–6.89 (m, 2H), 6.57 (d, 1H, J=8.5 Hz), 4.97 (s, 2H), 4.61 (s, 2H), 3.93 (s, 2H), 2.75 (t, 2H, J=7.5 Hz), 2.67 (t, 2H, J=7.5 Hz), 1.89 (pentet, 2H), 1.22 (s, 9H); MS m/z 475 (M−1). Anal. Calc'd for C$_{29}$H$_{32}$O$_4$S: C, 73.08; H, 6.77; found: C, 72.97; H, 6.84.

EXAMPLE 68
Synthesis of {7-[4-(4-Methoxy-benzyloxy)-benzylsulfanyl]-indan-4-yloxy}-acetic acid (compound 68)

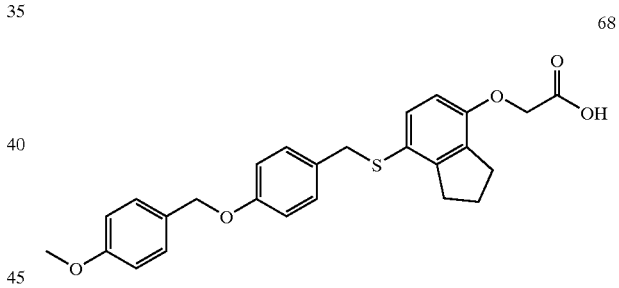

Step 1. Preparation of {7-[4-(4-Methoxy-benzyloxy)-benzylsulfanyl]-indan-4-yloxy}-acetic acid methyl ester (compound 68A)

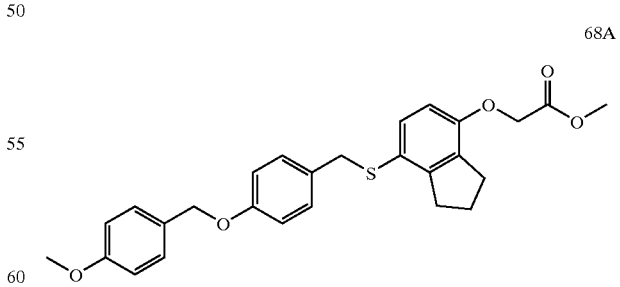

The title compound was prepared in the manner analogous to Example 1F using 12C and 4-chloromethyl-(4-methoxy-benzyloxy-benzene) prepared from 4-hydroxymethyl-phenol and 1-bromomethyl-4-methoxy-benzene in the manner analagous to Examples 14A and 14B. MS m/z 465 (M+1).

Step 2. Preparation of {7-[4-(4-Methoxy-benzyloxy)-benzylsulfanyl]-indan-4-yloxy}-acetic acid (compound 68)

The title compound was prepared in the manner analogous to Example 1 using 68A. mp 183–185° C.; IR (KBr) cm$^{-1}$: 3015, 2588, 1742, 1716, 1514, 1243; 400 MHz $^1$H NMR (DMSO-d$_6$): δ 12.97 (br(s), 1H), 7.26–7.34 (m, 2H), 7.06–7.13 (m, 2H) 7.04 (d, 1H, J=8.5 Hz), 6.80–6.92 (m, 4H), 6.56 (d, 1H, J=8.5 Hz), 4.92 (s, 2H), 4.60 (s, 2H), 3.93 (s, 2H), 3.69 (s, 3H), 2.75 (t, 2H, J=7.3 Hz), 2.67 (t, 2H, J=7.3 Hz), 1.89 (pentet, 2H); MS m/z 449 (M−1). Anal. Calc'd for C$_{26}$H$_{26}$O$_5$S: C, 69.31; H, 5.82; found: C, 69.00; H, 5.74.

EXAMPLE 69

Synthesis of [7-(4Benzyloxy-benzylsulfanyl)-indan-4-yloxy]-acetic acid (compound 69)

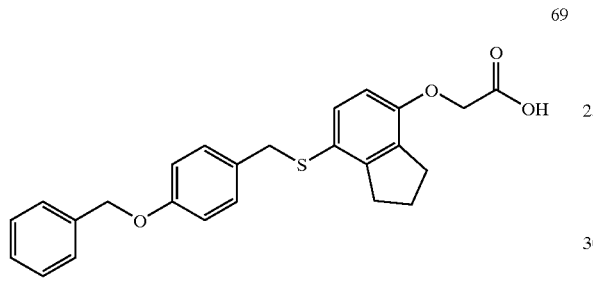

Step 1. Preparation of [7-(4-Benzyloxy-benzylsulfanyl)-indan-4-yloxy]-acetic acid methyl ester (compound 69A)

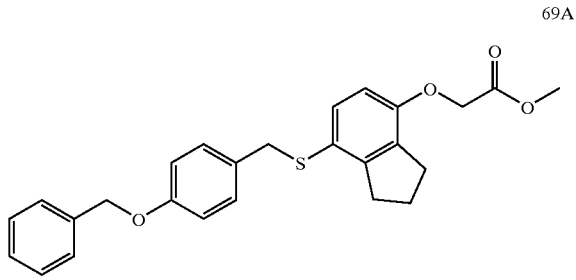

The title compound was prepared in the manner analogous to Example 1F using 12C and 1-benzyloxy-4-chloromethyl-benzene prepared from 4-hydroxymethyl-phenol and 4-bromomethyl-benzene in the manner analagous to Examples 14A and 14B. MS m/z 435 (M+1).

Step 2. Preparation of [7-(4-Benzyloxy-benzylsulfanyl)-indan-4-yloxy]-acetic acid (compound 69)

The title compound was prepared in the manner analogous to Example 1 using 69A. mp 145–147° C.; IR (KBr) cm$^{-1}$: 3066, 2584, 1742, 1511, 1234; 400 MHz $^1$H NMR (DMSO-d$_6$): δ 12.94 (br(s), 1H), 7.21–7.44 (m, 5H), 6.99–7.15 (m, 3H) 6.80–6.90 (m, 2H), 6.56 (d, 1H, J=8.3 Hz), 5.01 (s, 2H), 4.61 (s, 2H), 3.93 (s, 2H), 2.75 (t, 2H, J=7.3 Hz), 2.67 (t, 2H, J=7.3 Hz), 1.89 (pentet, 2H); MS m/z 419 (M−1). Anal. Calc'd for C$_{25}$H$_{24}$O$_4$S: C, 71.40; H, 5.75; found: C, 71.46; H, 5.75.

EXAMPLE 70

Synthesis of {7-[4-(4-Chloro-benzyloxy)-benzylsulfanyl]-indan-4-yloxy}-acetic acid (compound 70)

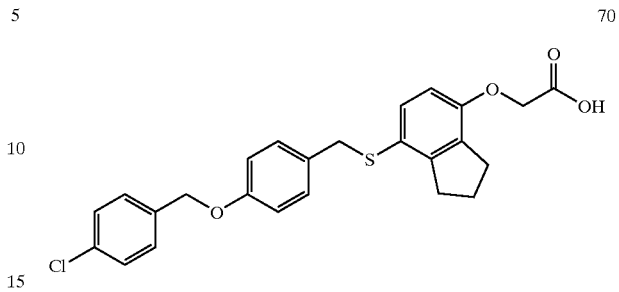

Step 1. Preparation of {7-[4(4Chloro-benzyloxy)-benzylsulfanyl]-indan-4-yloxy}-acetic acid methyl ester (compound 70A)

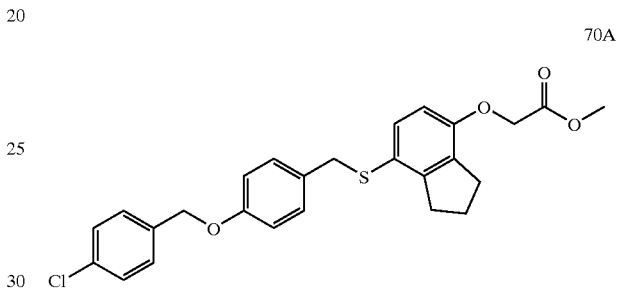

The title compound was prepared in the manner analogous to Example 1F using 12C and 1-(4-chloro-benzyloxy) 4chloromethyl benzene prepared from 1-bromomethyl-4-chloro-benzene and 4-hydroxymethyl-phenol in the manner analagous to Examples 14A and 14B. MS m/z 469 (M+1).

Step 4. Preparation of {7-[4-(4-Chloro-benzyloxy)-benzylsulfanyl]-indan-4-yloxy}-acetic acid (compound 70)

The title compound was prepared in the manner analogous to Example 1 using 70A. mp 170–172° C.; IR (KBr) cm$^{-1}$: 3054, 25.77, 1731, 1710, 1471, 1234; 400 MHz $^1$H NMR (DMSO-d$_6$): δ 12.95 (br(s), 1H), 7.39 (s, 4H), 6.99–7.25 (m, 3H), 6.79–6.97 (m, 2H), 6.56 (d, 1H, J=8.4 Hz), 5.01 (s, 2H), 4.60 (s, 2H), 3.93 (s, 2H), 2.74 (t, 2H, J=7.4 Hz), 2.66 (t, 2H, J=7.4 Hz), 1.88 (pentet, 2H); MS m/z 453 (M−1). Anal. Calc'd for C$_{25}$H$_{23}$ClO$_4$S: C, 66.00; H, 5.10; found: C, 65.95; H, 4.97.

EXAMPLE 71

Synthesis of {7-[4-(2,5-Dichloro-benzyloxy)-benzylsulfanyl]-indan-4-yloxy}-acetic acid (compound 71)

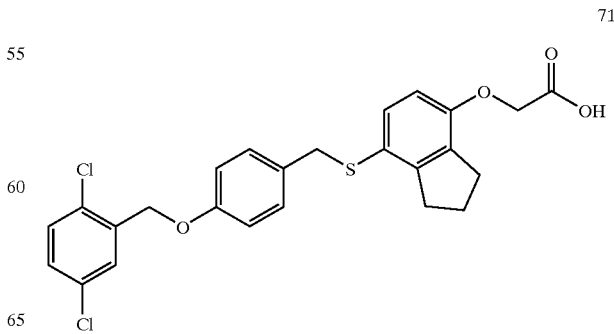

Step 1. Preparation of {7-[4(2,5-Dichloro-benzyloxy)-benzylsulfanyl]-indan-4-yloxy}-acetic acid methyl ester (compound 71A)

71A

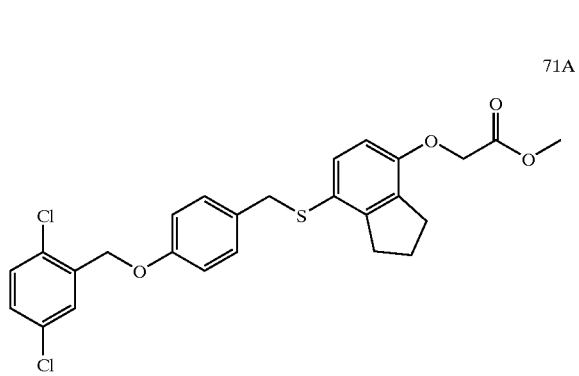

The title compound was prepared in the manner analogous to Example 1F using 12C and 1,4-Dichloro-2-(4-chloromethyl-phenoxymethyl)-benzene prepared from 1,4-dichloro-2-chloromethyl-benzene and 4-hydroxymethyl-phenol in the manner analagous to Examples 14A and 14B. MS m/z 265 (M−237).

Step 2. Preparation of {7-[4-(2,5-Dichloro-benzyloxy)-benzylsulfanyl]-indan-4-yloxy}acetic acid (compound 71)

The title compound was prepared in the manner analogous to Example 1 using 71A. mp 158–160° C.; IR (KBr) cm$^{-1}$: 3070, 2573, 1747, 1716, 1236, 1106; 400 MHz $^1$H NMR (DMSO-d$_6$): δ 12.95 (br(s), 1H), 7.57–7.62 (m, 1H) 7.47–7.53 (m, 1H), 7.38–7.45 (m, 1H), 7.08–7.16 (m, 2H), 7.04 (d, 1H, J=8.5 Hz), 6.85–6.92 (m, 2H), 6.56 (d, 1H, J=8.5 Hz), 5.06 (s, 2H), 4.61 (s, 2H), 3.94 (s, 2H), 2.75 (t, 2H, J=7.3 Hz), 2.67 (t, 2H, J=7.3 Hz), 1.89 (pentet, 2H); MS m/z 487 (M−1). Anal. Calc'd for C$_{25}$H$_{22}$Cl$_2$O$_4$S: C, 61.35; H, 4.53; found: C, 61.24; H, 4.43.

EXAMPLE 72

Synthesis of {7-[4-(3,4-Dichloro-benzyloxy)-benzylsulfanyl]-indan-4-yloxy}-acetic acid (compound 72)

72

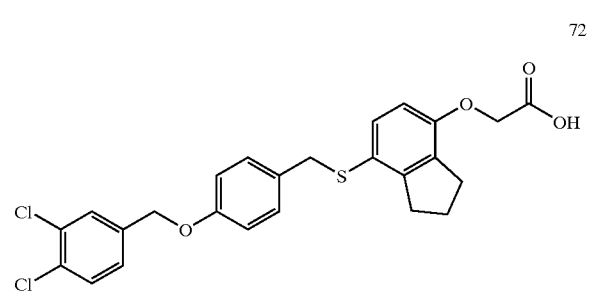

Step 1. Preparation of {7-[4(3,4Dichloro-benzyloxy)-benzylsulfanyl]-indan-4-yloxy}-acetic acid methyl ester (compound 72A)

72A

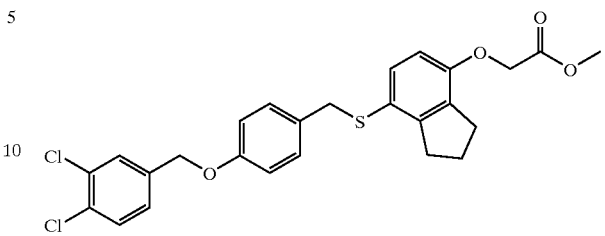

The title compound was prepared in the manner analogous to Example 1F using 12C and 1,2-Dichloro-4-(4-chloromethyl-phenoxymethyl)-benzene prepared from 1-bromomethyl-3,4-dichloro-benzene and 4-hydroxymethyl-phenol in the manner analagous to Examples 14A and 14B. MS m/z 503 (M+1).

Step 2. Preparation of {7-[4-(3,4Dichloro-benzyloxy)-benzylsulfanyl]-indan-4-yloxy}-acetic acid (compound 72)

The title compound was prepared in the manner analogous to Example 1 using 72A. mp 168° C.; IR (KBr) cm$^{-1}$: 3084, 3039, 1744, 1708, 1244, 1226; 400 Mz $^1$H NMR (DMSO-d$_6$): δ 12.95 (br(s), 1H), 7.57–7.67 (m, 2H) 7.37 (dd, 1H, J=8.3, 2.0 Hz), 7.01–7.14 (m, 3H), 6.82–6.89 (m, 2H), 6.56 (d, 1H, J=8.4 Hz), 5.04 (s, 2H), 4.61 (s, 2H), 3.93 (s, 2H), 2.75 (t, 2H, J=7.4 Hz), 2.66 (t, 2H, J=7.4 Hz), 1.88 (pentet, 2H); MS m/z 487 (M−1). Anal. Calc'd for C$_{25}$H$_{22}$Cl$_2$O$_4$S: C, 61.35; H, 4.53; found: C, 61.13; H, 4.38.

EXAMPLE 73

Synthesis of {7-[4-(4Chloro-3-trifluoromethyl-benzyloxy)-benzylsulfanyl]-indan-4-yloxy}-acetic acid (compound 73)

73

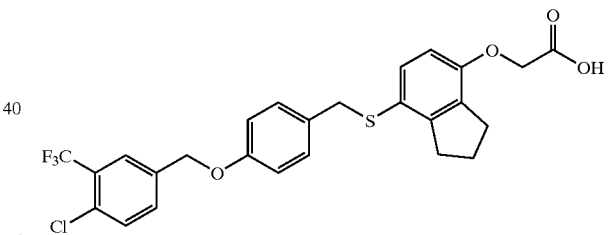

Step 1. Preparation of {7-[4-(4-Chloro-3-trifluoromethyl-benzyloxy)-benzylsulfanyl]-indan-4-yloxy}-acetic acid methyl ester (compound 73A)

73A

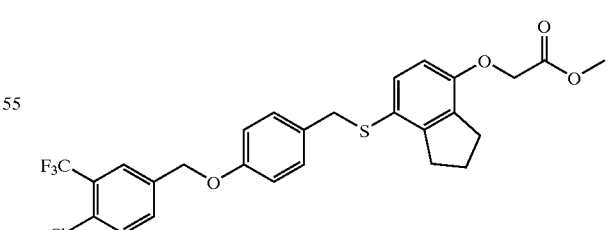

The title compound was prepared in the manner analogous to Example 1F using 12C and 1-Chloro-4-(4-chloromethyl-phenoxymethyl)-2-trifluoromethyl-benzene prepared from 1-bromomethyl-4-chloro-3-trifluoromethyl-benzene and 4-hydroxymethyl-phenol in the manner analagous to Examples 14A and 14B. MS m/z 299 (M−237).

Step 2. Preparation of {7-[4-(4-Chloro-3-trifluoromethyl-benzyloxy)-benzylsulfanyl]-indan-4-yloxy}-acetic acid (compound 73)

The title compound was prepared in the manner analogous to Example 1 using 73A. mp 151–152° C.; IR (KBr) cm$^{-1}$: 3076, 3050, 1748, 1426, 1244, 1109; 400 MHz $^1$H NMR (DMSO-d$_6$): δ 12.94 (br(s), 1H), 7.87 (s, 1H), 7.68–7.72 (m, 2H) 7.00–7.15 (m, 3H), 6.82–6.92 (m, 2H), 6.56 (d, 1H, J=8.5 Hz), 5.12 (s, 2H), 4.61 (s, 2H), 3.94 (s, 2H), 2.74 (t, 2H, J=7.5 Hz), 2.66 (t, 2H, J=7.5 Hz), 1.87 (pentet, 2H); MS m/z 521 (M−1). Anal. Calc'd for C26H$_{22}$ClF$_3$O$_4$S: C, 59.71; H, 4.24; found: C, 59.54; H, 4.11.

EXAMPLE 74

Synthesis of {7-[4-(4-Fluoro-3-trifluoromethyl-benzyloxy)-benzylsulfanyl]-indan-4-yloxy}-acetic acid (compound 74)

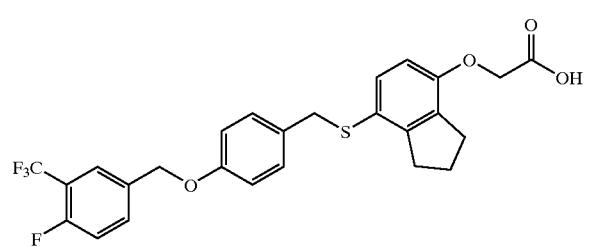

Step 1. Preparation of {7-[4-(4-Fluoro-3-trifluoromethyl-benzyloxy)-benzylsulfanyl]-indan-4-yloxy}-acetic acid methyl ester (compound 74A)

74A

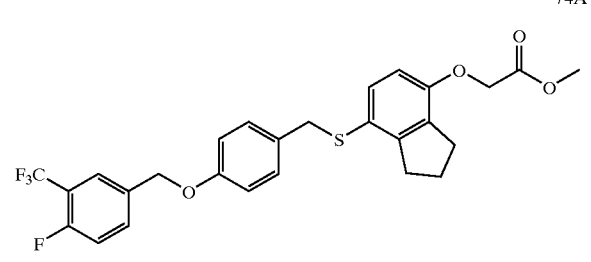

The title compound was prepared in the manner analogous to Example 1F using 12C and 4-(4-Chloromethyl-phenoxymethyl)-1-fluoro-2-trifluoromethyl-benzene prepared from 1-bromomethyl-4-fluoro-3-trifluoromethyl-benzene and 4-hydroxymethyl-phenol in the manner analagous to Examples 14A and 14B. MS m/z 283 (M−237).

Step 2. Preparation of {7-[4-(4-Fluoro-3-trifluoromethyl-benzyloxy)-benzylsulfanyl]-indan-4-yloxy}-acetic acid (compound 74)

The title compound was prepared in the manner analogous to Example 1 using 74A. mp 116–117° C.; IR (KBr) cm$^{-1}$: 3028, 1741, 1704, 1511, 1235, 1110; 400 MHz $^1$H NMR (DMSO-d$_6$): δ 12.96 (br(s), 1H), 7.74–7.85 (m, 2H) 7.45–7.54 (m, 1H), 7.08–7.15 (m, 2H), 7.04 (d, 1H, J=8.5 Hz), 6.84–6.91 (m, 2H), 6.56 (d, 1H, J=8.5 Hz), 5.09 (s, 2H), 4.61 (s, 2H), 3.94 (s, 2H), 2.75 (t, 2H, J=7.5 Hz), 2.66 (t, 2H, J=7.5 Hz), 1.88 (pentet, 2H); MS m/z 505 (M−1). Anal. Calc'd for C$_{26}$H$_{22}$F$_4$O$_4$S: C, 61.65; H, 4.38; found: C, 61.50; H, 4.07.

EXAMPLE 75

Synthesis of {7-[4-(4-Trifluoromethoxy-benzyloxy)-benzylsulfanyl]-indan-4-yloxy}-acetic acid (compound 75)

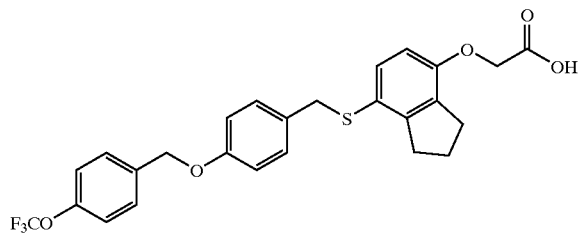

Step 1. Preparation of [7-(4-Acetoxy-benzylsulfanyl)-indan-4-yloxy]-acetic acid methyl ester (compound 75A)

75A

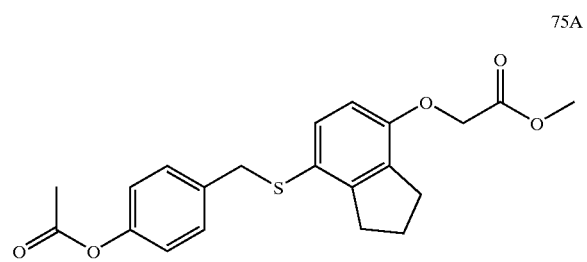

The title compound was prepared in the manner analogous to Example 35A using acetic acid 4-chloromethyl-phenyl ester and 12C. MS m/z 387 (M+1).

Step 2. Preparation of [7-(4-Hydroxy-benzysulfanyl)-indan-4-yloxy]-acetic acid (compound 75B)

75B

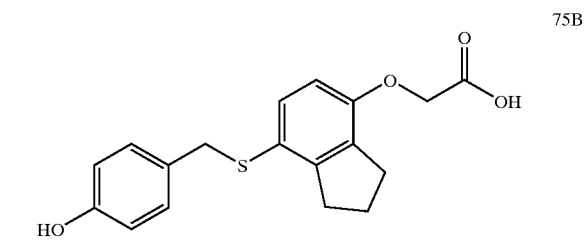

The title compound was prepared in the manner analogous to Example 35B using 75A. MS m/z 391 (M−1).

Step 3. Preparation of [7-(4-Hydroxy-benzylsulfanyl)-indan-4-yloxy]-acetic acid methyl ester (compound 75C)

75C

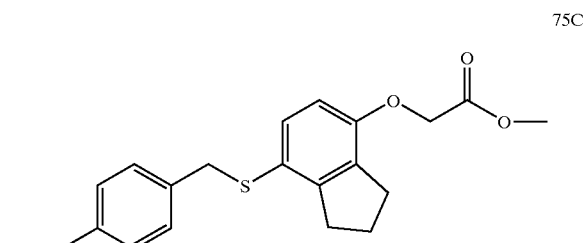

The title compound was prepared in the manner analogous to Example 35C using the product from Example 75B. MS m/z 237 (M−107).

Step 4. Preparation of {7-[4-(4-Trifluoromethoxy-benzyloxy)-benzylsulfanyl]-indan-4-yloxy}-acetic acid methyl ester (compound 75D)

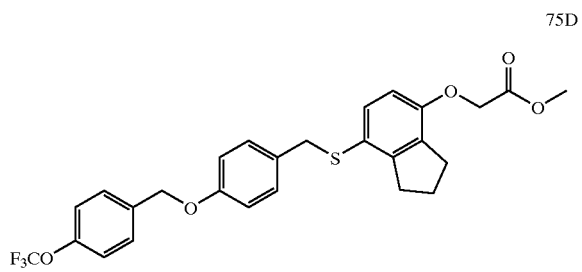

75D

The title compound was prepared in the manner analogous to Example 1F using 1-bromomethyl-4-trifluoromethoxy-benzene and 75C. MS m/z 519 (M+1).

Step 5. Preparation of {7-[4-(4-Trifluoromethoxy-benzyloxy)-benzylsulfanyl]-indan-4-yloxy}-acetic acid (compound 75)

The title compound was prepared in the manner analogous to Example 1 using 75D. mp 140–142° C.; IR (KBr) cm$^{-1}$: 3072, 3043, 1724, 1511, 1226, 1156; 400 MHz $^1$H NMR (DMSO-$_6$): δ 12.95 (br(s), 1H), 7.47–7.57 (m, 2H), 7.29–7.39 (m, 2H), 7.00–7.16 (m, 3H), 6.81–6.91 (m, 2H), 6.56 (d, 1H, J=8.5 Hz), 5.05 (s, 2H), 4.61 (s, 2H), 3.94 (s, 2H), 2.75 (t, 2H, J=7.4 Hz), 2.67 (t, 2H, J=7.4 Hz), 1.88 (pentet, 2H) MS m/z 503 (M–1). Anal. Calc'd for $C_{26}H_{23}F_3O_5S$: C, 61.90; H, 4.60; found: C, 61.53; H, 4.36.

EXAMPLE 76

Synthesis of {7-[4-(4-Fluoro-2-trifluoromethyl-benzyloxy)-benzylsulfanyl]-indan-4-yloxy}-acetic acid (compound 76)

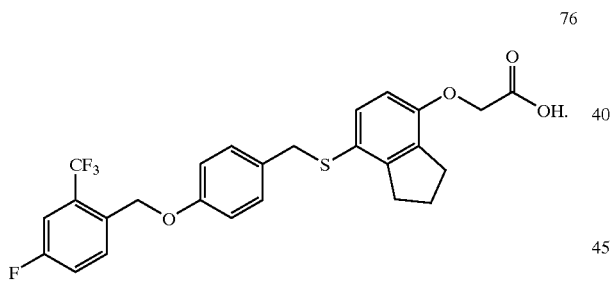

76

Step 1. Preparation of {7-[4-(4-Fuoro-2-trifluoromethyl-benzyloxy)-benzylsulfanyl]-indan-4-yloxy}-acetic acid methyl ester (compound 76A)

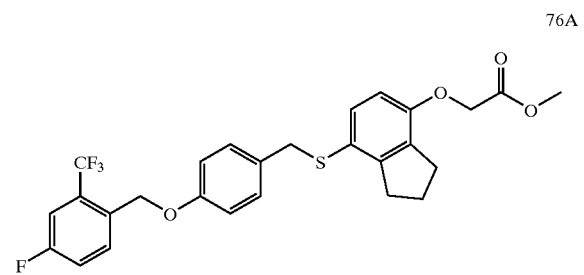

76A

The title compound was prepared in the manner analogous to Example 1F using 1-bromomethyl-fluoro-2-trifluoromethyl-benzene and the product prepared from Example 75C. MS m/z 283

Step 2. Preparation of {7-[4-(4-Fluoro-2-trifluoromethyl-benzyloxy)-benzylsulfanyl]-indan-4-yloxy}-acetic acid (compound 76)

The title compound was prepared in the manner analogous to Example 1 using 76A. mp 125–127° C.; IR (KBr) cm$^{-1}$: 3132, 3032, 1742, 1708, 1244, 1110; 400 MHz $^1$H NR (DMSO-$d_6$): δ 12.95 (br(s), 1H), 7.71–7.81 (m, 1H), 7.65 (dd, 1H, J=9.3, 2.6 Hz), 7.51–7.61 (m, 1H), 7.01–7.19 (m, 3H), 6.81–6.91 (m, 2H), 6.57 (d, 1H, J=8.5 Hz), 5.11 (s, 2H), 4.61 (s, 2H), 3.95 (s, 2H), 2.75 (t, 2H, J=7.4 Hz), 2.66 (t, 2H, J=7.4 Hz), 1.89 (pentet, 2H); MS m/z 502 (M–1). Anal. Calc'd for $C_{26}H_{22}F_4O_4S$: C, 61.65; H, 4.38; found: C, 61.28; H, 4.12.

EXAMPLE 77

Synthesis of {7-[4-(3,5-Dichloro-benzyloxy)-benzylsulfanyl]-indan-4-yloxy}-acetic acid (compound 77)

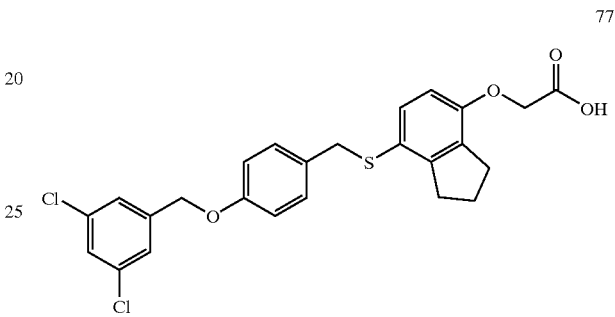

77

Step 1. Preparation of {7-[4(3,5-Dichloro-benzyloxy)-benzylsulfanyl]-indan-4-yloxy}-acetic acid methyl ester (compound 77A)

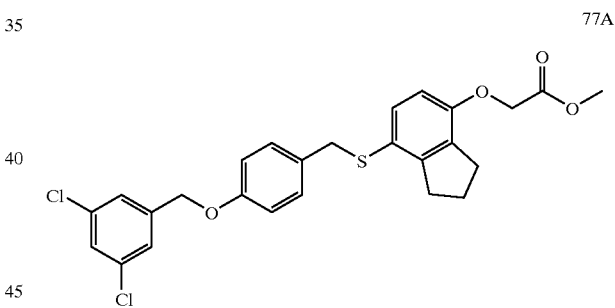

77A

The product from Example 75C (0.42 g, 1 mmoles), (3,5-dichlorophenyl)-methanol (0.24 g, 1.3 mmoles), triphenyl phosphine (0.38 g, 1.5 mmoles), and 0.23 mL of diethyl azodicarboxylate (0.25 g, 1.5 mmoles) were dissolved in 9 mL of tetrahydrofuran. The reaction mixture was stirred at room temperature under nitrogen for 18 hrs. The reaction mixture was evaporated to give a residue, which was flash chromatographed (silica gel, 20% ethyl acetate in hexane) to afford the title compound in good purity. MS m/z 265

Step 2. Preparation of {7-[4-(3,5-Dichloro-benzyloxy)-benzylsulfanyl]-indan-4-yloxy}-acetic acid (compound 77)

The title compound was prepared in the manner analogous to Example 1 using 77A. mp 134–135° C.; IR (KBr) cm$^{-1}$: 3070, 1747, 1708, 1572, 1432, 1244; 400 MHz $^1$H NMR (DMSO-$d_6$): δ 12.95 (br(s), 1H), 7.51–7.53 (m, 1H), 7.42–7.45 (m, 2H), 7.07–7.13 (m, 2H), 7.04 (d, 1H, J=8.6 Hz), 6.83–6.90 (m, 2H), 6.56 (d, 1H, J=8.6 Hz), 5.05 (s, 2H), 4.61 (s, 2H), 3.93 (s, 2H), 2.75 (t, 2H, J=7.5 Hz), 2.66 (t, 2H, 7.5 Hz), 1.88 (pentet, 2H); MS m/z 487 (M–1). Anal. Calc'd for $C_{25}H_{22}Cl_2O_4S$: C, 61.35; H, 4.53; found: C, 61.01; H, 436.

EXAMPLE 78

Synthesis of {7-[4-Methoxy-3-(4-trifluoromethyl-benzyloxy)-benzylsulfanyl]-indan-4-yloxy}-acetic acid (compound 78)

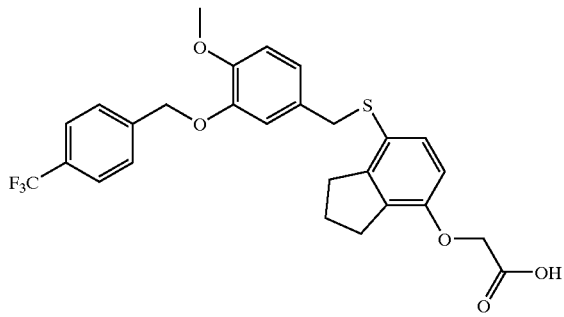

78

Step 1. Preparation of [4-Methoxy-3-(4-trifluoromethyl-benzyloxy)-phenyl]-methanol (compound 78A)

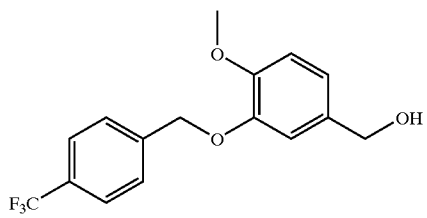

78A

The title compound was prepared in the manner analogous to Example 14A using 1-bromomethyl-4-trifluoromethyl-benzene and 5-hydroxymethyl-2-methoxy-phenol. MS m/z 295 (M-OH).

Step 2. Preparation of 4-Chloromethyl-1-methoxy-2-(4-trifluoromethyl-benzyloxy)-benzene (compound 78B)

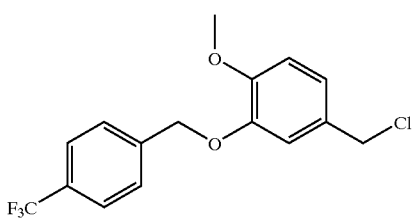

78B

The title compound was prepared in the manner analogous to Example 3B using 78A. MS m/z 295 (M-Cl).

Step 3. Preparation of {7-[4-Methoxy-3-(4-trifluoromethyl-benzyloxy)-benzylsulfanyl]-indan-4-yloxy}-acetic acid methyl ester (compound 78C)

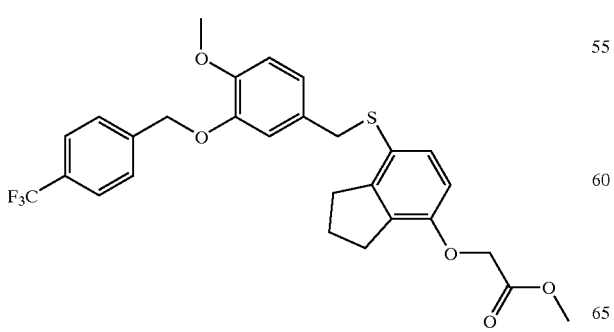

78C

The title compound was prepared in the manner analogous to Example 1F using 78B and 12C. MS m/z 373 (M-159).

Step 4. Preparation of {7-[4-Methoxy-3-(4-trifluoromethyl-benzyloxy)-benzylsulfanyl]-indan-4-yloxy}-acetic acid (compound 78)

The title compound was prepared in the manner analogous to Example 1 using 78C. mp 150–151° C.; IR (KBr) cm$^{-1}$: 3046, 1722, 1515, 1328, 1232, 1106; 400 MHz $^1$H NMR (DMSO-d$_6$): δ 12.95 (br(s), 1H), 7.71 (d, 2H, J=8.1 Hz), 7.58 (d, 2H, J=8.1 Hz), 7.03 (d, 1H, J=8.5 Hz), 6.70–6.86 (m, 3H), 6.57 (d, 1H, J=8.5 Hz), 5.01 (s, 2H), 4.61 (s, 2H), 3.89 (s, 2H), 3.69 (s, 3H), 2.75 (t, 2H, J=7.3 Hz), 2.62 (t, 2H, J=7.3 Hz), 1.87 (pentet, 2H); MS m/z 517 (M-1). Anal. Calc'd for C$_{27}$H$_{25}$F$_3$O$_5$S: C, 62.54; H, 4.86; found: C, 62.54; H, 4.71.

EXAMPLE 79

Synthesis of {7-[3-(4-Trifluoromethyl-benzyloxy)-benzylsulfanyl]-indan-4-yloxy}-acetic acid (compound 79)

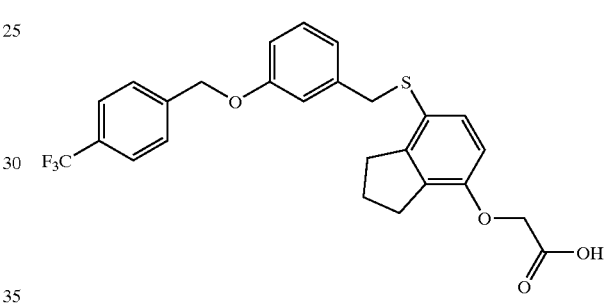

79

Step 1. Preparation of [3-(4-trifluoromethyl-benzyloxy)-phenyl]-methanol (compound 79A)

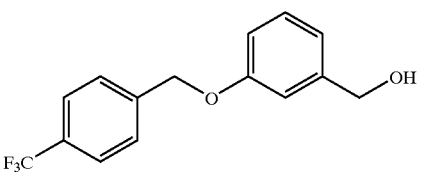

79A

The title compound was prepared in the manner analogous to Example 14A using 1-bromomethyl-4-trifluoromethyl-benzene and 3-hydroxymethyl-phenol. MS m/z 265 (M-OH).

Step 2. Preparation of 1-(4-trifluoromethyl-benzyloxy)-3-chloromethyl-benzene (Compound 79B)

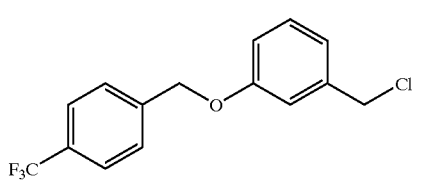

79B

The title compound was prepared in the manner analogous to Example 3B using 79A. MS m/z 265 (M-Cl).

Step 3. Preparation of {7-[3-(4-Trifluoromethyl-benzyloxy)-benzylsulfanyl]-indan-4-yloxy}-acetic acid methyl ester (compound 79C)

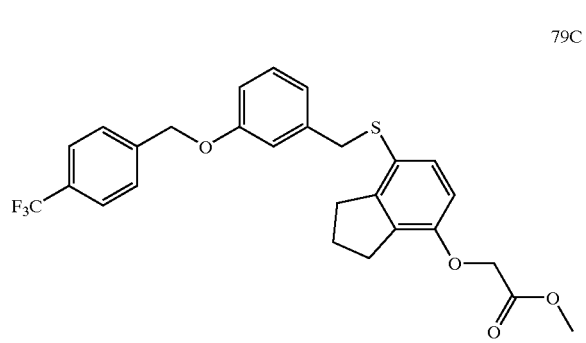

79C

The title compound was prepared in the manner analogous to Example 1F using 79B and 12C. MS m/z 503 (M+1).

Step 4. Preparation of {7-[3-(4-Trifluoromethyl-benzyloxy)-benzylsulfanyl]-indan-4-yloxy}-acetic acid (compound 79)

The title compound was prepared in the manner analogous to Example 1 using 79C. mp 145–146° C.; IR (KBr) cm$^{-1}$: 3076, 3028, 1705, 1318, 1232, 1109; 400 MHz $^1$H NMR (DMSO-d$_6$): δ 12.94 (br(s), 1H), 7.71 (d, 2H, J=8.2 Hz), 7.59 (d, 2H, J=8.0 Hz), 7.10–7.19 (m, 1H), 7.05 (d, 1H, J=8.5 Hz), 6.75–6.86 (m, 4H), 6.58 (d, 1H, J=8.5 Hz), 5.08 (s, 2H), 4.61 (s, 2H), 3.95 (s, 2H), 2.75 (t, 2H, J=7.5 Hz), 2.64 (t, 2H, J=7.5 Hz), 1.88 (pentet, 2H); MS m/z 487 (M−1). Anal. Calc'd for C$_{26}$H$_{23}$F$_3$O$_4$S: C, 63.92; H, 4.75; found: C, 63.78; H, 4.53.

EXAMPLE 80

Synthesis of {7-[3-(4-Chloro-3-trifluoromethyl-benzyloxy)-benzylsulfanyl]-indan-4-yloxy}-acetic acid (compound 80)

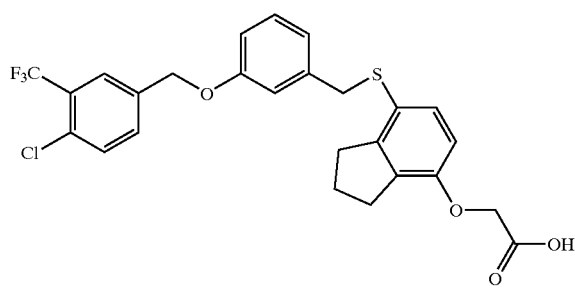

Step 1. Preparation of [3-(4Chloro-3-trifluoromethyl-benzyloxy)-phenyl]-methanol (compound 80A)

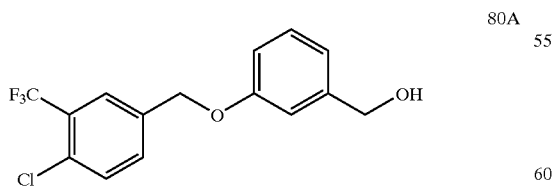

80A

The title compound was prepared in the manner analogous to Example 14A using 4-bromomethyl-1-chloro-2-trifluoromethyl-benzene and 3-hydroxymethyl-phenol. MS m/z 299 (M-OH).

Step 2. Preparation of 1-Chloro-4-(3-chloromethyl-phenoxymethyl)-2-trifluoromethyl-benzene (compound 80B)

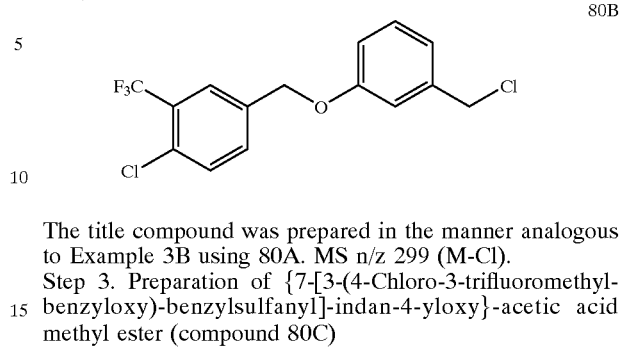

80B

The title compound was prepared in the manner analogous to Example 3B using 80A. MS n/z 299 (M-Cl).

Step 3. Preparation of {7-[3-(4-Chloro-3-trifluoromethyl-benzyloxy)-benzylsulfanyl]-indan-4-yloxy}-acetic acid methyl ester (compound 80C)

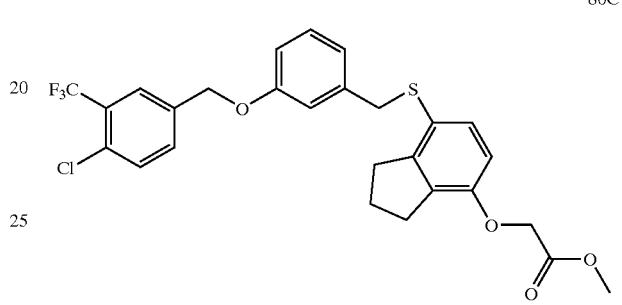

80C

The title compound was prepared in the manner analogous to Example 1F using 80B and 12C. MS m/z 537 (M+1).

Step 4. Preparation of {7-[3-(4-Chloro-3-trifluoromethyl-benzyloxy)-benzylsulfanyl]-indan-4-yloxy}-acetic acid (compound 80)

The title compound was prepared in the manner analogous to Example 1 using 80C. mp 121–122° C.; IR (KBr) cm$^{-1}$: 3027, 2584, 1742, 1255, 1129, 1109; 400 MHz $^1$H NMR (DMSO-d$_6$): δ 12.95 (br(s), 1H), 7.87 (s, 1H), 7.64–7.75 (m, 2H), 7.09–7.19 (m, 1H), 7.01–7.09 (m, 1H), 6.73–6.88 (m, 3H), 6.56 (d, 1H, J=8.5 Hz), 5.06 (s, 2H), 4.60 (s, 2H), 3.95 (s, 2H), 2.74 (t, 2H, J=7.4 Hz), 2.63 (t, 2H, J=7.4 Hz), 1.87 (pentet, 2H); MS m/z 523 (M+1). Anal. Calc'd for C$_{26}$H$_{22}$ClF$_3$O$_4$S: C, 59.71; H, 4.24; found: C, 59.45; H, 4.08.

EXAMPLE 81

Synthesis of {7-[2-(4-Trifluoromethyl-benzyloxy)-benzylsulfanyl]-indan-4-yloxy}-acetic acid (compound 81)

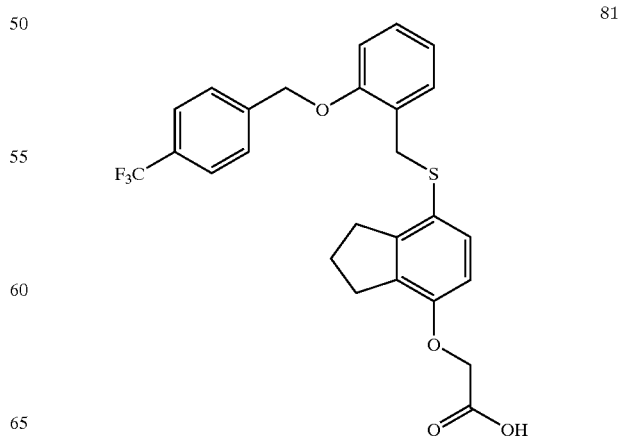

81

Step 1. Preparation of [2-(4-Trifluoromethyl-benzyloxy)-phenyl]-methanol (compound 81A)

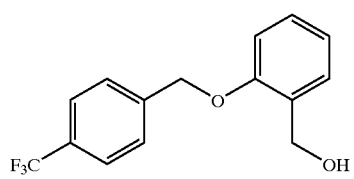
81A

The title compound was prepared in the manner analogous to Example 14A using 1-bromomethyl-4-trifluoromethyl-benzene and 2-hydroxymethyl-phenol. MS m/z 265 (M−OH).

Step 2. Preparation of 1-(4-trifluoromethyl-benzyloxy)-2-chloromethyl-benzene (compound 81B)

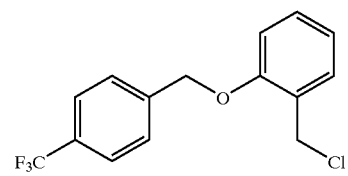
81B

The title compound was prepared in the manner analogous to Example 3B using 81A. MS m/z 265 (M−Cl).

Step 3. Preparation of {7-[2-(4-Trifluoromethyl-benzyloxy)-benzylsulfanyl]-indan-4-yloxy}-acetic acid methyl ester (compound 81C)

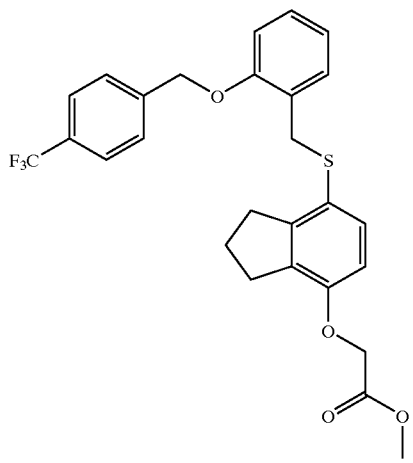
81C

The title compound was prepared in the manner analogous to Example 1F using 81B and 12C. MS m/z 503 (M+1).

Step 4. Preparation of {7-[2-(4-Trifluoromethyl-benzyloxy)-benzylsulfanyl]-indan-4-yloxy}-acetic acid (compound 81)

The title compound was prepared in the manner analogous to Example 1 using 81C. mp 150–152° C.; IR (KBr) cm$^{-1}$: 3074, 3042, 1701, 1324, 1124, 1099; 400 MHz $^1$H NMR (DMSO-d$_6$): δ 7.58–7.75 (m, 2H), 6.92–7.20 (m, 4H), 6.80 (t, 1H, J=7.5 Hz), 6.51 (d, 1H, J=8.5 Hz), 5.16 (s, 2H), 4.57 (s, 2H), 3.99 (s, 2H), 2.70 (t, 2H, J=7.5 Hz), 2.62 (t, 2H, J=7.5 Hz), 1.80 (pentet, 2H); MS m/z 487 (M−1). Anal. Calc'd for C$_{26}$H$_{23}$F$_3$O$_4$S: C, 63.92; H, 4.75; found: C, 63.54; H, 4.52.

EXAMPLE 82

Synthesis of {7-[3-Dichloro-4-(4-trifluoromethyl-benzyloxy)-benzylsulfonyl]-indan-4-yloxy}-acetic acid lithium salt (compound 82)

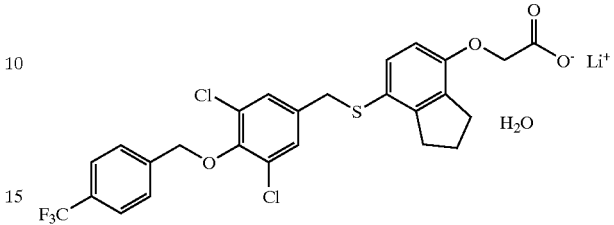
82

Step 1. Preparation of [3,5-Dichloro-4-(4-trifluoromethyl-benzyloxy)-phenyl]-methanol (compound 82A)

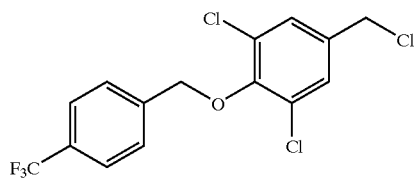
82A

The title compound was prepared in the manner analogous to Example 14A using 1-bromomethyl-4-trifluoromethyl-benzene and 2,6-dichloro-4-hydroxymethyl-phenol. MS m/z 191 (M−159).

Step 2. Preparation of 1,3-Dichloro-5-chloromethyl-2-(4-trifluoromethyl-benzyloxy)-benzene (compound 82B)

82B

The title compound was prepared in the manner analogous to Example 3B using 82A. MS m/z 333 (M−Cl).

Step 3. Preparation of {7-[3,5-Dichloro-4-(4-trifluoromethyl-benzyloxy)-benzylsulfonyl]-indan-4-yloxy}-acetic acid methyl ester (compound 82C)

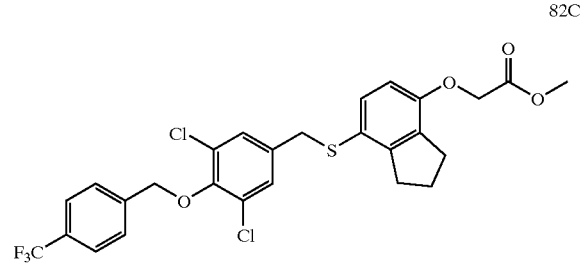
82C

The title compound was prepared in the manner analogous to Example 1F using 82B and 12C. MS m/z 571 (M+1).

Step 4. Preparation of The Lithium Salt of {7-[3,5-Dichloro-4(4-trifluoromethyl-benzyloxy)-benzylsulfonyl]-indan-4-yloxy}-acetic acid (compound 82)

The title compound, in unprotonated form, was prepared in the manner analogous to Example 1 using 82C. mp 235° C. dec; IR (KBr) cm$^{-1}$: 3414, 1622, 1591, 1472, 1326, 1265; 400 MHz $^1$H NMR (DMSO-d$_6$): δ 7.66–7.77 (m, 4H), 7.26 (s, 2H), 6.99 (d, 1H, J=8.5 Hz), 6.45 (d, 1H, J=8.5 Hz), 5.03 (s, 2H), 4.02 (s, 2H), 3.92 (s, 2H), 2.73 (t, 2H, J=7.3 Hz), 2.65 (t, 2H, J=7.3 Hz), 1.88 (pentet, 2H); MS m/z 555 (M−1). Anal. Calc'd for $C_{26}H_{20}Cl_2F_3O_4S$: Li: 0.50 H$_2$O: C, 54.56; H, 3.70; Li, 1.21; H$_2$O, 1.57; found: C, 54.63; H, 3.68; Li, 1.46; H$_2$O, 1.61.

EXAMPLE 83

Synthesis of {8-[4-(4Trifluoromethyl-benzyloxy)-benzylsulfanyl]-chroman-5-yloxy}-acetic acid (compound 83)

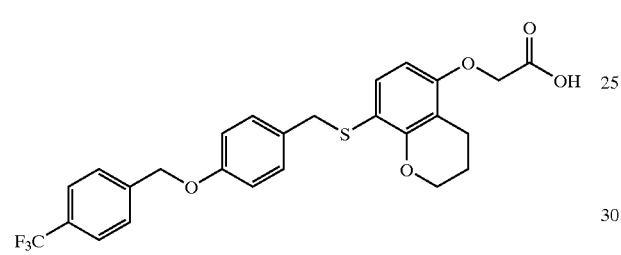

83

Step 1. Preparation of {8-[4-(4-Trifluoromethyl-benzyloxy)-benzylsulfanyl]-chroman-5-yloxy}-acetic acid methyl ester (compound 83A)

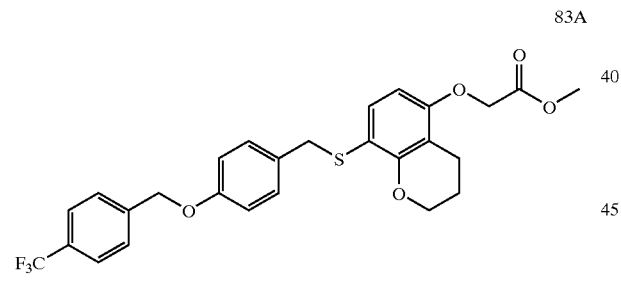

83A

The title compound was prepared in the manner analogous to Example 1F using (8-mercapto-chroman-5-yloxy)-acetic acid methyl ester and 14B. MS m/z 519 (M+1).

Step 2. Preparation of {8-[4(4-Trifluoromethyl-benzyloxy)-benzylsulfanyl]-chroman-5-yloxy}-acetic acid (compound 83)

The title compound was prepared in the manner analogous to Example 1 using 83A. mp 143–144° C.; HPLC: area %=96.02, r.t.=3.770 min, γ=214 nm, mobile phase=acetonitrile/water w/0.10% TFA; IR (KBr) cm$^{-1}$: 3042, 2581, 1739, 1714, 1325, 1116; 400 MHz $^1$H NMR (DMSO-d$_6$): δ 12.95 (br(s), 1H), 7.66–7.74 (m, 2H), 7.56–7.63 (m, 2H); 7.10–7.17 (m, 2H), 6.92 (d, 1H, J=8.7 Hz), 6.83–6.89 (m, 2H), 6.26 (d, 1H, J=8.5 Hz), 5.13 (s, 2H), 4.58 (s, 2H), 4.08 (t, 2H, J=4.8 Hz), 3.90 (s, 2H), 2.55 (t, 2H, J=6.5 Hz), 1.83 (pentet, 2H); MS m/z 503 (M−1). Anal. Calc'd for $C_{26}H_{23}F_3O_5S$: C, 61.90; H, 4.60; found: C, 61.41; H, 4.50.

EXAMPLE 84

Synthesis of {8-[3-(4-Trifluoromethyl-benzyloxy)-benzylsulfanyl]-chroman-5-yloxy}-acetic acid (compound 84)

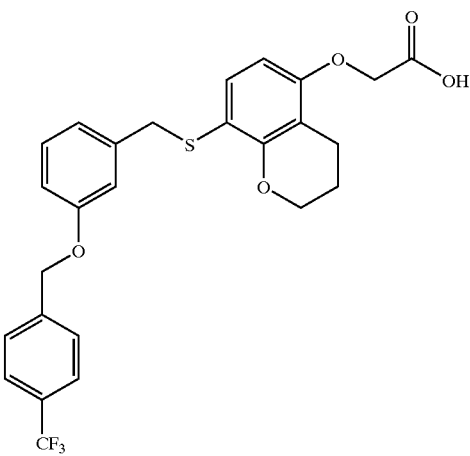

84

Step 1. Preparation of {8-[3-(4-Trifluoromethyl-benzyloxy)-benzylsulfanyl]-chroman-5-yloxy}-acetic acid methyl ester (compound 84A)

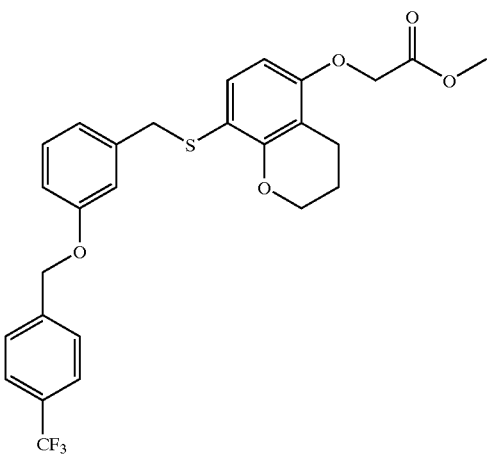

84A

The title compound was prepared in the manner analogous to Example 1F using (8-mercapto-chroman-5-yloxy)-acetic acid methyl ester and 79B. MS m/z 519 (M+1).

Step 2. Preparation of {8-[3-(4-Trifluoromethyl-benzyloxy)-benzylsulfanyl]-chroman-5-yloxy}-acetic acid (compound 84)

The title compound was prepared in the manner analogous to Example 1 using 84A. mp 113–115° C.; HPLC: area %=97.30, r.t.=3.140 min, γ=214 nm, mobile phase=acetonitrile/water w/0.10% TFA; IR (KBr) cm$^-$: 2952, 2577, 1742, 1582, 1323, 1120; 400 MHz $^1$H NMR (DMSO-d$_6$): δ 7.67–7.74 (m, 2H), 7.56–7.63 (m, 2H); 7.13 (t, 1H, J=7.8 Hz), 6.76–6.93 (m, 4H), 6.22 (d, 1H, J=8.7 Hz), 5.08 (s, 2H), 4.45 (s, 2H), 4.08 (t, 2H, J=4.8 Hz), 3.91 (s, 2H), 2.54 (t, 2H, J=6.6 Hz), 1.82 (pentet, 2H); MS m/z 505 (M+1). Anal. Calc'd for $C_{26}H_{23}F_3O_5S$: C, 61.90; H, 4.60; found: C, 61.49; H, 4.44.

EXAMPLE 85
Synthesis of {8-[4-(2,5-Dichloro-benzyloxy)-benzylsulfanyl]-chroman-5-yloxy}-acetic acid (compound 85)

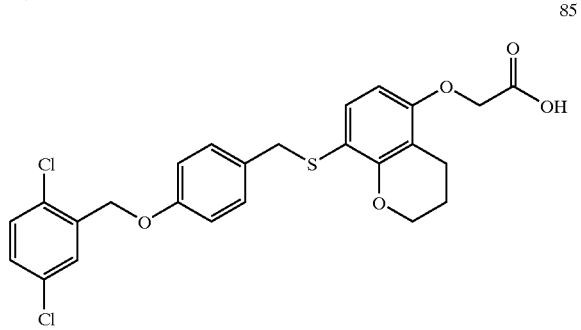

Step 1. Preparation of {8-[4-(2,5-Dichloro-benzyloxy)-benzylsulfanyl]-chroman-5-yloxy}-acetic acid methyl ester (compound 85A)

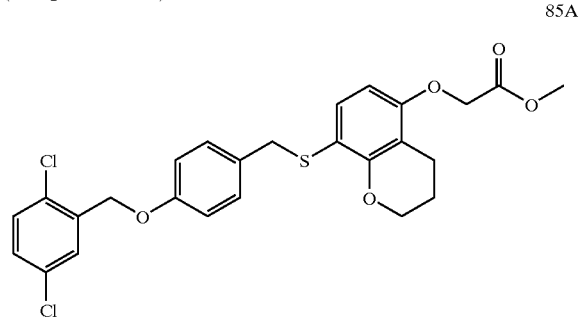

The title compound was prepared in the manner analogous to Example 1F using (8-mercapt-ochroman-5-yloxy)-acetic acid methyl ester and 1,4-Dichloro-2-(4-chloromethyl-phenoxymethyl)-benzene prepared in the manner analagous to Example 71A. m/z 519 (M+1).

Step 2. Preparation of {8-[4-(2,5-Dichloro-benzyloxy)-benzylsulfanyl]-chroman-5-yloxy}-acetic acid (compound 85)

The title compound was prepared in the manner analogous to Example 1 using 85A. mp 98–100° C.; IR (KBr) cm$^{-1}$: 3038, 2854, 1729, 1508, 1240, 1124; 400 MHz $^1$H NMR (MSOd-$_6$): δ 12.95 (br(s), 1H), 7.57–7.62 (m, 1H), 7.39–7.53 (m, 2H); 7.12–7.20 (m, 2H), 6.84–6.96 (m, 3H), 6.26 (d, 1H, J=8.6 Hz), 5.05 (s, 2H), 4.58 (s, 2H), 4.09 (t, 2H, J=4.9 Hz), 3.92 (s, 2H), 2.55 (t, 2H, J=6.5 Hz), 1.83 (pentet, 2H); MS m/z 503 (M−1). Anal. Calc'd for C$_{25}$H$_{22}$Cl$_2$O$_5$S: C, 59.41; H, 4.39; found: C, 59.20; H, 4.20.

EXAMPLE 86
Synthesis of {8-[4-(5-Trifluoromethyl-pyridine-2-yl)-benzylsulfanyl]-chroman-5-yloxy}-acetic acid (compound 86)

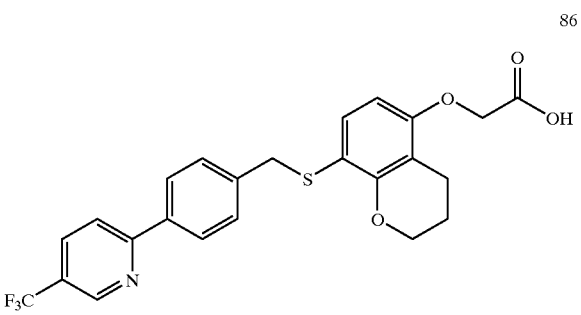

Step 1. {8-[4-(5-Trifluoromethyl-pyridine-2-yl)-benzylsulfanyl]-chroman-5-yloxy}-acetic acid methyl ester (compound 86A)

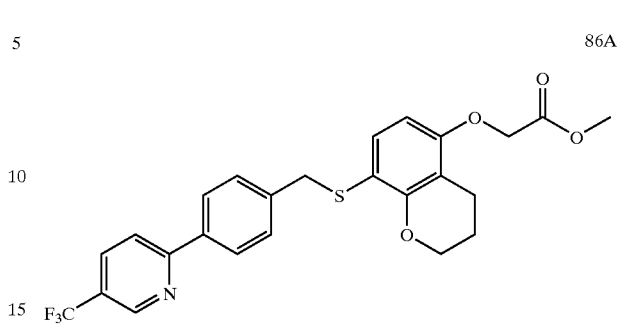

The title compound was prepared in the manner analogous to Example 1F using (8-mercapto-chroman-5-yloxy)-acetic acid methyl ester and 18B. MS m/z 490 (M+1).

Step 2. {8-[4-(5-Trifluoromethyl-pyridine-2-yl)-benzylsulfanyl]-chroman-5-yloxy}-acetic acid (compound 86)

The title compound was prepared in the manner analogous to Example 1 using 86A. mp 178–179° C.; IR (KBr) cm$^{-1}$: 3034, 2577, 1707, 1604, 1332, 1111; 400 MHz $^1$H NMR (DMSO-d$_6$): δ 12.95 (br(s), 1H), 8.97 (s, 1H), 7.99–8.24 (m, 4H), 7.33–7.40 (m, 2H), 6.95 (d, 2H, J=8.5 Hz), 6.26 (d, 2H, J=8.6 Hz), 4.57 (s, 2H), 4.11 (t, 2H, J=4.9 Hz), 4.04 (s, 2H), 2.56 (t, 2H, J=6.5 Hz), 1.84 (pentet, 2H); MS m/z 476 (M+1). Anal. Calc'd for C$_{24}$H$_{20}$F$_3$NO$_4$S: C, 60.63; H, 4.24; N, 2.95; found: C, 60.31; H, 4.24; N, 3.02.

EXAMPLE 87
Synthesis of {7-[5-(2-Chloro-phenyl)-isoxazol-3-ylmethylsulfanyl]-indan-4-yloxy}-acetic acid (compound 87)

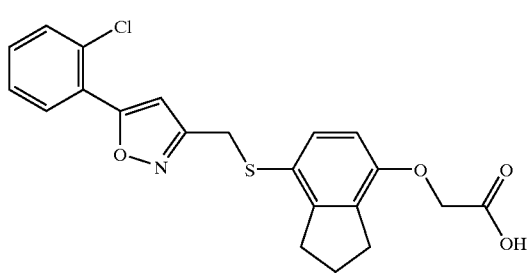

Step 1. Preparation of {7-[5-(2-Chloro-phenyl)-isoxazol-3-ylmethylsulfanyl]-indan-4-yloxy}-acetic acid methyl ester (compound 87A)

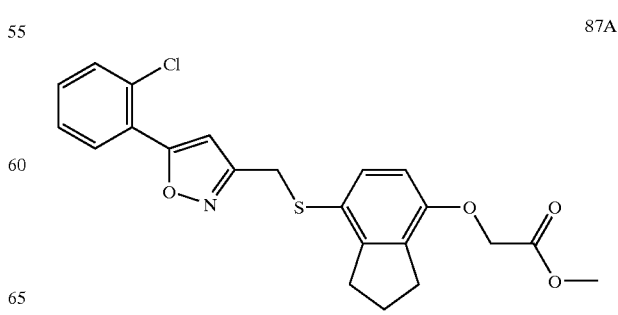

The title compound was prepared in the manner analogous to Example 1F using commercially available 3-chloromethyl-5-(2-chloro-phenyl)isoxazole and 12C. MS m/z 430 (M+1).

Step 2. Preparation of {7-[5-(2-Chloro-phenyl)-isoxazol-3-ylmethylsulfanyl]-indan-4-yloxy}-acetic acid (compound 87)

The title compound was prepared in the manner analogous to Example 1 using 87A. mp 161–162° C.; IR (KBr) cm$^{-1}$: 3177, 3065, 1706, 1475, 1432, 1233; 400 MHz $^1$H NMR (DMSO-d$_6$): δ 13.00 (bs, 1H), 7.78–7.85 (m, 1H), 7.58–7.64 (m, 1H), 7.42–7.53 (m, 2H), 7.15 (d, 1H, J=8.6 Hz), 6.84 (s, 1H), 6.60 ( d, 1H, J=8.6 Hz), 4.62 (s, 2H), 4.09 (s, 2H), 2.72–2.82 (m, 4H), 1.91 (pentet, 2H); MS m/z 416 (M+1). Anal. Calc'd for $C_{21}H_{18}ClNO_4S$: C, 60.65; H, 4.36; N, 3.37; found: C, 60.56; H, 4.28; N, 3.16.

EXAMPLE 88

Synthesis of {7-[3-(2,6-Dichloro-phenyl)-5-methyl-isoxazol-4-ylmethylsulfanyl]-indan-4-yloxy}-acetic acid (compound 88)

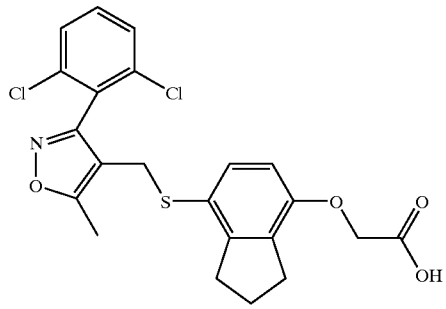

88

Step 1. Preparation of {7-[3-(2,6-Dichloro-phenyl)-5-methyl-isoxazol-4-ylmethylsulfanyl]-indan-4-yloxy}-acetic acid methyl ester (compound 88A)

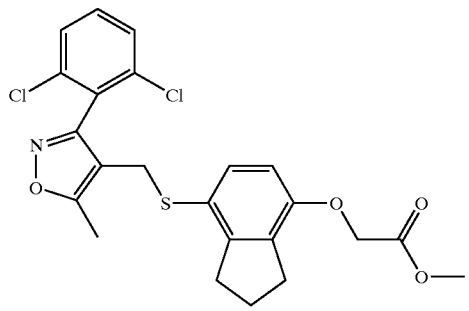

88A

The title compound was prepared in the manner analogous to Example 1F using commercially available 4-bromomethyl-3-(2,6-dichloro-phenyl)-5-methyl-isoxazole and 12C. MS m/z 478 (M+1).

Step 2. Preparation of {7-[3-(2,6-Dichloro-phenyl)-5-methyl-isoxazol-4-ylmethylsulfanyl]-indan-4-yloxy}-acetic acid (compound 88)

The title compound was prepared in the manner analogous to Example 1 using 88A. mp 151–152° C.; IR (KBr) cm$^{-1}$: 3084, 1743, 1430, 1277, 1245, 1106; 400 MHz $^1$H NMR (DMSO-d$_6$): δ 12.97 (br(s), 1H), 7.47–7.70 (m, 3H), 6.90 (d, 1H, J=8.5 Hz), 6.52 (d, 1H, J=8.5 Hz), 4.63 (s, 2H), 3.58 (s, 2H), 2.75 (t, 2H, J=7.6 Hz), 2.65 (t, 2H, J=7.6 Hz), 2.07 (s, 3H), 1.89 (pentet, 2H) MS m/z 464 (M+1). Anal. Calc'd for $C_{22}H_{19}Cl_2NO_4S$: C, 56.90; H, 4.12; N, 3.02; found: C, 56.51; H, 3.96; N, 2.95.

EXAMPLE 89

Synthesis of {7-[3-(4-Trifluoromethyl-phenyl)-isoxazol-5-ylmethylsulfanyl]-indan-4-yloxy}-acetic acid (compound 89)

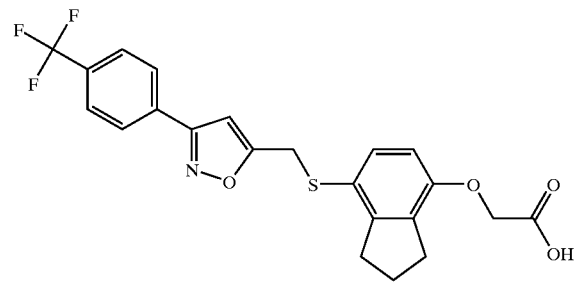

89

Step 1. Preparation of {7-[3-(4-Trifluoromethyl-phenyl)-isoxazol-5-ylmethylsulfanyl]-indan-4-yloxy}-acetic acid methyl ester (compound 89A)

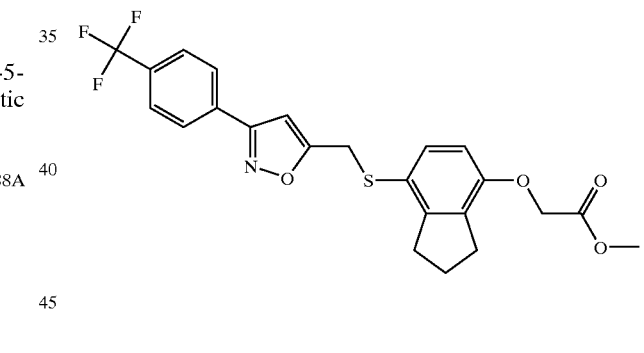

89A

The title compound was prepared in the manner analogous to Example 1F using 42C and 12C. MS m/z 464 (M+1).

Step 2. Preparation of {7-[3-(4-Trifluoromethyl-phenyl)-isoxazol-5-ylmethylsulfanyl]-indan-4-yloxy}-acetic acid (compound 89)

The title compound was prepared in the manner analogous to Example 1 using 89A. mp 166–168° C.; HPLC: area %=96.95, r.t.=3.140 min, γ=214 nm, mobile phase= acetonitrile/water w/0.10% TFA. IR (KBr) cm$^{-1}$: 3140, 3085, 1742, 1322, 1255, 1109; 400 MHz $^1$H NMR (DMSO-d$_6$): δ 12.96 (br(s), 1H), 7.99 (d, 2H, J=8.3 Hz), 7.81 (d, 2H, J=8.3 Hz), 7.14 (d, 1H, J=8.4 Hz), 6.81 (s, 1H), 6.61 (d, 1H, J=8.4 Hz), 4.63 (s, 2H), 4.23 (s, 2H), 2.76 (t, 4H, J=7.5 Hz), 1.91 (pentet, 2H); MS m/z 450 (M+1). Anal. Calc'd for $C_{22}H_{18}F_3NO_4S$: C, 58.79; H, 4.04; N, 3.12; found: C, 58.38; H, 3.92; N, 2.95.

EXAMPLE 90

Synthesis of {7-[2-(4'-Trifluoromethyl-biphenyl-4yl)-ethylsulfanyl]-indan-4-yloxy}-acetic acid (compound 90)

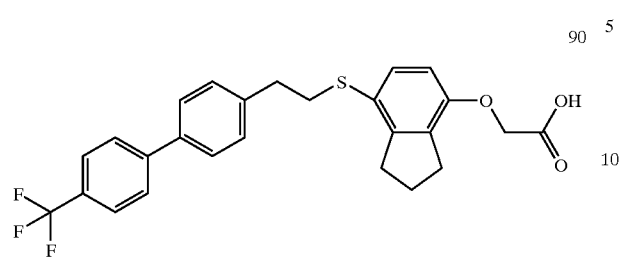

Step 1. Preparation of {7-[2-(4'-Trifluoromethyl-biphenyl-4-yl)-ethylsulfanyl]-indan-4-yloxy}-acetic acid methyl ester (compound 90A)

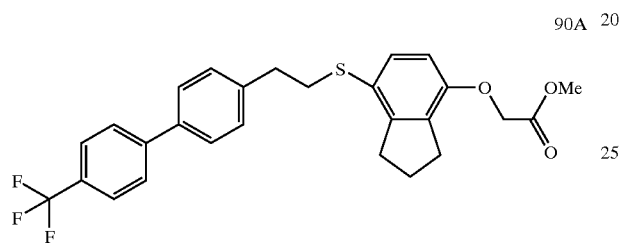

The title compound was prepared in the manner analogous to Example 1F using 12C and 4-(2-bromo-ethyl)-4'-trifluoromethyl-biphenyl (compound 22B). MS m/z 487 (M+1).

Step 2. Preparation of {7-[2-(4'-Trifluoromethyl-biphenyl-4-yl)-ethylsulfanyl]-indan-4-yloxy}-acetic acid (compound 90)

The title compound was prepared in the manner analogous to Example 1 using 90A. mp 170–172° C.; IR (thin film) cm$^{-1}$: 1724, 1471, 1327, 1239, 1175, 1110; 400 MHz $^1$H NMR (DMSO-d$_6$) δ 12.96 (br s, 1H), 7.82 (d, 2H, J=8.3 Hz), 7.74 (d, 2H, J=8.3 Hz), 7.61 (d, 2H, J=8.3 Hz), 7.31 (d, 2H, J=8.3 Hz), 7.12 (d, 2H, J=8.5 Hz), 6.62 (d, 1H, J=8.5 Hz), 4.63 (s, 2H), 3.08 (t, 2H, J=7.6 Hz), 2.80 (m, 6H), 1.96 (m, 2H); MS m/z 471 (M−1). Anal. Calc'd for C$_{26}$H$_{23}$F$_3$O$_3$S: C, 66.09; H, 4.91; found: C, 65.95; H, 4.63.

EXAMPLE 91

Synthesis of {7-[2-(4'-Trifluoromethyl-biphenyl-4-yl)-ethyl]-indan-4-yloxy}-acetic acid (compound 91)

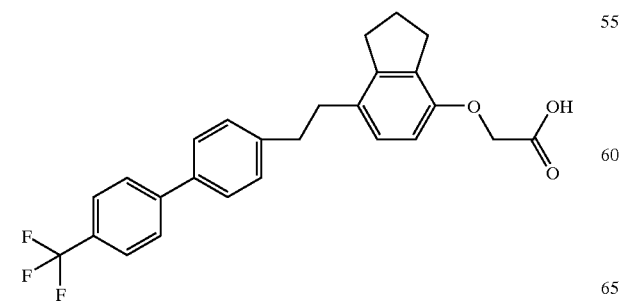

Step 1. Preparation of (Indan-4-yloxy)-acetic acid methyl ester (compound 91A)

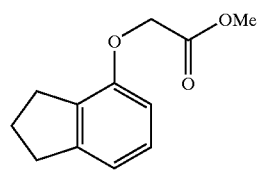

Compound 91A was prepared from indan-4-ol and bromoacetic acid methyl ester in the manner analogous to Example 1C. 400 MHz $^1$H NMR (DMSO-d$_6$) δ 7.00 (t, 1H, J=7.8 Hz), 6.79 (d, 1H, J=7.3 Hz), 6.56 (d, 1H, J=8.1 Hz), 4.74 (s, 2H), 3.63 (s, 3H), 2.77 (m, 4H), 1.95 (m, 2H).

Step 2. Preparation of (4'-Trifluoromethyl-biphenyl-4-yl)-acetic acid (compound 91B)

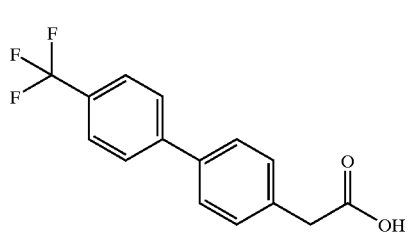

A mixture of (4-bromo-phenyl)-acetic acid (10.2 g, 47.4 mmol), 4-trifluoromethylphenylboronic acid (10.0 g, 52.7 mmol), and 50% water-wet 5% palladium on charcoal catalyst (4.6 g) in 50 ml of water and 8.0 ml of 2-propanol was treated dropwise over 30 minutes with a solution of sodium carbonate (6.8 g, 64.2 mmol) in 18 ml of water. The mixture was heated at 65–70° C. for 3 h, then cooled to 40° C. and treated with 13.0 ml of a solution of 2-propanol/water/2.0 N aqueous sodium hydroxide solution (70/15/1). The reaction mixture was filtered through a bed of Celite filter-aid, and the filter cake was washed 5× with the above 2-propanol/water/2.0 N aqueous sodium hydroxide solution. The combined filtrates were diluted with 125 ml of water, and the solution was digested on the steam bath with charcoal and filtered. The filtrate was diluted with an additional 150 ml of water and made strongly acidic by the addition of 4.0 N hydrochloric acid. The precipitated product was filtered and suspended in 350 ml of water plus 50 ml of methanol. The new mixture was stirred for several hours and filtered again. The crude product was recrystallized from aqueous acetonitrile. A sample recrystallized a second time from aqueous acetonitrile had mp 158–160° C.; MS m/z 280 (M).

Step 3. Preparation of (4'-Trifluoromethyl-biphenyl-4-yl)-acetyl chloride (compound 91C)

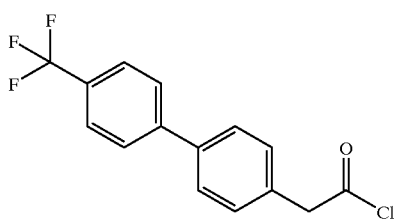

A suspension 91B (2.0 g, 7.1 mmol) and 5 drops of N,N-dimethylformamide in 30 ml of dichloromethane was cooled in ice and treated dropwise with a solution of oxalyl chloride (0.70 ml, 1.0 g, 8.0 mmol) in 10 ml of dichloromethane. The ice bath was removed, and the mixture was stirred at room temperature for 3 h. The solution was filtered, and the filtrate was evaporated. The residue quickly crystallized to yield the acid chloride intermediate, which was used immediately in the next step.

Step 4. Preparation of {7-[2-(4'-Trifluoromethyl-biphenyl-4-yl-acetyl]-indan-4-yloxy)-acetic acid methyl ester (compound 91D)

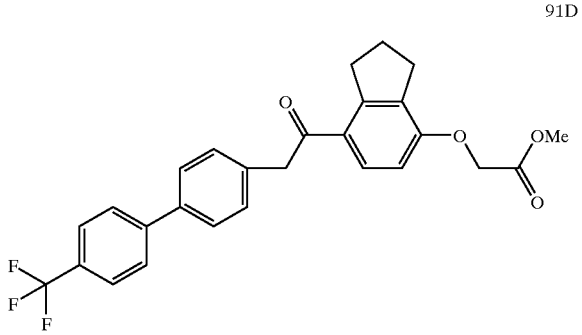

91D

A solution of 91C (2.1 g, 7.0 mmol) in 25 ml of 1,2-dichloroethane was cooled in ice and treated with anhydrous ferric chloride (1.2 g, 7.4 mmol). The mixture was stirred, and a solution of 91A (1.5 g, 7.3 mmol) in 10 ml of 1,2-dichloroethane was added dropwise. The mixture was stirred at room temperature for 18 h. The reaction mixture was added to 300 g of ice and of brine and extracted with ethyl acetate (4×10 ml). The combined extracts were washed with 5% aqueous sodium bicarbonate solution (4×250 ml) and brine (1×250 ml), then dried over anhydrous sodium sulfate and concentrated. The crude product was purified by normal phase chromatography. A sample recrystallized from ethyl acetate/hexane had mp 141–143° C.; MS m/z 467 (M−1).

Step 5. Preparation of {7-[2-(4'-Trifluoromethyl-biphenyl-4-yl)-ethyl]-indan-4-yloxy}-acetic acid methyl ester (compound 91E)

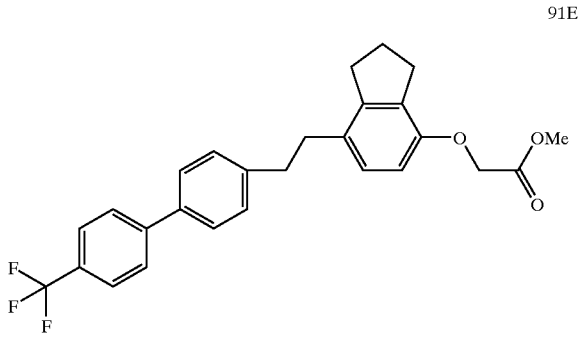

91E

A solution of 91D (1.0 g, 2.1 mmol) in 10.0 ml of trifluoroacetic acid was treated dropwise with triethylsilane (1.5 ml, 1.1 g, 9.4 mmol). The mixture was stirred at room temperature for 3 h and then added to 200 g of ice and water. The precipitated solid was extracted out with ethyl acetate (4×100 ml). The combined extracts were washed with brine (1×250 ml), 5% aqueous sodium bicarbonate solution (4×250 ml), and brine again, then dried over anhydrous sodium sulfate and concentrated. The crude product was purified by normal phase chromatography. 400 MHz $^1$H NMR (DMSO-$d_6$) δ 7.82 (d, 2H, J=8.3 Hz), 7.75 (d, 2H, J=8.3 Hz), 7.61 (d, 2H, J=8.3 Hz), 7.30 (d, 2H, J=8.3 Hz), 6.90 (d, 1H, J=8.3 Hz), 6.53 (d, 1H, J=8.3 Hz), 4.71 (s, 2H), 3.63 (s, 2H), 2.77 (m, 8H), 1.94 (m, 2H).

Step 6. Preparation of {7-[2-(4'-Trifluoromethyl-biphenyl-4-yl)-ethyl]-indan-4-yloxy}-acetic acid (compound 91)

The title compound was prepared in the manner analogous to Example 1 using 91E. mp 188–190° C.; IR (thin film) cm$^{-1}$: 1745, 1322, 1252, 1170, 1112, 1071; 400 MHz $^1$H NMR (DMSO-$d_6$) δ 12.89 (br s, 1H), 7.83 (d, 2H, J=8.1 Hz), 7.74 (d, 2H, J=8.5 Hz), 7.61 (d, 2H, J=8.1 Hz), 7.30 (d, 2H, J=8.3 Hz), 6.90 (d, 1H, J=8.3 Hz), 6.51 (d, 1H, J=8.3 Hz), 4.58 (s, 2H), 2.75 (m, 8H), 2.45 (m, 2H); MS m/z 439 (M−1). Anal. Calc'd for $C_{26}H_{23}F_3O_3$: C, 70.90; H, 5.26; found: C, 70.92; H, 5.01.

EXAMPLE 92

Synthesis of {5-Methyl-7-[4-(5-trifluoromethyl-pyridin-2-yl)-benzylsulfanyl]-2,3-dihydro-benzofuran-4-yloxy}-acetic acid (compound 92)

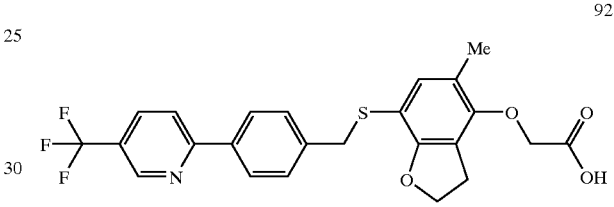

92

Step 1. Preparation of {5-Methyl-7-[4-(5-trifluoromethyl-pyridin-2-yl)-benzylsulfanyl]-2,3-dihydro-benzofuran-4-yloxy}-acetic acid methyl ester (compound 92A)

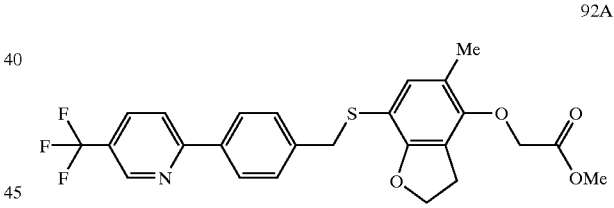

92A

The title compound was prepared in the manner analogous to Example 1F using 18B and 7-mercapto-5-methy-2,3-dihydro-benzofuran-4-yloxy)-acetic acid methyl ester (prepared in a similar manner as described for Example 12C). mp 94–95° C.; MS m/z 490 (M+1).

Step 2. Preparation of (5-Methyl-7-[4(5-trifluoromethyl-pyridin-2-yl)-benzylsulfanyl]-2,3-dihydro-benzofuran-4-yloxy)-acetic acid (compound 92)

The title compound was prepared in the manner analogous to Example 1 using 92A. mp 155–157° C.; IR (thin film) cm$^{-1}$: 1732, 1587, 1416, 1331, 1211, 1129; 400 MHz $^1$H NMR (DMSO-$d_6$) δ 12.89 (br s, 1H), 8.97 (m, 1H), 8.21 (dd, 1H, J=2.0, 8.5 Hz), 8.12 (d, 1H, J=8.3 Hz), 8.02 (d, 2H, J=8.3 Hz), 7.34 (d, 2H, J=8.5 Hz), 6.83 (s, 1H), 4.56 (s, 2H), 4.48 (t, 2H, J=8.7 Hz), 4.08 (s, 2H), 3.24 (t, 2H, J=8.7 Hz), 2.02 (s, 3H); MS m/z 474 (M−1). Anal. Calc'd for $C_{24}H_{20}F_3NO_4S$: C, 60.63; H, 4.24; N, 2.95; found: C, 60.54; H, 4.19; N, 2.94.

EXAMPLE 93

Synthesis of [8-(4'-Trifluoromethyl-biphenyl-4-ylmethylsulfanyl)-chroman-5-yloxy]-acetic acid (compound 93)

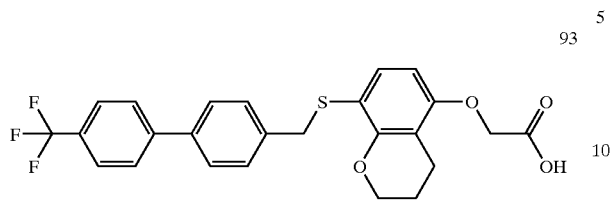

93

Step 1. Preparation of [8-(4'-Trifluoromethyl-biphenyl-4-ylmethylsulfanyl)-chroman-5-yloxy]-acetic acid methyl ester (compound 93A)

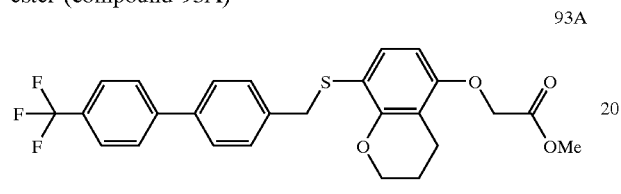

93A

The title compound was prepared in the manner analogous to Example 1F using 18B and (8-mercapto-chroman-5-yloxy)-acetic acid methyl ester. mp 122–124° C.; MS m/z 489 (M+1).

Step 2. Preparation of [8-(4'-Trifluoromethyl-biphenyl-4-ylmethylsulfanyl)-chroman-5-yloxy]-acetic acid (compound 93)

The title compound was prepared in the manner analogous to Example 1 using 93A. mp 170–172° C.; IR (thin film) cm$^{-1}$: 1717, 1584, 1473, 1330, 1231, 1118; 400 MHz $^1$H NMR (DMSO-d$_6$) δ 12.94 (br s, 1H), 7.82 (d, 2H, J=8.1 Hz), 7.74 (d, 2H, J=8.5 Hz), 7.60 (d, 2H, J=8.3 Hz), 7.34 (d, 2H, J=8.3 Hz), 6.96 (d, 2H, J=8.8 Hz), 6.28 (d, 2H, J=8.8 Hz), 4.58 (s, 2H), 4.11 (t, 2H, J=5.0 Hz), 4.03 (s, 2H), 2.56 (t, 2H, J=6.5 Hz), 1.84 (m, 2H); MS m/z 473 (M−1). Anal. Calc'd for C$_{25}$H$_{21}$F$_3$O$_4$S: C, 63.28; H, 4.46; found: C, 63.28; H, 4.26.

EXAMPLE 94

Synthesis of {8-[5-(4-Trifluoromethyl-phenyl)-isoxazol-3-ylmethylsulfanyl]-chroman-5-yloxy-}-acetic acid (compound 94)

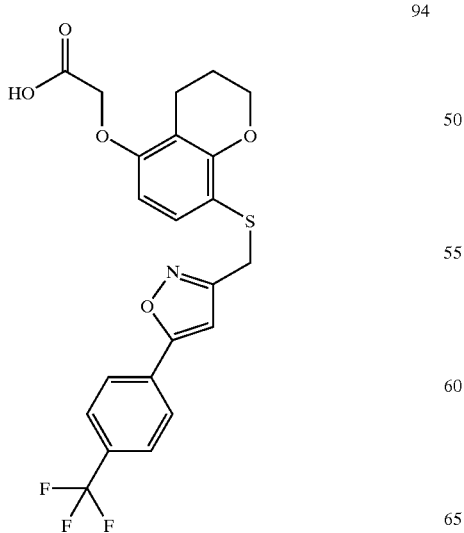

94

Step 1. Preparation of {8-[5-(4-Trifluoromethyl-phenyl)-isoxazol-3-ymethylsulfanyl]-chroman-5-yloxy}acetic acid methyl ester (compound 94A)

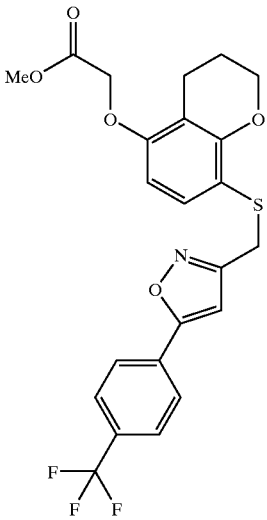

94A

The title compound was prepared in the manner analogous to Example 1F using 42C and (8-mercapto-chroman-5-yloxy)-acetic acid methyl ester. mp 112–113° C.; MS m/z 480 (M+1).

Step 2. Preparation of {8-[5-(4-Trifluoromethyl-phenyl)-isoxazol-3-ylmethylsulfanyl]-chroman-5-yloxy}-acetic acid (compound 94)

The title compound was prepared in the manner analogous to Example 1 using 94A. The crude product was recrystallized from ethyl acetate/hexane to yield the final product. mp 171–173° C.; IR (thin film) cm$^{-1}$: 1722, 1432, 1322, 1232, 1103, 1065; 400 MHz $^1$H NMR (DMSO-d$_6$) δ 12.94 (br s, 1H), 8.01 (d, 2H, J=8.1 Hz), 7.84 (d, 2H, J=8.3 Hz), 7.09 (s, 1H), 7.03 (d, 1H, J=8.5 Hz), 6.29 (d, 1H, J=8.5 Hz), 4.59 (s, 2H), 4.08 (t, 2H, J=5.0 Hz), 4.04 (s, 2H), 2.55 (t, 2H, J=6.5 Hz), 1.83 (m, 2H); MS m/z 464 (M−1). Anal. Calc'd for C$_{22}$H$_{18}$F$_3$NO$_5$S: C, 56.77; H, 3.90; N, 3.01; found: C, 56.80; H, 3.58; N, 3.07.

EXAMPLE 95

Synthesis of {8-[5-(4-Chloro-phenyl)-isoxazol-3-ylmethylsulfanyl]-chroman-5-yloxy}-acetic acid (compound 95)

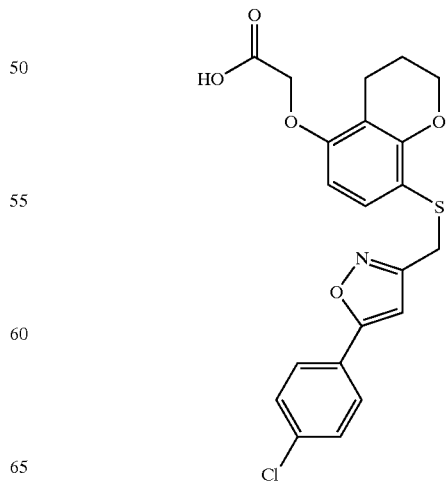

95

Step 1. Preparation of {8-[5-(4-Chloro-phenyl)-isoxazol-3-ylmethylsulfanyl]-chroman-5-yloxy}-acetic acid methyl ester (compound 95A)

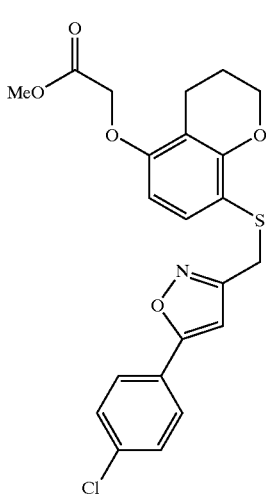

95A

The title compound was prepared in the manner analogous to Example 1F using 3-chloromethyl-5-(4-chloro-phenyl)-isoxazole and (8-mercapto-chroman-5-yloxy)-acetic acid methyl ester. mp 131–133° C.; MS m/z 446 (M+1).

Step 2. Preparation of {8-[5-(4Chloro-phenyl)-isoxazol-3-ylmethylsulfanyl]-chroman-5-yloxy}-acetic acid (compound 95)

The title compound was prepared in the manner analogous to Example 1 using 95A. mp 181–183° C.; IR (thin film) cm$^{-1}$: 1723, 1612, 1479, 1428, 1231, 1134; 400 MHz $^1$H NMR (DMSO-d$_6$) δ 12.95 (br s, 1H), 7.82 (m, 2H), 7.54 (m, 2H), 7.02 (d, 1H, J=8.8 Hz), 6.94 (s, 1H), 6.29 (d, 1H, J=8.5 Hz), 4.59 (s, 2H), 4.08 (t, 2H, J=5.0 Hz), 4.01 (s, 2H), 2.55 (t, 2H, J=6.6 Hz), 1.83 (m, 2H); MS m/z 430 (M−1). Anal. Calc'd for C$_{21}$H$_{18}$ClNO$_5$S: C, 58.40; H, 4.20; N, 3.24; found: C, 58.30; H, 3.91; N, 3.28.

EXAMPLE 96

Synthesis of {4-[5-(4-Chloro-phenyl)-isoxazol-3-ylmethylsulfanyl]-2-methyl-phenoxy}-acetic acid (compound 96)

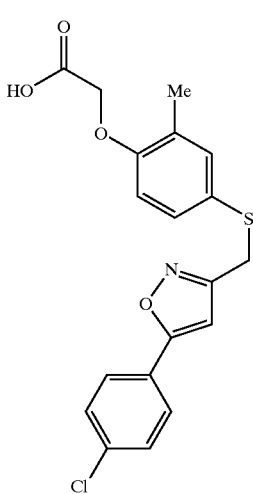

96

Step 1. Preparation of {4-[5-(4-Chloro-phenyl)-isoxazol-3-ylmethylsulfanyl]-2-methyl-phenoxy}-acetic acid methyl ester (compound 96A)

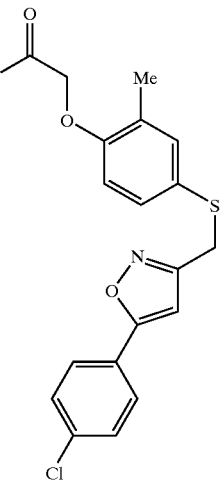

96A

The title compound was prepared in the manner analogous to Example 1F using 3-chloromethyl-5-(4-chloro-phenyl)-isoxazole and 2C. mp 79–80° C.; MS m/z 404 (M+1).

Step 2. Preparation of {4-[5-(4-Chloro-phenyl)-isoxazol-3-ylmethylsulfanyl]-2-methyl-phenoxy}-acetic acid (compound 96)

The title compound was prepared in the manner analogous to Example 1 using 96A. mp 152–153° C.; IR (thin film) cm$^{-1}$: 1724, 1495, 1433, 1309, 1225, 1196; 400 MHz $^1$H NMR (DMSO-d$_6$) δ 12.96 (br s, 1H), 7.82 (m, 2H), 7.54 (m, 2H), 7.19 (d, 1H, J=1.5 Hz), 7.12 (dd, 1H, J=2.1, 8.4 Hz), 6.97 (s, 1H), 6.72 (d, 1H, J=8.5 Hz), 4.63 (s, 2H), 4.11 (s, 2H), 2.09 (s, 3H); MS m/z 388 (M−1). Anal. Calc'd for C$_{19}$H$_{16}$ClNO$_4$S: C, 58.54; H, 4.14; N, 3.59; found: C, 58.53; H, 4.08; N, 3.50.

EXAMPLE 97

Synthesis of {7-[5-(4-Chloro-phenyl)-isoxazol-3-ylmethylsulfanyl]-indan-4-yloxy}-acetic acid (compound 97)

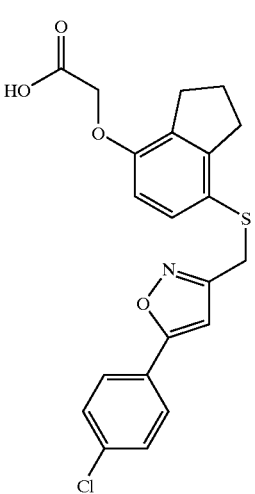

97

137

Step 1. Preparation of {7-[5-(4-Chloro-phenyl)-isoxazol-3-ylmethylsulfanyl]-indan-4-yloxy}-acetic acid methyl ester (compound 97A)

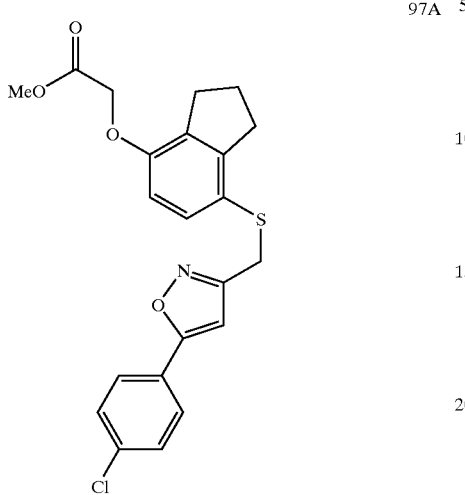

The title compound was prepared in the manner analogous to Example 1F using 3-chloromethyl-5-(4-chloro-phenyl)-isoxazole and 12C. mp 112–114° C.; MS m/z 430 (M+1).

Step 2. Preparation of {7-[5-(4-Chloro-phenyl)-isoxazol-3-ylmethylsulfanyl]-indan-4-yloxy}-acetic acid (compound 97)

The title compound was prepared in the manner analogous to Example 1 using 97A. mp 157–159° C.; IR (thin film) cm$^{-1}$: 1731, 1612, 1465, 1433, 1231, 1110; 400 MHz $^1$H NMR (DMSO-d$_6$) δ 7.81 (m, 2H), 7.54 (m, 2H), 7.10 (d, 1H, J=8.3 Hz), 6.95 (s, 1H), 6.59 (d, 1H, J=8.5 Hz), 4.62 (s, 2H), 4.06 (s, 2H), 2.77 (m, 4H), 1.92 (m, 2H); MS m/z 414 (M−1). Anal. Calc'd for C$_{21}$H$_{18}$ClNO$_4$S: C, 60.65; H, 4.36; N, 3.37; found: C, 60.62; H, 4.10; N, 3.31.

EXAMPLE 98

Synthesis of {7-[3-(4-Chloro-phenyl)-isoxazol-5-ylmethylsulfanyl]-indan-4-yloxy}-acetic acid (compound 98)

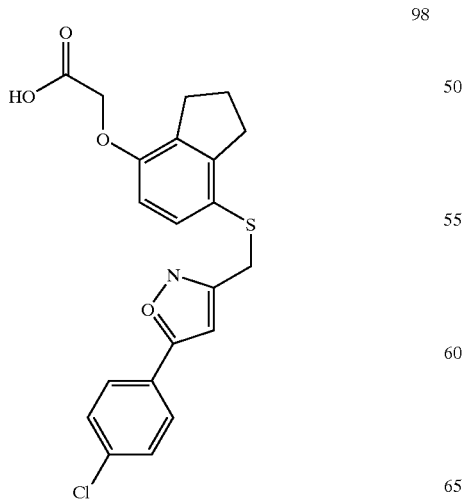

138

Step 1. Preparation of {7-[3-(4-Chloro-phenyl)-isoxazol-5-ylmethylsulfanyl]-indan-4-yloxy}-acetic acid methyl ester (compound 98A)

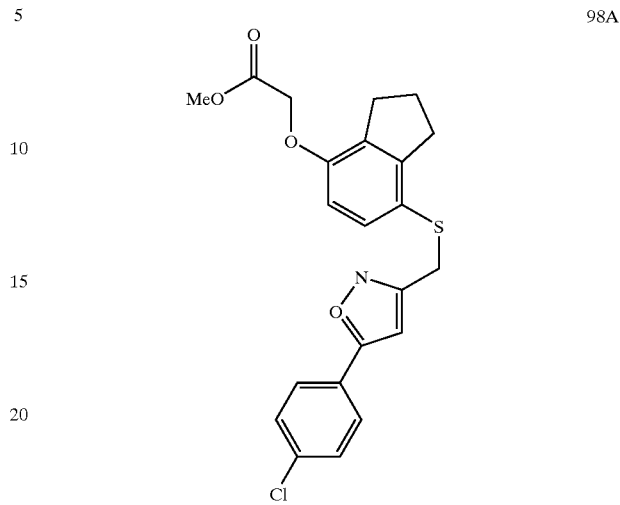

The title compound was prepared in the manner analogous to Example 1F using 5-chloromethyl-3-(4-chloro-phenyl)-isoxazole and 12C. mp 92–94° C.; MS m/z 430 (M+1).

Step 2. Preparation of {7-[3-(4-Chloro-phenyl)-isoxazol-5-ylmethylsulfanyl]-indan-4-yloxy}-acetic acid The title compound was prepared in the manner analogous to Example 1 using 98A. mp 158–160° C.; IR (thin film) cm$^{-1}$: 1741, 1574, 1476, 1429, 1252, 1110; 400 MHz $^1$H NMR (DMSO-d$_6$) δ 7.78 (m, 2H), 7.51 (m, 2H), 7.13 (d, 1H, J=8.6 Hz), 6.72 (s, 1H), 6.60 (d, 1H, J=8.5 Hz), 4.62 (s, 2H), 4.20 (s, 2H), 2.76 (m, 4H), 1.91 (m, 2H); MS m/z 414 (M−1). Anal. Calc'd for C$_{21}$H$_{18}$ClNO$_4$S: C, 60.65; H, 4.36; N, 3.37; found: C, 60.55; H, 4.17; N, 3.34.

EXAMPLE 99

Synthesis of {5-Chloro-2-methyl-4-[5-(4-trifluoromethyl-phenyl)-isoxazol-3-ylmethylsulfanyl]-phenoxy}-acetic acid (compound 99)

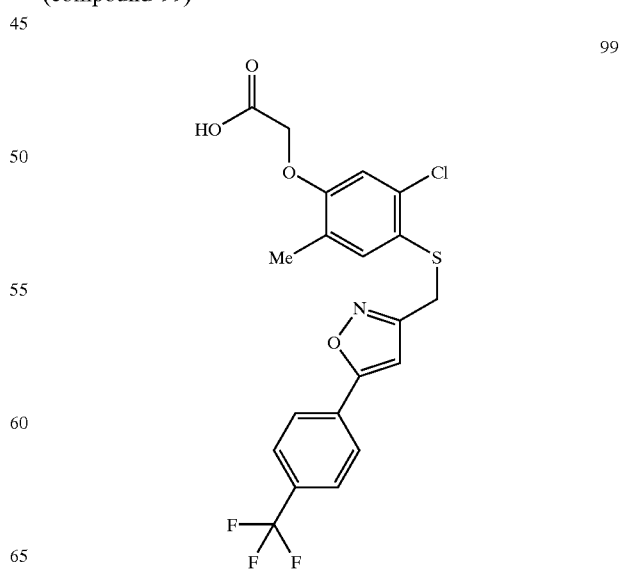

Step 1. Preparation of {5-Chloro-2-methyl-4-[5-(4-trifluoromethyl-phenyl)-isoxazol-3-ylmethylsulfanyl]-phenoxy}-acetic acid methyl ester (compound 99A)

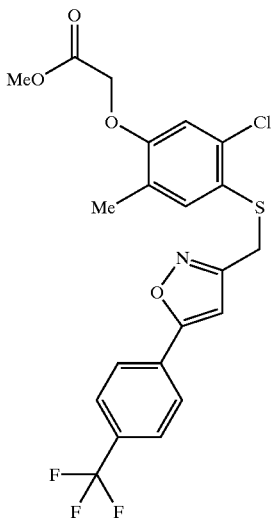

99A

The title compound was prepared in the manner analogous to Example 1F using 3-chloromethyl-5-(4-chloro-phenyl)-isoxazole and 20C. mp 120–121° C.; MS m/z 472 (M+1).

Step 2. Preparation of {5-Chloro-2-methyl-4-[5-(4-trifluoromethyl-phenyl)-isoxazol-3-ylmethylsulfanyl]-phenoxy}-acetic acid (compound 99)

The title compound was prepared in the manner analogous to Example 1 using 99A. mp 180–182° C.; IR (thin film) cm$^{-1}$: 1743, 1484, 1325, 1236, 1165, 1111; 400MHz $^1$H NMR (DMSO-d$_6$) δ 13.03 (br s, 1H), 8.03 (d, 2H, J=8.1 Hz), 7.84 (d, 2H, J=8.3 Hz), 7.33 (s, 1H), 7.14 (s, 1H), 6.96 (s, 1H), 4.71 (s, 2H), 4.23 (s, 2H), 2.07 (s, 3H); MS m/z 456 (M-1). Anal. Calc'd for C$_{20}$H$_{15}$ClF$_3$NO$_4$S: C, 52.47; H, 3.30; N, 3.06; found: C, 52.39; H, 3.02; N, 2.86.

EXAMPLE 100

Synthesis of 2-[2-butyl-4-({4-[4-(trifluoromethyl)phenyl]phenyl}methylthio)phenoxy]acetic acid (compound 100)

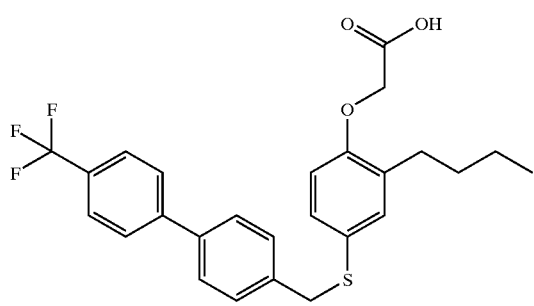

100

Step 1. Preparation of 2-((1E)buta-1,3-dienyl)-1-methoxybenzene (compound 100A)

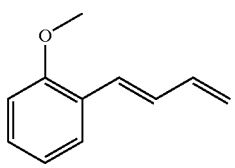

100A

Methyltriphenylphosphonium bromide (42.9 g, 0.12 mol) was suspended in 400 ml of anhydrous THF under nitrogen and cooled to −78° C. Sodium hydride (60% in mineral oil, 6.0 g, 0.15 mol) was added portionwise. The reaction mixture was allowed to warm up slowly to room temperature and stirred at the same temperature for 1 h, then 2-methoxycinnamaldehyde (16.2 g, 0.10 mol) in 200 ml of THF was added dropwise at room temperature, and stirred at the same temperature for 3 h. Water (200 ml) and diethyl ether (800 ml) were added. The organic layer was separated, dried over sodium sulfate, concentrated, and purified using normal phase chromatography to afford the title product. 400 MHz $^1$H NMR (CDCl$_3$) δ 7.48–6.56 (m, 7H), 5.32 (d, 1H), 5.16 (d, 11H), 3.84 (s, 3H).

Step 2. Preparation of 2-butyl-1-methoxybenzene (compound 100B)

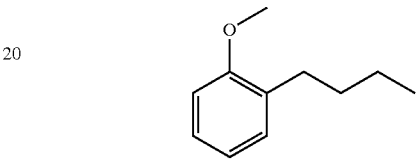

100B

A mixture of the product from example 100A (12.8 g, 0.08 mol) and palladium/carbon (10%, 50% water, 12 g) in 400 ml of ethyl acetate was hydrogenated at 50 psi, at room temperature overnight, then filtered through Celite®, and concentrated to give 100B. 400 MHz$^1$H NMR (CDCl$_3$) δ 7.16 (m, 2H), 6.85 (m, 2H), 3.81 (s, 3H), 2.61 (m, 2H), 1.57 (m, 2H), 1.38 (m, 2H), 0.92 (t, 3H).

Step 3. Preparation of 2-butylphenol (compound 100C)

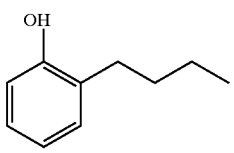

100C

To a stirred solution of the product from example 100B (13.1 g, 0.08 mol) in 400 ml of dichloromethane at −78° C. was added dropwise a solution of boron tribromide (100.2 g, 0.4 mol) in 200 ml of dichloromethane. After the completion of addition of boron tribromide, the reaction mixture was maintained at −78° C. for 1 h, then allowed to reach room temperature and stirred at the same temperature overnight. The mixture was cooled to 0° C., and carefully quenched with 100 ml of water. The mixture was extracted with ethyl acetate, washed with brine, dried over sodium sulfate, and concentrated to give 100C. 400 MHz $^1$H NMR (CDCl$_3$) δ 7.10 (m, 2H), 6.86 (m, 1H), 6.78 (d, 1H), 4.61 (brs, 1H), 2.61 (m, 2H), 1.60 (m, 2H), 1.40 (m, 2H), 0.96 (t, 3H).

Step 4. Preparation of (3-butyl-4-hydroxyphenyl)thiocarbonitrile (compound 100D)

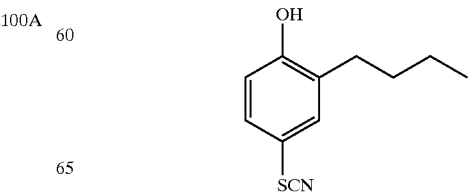

100D

The title compound was prepared in the manner analogous to Example 1B with the product from example 100C (2.38 g, 0.016 mol), sodium thiocyanate (5.14 g, 0.063 mol), sodium bromide (1.63 g, 0.016 mol), and bromine (2.8 g, 0.017 mol) in methanol. 400 MHz $^1$H NMR (CDCl$_3$) δ 7.30 (m, 2H), 6.81 (d, 1H), 5.49 (brs, 1H), 2.60 (m, 2H), 1.59 (m, 2H), 1.38 (m, 2H), 0.95 (t, 3H).

Step 5. Preparation of methyl 2-(2-butyl-4-cyanothiophenoxy)acetate (compound 100E)

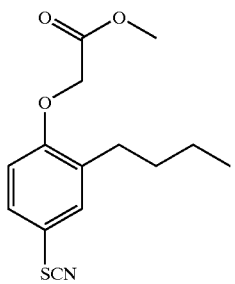

100E

The title compound was prepared in the manner analogous to Example 1C with the product from example 100D (2.80 g, 0.014 mol), methyl bromoacetate (2.28 g, 0.015 mol), and cesium carbonate (6.60 g, 0.020 mol) in 100 ml of acetonitrile. 400 MHz $^1$H NMR (CDCl$_3$) δ 7.38 (m, 2H), 6.72 (d, 1H), 4.66 (s, 2H), 3.80 (s, 3H), 2.67 (m, 2H), 1.57 (m, 2H), 1.38 (m, 2H), 0.98 (t, 3H).

Step 6. Preparation of methyl 2-(2-butyl-4-sulfanylphenoxy)acetate (compound 100F)

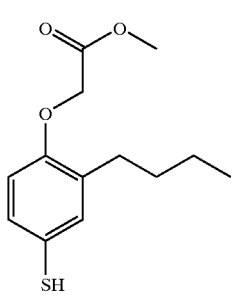

100F

The title compound was prepared in the manner analogous to Example 1D with the product from example 100E (2.79 g, 10.0 mmol), dithiothreitol (3.08 g, 20.0 mmol), and 0.2 M potassium dihydrogenphosphate (15 ml) in 60 ml of methanol. 400 MHz $^1$H NMR (CDCl$_3$) δ 7.11 (m, 2H), 6.60 (d, 1H), 4.61 (s, 2H), 3.81 (s, 3H), 3.36 (s, 1H), 2.63 (m, 2H), 1.57 (m, 2H), 1.38 (m, 2H), 0.98 (t, 3H).

Step 7. Preparation of methyl 2-[2-butyl-4-({4-[4-(trifluoromethyl)phenyl]phenyl}methylthio)phenoxy]acetate (compound 100G)

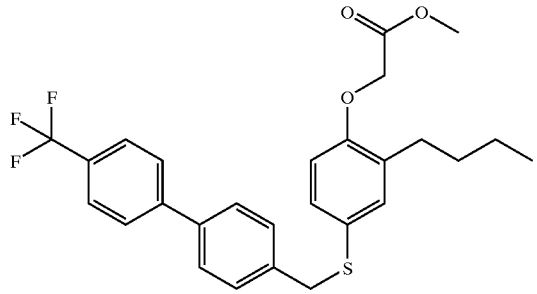

100G

The title compound was prepared in the manner analogous to Example 1F using 100F and 1-(bromomethyl)-4-[4-(trifluoromethyl)phenyl]benzene prepared from and phosphorous tribromide and (4'-trifluoromethyl-biphenyl-4-yl)-methanol in a manner analagous to Example 3B. 400 MHz $^1$H NMR (CDCl$_3$) δ 7.68 (m, 4H), 7.51 (d, 2H), 7.29 (d, 2H), 7.15 (m, 2H), 6.60 (d, 1H), 4.62 (s, 2H), 4.04 (s, 2H), 3.79 (s, 3H), 2.60 (m, 2H), 1.55 (m, 2H), 1.35 (m, 2H), 0.88 (t, 3H).

Step 8. Preparation of 2-[2-butyl-4-({4-[4-(trifluoromethyl)phenyl]phenyl}methylthio)phenoxy]acetic acid (compound 100)

The title compound was prepared in the manner analogous to Example 1 with the product from example 100G. mp 155–157° C.; 400 MHz $^1$H NMR (DMSOd-$_6$) δ 7.88 (d, 2H), 7.80 (d, 2H), 7.65 (d, 2H), 7.38 (d, 2H), 7.17 (dd, 1H), 7.09 (d, 1H), 6.79 (d, 1H), 4.65 (s, 2H), 4.17 (s, 2H), 2.50 (m, 2H), 1.43 (m, 2H), 1.22 (m, 2H), 0.81 (t, 3H). MS m/z 473 (M−1). Anal. Calc'd for C$_{26}$H$_{25}$O$_3$SF$_3$: C, 65.81; H, 5.31; Found: C, 65.95; H, 5.36.

EXAMPLE 101

Preparation of {6-methyl-8-[4-(4-trifluoromethyl-benzyloxy)-benzyl-sulfanyl]-chroman-5-yloxy}-acetic acid (compound 101)

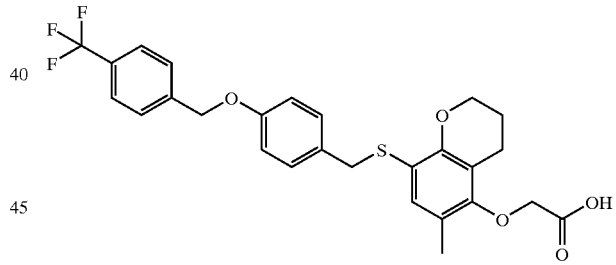

101

Step 1. {6-methyl-8-[4-(4-trifluoromethyl-benzyloxy)-benzylsulfanyl]-chroman-5-yloxy}-acetic acid methyl ester (compound 101A)

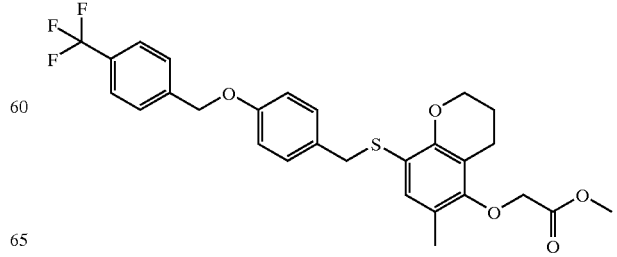

101A

The title compound was prepared in the manner analogous to Example 1F using (8-mercapto-6-methyl-chroman-5-yloxy)-acetic acid methyl ester and the product from Example 14B. MS m/z 533 (M+1).

Step 2. {6-methyl-8-[4-(4-trifluoromethyl-benzyloxy)-benzylsulfanyl]-chroman-5-yloxy}-acetic acid (compound 101)

2N KOH solution (5 ml) was added to a stirred slurry of the product from Example 101A (0.4g, 0.75 mmol) in 2–3 ml of methanol, and the mixture was heated briefly on a steambath until nearly clear, then stirred at room temp. After 3 hours the mixture was diluted with 15–20 ml of ice-water and acidified with $H_3PO_4$. After 15 minutes the precipitate was filtered off, rinsed 3x with water, and dried to afford the title product, 0.2g, 51%. 400 MHz $^1$H NMR (DMSO-$d_6$) δ 7.70 (d, 2H, J=8 Hz), 7.59 (d, 2H, J=8 Hz), 7.18 (d, 2H, J=8.5 Hz), 6.88 (d, 2H, J=8.5 Hz), 6.83 (s, 1H), 5.14 (s, 2H), 4.21 (s, 2H), 4.06 (t, 2H, J=4.9Hz), 3.95 (s, 2H), 2.63 (t, 2H, J=6.3Hz), 2.03 (s, 3H), 1.79 (quint, 2H); MS m/z 517 (M−1).

EXAMPLE 102

Preparation of {4-[5-(4-trifluoromethyl-phenyl)-isoxazol-3-ylmethylsulfanyl]-5,6,7,8-tetrahydro-naphthalen-1-yloxy}-acetic acid (compound 102)

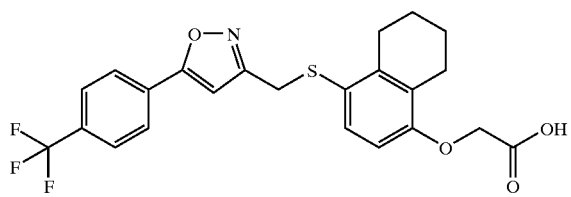

102

Step 1. {4-[5-(4-trifluoromethyl-phenyl)-isoxazol-3-ylmethylsulfanyl]-5,6,7,8-tetrahydro-naphthalen-1-yloxy}-acetic acid methyl ester (compound 102A)

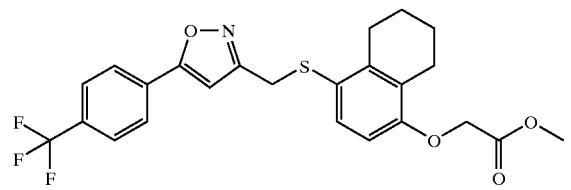

102A

The title compound was prepared in the manner analogous to Example 1F using (4-mercapto-5,6,7,8-tetrahydro-naphthalen-1-yloxy)-acetic acid methyl ester and the product from Example 42C; recrystallization from methanol afforded the title compound. MS m/z 478 (M+1).

Step 2. {4-[5-(4-trifluoromethyl-phenyl)-isoxazol-3-ylmethylsulfanyl]-5,6,7,8-tetrahydro-naphthalen-1-yloxy}-acetic acid (compound 102)

The title compound was prepared in the manner analogous to Example 1 using the product from Example 102A. mp 167–170° C; 400 MHz $^1$H NMR (DMSO-$d_6$) δ 8.01 (d, 2H, J=8 Hz), 7.83 (d, 2H, J=8.3 Hz), 7.14 (d, 2H, J=8.5 Hz), 7.07 (s, 1H), 6.58 (d, 2H, J=8.8 Hz), 4.56 (s, 2H), 4.07 (s, 2H), 2.64 (m, 2H), 2.53 (m, 2H), 1.60 (m, 4H,); MS m/z 464 (M+1).

The compounds of the present invention can also be prepared using combinatorial chemistry methods. In particular, compounds of Examples 103–134 were prepared using combinatorial chemistry analagous to that previously described in Examples 1–102. The combinatorial chemistry methods useful in the present invention include those where an activated alcohol is contacted with a thiol followed by saponification of the resulting ester to afford the desired products. Such methods can be illustrated by previously described Scheme 1 where compound D is an exemplary thiol, compound Y is an exemplary activated alcohol, and compound F is an exemplary desired product.

EXAMPLES 103–134

| Example No. | Name | MS m/z |
|---|---|---|
| 103 | (4-{2-Butyl-5-chloro-1-[4-(1-cyano-cyclopentyl)-benzyl]-1H-imidazol-4-ylmethylsulfanyl}-2-methyl-phenoxy)-acetic acid | 552.37 |
| 104 | [4-(5-Biphenyl-4-yl-2-thiophen-2-yl-4,5-dihydro-oxazol-4-ylmethylsulfanyl)-5-methoxy-2-methyl-phenoxy]-acetic acid | 546.33 |
| 105 | {4-[2-(4-Bromo-phenoxy)-ethylsulfanyl]-2,6-dimethyl-phenoxy}-acetic acid | 451.33 |
| 106 | [4-(3-{2-[4-(2-Diethylamino-ethoxy)-phenyl]-benzimidazol-1-yl}-propylsulfanyl)-5-methoxy-2-methyl-phenoxy]-acetic acid | 578.43 |
| 107 | [4-(5-Biphenyl-4-yl-2-thiophen-2-yl-4,5-dihydro-oxazol-4-ylmethylsulfanyl)-2-methyl-phenoxy]-acetic acid | 516.31 |
| 108 | (4-{2-[3-(4-Fluoro-phenyl)-benzo[b]thiopben-7-yl]-ethylsulfanyl}-2-methyl-phenoxy)-acetic acid | 451.24 |
| 109 | {2-Methyl-4-[2-(5-phenyl-naphthalen-1-yloxy)-ethylsulfanyl]-phenoxy}-acetic acid | 443.3 |
| 110 | [2-Methyl-4-(3-phenoxy-benzylsulfanyl)-phenoxy]-acetic acid | 379.23 |
| 111 | [2,5-Dimethyl-4-(5-p-tolyl-1,3,4-oxadiazol-2-ylmethylsulfanyl)-phenoxy]-acetic acid | 385.22 |
| 112 | [2-Methyl-4-(4-pyrazol-1-yl-benzylsulfanyl)-phenoxy]-acetic acid | 355.2 |
| 113 | [2-Methyl-4-(5-methyl-3-phenyl-isoxazol-4-ylmethylsulfanyl)-phenoxy]-acetic acid | 370.2 |
| 114 | [4-(Biphenyl-2-ylmethylsulfanyl)-2-methyl-phenoxy]-acetic acid | 363.2 |
| 115 | {4-[5-(4-Chloro-phenyl)-isoxazol-3-ylmethylsulfanyl]-2-methyl-phenoxy}-acetic acid | 390.16 |
| 116 | [2-Methyl-4-(5-p-tolyl-1,3,4-oxadiazol-2-ylmethylsulfanyl)-phenoxy]-acetic acid | 371.19 |
| 117 | {4-[3-(4-Chloro-phenyl)-1,2,4-oxadiazol-5-ylmethylsulfanyl]-2-methyl-phenoxy}-acetic acid | 391.14 |
| 118 | [2,5-Dimethyl-4-(4-pyrazol-1-yl-benzylsulfanyl)-phenoxy]-acetic acid | 369.2 |
| 119 | [4-(Biphenyl-2-ylmethylsulfanyl)-2,5-dimethyl-phenoxy]-acetic acid | 377.19 |
| 120 | [4-(4-Benzyloxy-benzylsulfanyl)-5,6,7,8-tetrahydro-naphthalen-1-yloxy]-acetic acid | 433.41 |
| 121 | [4-(4-Benzyloxy-benzylsulfanyl)-2,6-dimethyl-phenoxy]-acetic acid | 407.39 |
| 122 | [4-(4-Benzyloxy-benzylsulfanyl)-2,5-dimethyl-phenoxy]-acetic acid | 407.38 |
| 123 | [4-(4-Benzyloxy-benzylsulfanyl)-2-methyl-phenoxy]-acetic acid | 393.38 |
| 124 | [4-(4-Benzyloxy-benzylsulfanyl)-phenoxy]-acetic acid | 379.35 |
| 125 | [4-(Biphenyl-4-ylmethylsulfanyl)-5,6,7,8-tetrahydro-naphthalen-1-yloxy]-acetic acid | 403.4 |
| 126 | [4-(Biphenyl-4-ylmethylsulfanyl)-2,6-dimethyl-phenoxy]-acetic acid | 377.38 |
| 127 | [4-(Biphenyl-4-ylmethylsulfanyl)-2,5-dimethyl-phenoxy]-acetic acid | 377.37 |
| 128 | [4-(Biphenyl-4-ylmethylsulfanyl)-phenoxy]-acetic acid | 349.32 |
| 129 | {4-[3-(2-Fluoro-phenoxy)-benzylsulfanyl]-2,6-dimethyl-phenoxy}-acetic acid | 411.2 |
| 130 | [4-(2-{4-[2-(3-Chloro-4-cyclohexyl-phenyl)-ethyl]-piperazin-1-yl}-ethylsulfanyl)-2-methyl-phenoxy]-acetic acid | 531.31 |

-continued

| Example No. | Name | MS m/z |
|---|---|---|
| 131 | [5-Methoxy-2-methyl-4-(2-{4-[2-(3-phenyl-benzofuran-7-yl)-ethyl]-piperazin-1-yl}-ethylsulfanyl)-phenoxy]-acetic acid | 561.37 |
| 132 | {4-[2-(2,6-Diphenyl-piperidin-1-yl)-ethylsulfanyl]-5-methoxy-2-methyl-phenoxy}-acetic acid | 492.31 |
| 133 | [2-Methyl-4-(2-{4-[2-(3-phenyl-benzofuran-7-yl)-ethyl]-piperazin-1-yl}-ethylsulfanyl)-phenoxy]-acetic acid | 531.32 |
| 134 | {4-[2-(2,6-Diphenyl-piperidin-1-yl)-ethylsulfanyl]-2-methyl-phenoxy}-acetic acid | 462.25 |

The preparation of Examples 103–134 is further described below.

Preparation of Thiols used in Combinatorial Methods

Thiol WW

Preparation of 2,5-Dimethyl-4-thiocyanato-phenol (compound WWA)

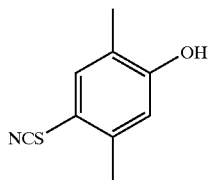

WWA

The title compound was prepared in a manner analogous to compound 1B. 400 MHz $^1$H NMR (DOMSO-d$_6$) δ 10.0 (s, 1H), 7.35 (s, 1H), 6.73 (s, 1H), 2.3 (s, 3H), 2.04 (s, 3H); MS m/z 180 (m+1).

Preparation of (2,5-Dimethyl-4-thiocyanato-phenoxy)-acetic acid methyl ester (compound WWB)

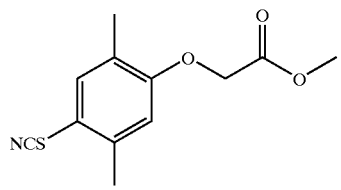

WWB

The title compound was prepared from compound WWA in a manner analogous to compound 1C. 400 MHz $^1$H NMR (DMSO-d$_6$) δ 7.07 (s, 1H), 6.50 (s, 1H), 4.56 (s, 2H), 3.76 (s, 3H), (s, 1H), 2.26 (s, 3H), 2.17 (s, 3H); MS m/z 252 (m+1).

Preparation of (4-Mercapto-2,5-dimethyl-phenoxy)-acetic acid methyl ester (compound WW)

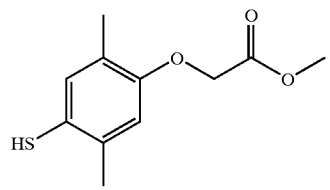

WW

The title compound was prepared from compound WWB in a manner analogous to compound 1D. 400 MHz $^1$H NMR (DMSO-d$_6$) δ 7.07 (s, 1H), 6.50 (s, 1H), 4.56 (s, 2H), 3.76 (s, 3H), 3.07 (s, 1H), 2.26 (s, 3H), 2.17 (s, 3H); MS m/z 227 (M+1).

Thiol XX

Preparation of 2,6-Dimethyl-4-thiocyanato-phenol (compound XXA)

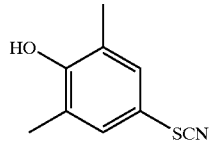

XXA

Compound XXA was prepared from 2,6-dimethylphenol in a similar manner as described for compound 1B. 400 MHz $^1$H NMR (DMSO-d$_6$) δ 8.96 (s, 1H), 7.22 (s, 2H), 2.13 (s, 6H).

Preparation of (2,6-Dimethyl-4-thiocyanato-phenoxy)-acetic acid methyl ester (compound XXB)

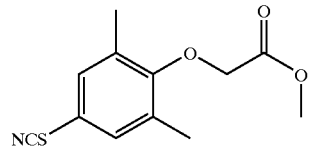

XXB

Compound XXB was prepared from compound XXA in a similar manner as described for compound 1C to give 2.5 g (46%) of the title compound pure enough for subsequent use 400 MHz $^1$H NMR (DMSO-d$_6$) δ 7.11 (s, 2H), 4.41 (s, 2H), 3.63 (s, 3H), 2.14 (s, 6H).

Preparation of (4-Mercapto-2,6-dimethyl-phenoxy)-acetic acid methyl ester (compound XX)

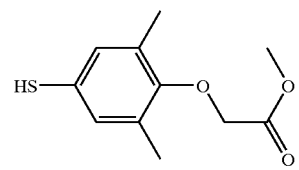

XX

Compound XX was prepared from compound XXB in a similar manner as described for compound 1D to give, after purification by flash column chromatography (gradient elution: 100% hexanes to 30% EtOAc/hexanes), 1.8 g (82%) of the title compound. 400 MHz $^1$H NMR (DMSO-d$_6$) δ 6.90 (s, 2H), 5.51 (s, 1H), 4.39 (s, 2H), 3.66 (s, 3H), 2.10 (s, 6H); MS m/z 225 (M–1).

Thiol YY

Preparation of 4-Thiocyanato-5,6,7,8-tetrahydro-naphthalen-1-ol (compound YYA)

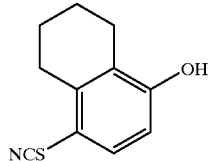

YYA 5,6,7,8-Tetrahydro-naphthalen-1-ol (1 g, 6.8 mmol) was dissolved in 25 ml acetonitrile. Sodium thiocyanate (1.76 g, 22 mmol) and sodium bromide (0.7 g, 6.8 mmol) were added and stirred for 5 minutes at ambient temperature. Bromine (1.2 g, 7.48 mmol) was added drop wise over 5 minutes. The orange solution was allowed to stir two hours. Brine was added and the crude product was extracted twice into ethyl acetate. The combined organic extracts were washed once with brine, dried over anhydrous sodium sulfate, decanted and concentrated. Normal phase chromatography afforded the title product, 1.28 g, 92%. 400 MHz $^1$H N MR (DMSO-$d_6$) δ 11.1 (s, 1H), 7.40 (d, 1H, J=8.8 Hz), 6.61 (d, 1H, 8.8 Hz), 2.78 (m, 2H), 2.59 (m, 2H), 1.70 (m, 4H). MS m/z 278 (m+1)

Preparation of (4-Thiocyanato-5,6,7,8-tetrahydro-naphthalen-1-yloxy)-acetic acid methyl ester (compound YYB)

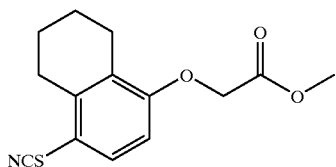

YYB

The title compound was prepared in the manner analogous to example 1C utilizing compound YYA. 400 MHz $^1$H NMR (DMSO-$d_6$) δ 7.4 (d, 1H, J=8.8 Hz), 6.80 (d, 1H, 8.8 Hz), 4.84 (s, 2H), 3.64 (s, 3H), 2.78 (m, 2H), 2.59 (m, 2H), 1.70 (m, 4H). MS m/z 278 (m+1).

Preparation of (4-Mercapto-5,6,7,8tetrahydro-naphthalen-1-yloxy)-acetic acid methyl ester (compound YY)

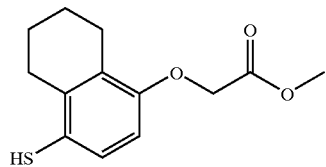

YY

The title compound was prepared in the manner analogous to example 1D utilizing compound YYB. 400 MHz $^1$H NMR (DMSO-$d_6$) δ 7.08 (d, 1H, J=8.8 Hz), 6.55 (d, 1H, 8.8 Hz), 4.71 (s, 1H), 4.70 (s, 2H), 3.63 (s, 3H), 2.45 (m, 2H), 2.44 (m, 2H), 1.65 (m, 4H). MS m/z 253 (M+1).

Thiol ZZ

Preparation of 4-Thiocyanato-phenol (compound ZZA)

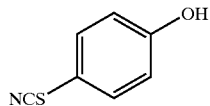

ZZA

The title compound was prepared in the manner analogous to Example 1B using phenol. MS m/z 152 (M+1)

Preparation of [(4-Thiocyanato-phenoxy)-acetic acid methyl ester (compound ZZB)

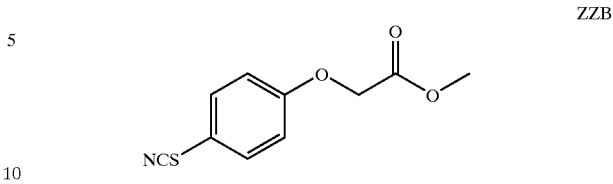

ZZB

The title compound was prepared in the manner analogous to Example 1C using ZZA. MS m/z 224 (M+1)

Preparation of (4-Mercapto-phenoxy)-acetic acid methyl ester (compound ZZ)

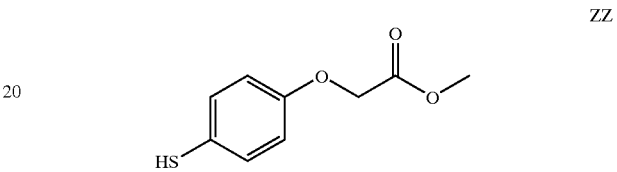

ZZ

The title compound was prepared in the manner analogous to Example 1D using ZZB. MS m/z 197 (M−1)

Preparation of Examples 103–134

Alcohol Preparation:

The appropriate alcohols in the salt form (0.65mmol) were dissolved in 3.0 mL of low water MeOH. MP-$CO_3$ (3.21 mmol/g, 3.70 equivalents to alcohol, 2.41 mmol) was then added to each vial containing the alcohol and shaken at ambient temperature for 3 h. The samples were then filtered into tared vials and concentrated.

Alcohol Activation:

Each alcohol sample was then diluted to 0.15M with DCM and 1.0 ML of each delivered to a reaction tube. PS-morpholine (4.0 mmol/g, 2 equivalents to alcohol, 0.3 mmol) and 25 μL methanesulfonyl chloride was then added to each reaction tube. The reaction tubes were shaken at ambient temperature for 16 h. The samples were then filtered into collection tubes, the resin rinsed with two 1.0 mL aliquots of DCM, and concentrated.

Alkylation:

Examples 103–134 were synthesized in the following fashion using either the thiol products 2C, 1D, WW, XX, YY or ZZ and the appropriate activated alcohol or alkyl halide. Each thiol was diluted to 0.15M with $CH_3CN$ and each activated alcohol diluted to 0.15M with $CH_3CN$. 1.0 mL aliquots of each thiol (0.15 mmol) and 1.0 mL aliquots of each activated alcohol (1.0 equivalents, 0.15 mmol) were then delivered to a reaction tube and 100 mg $Cs_2CO_3$ (2 equivalents, 0.3 mmol) was added. The reaction tubes were shaken at 60° C. for 2.5 h. The reacion mixtures were filtered into collection tubes, the resin rinsed with two 1.0 mL aliquots of $CH_3CN$, and concentrated.

Saponification:

Examples 103–134 were synthesized in the following fashion using the products from the alkylation step discussed above. Each alkylation product was diluted with 3.0 mL of 0.5M LiOH in 4:1 methoxyethanol:$H_2O$, shaken at 60° C. for 4 h and cooled to ambient temperature. To each reaction, was then added 1.0 mL 1N HCl and 1.0 mL brine. Each reaction was extracted twice with 2.0 mL EtOAc, and the organic layers concentrated to afford the desired products.

Biological Assays

The compounds of the present invention have demonstrated PPAR modulating activity in the standard assays commonly employed by those skilled in the art. Accordingly, such compounds and formulations comprising such compounds are useful for supressing appetite, modulating leptin, and treating, preventing or controlling hypercholesterolemia, dyslipidemia, obesity, eating disorders, hyperglycemia, atherosclerosis, hypertriglyceridemia, hyperinsulinemia and diabetes.

A. Selectivity Measurements

1. Test A. Transient Transfections Assay using the HepG2Hepatoma Cell Line.

HepG2 cells were transiently transfected with an expression plasmids encoding hPPARα, hPPARβ or mPPARγ chimeric receptors and a reporter containing the yeast upstream activating sequence (UAS) upstream of the viral E1B promoter controlling a luciferase reporter gene. In addition, the plasmid pRSVβ-gal was used to control for transfection efficiency. HepG2 cells were grown in DMEM supplemented with 10% FBS and 1 μM non-essential amino acid. On the first day, cells were split into 100 mm dishes at $2.5 \times 10^6$/dish and incubated overnight at 37° C./5% $CO_2$. On the second day the cells were transiently transfected with plasmid DNA encoding a chimeric receptor, the luciferase reporter gene; and β-gal. For each 100 mm dish, 15 μg of lucifease reporter (PG5E1b) DNA, 15 μg of Gal4-PPAR chimeric receptor DNA, and 1.5 μg of β-gal plasmid DNA were mixed with 1.4 ml of opti-MEM in the tube. 28 μl of LipoFectamine-2000 reagent was added to 1.4 ml of opti-MEM in the tube, and incubate for 5 min at RT. The diluted LipoFectamine-2000 reagent was combined with the DNA mixture, and incubate for 20 min at RT. After fresh medium was added to each 100 mm dish of cells, 2.8 ml of Lipofectamine2000-DNA mixture was added dropwise to the 100 mm dish containing 14 ml of medium, and incubate 37° C. overnight. On day three cells were trypsinized off the100 mm dishes and re-plated on 96 well plates. Cells were plated at $2.5 \times 10^4$ cells per well in 150 μl of media and 50 μl of compound diluted by media was added. The test compound added were in the range from 50 μM to 50 pM. After addition of compounds, the plates were incubated at 37° C. for 24 hours. Subsequently cells were washed with once with 100 μl of PBS, lysed, and processed for measuring luciferase and β-gal activity using Dual-Light luciferase kit from Tropix®, according to the manufacturer's recommendations, on an EG&G Bethold MicroLumat LB96P luminometer. $EC_{50}$ values were obtained using the GraphPad Prism™ program. Surprisingly, the compounds of the present invention exhibit activity for both PPARα and PPARβ. Compounds of the present invention exhibited a range of Hep G2-hBeta $EC_{50}$'s ("$EC_{50}β$") and Hep G2-hAlpha $EC_{50}$'s ("$EC_{50}α$") from greater than zero to about 20 μM. Specifically, as shown in Table 1, the Hep G2-hBeta $EC_{50}$'s and Hep G2-hAlpha $EC_{50}$'s for the compounds of the present invention fall within the following 6 groups:

I) >0–300 nM
II) >300–500 nM
III) >500–1000 nM
IV) >1000–2000 nM
V) >2000–5000 nM
VI) >5000 nM

TABLE 1

| Compound | $EC_{50}β$ nM (Group) | $EC_{50}α$ nM (Group) |
| --- | --- | --- |
| 1 | I | I |
| 3 | I | V |
| 4 | I | I |
| 5 | IV | — |
| 7 | I | I |
| 9 | I | I |
| 10 | I | II |
| 11 | I | III |
| 12 | I | — |
| 14 | I | I |
| 15 | I | — |
| 16 | I | I |
| 17 | IV | V |
| 18 | I | VI |
| 19 | I | I |
| 20 | I | V |
| 21 | I | I |
| 22 | IV | III |
| 23 | I | I |
| 25 | V | IV |
| 26 | I | — |
| 27 | V | III |
| 28 | IV | IV |
| 29 | I | I |
| 30 | IV | IV |
| 31 | VI | IV |
| 32 | II | IV |
| 33 | IV | IV |
| 34 | I | I |
| 35 | II | I |
| 36 | V | I |
| 37 | I | — |
| 38 | I | — |
| 39 | I | — |
| 40 | III | — |
| 41 | I | V |
| 42 | I | V |
| 43 | I | III |
| 44 | III | VI |
| 45 | I | — |
| 46 | I | I |
| 47 | VI | — |
| 48 | I | V |
| 49 | I | II |
| 50 | V | — |
| 51 | V | — |
| 52 | I | III |
| 53 | I | IV |
| 54 | II | — |
| 57 | V | IV |
| 58 | V | — |
| 59 | IV | VI |
| 60 | VI | — |
| 61 | II | — |
| 62 | IV | VI |
| 63 | I | V |
| 64 | VI | — |
| 65 | VI | — |
| 66 | VI | — |
| 67 | I | — |
| 68 | IV | — |
| 69 | V | — |
| 70 | III | — |
| 71 | III | — |
| 72 | IV | — |
| 73 | I | V |
| 74 | I | V |
| 75 | III | — |
| 76 | IV | — |
| 77 | II | — |
| 78 | II | — |
| 79 | II | VI |
| 80 | IV | — |
| 81 | I | VI |
| 84 | II | VI |
| 85 | IV | — |

TABLE 1-continued

| Compound | EC$_{50}\beta$ nM (Group) | EC$_{50}\alpha$ nM (Group) |
|---|---|---|
| 87 | V | — |
| 88 | VI | — |
| 89 | IV | — |
| 90 | III | — |
| 91 | V | — |
| 92 | I | I |
| 93 | III | — |
| 97 | III | VI |
| 98 | V | — |
| 99 | II | — |
| 100 | III | — |

B. Effect of PPAR Modulators on Lipid and Human Apoprotein A1 Concentrations in the hApoA1 Transgenic Mouse Mice, transgenic for human apoA1, were purchased from Jackson laboratories. All animals were allowed normal chow (Ralston-Purina) and water ad libitum in temperature controlled rooms, under a 12-h light, 12-h dark cycle beginning with lights on at 6 AM. During the treatment phase of the study the mice were dosed daily between 6 and 9 AM by oral gavage using a suspension vehicle of 1.5% carboxymethyl-cellulose plus 0.2 percent Tween-20 (CMC/Tween) containing the specified compounds. Control animals received vehicle alone. Vehicle volume represented 0.25 percent of body weight. Under anesthesia, tail blood was obtained weekly in the morning at the indicated days of study. At termination, tissue samples (liver, intestine, fat, and muscle) were taken to study effects on genes effecting lipid metabolism. Each of the compounds of the present invention that were tested effected a significant increase in HDL over the values observed for the control animals. Furthermore, these compounds resulted in triglyceride levels which were lower than observed in controls. Compounds of the present invention tested in the hApoAI transgenic mouse model showed a range of HDL-c elevation and triglyceride lowering when dosed at 30 mg/kg/day. For instance, Example 4 raised HDL-c 97% and lowered triglycerides 65 % relative to the control population, Example 6 raised HDL-c 24% and lowered triglycerides 59 % relative to the control population, and Example 3 raised HDL-c 9% and lowered triglycerides 70% relative to the control population.

C. Effect of Compounds of the Invention on Insulin Resistant or Diabetic Cynomolgus Monkeys Cynomolgus monkeys that were either insulin resistant or diabetic (type II) were treated for eight weeks with [5-Methoxy-2-methyl-4-(4'-trifluoromethyl-biphenyl-4-ylmethylsulfanyl)-phenoxy]-acetic acid in a rising dose fashion (0.1 to 1 mg/kg). Plasma was sampled bi-weekly and analyzed for glycemics and leptin. Body weight was also measured at various time points across the study. The diabetic monkey mean body weight data is presented in Table 2 and the insulin resistant monkey mean body weight data is presented in Table 3.

TABLE 2

Diabetic Monkey Mean Body Weight

|  | −7 wk | −4 wk | Mean Baseline | 2 wk | 5 wk | 7 wk | 8 wk |
|---|---|---|---|---|---|---|---|
| Diab Ctl Mean | 8.10 | 8.05 | 8.08 | 8.17 | 8.18 | 8.17 | 8.19 |
| Diab Ctl StDev | 3.77 | 3.77 | 3.77 | 3.74 | 3.70 | 3.70 | 3.64 |
| Diab Ctl SEM | 1.89 | 1.88 | 1.89 | 1.87 | 1.85 | 1.85 | 1.82 |
| Diab Txt Mean | 8.84 | 8.91 | 8.87 | 8.75 | 8.37 | 8.08 | 7.80 |
| Diab Txt StDev | 3.73 | 3.68 | 3.70 | 3.61 | 3.52 | 3.34 | 3.20 |
| Diab Txt SEM | 1.32 | 1.30 | 1.31 | 1.28 | 1.24 | 1.18 | 1.13 |

IR = insulin resistant, Diab = diabetic, Ctl = control, Txt = experimental, StDev = standard deviation, SEM = standard error of the mean

TABLE 3

Insulin Resistant Monkey Mean Body Weight

|  | −7 wk | −4 wk | Mean Baseline | 2 wk | 4 wk | 6 wk | 8 wk |
|---|---|---|---|---|---|---|---|
| IR Ctl Mean | 6.18 | 6.15 | 6.17 | 6.04 | 6.00 | 5.94 | 5.91 |
| IR Ctl StDev | 3.48 | 3.43 | 3.46 | 3.22 | 3.19 | 3.16 | 3.17 |
| IR Ctl SEM | 1.74 | 1.72 | 1.73 | 1.61 | 1.60 | 1.58 | 1.59 |
| IR Txt Mean | 5.25 | 5.32 | 5.29 | 5.26 | 5.04 | 4.91 | 4.71 |
| IR Txt StDev | 3.17 | 3.22 | 3.19 | 3.42 | 3.40 | 3.34 | 3.20 |
| IR Txt SEM | 0.95 | 0.97 | 0.96 | 1.03 | 1.03 | 1.01 | 0.96 |

IR = insulin resistant, Diab = diabetic, Ctl = control, Txt = treated, StDev = standard deviation, SEM = standard error of the mean Plasma leptin values, presented as baseline values vs. 8-week treatment, were determined by ELISA and are presented in Table 4. The effect of [5-Methoxy-2-methyl-4-(4'-trifluoromethyl-biphenyl-4-ylmethylsulfanyl)-phenoxy]-acetic acid on plasma leptin values in diabetic and insulin resistant obese cynomolgus monkeys is demonstrated. by the lesser increase in plasma leptin values seen in the treated animals.

The amount of exogenous insulin the diabetic monkeys received to maintain proper glucose levels, the exogenous insulin requirement, is also presented in Table 4 as baseline values vs. 8-week treatment. By definition, insulin resistant monkeys are not yet diabetic and do not receive exogenous insulin. A reduction in exogenous insulin requirements is a measure of improved insulin sensitivity and glucose control.

TABLE 4

Leptin and Exogenous Insulin

|  | Pre-Treatment | Post-Treatment |
|---|---|---|
| Exogenous Insulin Requirement (u/day) |  |  |
| Diabetic Controls | 89 ± 71 | 101 ± 73 |
| Diabetic Treated | 66 ± 16 | 18 ± 4 |
| Leptin (ng/ml) |  |  |
| Diabetic Controls | 6.55 ± 1.38 | 18.83 ± 0.24 |
| Diabetic Treated | 7.22 ± 0.93 | 10.89 ± 2.7 |
| Insulin Resistant Controls | 9.85 ± 0.45 | 13.60 ± 3.45 |
| Insulin Resistant Treated | 7.33 ± 1.16 | 5.73 ± 2.14 |

Formulations

The compounds of the present invention can be administered alone or in combination with one or more therapeutic agents. These include, for example, other agents for the treatment, control, or prevention of hypercholesteremia, dyslipidemia, obesity, hyperglycemia, hypercholesteremia, atherosclerosis, hypertriglyceridemia, and hyperinsulinemia. The compounds of the present invention can be administered alone or in combination with one or more therapeutic agents for the supression of appetite and modulation of leptin.

The compounds are thus well suited to formulation for convenient administration to mammals for the prevention and treatment of such disorders.

The following examples further illustrate typical formulations provided by the invention.

Formulation 1

| Ingredient | Amount |
|---|---|
| compound of Formulas I–V | 0.5 to 800 mg |
| sodium benzoate | 5 mg |
| isotonic saline | 1000 mL |

The above ingredients are mixed and dissolved in the saline for IV administration to a patient.

Formulation 2

| Ingredient | Amount |
|---|---|
| compound of Formulas I–V | 0.5 to 800 mg |
| cellulose, microcrystalline | 400 mg |
| stearic acid | 5 mg |
| silicon dioxide | 10 mg |
| sugar, confectionery | 50 mg |

The ingredients are blended to uniformity and pressed into a tablet that is well suited for oral administration to a patient.

Formulation 3

| Ingredient | Amount |
|---|---|
| compound of Formulas I–V | 0.5 to 800 mg |
| starch, dried | 250 mg |
| magnesium stearate | 10 mg |

The ingredients are combined and milled to afford material suitable for filling hard gelatin capsules administered to a patient.

Formulation 4

| Ingredient | Amount % wt./(total wt.) |
|---|---|
| compound of Formulas I–V | 1 to 50 |
| Polyethylene glycol 1000 | 32 to 75 |
| Polyethylene glycol 4000 | 16 to 25 |

The ingredients are combined via melting and then poured into molds containing 2.5 g total weight.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A compound of formula (I):

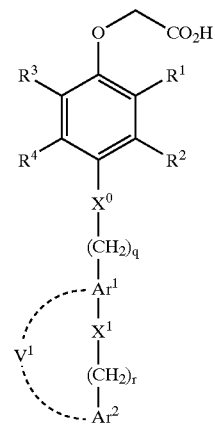

and pharmaceutically acceptable salts thereof, wherein:

$X^0$ is S; $X^1$ is absent, O, S, —$CH_2$—, —$CH_2$—$CH_2$—, or —CH=CH—;

$Ar^1$ and $Ar^2$ are each independently unsubstituted or substituted phenyl or pyridinyl;

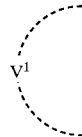

is absent;

$R^1$ and $R^2$ are selected from hydrogen, lower alkyl, lower alkoxy, haloalkyl, —O—$(CH_2)_m CF_3$, halogen, nitro, cyano, —OH, —SH or —$CF_3$;

$R^3$ and $R^4$ are selected from hydrogen, lower alkyl, lower alkoxy, haloalkyl, —O—$(CH_2)_m CF_3$, halogen, nitro, cyano, —OH, —SH or —$CF_3$;

provided that at least one of $R_1$–$R_4$ is H, lower alkyl, lower alkoxy, haloalkyl, —O—$(CH_2)_m CF_3$, halogen, nitro, cyano, —OH, —SH or —$CF_3$;

m is 0 to 5;

q is 0 to 1; and r is 0 to 1.

2. The compound of claim 1, wherein $X^1$ is absent or O;

$Ar^1$ and $Ar^2$ are each independently unsubstituted or substituted phenyl or pyridinyl;

$R^1$ is hydrogen;

$R^2$ is lower alkyl, lower alkoxy, haloalkyl, —O—$(CH_2)_m CF_3$, halogen, nitro, cyano, —OH, —SH or —$CF_3$;

$R^3$ is lower alkyl, lower alkoxy, haloalkyl, —O—$(CH_2)_m CF_3$, halogen, nitro, cyano, —OH, —SH or $CF_3$;

$R^4$ is hydrogen, lower alkyl, lower alkoxy, haloalkyl, —O—$CH_2)_m CF_3$, halogen, nitro, cyano, —OH, —SH or —$CF_3$;

m is 0 to 5;

q is 1; and r is 0 to 1.

3. The compound of claim 1, wherein
$X^1$ is absent;
$Ar^1$ is phenyl;
$Ar^2$ is substituted phenyl or pyridinyl;
$R^1$ is hydrogen;
$R^2$ is lower alkyl, lower alkoxy, haloalkyl, —O—(CH$_2$)$_m$CF$_3$, —OH or —SH;
$R^3$ is lower alkyl or haloalkyl;
$R^4$ is hydrogen;
m is 0 to 5;
q is 1; and
r is 0.

4. The compound of claim 1, wherein
$X^1$ is absent or 0;
$Ar^1$ is phenyl;
$Ar^2$ is substituted phenyl;
$R^1$ is hydrogen;
$R^2$ is lower alkoxy;
$R^3$ is lower alkyl;
$R^4$ is hydrogen;
q is 1; and
r is 0 to 1.

5. The compound of claim 1, wherein
$X^1$ is absent or 0;
$Ar^1$ is phenyl;
$Ar^2$ is substituted phenyl;
$R^1$ is hydrogen;
$R^2$ is methoxy;
$R^3$ is methyl;
$R^4$ is hydrogen;
q is 1; and
r is 0 to 1.

6. The compound of claim 1, wherein q is 1.

7. The compound of claim 1, wherein $Ar^1$ is substituted or unsubstituted phenyl.

8. The compound of claim 1, wherein $Ar^2$ is 4-trifluoromethylphenyl.

9. The compound of claim 1, wherein:
$R^1$, $R^2$, $R^3$, and $R^4$ are selected from hydrogen, alkyl, or alkoxy.

10. The compound of claim 1, wherein:
$R^2$ and $R^3$ are hydrogen; and
$R^1$ and $R^4$ are alkyl or alkoxy.

11. The compound of claim 1, wherein:
$R^1$ is alkyl;
$R^2$ and $R^3$ are hydrogen; and
$R^4$ is alkoxy.

12. The compound of claim 1, wherein:
$R^1$ is methyl, ethyl, isopropyl, n-propyl, t-butyl, n-butyl, or isobutyl;
$R^2$ and $R^3$ are hydrogen; and
$R^4$ is methyoxy, ethoxy, isopropoxy, n-propoxy, t-butoxy, n-butoxy, or isobutoxy.

13. A compound selected from:
[4-(Biphenyl-4-ylmethylsulfanyl)-5-methoxy-2-methyl-phenoxy]-acetic acid;
[5-Methoxy-2-methyl-4-(4'-trifluoromethyl-biphenyl-4-ylmethylsulfanyl)-phenoxy]-acetic acid;
[4-(2',4'-Dichloro-biphenyl-4-ylmethylsulfanyl)-5-methoxy-2-methyl-phenoxy]-acetic acid;
[5-Methoxy-2-methyl-4-(3'-trifluoromethyl-biphenyl-4-ylmethylsulfanyl)-phenoxy]-acetic acid;
[4-(4'-Fluoro-biphenyl-4-ylmethylsulfanyl)-5-methoxy-2-methyl-phenoxy]-acetic acid;
{5-Methoxy-2-methyl-4-[4-(4-trifluoromethyl-benzyloxy)-benzylsulfanyl]-phenoxy}-acetic acid;
[5-Methoxy-2-methyl-4-(3'-trifluoromethoxy-biphenyl-3-ylmethylsulfanyl)-phenoxy]-acetic acid;
{{-Methoxy-2-methyl-4-[4-(5-trifluoromethyl-pyridin-2-yl)-benzylsulfanyl]-phenoxy}-acetic acid;
{5-Methoxy-2-methyl-4-[6-(4-trifluoromethyl-phenyl)-pyridin-3-ylmethylsulfanyl]-phenoxy}-acetic acid;
[3-Methoxy-4-(4'-trifluoromethyl-biphenyl-4-ylmethylsulfanyl)-phenoxy]-acetic acid;
(4-{4-[2-(3-Fluoro-phenyl)-vinyl]-benzylsulfanyl}-5-methoxy-2-methyl-phenoxy)-acetic acid;
[5-Methoxy-2-methyl-4-(3-methyl-4'-trifluoromethyl-biphenyl-4-ylmethylsulfanyl)-phenoxy]-acetic acid;
[5-Methoxy-2-methyl-4-(4'-trifluoromethyl-biphenyl-3-ylmethylsulfanyl)-phenoxy]-acetic acid;
and pharmaceutically acceptable salts thereof.

14. A pharmaceutical composition comprising a compound of claim 1 or a pharmaceutically acceptable salt thereof admixed with a carrier, diluent, or excipient.

15. A method of treating or controlling non-insulin dependent diabetes mellitus in a mammal comprising administering to the mammal in need thereof a therapeutically effective amount of a compound of claim 1.

16. A method of treating or controlling obesity in a mammal comprising administering to the mammal in need thereof a therapeutically effective amount of a compound of claim 1.

17. A method of treating or controlling eating disorders in a mammal comprising administering to the mammal in need thereof a therapeutically effective amount of a compound of claim 1.

18. A method of supressing appetite in a mammal comprising administering to the mammal in need thereof a therapeutically effective amount of a compound of claim 1.

19. A method of modulating leptin levels in a mammal comprising administering to the mammal in need thereof a therapeutically effective amount of a compound of claim 1.

20. A method of treating or controlling hyperglycemia in a mammal comprising administering to the mammal in need thereof a therapeutically effective amount of a compound of claim 1.

21. A method of treating or controlling hyperinsulinemia in a mammal comprising administering to the mammal in need thereof a therapeutically effective amount of a compound of claim 1.

22. A method of treating a patient exhibiting glucose disorders associated with circulating glucocorticoids, growth hormone, catecholamines, glucagon, or parathyroid hormone, comprising administering to the patient a therapeutically effective amount of a compound of claim 1.

23. A method d of treating non-insulin dependent diabetes mellitus in a patient comprising administering to the patient in need of treatment a composition according to claim 14.

24. A method of treating metabolic syndrome in a patient comprising administering to the patient in need of treatment a composition according to claim 14.

* * * * *